US012569679B2

(12) United States Patent
Kendall et al.

(10) Patent No.: US 12,569,679 B2
(45) Date of Patent: Mar. 10, 2026

(54) TREATMENT DELIVERY SYSTEM

(71) Applicant: WearOptimo Pty Ltd, South Brisbane (AU)

(72) Inventors: Mark Anthony Fernance Kendall, South Brisbane (AU); Stephen James Wilson, South Brisbane (AU); Anthony Mark Brewer, South Brisbane (AU)

(73) Assignee: WearOptimo Pty Ltd, South Brisbane (AU)

( * ) Notice: Subject to any disclaimer, the term of this patent is extended or adjusted under 35 U.S.C. 154(b) by 1020 days.

(21) Appl. No.: 17/282,296

(22) PCT Filed: Oct. 1, 2019

(86) PCT No.: PCT/AU2019/051063
§ 371 (c)(1),
(2) Date: Apr. 1, 2021

(87) PCT Pub. No.: WO2020/069568
PCT Pub. Date: Apr. 9, 2020

(65) Prior Publication Data
US 2021/0402182 A1      Dec. 30, 2021

(30) Foreign Application Priority Data

Oct. 2, 2018      (AU) ................................ 2018903711

(51) Int. Cl.
*A61N 1/36*          (2006.01)
*A61B 5/00*          (2006.01)
(Continued)

(52) U.S. Cl.
CPC ...... *A61N 1/36031* (2017.08); *A61B 5/14546* (2013.01); *A61B 5/4836* (2013.01);
(Continued)

(58) Field of Classification Search
CPC ....... A61B 5/4848; A61B 5/685; A61B 5/145; A61B 5/00; A61B 5/14514; A61N 1/0575; A61N 1/08; A61M 2037/0023
See application file for complete search history.

(56) References Cited

U.S. PATENT DOCUMENTS

| | | | |
|---|---|---|---|
| 4,837,049 A | 6/1989 | Byers et al. | |
| 4,969,468 A | 11/1990 | Byers et al. | |

(Continued)

FOREIGN PATENT DOCUMENTS

| | | |
|---|---|---|
| CN | 102660547 A | 9/2012 |
| CN | 102703455 A | 10/2012 |

(Continued)

OTHER PUBLICATIONS

Miller, Philip R. et al., Multiplexed microneedle-based biosensor array for characterization of metabolic acidosis, Talanta, Jan. 15, 2012, pp. 739-742, vol. 88, Elsevier.

(Continued)

*Primary Examiner* — James D Ponton
*Assistant Examiner* — John A Doubrava
(74) *Attorney, Agent, or Firm* — Howard & Howard Attorneys PLLC

(57) ABSTRACT

A system for delivering treatment to a biological subject, the system including: at least one substrate including a plurality of microstructures configured to breach a stratum corneum of the subject; at least one sensor operatively connected to at least one microstructure, the at least one sensor being configured to measure response signals from the at least one microstructure; at least one treatment delivery mechanism operatively coupled to at least one microstructure to deliver treatment via at least one microstructure; and, one or more electronic processing devices that are configured to control the at least one treatment delivery mechanism to thereby (Continued)

deliver treatment to the subject at least partially in accordance with the measured response signals.

19 Claims, 65 Drawing Sheets

Specification includes a Sequence Listing.

(51) Int. Cl.

| | | |
|---|---|---|
| *A61B 5/145* | (2006.01) | |
| *A61N 1/05* | (2006.01) | |
| *A61N 1/08* | (2006.01) | |

(52) U.S. Cl.
CPC ............ *A61B 5/4848* (2013.01); *A61B 5/685* (2013.01); *A61N 1/0575* (2013.01); *A61N 1/08* (2013.01)

(56) References Cited

U.S. PATENT DOCUMENTS

| | | | |
|---|---|---|---|
| 5,582,981 | A | 12/1996 | Toole et al. |
| 5,595,877 | A | 1/1997 | Gold et al. |
| 6,052,652 | A | 4/2000 | Lee |
| 6,091,975 | A | 7/2000 | Daddona et al. |
| 6,256,533 | B1 | 7/2001 | Yuzhakov et al. |
| 6,267,724 | B1 | 7/2001 | Taylor |
| 6,558,361 | B1 | 5/2003 | Yeshurun |
| 6,589,202 | B1 | 7/2003 | Powell |
| 6,591,124 | B2 | 7/2003 | Sherman et al. |
| 6,908,453 | B2 | 6/2005 | Fleming et al. |
| 6,923,764 | B2 | 8/2005 | Aceti et al. |
| 6,972,013 | B1 | 12/2005 | Zhang et al. |
| 7,285,090 | B2 | 10/2007 | Stivoric et al. |
| 8,506,529 | B1 | 8/2013 | Yang |
| 8,543,179 | B2 | 9/2013 | Chen et al. |
| 8,588,884 | B2 | 11/2013 | Hegde et al. |
| 9,700,245 | B2 | 7/2017 | Bandura et al. |
| 9,974,471 | B1 | 5/2018 | Kam et al. |
| 10,098,574 | B1 | 10/2018 | Kam |
| 12,048,558 | B2 | 7/2024 | Kendall et al. |
| 2002/0028991 | A1 | 3/2002 | Thompson |
| 2002/0082543 | A1 | 6/2002 | Park et al. |
| 2002/0133129 | A1 | 9/2002 | Arias et al. |
| 2003/0069509 | A1 | 4/2003 | Matzinger et al. |
| 2003/0162190 | A1 | 8/2003 | Gorenstein et al. |
| 2003/0181936 | A1 | 9/2003 | Trautman et al. |
| 2004/0006264 | A1 | 1/2004 | Mojarradi et al. |
| 2004/0039254 | A1 | 2/2004 | Stivoric et al. |
| 2005/0070778 | A1 | 3/2005 | Lackey et al. |
| 2005/0261606 | A1 | 11/2005 | Sohrab |
| 2005/0261632 | A1 | 11/2005 | Xu |
| 2006/0172320 | A1 | 8/2006 | Stojanovic |
| 2006/0264782 | A1 | 11/2006 | Holmes et al. |
| 2007/0016268 | A1 | 1/2007 | Carter et al. |
| 2007/0020641 | A1 | 1/2007 | Heeger et al. |
| 2007/0134721 | A1 | 6/2007 | Laitenberger et al. |
| 2007/0142885 | A1 | 6/2007 | Hantash et al. |
| 2007/0276211 | A1 | 11/2007 | Mir et al. |
| 2008/0009763 | A1 | 1/2008 | Chiou et al. |
| 2008/0221407 | A1 | 9/2008 | Baker |
| 2008/0269666 | A1 | 10/2008 | Wang et al. |
| 2009/0062752 | A1 | 3/2009 | Gonnelli |
| 2009/0187167 | A1 | 7/2009 | Sexton et al. |
| 2010/0069726 | A1 | 3/2010 | Levinson |
| 2010/0075432 | A1 | 3/2010 | Piletsky et al. |
| 2010/0100005 | A1 | 4/2010 | Mir et al. |
| 2010/0121163 | A1 | 5/2010 | Vestel et al. |
| 2010/0256524 | A1 | 10/2010 | Levinson et al. |
| 2010/0286491 | A1 | 11/2010 | Chen et al. |
| 2011/0087195 | A1 | 4/2011 | Uhland et al. |
| 2011/0105871 | A1 | 5/2011 | Zimmermann et al. |
| 2011/0125058 | A1 | 5/2011 | Levinson et al. |
| 2011/0139636 | A1 | 6/2011 | Lai et al. |
| 2011/0224515 | A1 | 9/2011 | Mir et al. |

| | | | |
|---|---|---|---|
| 2011/0237925 | A1 | 9/2011 | Yue et al. |
| 2011/0295100 | A1 | 12/2011 | Hegde et al. |
| 2011/0318846 | A1 | 12/2011 | Lee et al. |
| 2011/0319786 | A1 | 12/2011 | Rebello et al. |
| 2012/0040865 | A1 | 2/2012 | Kim |
| 2012/0135540 | A1 | 5/2012 | Bruno |
| 2012/0316326 | A1 | 12/2012 | Ban et al. |
| 2013/0225956 | A1 | 8/2013 | Huang et al. |
| 2013/0338746 | A1 | 12/2013 | Guvanasen et al. |
| 2014/0170299 | A1 | 6/2014 | Gill et al. |
| 2014/0259652 | A1 | 9/2014 | Pushpala et al. |
| 2014/0303471 | A1 | 10/2014 | Rajaraman et al. |
| 2015/0208984 | A1 | 7/2015 | Huang |
| 2015/0247816 | A1 | 9/2015 | Bhansali et al. |
| 2015/0257685 | A1 | 9/2015 | Pushpala et al. |
| 2015/0335288 | A1 | 11/2015 | Toth et al. |
| 2015/0351690 | A1 | 12/2015 | Toth et al. |
| 2015/0367117 | A1 | 12/2015 | Ross et al. |
| 2016/0029962 | A1 | 2/2016 | Hyde et al. |
| 2016/0051195 | A1 | 2/2016 | Pang et al. |
| 2016/0082242 | A1 | 3/2016 | Burton et al. |
| 2016/0131668 | A1 | 5/2016 | Roncancio et al. |
| 2016/0166184 | A1 | 6/2016 | Teng et al. |
| 2016/0166185 | A1 | 6/2016 | Liepmann et al. |
| 2016/0220808 | A1 | 8/2016 | Hyde et al. |
| 2016/0256091 | A1 | 9/2016 | Cho et al. |
| 2016/0278638 | A1 | 9/2016 | Schwartz et al. |
| 2016/0278672 | A1 | 9/2016 | Cho et al. |
| 2016/0296149 | A1 | 10/2016 | Polsky et al. |
| 2016/0302687 | A1 | 10/2016 | Lee et al. |
| 2016/0331290 | A1 | 11/2016 | Oh et al. |
| 2016/0338639 | A1 | 11/2016 | Myers et al. |
| 2016/0345872 | A1 | 12/2016 | Wasson et al. |
| 2017/0007813 | A1 | 1/2017 | Negi et al. |
| 2017/0065186 | A1* | 3/2017 | Joseph ................. A61B 5/6876 |
| 2017/0128009 | A1 | 5/2017 | Pushpala et al. |
| 2017/0188916 | A1 | 7/2017 | Wang et al. |
| 2017/0233738 | A1 | 8/2017 | Jackson |
| 2017/0347925 | A1 | 12/2017 | Wang et al. |
| 2018/0059099 | A1 | 3/2018 | Kaushik et al. |
| 2018/0133447 | A1* | 5/2018 | McAllister ........ A61M 37/0015 |
| 2018/0177439 | A1 | 6/2018 | Sia et al. |
| 2018/0236215 | A1 | 8/2018 | Liu et al. |
| 2018/0326208 | A1 | 11/2018 | Ingman et al. |
| 2018/0327746 | A1 | 11/2018 | Minagawa et al. |
| 2018/0338713 | A1 | 11/2018 | Polsky et al. |
| 2019/0013425 | A1 | 1/2019 | Huang |
| 2019/0125223 | A1 | 5/2019 | Wang et al. |
| 2019/0219595 | A1 | 7/2019 | Leung |
| 2019/0223795 | A1* | 7/2019 | Patolsky ............ A61B 5/14865 |
| 2019/0256852 | A1 | 8/2019 | Xiao et al. |
| 2019/0328938 | A1 | 10/2019 | Son |
| 2020/0081001 | A1 | 3/2020 | Cleveland et al. |
| 2020/0172907 | A1 | 6/2020 | Yang et al. |
| 2020/0297945 | A1* | 9/2020 | Cottenden ........... A61M 15/009 |
| 2021/0033158 | A1 | 2/2021 | Sakamoto |
| 2021/0060322 | A1* | 3/2021 | Burton ................. A61B 5/4839 |
| 2021/0077019 | A1 | 3/2021 | Kendall et al. |
| 2021/0196164 | A1 | 7/2021 | Ivosevic |
| 2021/0204845 | A1 | 7/2021 | Pushpala et al. |
| 2021/0321916 | A1 | 10/2021 | Kendall et al. |
| 2021/0321942 | A1 | 10/2021 | Pushpala et al. |
| 2021/0338158 | A1 | 11/2021 | Kendall et al. |
| 2022/0031244 | A1 | 2/2022 | Windmiller et al. |
| 2023/0320636 | A1 | 10/2023 | Tehrani et al. |

FOREIGN PATENT DOCUMENTS

| | | |
|---|---|---|
| CN | 104745585 A | 7/2015 |
| CN | 105136754 A | 12/2015 |
| CN | 105349545 A | 2/2016 |
| CN | 106618598 A | 5/2017 |
| CN | 110876711 A | 3/2020 |
| CN | 115515488 A | 12/2022 |
| DE | 19758804 B4 | 10/2009 |
| EP | 1266608 A2 | 12/2002 |
| EP | 1 006 868 B1 | 6/2004 |
| EP | 2 532 749 A1 | 12/2012 |
| EP | 2 898 821 A1 | 7/2015 |

(56) References Cited

FOREIGN PATENT DOCUMENTS

| EP | 2 898 921 A1 | 7/2015 |
| EP | 3 517 023 | 7/2019 |
| EP | 3 564 672 A1 | 11/2019 |
| JP | 2001-523993 A | 11/2001 |
| JP | 2003-501161 A | 1/2003 |
| JP | 2003-501163 A | 1/2003 |
| JP | 2004-526581 A | 9/2004 |
| JP | 2009-519062 A | 5/2009 |
| JP | 4672142 B2 | 1/2011 |
| JP | 2013-512062 A | 4/2013 |
| JP | 2014-533523 A | 12/2014 |
| KR | 20170041375 A | 10/2015 |
| KR | 10-2016-0021488 A | 2/2016 |
| KR | 10-2016-0041667 A | 4/2016 |
| KR | 20170041473 | 4/2017 |
| NO | 2014/197822 | 12/2014 |
| WO | 1998/46124 | 10/1998 |
| WO | 2000/074763 | 12/2000 |
| WO | 2000/074766 | 12/2000 |
| WO | 01/91846 A2 | 12/2001 |
| WO | 03/050290 A2 | 6/2003 |
| WO | 2005/060621 A2 | 7/2005 |
| WO | 2005/072630 | 8/2005 |
| WO | 2006101798 A2 | 9/2006 |
| WO | 2006/116242 A2 | 11/2006 |
| WO | 2009/012420 A1 | 1/2009 |
| WO | 2009/140735 | 11/2009 |
| WO | 2010/070619 A1 | 6/2010 |
| WO | 2011/135531 A2 | 11/2011 |
| WO | 2012/040243 A1 | 3/2012 |
| WO | 2012/130948 A1 | 10/2012 |
| WO | 2013/058879 | 4/2013 |
| WO | 2013058879 A2 | 4/2013 |
| WO | 2014/120114 A1 | 8/2014 |
| WO | 2014/143427 A1 | 9/2014 |
| WO | 2014/159669 A2 | 10/2014 |
| WO | 2015/197706 A1 | 12/2015 |
| WO | 2016/009228 | 1/2016 |
| WO | 2016/009228 A1 | 1/2016 |
| WO | 2016/019250 | 2/2016 |
| WO | 2016/172554 A1 | 10/2016 |
| WO | 2016164208 A1 | 10/2016 |
| WO | 2017/156223 A1 | 9/2017 |
| WO | 2017/164982 A1 | 9/2017 |
| WO | 2017/210683 A1 | 12/2017 |
| WO | 2018/017196 | 1/2018 |
| WO | 2018/026931 A1 | 2/2018 |
| WO | 2018/031559 A1 | 2/2018 |
| WO | 2018/037407 | 3/2018 |
| WO | 2018/124327 | 7/2018 |
| WO | 2018/202922 A1 | 11/2018 |
| WO | 2018/223105 A2 | 12/2018 |
| WO | 2018/237380 A1 | 12/2018 |
| WO | 2019/032461 | 2/2019 |
| WO | 2019/050933 A1 | 3/2019 |
| WO | 2019044993 A1 | 3/2019 |
| WO | 2019/067383 A1 | 4/2019 |
| WO | 2019/094315 A1 | 5/2019 |
| WO | 2019/099856 A1 | 5/2019 |
| WO | 2019/121324 | 6/2019 |
| WO | 2019/139827 A1 | 7/2019 |
| WO | 2019/143923 A1 | 7/2019 |
| WO | 2019/170775 A1 | 9/2019 |
| WO | 2019/186129 | 10/2019 |
| WO | 2019/190596 | 10/2019 |
| WO | 2020/069564 A1 | 4/2020 |
| WO | 2020/069565 A1 | 4/2020 |
| WO | 2020/069568 A1 | 4/2020 |
| WO | 2020/069570 A1 | 4/2020 |
| WO | 2020069567 A1 | 4/2020 |
| WO | 2020/102277 A1 | 5/2020 |
| WO | 2021062475 A1 | 4/2021 |
| WO | 2021062476 A1 | 4/2021 |
| WO | 2022217304 A1 | 10/2022 |

OTHER PUBLICATIONS

Miller, Philip R. et al., Integrated carbon fiber electrodes within hollow polymer microneedles for transdermal electrochemical sensing, Biomicrofluidics, 2011, pp. 013415-1 to 013415-14, vol. 5, No. 1.

Szeitner, Zsuzsanna et al., A rational approach for generating cardiac troponin I selective Spiegelmers, The Royal Society of Chemistry, 2014, pp. 6801-6804, vol. 50.

Kiao, Yi et al., Preparation of electrode-immobilied, redox-modified oligonucleotides for electrochemical DNA and aptamer-based sensing, Nature Protocols, 2007, pp. 2875-2880, vol. 2, No. 11, Santa Barbara, California.

Xiao, Yi et al., Label-Free Electronic Detection of Thrombin in Blood Serum by Using an Aptamer-Based Sensor, Angew. Chem. Int. Ed., 2005, pp. 5456-5459, vol. 44, Wiley-VCH Verlag GmbH 7 Co. KGaA, Weinheim.

Pfeiffer, Franziska et al., Selection and Biosensor Application of Aptamers for Small Molecules, Frontiers in Chemistry, Jun. 15, 2016, 21 pages, vol. 4, Bonn, Germany.

Negahdary, M. et al., Electrochemical aptasensing of human cardiac troponin I based on an array of gold hanodumbells-Applied to early detection of myocardial infarction, Elsevier, 2017, pp. 62-71.

Stojanovic, Milan N. et al., Fluorescent Sensors Based on Aptamer Self-Assembly, American Chemical Society, 2000, pp. 11547-11548, vol. 122.

Gupta, Shashi et al., Chemically Modified DNA Aptamers Bind Interleukin-6 with High Affinity and Inhibit Signaling by Blocking Its Interaction with Interleukin-6 Receptor, The Journal of Biological Chemistry, Mar. 21, 2014, pp. 8706-8719, vol. 289, No. 12, USA.

Jo, Hunho et al., Electrochemical Aptasensor of Cardiac Troponin I for the Early Diagnosis of Acute Myocardial Infarction, analytical chemistry, 2015, pp. 9869-9875, vol. 87, ACS Publications,.

Negahdary, M. et al., An Aptamer-based Biosensor for Troponin I Detection in Diagnosis of Myocardial Infarction, J Biomed Phys Eng, 2018, pp. 167-178, vol. 8, No. 2.

Mishra, Geetesh Kumar et al., Electrochemical Aptasensors for Food and Environmental Safeguarding: A Review, Biosensors, Mar. 23, 2018, pp. 1-13, vol. 8, No. 28.

Meng, Ellis et al., Plasma Removal of Parylene C, Journal of Micromechanics and Microengineering, Feb. 22, 2008, pp. 1-13, vol. 18, IOP Publishing.

Liu, Ying et al., Aptamer-Based Electrochemical Biosensor for Interferon Gamma Detection, Analytical Chemistry, Oct. 1, 2010, pp. 8131-8136, vol. 82, No. 19.

Kumar, L.S. Selva et al., Label free nano-aptasensor for interleukin-6 in protein-dilute bio fluids such as sweat, Analytical Methods, 2015, pp. 1-5, vol. xx.

Lai, Rebecca Y et al., Comparison of the Signaling and Stability of Electrochemical DNA Sensors Fabricated from 6- or 11-Carbon Self-Assembled Monolayers, Lanmuir, Jun. 13, 2006, pp. 10796-10800, vol. 22, Santa Barbara, California.

Hirota, Masao et al., Chemically Modified Interleukin-6 Aptamer Inhibits Development of Collagen-Induced Arthritis n Cynomolgus Monkeys, Nucleic Acid Therapeutics, 2016, pp. 10-20, vol. 26, No. 1, Mary Ann Liebert, Inc.

Ricci, Francesco et al., Using Nature's "Tricks" To Rationally Tune the Binding Properties of Biomolecular Receptors, American Chemical Society, Aug. 26, 2016, pp. 1884-1892, vol. 49, ACS Publications.

Jiang, Wensen et al., One-dimensional microstructure-assisted intradermal and intracellular delivery, Bio-Design and Manufacturing, vol. 2, Feb. 1, 2019, pp. 24-30.

Sharma, Kabita; Scienceinfo "www.scienceinfo.com/potentiometry-types-electrodes-advantages/", Potentiometry definition, accessed Nov. 2024 (Year: 2023).

Sharma, Kabita, "Potentiometry: Principle, Types, Electrodes, Advantages", Science Info, Aug. 13, 2023, 13 pages.

English language abstract and machine-assisted English translation for DE 197 58 804 B4 extracted from espacenet. com database on Jun. 17, 2025, 42 pages.

(56) References Cited

OTHER PUBLICATIONS

English language abstract and machine-assisted English translation
for WO 2019/044993 A1 extracted from espacenet.com database on
Jun. 17, 2025, 24 pages.

* cited by examiner

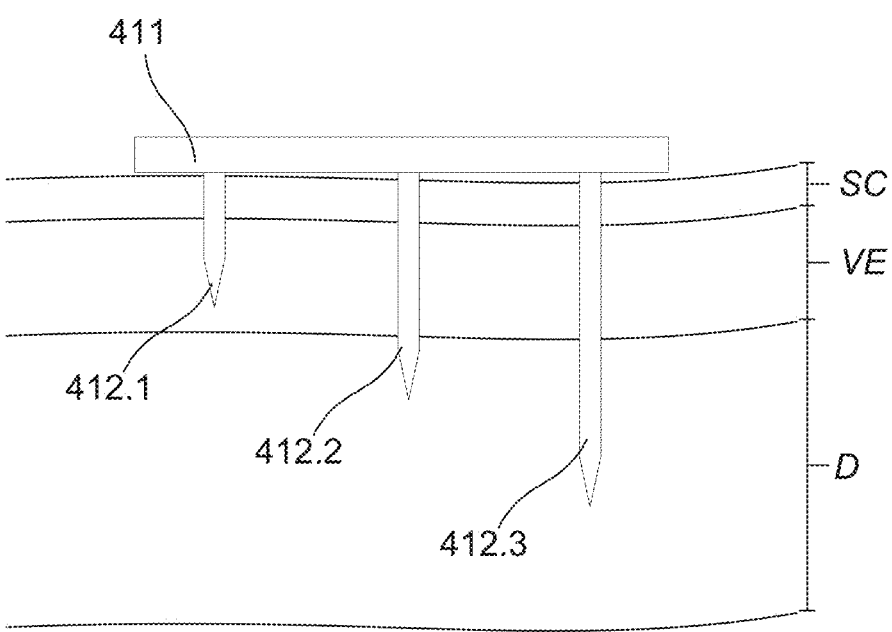
Fig. 4A
Fig. 4B
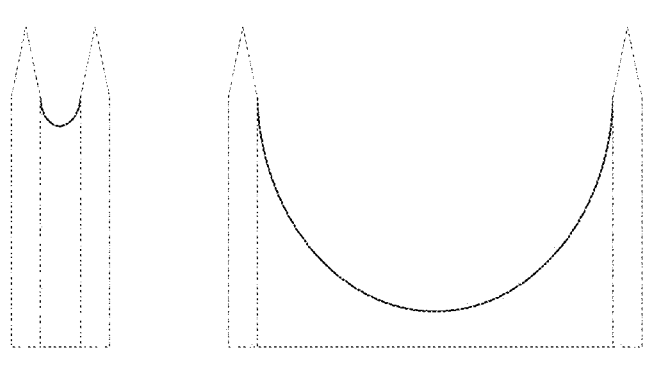
Fig. 4C          Fig. 4D

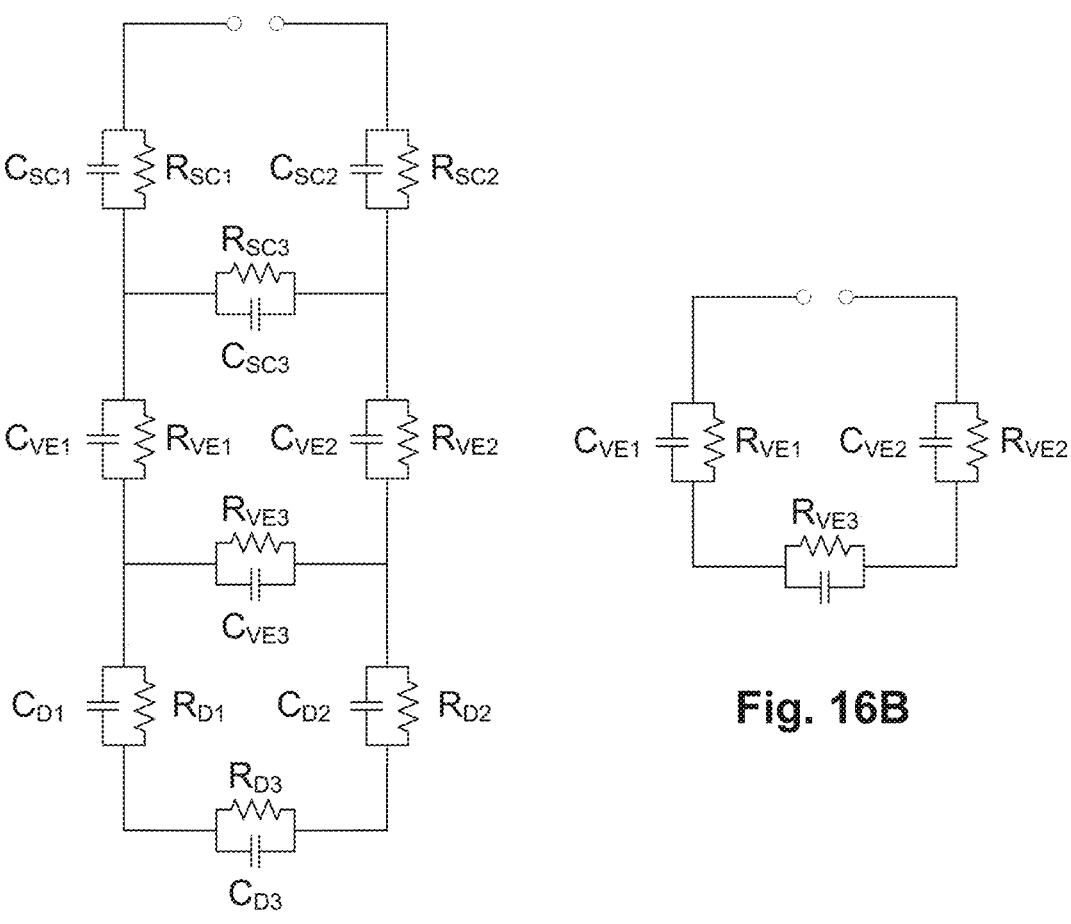
Fig. 16A
Fig. 16B
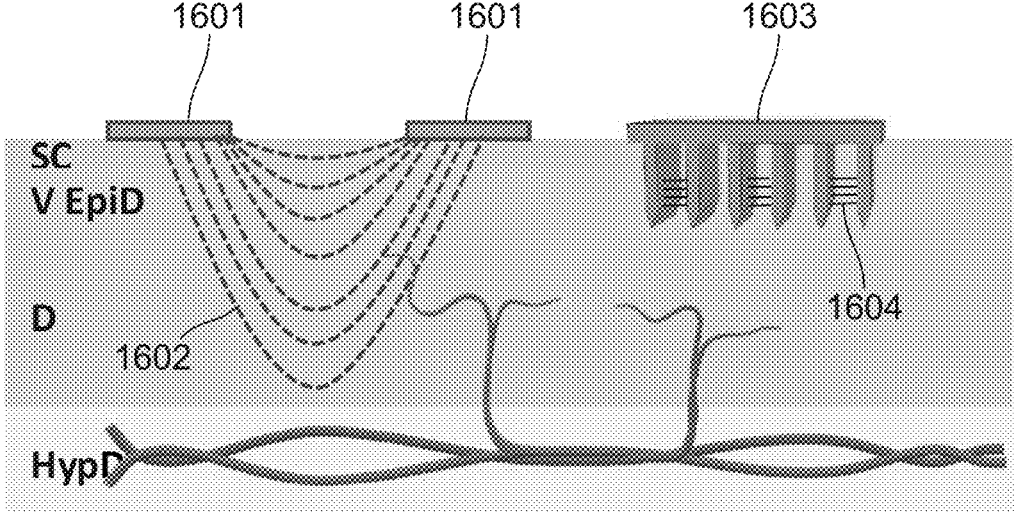
Fig. 16C

TREATMENT DELIVERY SYSTEM

CROSS-REFERENCE TO RELATED APPLICATIONS

The present application is the National Stage of International Patent Application No. PCT/AU2019/051063, filed Oct. 1, 2019, which claims priority to and all the benefits of Australian Patent Application No. 2018903711, filed Oct. 2, 2018, all disclosures of which are expressly incorporated herein by reference in their entirety.

SEQUENCE LISTING

This disclosure, in accordance with 37 C.F.R. § 1.52, incorporated by reference the sequence listing material contained within text file titled "Sequencelisting_ST25.txt", created on Dec. 11, 2025, and totaling 5,203 bytes.

BACKGROUND OF THE INVENTION

The present invention relates to a system and method for delivery treatment to a biological subject, and in one particular example, to delivering treatment, such as therapy, to a biological subject by breaching a functional barrier of the subject using microstructures.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Biological markers, such as proteins, antibodies, cells, small chemicals, hormones and nucleic acids, whose presence in excess or deficiency may indicate a diseased state, have been found in blood serum and their levels are routinely measured for research and for clinical diagnosis. Standard tests include antibody analysis for detecting infections, allergic responses, and blood-borne cancer markers (e.g. prostate specific antigen analysis for detecting prostate cancer). The biological markers may originate from many organ systems in the body but are extracted from a single compartment, the venous blood.

However, this is not suitable for all conditions as often blood does not contain key biological markers for diseases originating in solid tissues, and whilst this problem has been partially overcome by taking tissue biopsies, this is time-consuming, painful, risky, costly and can require highly-skilled personnel such as surgeons.

Another serum-rich fluid is the interstitial fluid (ISF) which fills the intercellular spaces in solid tissues and facilitates the passage of nutrients, biomarkers, and excretory products via the blood stream.

WO2005/072630 describes devices for delivering bioactive materials and other stimuli to living cells, methods of manufacture of the device and various uses of the device, including a number of medical applications. The device comprises a plurality of structures which can penetrate a body surface so as to deliver the bioactive material or stimulus to the required site. The structures are typically solid and the delivery end section of the structure is so dimensioned as to be capable of insertion into targeted cells to deliver the bioactive material or stimulus without appreciable damage to the targeted cells or specific sites therein.

The use of microneedle versions of such arrays in sampling fluids is also known. However, the techniques focus on the use of micro-fluidic techniques such as capillary or pumping actions to extract fluid, as described for example in U.S. Pat. Nos. 6,923,764, 6,052,652, 6,591,124, 6,558,361, 6,908,453, and US2005/0261632, US2006/0264782, US2005/0261632, US2005/0261632, U.S. Pat. No. 6,589,202.

However, these systems suffer from a number of drawbacks. Firstly, use of capillary or pumping actions can only be achieved using relatively largely structures, which typically pass through the dermis and consequently can end up sampling blood as opposed to interstitial fluid. This can also cause discomfort and irritation to the subject being sampled. Secondly, the requirement for capillary or pumping actions renders the arrays complex, in structure and requiring power sources resulting in arrays that are difficult and expensive to manufacture, liable to infection, making them unsuitable for general use.

Other in vitro diagnostic devices are known, such as the use of arrays that include silicon nanowires, or other complex detection mechanisms, such as direct radio-frequency detection of nucleotide hybridization to perform the detection. Again, the fabrication of such systems is complex and expensive, again making these unsuitable for practical applications.

U.S. Pat. No. 9,974,471 describes a device and system for measuring and/or monitoring an analyte present on the skin is provided. The system includes a skin-mountable device that may be attached to an external skin surface and a reader device. The skin-mountable device includes a substrate, a plurality of microneedles, and nanosensors. The microneedles are attached to the substrate such that attachment of the substrate to an external skin surface causes to the microneedles to penetrate into the epidermis, intradermis, or dermis. The nanosensors include a detectable label and are configured to interact with a target analyte present in the interstitial fluid in the epidermis, intradermis, or dermis. The reader device is configured to detect the analyte in interstitial fluid via interaction with the skin-mountable device.

US20070142885 describes a system and method for revitalizing aging skin using electromagnetic energy that is delivered using a plurality of needles that are capable of penetrating the skin to desired depths. A particular aspect of the invention is the capability to spare zones of tissue from thermal exposure. This sparing of tissue allows new tissue to be regenerated while the heat treatment can shrink the collagen and tighten the underlying structures. Additionally, the system is capable of delivering therapeutically beneficial substances either through the penetrating needles or through channels that have been created by the penetration of the needles.

U.S. Pat. No. 6,972,013 describes methods for using an electric field to delivery therapeutic or immunizing treatment to a subject by applying non-invasive, user-friendly electrodes to the surface of the skin. Thus, therapeutic or immunizing agents can be delivered into cells of skin for local and systemic treatments or for immunization with optimal gene expression and minimal tissue damage. In particular, therapeutic agents include naked or formulated nucleic acid, polypeptides and chemotherapeutic agents.

U.S. Pat. No. 7,285,090 describes a monitoring apparatus that includes a sensor device and an I/O device in communication with the sensor device that generates derived data using the data from the sensor device. The derived data cannot be directly detected by the associated sensors. Alternatively, an apparatus that includes a wearable sensor device and an I/O device in communication with the sensor device that includes means for displaying information and a dial for entering information. Alternatively, an apparatus for tracking caloric consumption and caloric expenditure data that includes a sensor device and an I/O device in communication with the sensor device. The sensor device includes a processor programmed to generate data relating to caloric expenditure from sensor data. Alternatively, an apparatus for tracking caloric information for an individual that utilizes a plurality of classification identifiers for classifying meals consumed by the individual, each of the classification identifiers having a corresponding caloric amount.

US20110295100 describes methods, systems and/or devices for enhancing conductivity of an electrical signal through a subject's skin using one or more microneedle electrodes are provided. A microneedle electrode may be applied to the subject's skin by placing the microneedle electrode in direct contact with the subject's skin. The microneedles of the microneedle electrode may be inserted into the skin such that the microneedles pierce stratum corneum of the skin up to or through dermis of the skin. An electrical signal passes or is conducted through or across the microneedle electrode and the subject's skin, where impedance of the microneedle electrode is minimal and greatly reduced compared to existing technologies.

WO2009140735 describes an apparatus for use in detecting analytes in a subject, wherein the apparatus includes a number of structures provided on a patch, such that applying the patch to the subject causes at least some of the structures to be inserted into the subject and target one or more analytes and a reagent for detecting the presence or absence of analytes.

U.S. Pat. No. 10,098,574 describes device and system for measuring and/or monitoring an analyte present on the skin is provided. The system includes a skin-mountable device that may be attached to an external skin surface and a reader device. The skin-mountable device includes a substrate, a plurality of micro-needles, and nanosensors encapsulated in the micro-needles. The micro-needles are attached to the substrate such that attachment of the substrate to an external skin surface causes to the micro-needles to penetrate into the skin to contact interstitial fluid. The micro-needles can include a sacrificial agent and are configured to become porous on contact with a solvent, e.g., interstitial fluid, which dissolves at least a portion of the sacrificial agent. The nanosensors encapsulated in the micro-needles include a detectable label and are configured to interact with a target analyte present in the interstitial fluid. The reader device is configured to detect the analyte in interstitial fluid via interaction with the skin-mountable device.

US 2016/0256091 describes a bio information measuring device is provided. The bio information measuring device includes a sensor portion and a needle portion including a plurality of needles projecting from a plurality of openings formed in a surface of the sensor portion. The plurality of needles are configured to pierce tissue, wherein the plurality of needles include a biocompatible organic material which includes an enzyme member that reacts with an analysis material and a conductive polymer for transferring an electrical signal generated as a result of a reaction of the enzyme member with the analysis material.

US 2018/0177439 describes at least one microneedle comprises a hydrogel material that includes a substance that fluoresces when the substance interacts with an analyte. A magnitude of the fluorescence varies as a function of the concentration of the analyte. During use, the hydrogel material is illuminated with illumination light in a first wavelength range while the hydrogel material interfaces with the dermal interstitial fluid layer of a subject, and a photosensor generates an output that corresponds to an amount of light received in a second wavelength range.

US 2007/0276211 describes a biomedical monitor is disclosed. The biomedical monitor has an array of moveable microneedles coated with a first chemical sensing media. The biomedical monitor also has an actuator configured to move at least one microneedle in the array of microneedles from a retracted position to an engaged position whereby the at least one microneedle enters a subject's skin. The biomedical monitor further has an optical system configured to illuminate the at least one microneedle during or after entering the subject's skin and monitor the first chemical sensing media from the at least one microneedle, whereby at least one biomedical characteristic is determined based on at least one spectral property of the monitored first chemical sensing media. A method of monitoring at least one biomedical characteristic is also disclosed.

WO2013058879A2 describes methods, structures, and systems are disclosed for biosensing and drug delivery techniques. In one aspect, a device for detecting an analyte and/or releasing a biochemical into a biological fluid can include an array of hollowed needles, in which each needle includes a protruded needle structure including an exterior wall forming a hollow interior and an opening at a terminal end of the protruded needle structure that exposes the hollow interior, and a probe inside the exterior wall to interact with one or more chemical or biological substances that come in contact with the probe via the opening to produce a probe sensing signal, and an array of wires that are coupled to probes of the array of hollowed needles, respectively, each wire being electrically conductive to transmit the probe sensing signal produced by a respective probe.

US20150208984 describes a transdermal microneedle continuous monitoring system. The continuous system monitoring includes a substrate, a microneedle unit, a signal processing unit and a power supply unit. The microneedle unit at least comprises a first microneedle set used as a working electrode and a second microneedle set used as a reference electrode, the first and second microneedle sets arranging on the substrate. Each microneedle set comprises at least a microneedle. The first microneedle set comprises at least a sheet having a through hole on which a barbule forms at the edge. One of the sheets provides the through hole from which the barbules at the edge of the other sheets go through, and the barbules are disposed separately.

US 2016/0302687 describes a biometric information measuring sensor is provided that includes a base comprising a plurality of bio-marker measuring areas and a plurality of electrodes. Each of the plurality of electrodes is disposed on a respective one of the plurality of bio-marker measuring areas, and each of the plurality of electrodes includes a working electrode and a counter electrode spaced apart from the working electrode. The biometric information measuring sensor also includes a plurality of needles. Each of the needles is disposed on a respective one of the plurality of electrodes. Two or more of the plurality of needles have different lengths.

US 2016/0166184 describes a microneedle device (200) including at least one microneedle (1) having one or more nanowires (203) on a surface of said at least one microneedle. The microneedle device is typically used in a sensor such as a sensor for monitoring glucose levels in the body and the nanowires may have a membrane (207) covering at least part of the nanowires.

KR 20170041375 describes a micro-needle skin patch functionalized with early diagnosis aptamer coated carbon nanotubes of various diseases.

U.S. Pat. No. 8,543,179 describes a biomedical sensor device includes a light source, a probe array, and a photo detector. The light source is configured for emitting infrared radiation. The probe array is contacted to a user's skin to detect an electric wave signal transmitted through the probe array from the skin. The probe array includes a substrate and a plurality of probes mounted on the substrate, wherein the substrate and the probes are non-opaque so that the infrared radiation may be transmitted through the probe array into the skin. The photo detector is configured to detect an infrared signal by measuring the infrared radiation absorption by the skin.

U.S. Pat. No. 8,588,884 describes devices for enhancing conductivity of an electrical signal through a subject's skin using one or more microneedle electrodes are provided. A microneedle electrode may be applied to the subject's skin by placing the microneedle electrode in direct contact with the subject's skin. The microneedles of the microneedle electrode may be inserted into the skin such that the microneedles pierce stratum corneum of the skin up to or through dermis of the skin. An electrical signal passes or is conducted through or across the microneedle electrode and the subject's skin, where impedance of the microneedle electrode is minimal and greatly reduced compared to existing technologies.

US 2016/0051195 describes skin-conformal sensor devices and methods of using the same. As consistent with one or more embodiments, a sensor device includes an upper portion and lower portion. The upper portion includes a plurality of layers including at least one sensor. The lower portion includes a layer of microstructures configured and arranged to interface with skin of a subject and to interlock the skin with the at least one sensor.

US 2005/0261606 describes a device for sampling at least one biological fluid constituent and measuring at least one target constituent within the biological fluid. The device has at least one micro-needle having an open distal end used to penetrate the skin to a depth where pain and bleeding are minimized. The device further includes a hydrophilic gel within the micro-needle for sampling the biological fluid constituents and an electrochemical cell for measuring the concentration of targeted constituents within the sampled biological fluid constituents. In certain embodiments, the electrochemical cell is integrated within the micro-needle whereby the steps of sampling and measuring are performed completely in-situ. In other embodiments, the electrochemical cell is located external to the micro-needle at its proximal end. Constituent sampling and measurement systems, methods and kits are also provided.

WO 2018/124327 describes a method for fabricating an aptamer-coated, microneedle-based diagnostic skin patch and a patch fabricated thereby. The patch has the advantage of attaching a great number of aptamers, which are much smaller in size than antibodies, onto a relatively great number of microneedle tip surfaces. Allowing the attachment of aptamers for various kinds of biomarkers all together thereto, the patch can also simultaneously detect various kinds of materials (multiplexing). Therefore, a microneedle tip-based skin patch can also be used as a protein chip using an aptamer.

SUMMARY OF THE PRESENT INVENTION

In one broad form, an aspect of the present invention seeks to provide a system for delivering treatment to a biological subject, the system including: at least one substrate including a plurality of microstructures configured to breach a stratum corneum of the subject; at least one sensor operatively connected to at least one microstructure, the at least one sensor being configured to measure response signals from the at least one microstructure; at least one treatment delivery mechanism operatively coupled to at least one microstructure to deliver treatment via at least one microstructure; and, one or more electronic processing devices that are configured to control the at least one treatment delivery mechanism to thereby deliver treatment to the subject at least partially in accordance with the measured response signals.

In one broad form, an aspect of the present invention seeks to provide a method for delivering treatment to a biological subject, the method including: using at least one substrate including one or more microstructures to breach a functional barrier of the subject; using at least one sensor operatively connected to at least one microstructure to measure response signals from the at least one microstructure; using at least one treatment delivery mechanism operatively coupled to at least one microstructure to deliver treatment via at least one microstructure; and, in one or more electronic processing devices, controlling the at least one treatment delivery mechanism to thereby deliver treatment to the subject at least partially in accordance with the measured response signals.

In one broad form, an aspect of the present invention seeks to provide a method treating to a biological subject, the method including: using at least one substrate including one or more microstructures to breach a functional barrier of the subject; using at least one sensor operatively connected to at least one microstructure to measure response signals from the at least one microstructure; using at least one treatment delivery mechanism operatively coupled to at least one microstructure to deliver treatment via at least one microstructure; and, in one or more electronic processing devices, controlling the at least one treatment delivery mechanism to thereby deliver treatment to the subject at least partially in accordance with the measured response signals.

In one embodiment the treatment is at least one of: therapeutic; and, cosmetic.

In one embodiment at least one treatment delivery mechanism includes a signal generator operatively connected to at least one microstructure to apply stimulation to the at least one microstructure.

In one embodiment at least one microstructure includes a material, and wherein at least one treatment delivery mechanism controls release of the material.

In one embodiment release of the material is controlled by applying at least one of optical and electrical stimulation to the at least one microstructure.

In one embodiment the stimulation is used to at least one of: control a rate of release of material from the at least one microstructure; vary a rate of release of material from the at least one microstructure; control a quantity of material released from the at least one microstructure; control a dose of material released from the at least one microstructure; substantially prevent release of material from the at least one microstructure; substantially slow release of material from the at least one microstructure; and, release material from the at least one microstructure.

In one embodiment at least one of: a change in an electrical stimulation signal applied to the at least one microstructure is used to trigger release of the material; a first electrical stimulation signal is applied to the at least one microstructure to substantially prevent release of the material; and, a second electrical stimulation signal is applied to the at least one microstructure to release the material.

In one embodiment the material is contained in at least one of: a coating on the at least one microstructure; and, a selectively dissolvable coating on the at least one microstructure.

In one embodiment the stimulation is used to at least one of: release material from the coating on the at least one microstructure; disrupt the coating on the at least one microstructure; dissolve the coating on the at least one microstructure; and, release the coating on the at least one microstructure.

In one embodiment at least one of: at least some microstructures are uncoated; at least some microstructures are porous with an internal coating; at least some microstructures are partially coated; different microstructures have different coatings; different parts of microstructures include different coatings; and, at least some microstructures include multiple coatings.

In one embodiment at least one microstructure includes a selectively dissolvable coating and wherein the selectively dissolvable coating dissolves at least one of: after a defined time period; in response to breaching or penetration of the functional barrier; in response to application of a stimulatory signal; in response to a presence, absence, level or concentration of analytes; and, upon breaching or penetration of the functional barrier.

In one embodiment the system is configured to: detect the coating dissolving; and, at least one of: perform at least one measurement after the coating has dissolved; and, deliver treatment after the coating has dissolved.

In one embodiment the system is configured to detect the coating dissolving based on a change in a response signal.

In one embodiment at least some of the microstructures including a coating that at least one of: undergoes a shape change to selectively anchor microstructures; modifies surface properties to at least one of: increase hydrophilicity; increase hydrophobicity; and, minimize biofouling; attracts at least one substance to the microstructures; repels at least one substance from the microstructures; attracts at least one analyte to the microstructures; repels at least one analyte from the microstructures; provides a physical structure to at least one of: facilitate penetration of the barrier; strengthen the microstructures; and, anchor the microstructures in the subject; dissolves to at least one of: expose a microstructure; expose a further coating; and, expose a material; provides stimulation to the subject; contains a material; selectively releases a material; acts as a barrier to preclude at least one substance from the microstructures; and, includes at least one of: polyethylene; polyethylene glycol; polyethylene oxide; zwitterions; peptides; hydrogels; and, self-assembled monolayer.

In one embodiment at least some of the microstructures include a material.

In one embodiment different microstructures include at least one of: different materials; and, different doses of a therapeutic material.

In one embodiment the one or more processing devices are configured to control at least one treatment delivery mechanism to release material from selected microstructures.

In one embodiment the material includes at least one of: antivirals; antibacterials; anti-inflammatories or inflammatories; agonists or antagonists; adjuvants; vaccines; nanoparticles; a nucleic acid; an antigen or allergen; parasites, bacteria, viruses, or virus-like particles; metals or metallic compounds; molecules, elements or compounds; DNA; protein; RNA, siRNA, sfRNA, iRNA; synthetic biological materials; polymers; drugs; hormones; and, neurotransmitters.

In one embodiment the system includes one or more switches for selectively connecting a signal generator to one or more of the microstructures, and wherein the one or more processing devices are configured to control the switches and the signal generator to thereby controllably release material from one or more selected microstructures.

In one embodiment the one or more processing devices are configured to: perform an analysis, at least in part, using the measured response signals; and, use results of the analysis to control the at least one treatment delivery mechanism.

In one embodiment the one or more electronic devices are configured to analyse the measured response signals using at least one of: pattern matching; a longitudinal analysis; comparison to a threshold; and, machine learning techniques.

In one embodiment the system includes a monitoring device and a patch including the substrate and microstructures.

In one embodiment the monitoring device is at least one of: inductively coupled to the patch; attached to the patch; and, brought into contact with the patch when a reading is to be performed.

In one embodiment the monitoring device is configured to at least one of: cause a measurement to be performed; at least partially analyse measurements; control delivery of therapy; control stimulation applied to at least one microstructure; generate an output; and, cause an action to be performed.

In one embodiment the system includes a transmitter that transmits at least one of: measured response signals; subject data derived from the measured response signals; and, at least one metric derived from the measured response signals.

In one embodiment the system includes: a wearable monitoring device configured to: perform the measurements; and, control delivery of the therapy; and, a processing system that: receives subject data derived from the measured response signals; and, analyses the subject data to at least one of: generate at least one indicator, the at least one indicator being at least partially indicative of a physiological status associated with the subject; determine treatment requirements; and, cause treatment to be delivered.

In one embodiment the physiological status is indicative of at least one of: organ function; tissue function; cell function; a presence, absence or degree of a medical condition; a prognosis associated with a medical condition; a presence, absence, level or concentration of a biomarker; a presence, absence, level or concentration of an analyte; a presence, absence or grade of cancer; fluid levels in the subject; tissue inflammation; blood oxygenation; and, bioelectric activity.

In one embodiment the system includes a client device that: receives measurement data from the wearable monitoring device; generates subject data using the measurement data; transfers the subject data to the processing system; stores a representation of the indicator; receives an indicator from the processing system; and, displays a representation of the indicator.

In one embodiment the substrate includes at least one of: electrical connections to allow electrical signals to be communicated with respective microstructures; and, optical connections to allow optical signals to be communicated with respective microstructures.

In one embodiment the response signals are indicative of at least one of: a visualization; a mapping; mechanical properties; forces; pressures; muscle movement; blood pulse wave; an analyte concentration; a blood oxygen saturation; a tissue inflammation state; a bioimpedance; a biocapacitance; a bioconductance; and, electrical signals within the body.

In one embodiment at least one of the substrate and the microstructures include at least one of: metal; polymer; and, silicon.

In one embodiment the substrate is at least one of: at least partially flexible; configured to conform to an outer surface of the functional barrier; and, configured to conform to a shape of at least part of a subject.

In one embodiment at least some of the microstructures are plate microstructures having a substantially rounded rectangular cross sectional shape.

In one embodiment the microstructures include anchor microstructures used to anchor the substrate to the subject and wherein the anchor microstructures at least one of: undergo a shape change; undergo a shape change in response to at least one of substances in the subject and applied stimulation; swell; swell in response to at least one of substances in the subject and applied stimulation; include anchoring structures; have a length greater than that of other microstructures; are rougher than other microstructures; have a higher surface friction than other microstructures; are blunter than other microstructures; are fatter than other microstructures; and, enter the dermis.

In one embodiment at least some of the microstructures have at least one of: a length that is at least one of: less than 2500 μm; less than 1000 μm; less than 750 μm; less than 450 μm; less than 300 μm; less than 250 μm; about 250 μm; about 150 μm; greater than 100 μm; greater than 50 μm; and, greater than 10 μm; a maximum width that is at least one of: less than 2500 μm; less than 1000 μm; less than 750 μm; less than 450 μm; less than 300 μm; less than 250 μm; of a similar order of magnitude to the length; greater than the length; greater than the length; about the same as the length; about 250 μm; about 150 μm; and, greater than 50 μm; and, a maximum thickness that is at least one of: less that the width; significantly less that the width; of a smaller order of magnitude to the length; less than 300 μm; less than 200 μm; less than 50 μm; about 25 μm; and, greater than 10 μm.

In one embodiment at least some of the microstructures include at least one of: a shoulder that is configured to abut against the stratum corneum to control a depth of penetration; and, a shaft extending from a shoulder to the tip, the shaft being configured to control a position of the tip in the subject.

In one embodiment the microstructures have at least one of: a density that is at least one of: less than 5000 per cm$^2$; greater than 100 per cm$^2$; and, about 600 per cm$^2$; and, a spacing that is at least one of: less than 1 mm; about 0.5 mm; about 0.2 mm; about 0.1 mm; and, more than 10 μm.

In one embodiment at least some of the microstructures include an electrode.

In one embodiment at least one electrode at least one of: extends over a length of a distal portion of the microstructure; extends over a length of a portion of the microstructure spaced from the tip; is positioned proximate a distal end of the microstructure; is positioned proximate a tip of the microstructure; extends over at least 25% of a length of the microstructure; extends over less than 50% of a length of the microstructure; extends over about 60 μm of the microstructure; is configured to be positioned in a viable epidermis of the subject in use; and, has a surface area of at least one of: less than 200,000 μm$^2$; about 22,500 μm$^2$; and, at least 2,000 μm$^2$.

In one embodiment at least some of microstructures include at least part of an active sensor.

In one embodiment at least some of the microstructures include an electrically conductive material.

In one embodiment at least some of the microstructures include an insulating layer extending over at least one of: part of a surface of the microstructure; a proximal end of the microstructure; at least half of a length of the microstructure; about 60 μm, 90 μm or 150 μm of a proximal end of the microstructure; and, at least part of a tip portion of the microstructure.

In one embodiment at least some of the microstructures include plates having a substantially planar face including at least one electrode.

In one embodiment at least some of the microstructures are arranged in groups, and wherein at least one of: response signals are measured between microstructures in a group; and, stimulation is applied between microstructures in a group.

In one embodiment the group is a pair of microstructures including spaced apart plate microstructures having substantially planar electrodes in opposition.

In one embodiment at least one of: at least some pairs of microstructures are angularly offset; at least some pairs of microstructures are orthogonally arranged; adjacent pairs of microstructures are orthogonally arranged; pairs of microstructures are arranged in rows, and the pairs of microstructures in one row are angularly offset relative to pairs of microstructures in other rows; and, pairs of microstructures are arranged in rows, and the pairs of microstructures in one row are orthogonally arranged relative to pairs of microstructures in other rows.

In one embodiment at least one of: the spacing between the electrodes in each group are at least one of: less than 10 mm; less than 1 mm; about 0.1 mm; and, more than 10 μm; and, a spacing between groups of microstructures is at least one of: less than 50 mm; more than 20 mm; less than 20 mm; less than 10 mm; more than 10 mm; less than 1 mm; more than 1 mm; about 0.5 mm; and, more than 0.2 mm.

In one embodiment one or more microstructure electrodes interact with one or more analytes of interest such that a response signal is dependent on a presence, absence, level or concentration of analytes of interest.

In one embodiment the analytes interact with a coating on the microstructures to change electrical and/or optical properties of the coating, thereby allowing the analytes to be detected.

In one embodiment the microstructures include a material including at least one of: a bioactive material; a reagent for reacting with analytes in the subject; a binding agent for binding with analytes of interest; a material for binding one or more analytes of interest; a probe for selectively targeting analytes of interest; an insulator; a material to reduce biofouling; a material to attract at least one substance to the microstructures; a material to repel at least one substance from the microstructures; a material to attract at least some analytes to the microstructures; and, a material to repel at least some analytes from the microstructures.

In one embodiment the substrate includes a plurality of microstructures and wherein different microstructures are at least one of: differentially responsive to analytes; responsive to different analytes; responsive to different combination of analytes; and, responsive to different levels or concentrations of analytes.

In one embodiment at least some of the microstructures at least one of: attracts at least one substance to the microstructures; repels at least one substance from the microstructures; attracts at least one analyte to the microstructures; and, repels at least one analyte from the microstructures.

In one embodiment the at least one treatment delivery mechanism includes an actuator configured to cause at least some of the microstructures to breach the functional barrier and deliver a treatment to the subject.

In one embodiment the system includes a housing containing the at least one sensor and at least one electronic processing device.

In one embodiment the housing selectively couples to the substrate.

In one embodiment the housing couples to the substrate using at least one of: electromagnetic coupling; mechanical coupling; adhesive coupling; and, magnetic coupling.

In one embodiment at least one of the housing and substrate are at least one of: secured to the subject; secured to the subject using anchor microstructures; secured to the subject using an adhesive patch; and, secured to the subject using a strap.

In one embodiment the housing includes housing connectors that operatively connect to substrate connectors on the substrate to communicate signals with the microstructures.

In one embodiment the system is configured to perform repeated measurements over a time period and wherein the microstructures are configured to remain in the subject during the time period.

In one embodiment the time period is at least one of: less than 0.01 seconds; at least one minute; at least one hour; at least one day; and, at least one week.

In one embodiment the system is configured to perform repeated measurements with a frequency that is at least one of: substantially continuously; every second; every minute; every 5 to 10 minutes; and, hourly.

In one embodiment system includes: a substrate coil positioned on the substrate and operatively coupled to one or more microstructure electrodes; and, an excitation and receiving coil positioned in proximity to the substrate coil such that attenuation of a drive signal applied to the excitation and receiving coil acts as a response signal.

It will be appreciated that the broad forms of the invention and their respective features can be used in conjunction and/or independently, and reference to separate broad forms is not intended to be limiting. Furthermore, it will be appreciated that features of the method can be performed using the system or apparatus and that features of the system or apparatus can be implemented using the method.

BRIEF DESCRIPTION OF THE DRAWINGS

Various examples and embodiments of the present invention will now be described with reference to the accompanying drawings, in which:—

FIG. 4A is a schematic side view of a first example of a microstructure configuration;

FIG. 4B is a schematic side view of a second example of a microstructure configuration;

FIG. 4C is a graph illustrating the electric field between closely spaced electrodes;

FIG. 4D is a graph illustrating the electric field between distant spaced electrodes;

FIG. 5A is a schematic side view of an example of a plate microstructure;

FIG. 5B is a schematic front view of the microstructure of FIG. 5A;

FIG. 16A is an equivalent circuit for skin based impedance measurements;

FIG. 16B is an equivalent circuit for epidermal based impedance measurements;

FIG. 16C is a schematic diagram comparing skin and microstructure based impedance measurements;

FIGS. 37A to 37C are schematic diagrams illustrating manufacture of an antibody functionalised electrode for analyte sensing;

DETAILED DESCRIPTION OF THE PREFERRED EMBODIMENTS

Definitions

Figure 1:
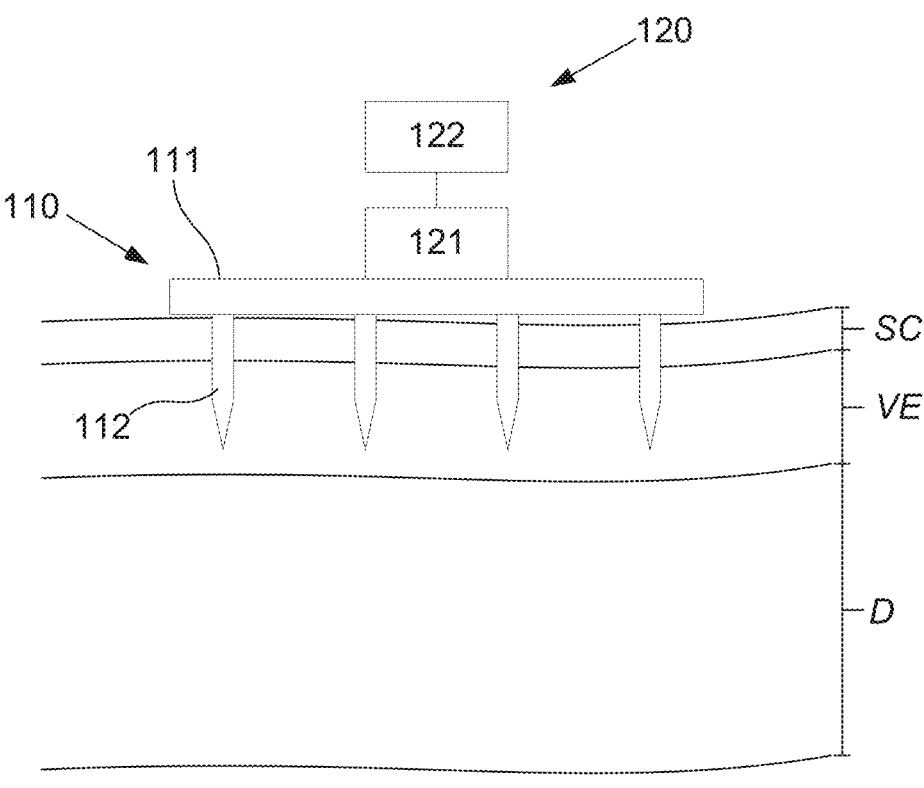
FIG. 1 is a schematic diagram of an example of a system for delivering treatment to a biological subject.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

The terms "about" and "approximately" are used herein to refer to conditions (e.g. amounts, levels, concentrations, time, etc.) that vary by as much as 20% (i.e. +20%), especially by as much as 10%, 9%, 8%, 7%, 6%, 5%, 4%, 3%, 2% or 1% to a specified condition.

As used herein, the term "analyte" refers to a naturally occurring and/or synthetic compound, which is a marker of a condition (e.g., drug abuse), disease state (e.g., infectious diseases), disorder (e.g., neurological disorders), or a normal or pathologic process that occurs in a subject (e.g., drug metabolism), or a compound which can be used to monitor levels of an administered or ingested substance in the subject, such as a medicament (substance that treats, prevents and/or alleviates the symptoms of a disease, disorder or condition, e.g., drug, vaccine etc.), an illicit substance (e.g. illicit drug), a non-illicit substance of abuse (e.g. alcohol or prescription drug taken for non-medical reasons), a poison or toxin (including an environmental contaminant), a chemical warfare agent (e.g. nerve agent, and the like) or a metabolite thereof. The term "analyte" can refer to any substance, including chemical and/or biological agents that can be measured in an analytical procedure, including nucleic acids, proteins, illicit drugs, explosives, toxins, pharmaceuticals, carcinogens, poisons, allergens, and infectious agents, which can be measured in an analytical procedure. The analyte may be a compound found directly in a sample such as biological tissue, including body fluids (e.g. interstitial fluid), from a subject, especially in the dermis and/or epidermis. In particular embodiments, the analyte is a compound found in the interstitial fluid. In some embodiments, the analyte is a compound with a molecular weight in the range of from about 30 Da to about 100 kDa, especially about 50 Da to about 40 kDa. Other suitable analytes are as described herein.

As used herein, the term "and/or" refers to and encompasses any and all possible combinations of one or more of the associated listed items, as well as the lack of combinations when interpreted in the alternative (or).

As used herein, the term "aptamer" refers to a single-stranded oligonucleotide (e.g. DNA or RNA) that binds to a specific target molecule, such as an analyte. An aptamer may be of any size suitable for binding such target molecule, such as from about 10 to about 200 nucleotides in length, especially from about 30 to about 100 nucleotides in length.

The term "bind" and variations such as "binding" are used herein to refer to an interaction between two substances, such as an analyte and an aptamer or an analyte and a molecularly imprinted polymer. The interaction may be a covalent or non-covalent interaction, particularly a non-covalent interaction.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. Thus, the use of the term "comprising" and the like indicates that the listed integers are required or mandatory, but that other integers are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The term "plurality" is used herein to refer to more than one, such as 2 to $1 \times 10^{15}$ (or any integer therebetween) and upwards, including 2, 10, 100, 1000, 10000, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, etc. (and all integers therebetween).

As used herein, the term "predetermined threshold" refers to a value, above or below which indicates the presence, absence or progression of a disease, disorder or condition; the presence or absence of an illicit substance or non-illicit substance of abuse; or the presence or absence of a chemical warfare agent, poison and/or toxin. For example, for the purposes of the present invention, a predetermined threshold may represent the level or concentration of a particular analyte in a corresponding sample from an appropriate control subject, such as a healthy subject, or in pooled samples from multiple control subjects or medians or averages of multiple control subjects. Thus, a level or concentration above or below the threshold indicates the presence, absence or progression of a disease, disorder or condition; the presence or absence of an illicit substance or non-illicit substance of abuse; or the presence or absence of a chemical warfare agent, poison and/or toxin, as taught herein. In other examples, a predetermined threshold may represent a value larger or smaller than the level or ratio determined for a control subject so as to incorporate a further degree of confidence that a level or ratio above or below the predetermined threshold is indicative of the presence, absence or progression of a disease, disorder or condition; the presence or absence of an illicit substance or non-illicit substance of abuse; or the presence or absence of a chemical warfare agent, poison and/or toxin. Those skilled in the art can readily determine an appropriate predetermined threshold based on analysis of samples from appropriate control subjects.

The terms "selective" and "selectivity" as used herein refer to molecularly imprinted polymers or aptamers that bind an analyte of interest without displaying substantial binding of one or more other analytes. Accordingly, a molecularly imprinted polymer or aptamers that is selective for an analyte, such as troponin or a subunit thereof, exhibits selectivity of greater than about 2-fold, 5-fold, 10-fold, 20-fold, 50-fold, 100-fold or greater than about 500-fold with respect to binding of one or more other analytes.

The term "subject" as used herein refers to a vertebrate subject, particularly a mammalian subject, for whom monitoring and/or diagnosis of a disease, disorder or condition is desired. Suitable subjects include, but are not limited to, primates; avians (birds); livestock animals such as sheep, cows, horses, deer, donkeys and pigs; laboratory test animals such as rabbits, mice, rats, guinea pigs and hamsters; companion animals such as cats and dogs; bats and captive wild animals such as foxes, deer and dingoes. In particular, the subject is a human.

System for Delivering Therapy

An example of a system for delivering treatment to a biological subject will now be described with reference to FIG. 1.

In this example, the system includes at least one substrate 111 having one or more microstructures 112. In use, the microstructures are configured to breach a functional barrier associated with a subject. In the current example, the functional barrier is the stratum corneum SC, and the microstructures are configured to breach the stratum corneum SC by penetrating the stratum corneum SC and entering at least the viable epidermis VE. In one particular example, the microstructures are configured to not penetrate a boundary between the viable epidermis VE and the dermis D, although this is not essential and structures that penetrate into the dermis could be used as will be described in more detail below.

Whilst this example is described with respect to breaching of the stratum corneum SC, it will be appreciated that this is not essential, and the techniques could equally be applied to other functional barriers. In this regard, a functional barrier will be understood to include any structure, boundary, or feature, whether physical or otherwise, that prevents passage of signals, and/or analytes, such as biomarkers. For example, functional barriers could include one or more layers, a mechanical discontinuity, such as a discrete change in tissue mechanical properties, a tissue discontinuity, a cellular discontinuity, a neural barrier, a sensor barrier, a cellular layer, skin layers, mucosal layers, internal or external barriers, an inner barrier within an organ, an outer barrier of organs other than the skin, epithelial layers or endothelial layers, or the like. Functional barriers could also include other internal layers or boundaries, including optical barriers such as a melanin layer, electrical barriers, molecular weight barriers that prevent passage of a biomarkers with certain molecular weights, a basal layer boundary between the viable epidermis and dermis, or the like.

The nature of the microstructure will vary depending upon the preferred implementation. In one example, the microstructures could include needles, but this is not essential and more typically structures, such as plates, blades, or the like, are used, as will be described in more detail below.

The substrate and microstructures could be manufactured from any suitable material, and the material used may depend on the intended application, for example depending on whether there is a requirement for the structures to be optically and/or electrically conductive, or the like. The substrate can form part of a patch 110, which can be applied to a subject, although other arrangements could be used for example, having the substrate form part of a housing containing other components.

In one example at least one sensor 121 is provided, which is operatively connected to at least one microstructure 112, thereby allowing response signals to be measured from respective microstructures 112. In this regard, the term response signal will be understood to encompass signals that are intrinsic within the subject, such ECG (Electrocardiogramals, or the like, or signals that are induced as a result of the application of stimulation, such as bioimpedance signals, or the like.

The nature of the sensor will vary depending on the preferred implementation and the nature of the sensing being performed. For example, the sensing could include sensing electrical signals, in which case the sensor could be a voltage or current sensor, or the like. Alternatively, optical signals could be sensed, in which case the sensor could be an optical sensor, such as a photodiode, CCD (Charge Coupled Device) array, or similar, whilst temperature signals could be sensed using a thermistor or the like.

The manner in which the sensor 121 is connected to the microstructure(s) 112 will also vary depending on the preferred implementation. In one example, this is achieved using connections between the microstructure(s) 112 and the sensor, with the nature of the connections varying depending upon the signals being sensed, so that the connections could include electrically conductive elements to conduct electrical signals, a wave guide, optical fibre or other conductor to conduct electromagnetic signals, or thermal conductor to conduct thermals signals. Connections could also include wireless connections, allowing the sensor to be located remotely. Ionic connections could also be used. Furthermore, connections could be provided as discrete elements, although in other examples, the substrate provides the connection, for example, if the substrate is made from a conductive plate which is then electrically connected to all of the microstructures.

As a further alternative, the sensor could be embedded within or formed from part of the microstructure, in which connections may not be required.

The sensor 121 can be operatively connected to all of the microstructures 112, with connections being collective and/or independent. For example, one or more sensors could be connected to different microstructures to allow different measured response signals to be measured from different groups of microstructures 112. However, this is not essential, and any suitable arrangement could be used.

In addition to providing sensing, the system can also include a treatment delivery mechanism 128, which is configured to deliver treatment to the subject. The nature of the treatment and the manner in which it is delivered will vary depending on the preferred implementation. In one example, the treatment includes stimulation, in which case the microstructures could be coupled to a signal generator that generates a stimulatory signal, as will be described in more detail below. Such stimulation could again include electrical stimulation, using a voltage or current source, optical stimulation, using a visible or non-visible radiation source, such as an LED or laser, thermal stimulation, or the like, and could be delivered via the same microstructures used for measuring response signals, or different microstructures, depending on the preferred implementation. Additionally, and/or alternatively, treatment could be achieved using other techniques, such as through exposure of the subject to the microstructures and materials thereon or therein. For example, coatings can be applied to the microstructures, allowing material to be delivered into the subject beyond the barrier, thereby stimulating a response within the subject.

These options allow a range of different types of sensing to be performed, including detecting electrical signals within the body, such as ECG signals, plethysmographic signals, electromagnetic signals, or electrical potentials generated by muscles, neural tissue, blood, or the like, detecting photoplethysmographic effects, electromagnetic effects, such as fluorescence, detecting mechanical properties, such as stress or strain, or the like. Sensing could include detecting the body's response to applied electrical signals, for example to measure bioimpedance, bioconductance, or biocapacitance, detecting the presence, absence, level or concentration of analytes, for example by detecting electrical or optical properties, or the like.

The system further includes one or more electronic processing devices 122, which can form part of a measuring device, and/or could include electronic processing devices forming part of one or more processing systems, such as computer systems, servers, client devices, or the like as will be described in more detail below. In use, the processing devices 122 are adapted to receive signals from the sensor 121 and analyse signals, using results of the analysis to control the treatment delivery mechanism 128. For ease of illustration the remaining description will refer generally to a processing device, but it will be appreciated that multiple processing devices could be used, with processing distributed between the devices as needed, and that reference to the singular encompasses the plural arrangement and vice versa.

Figure 2:
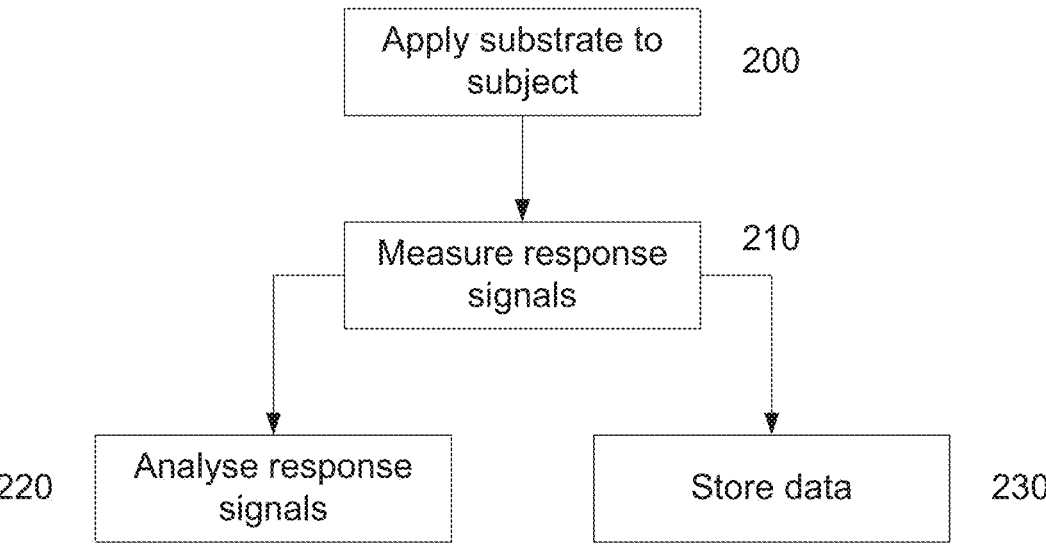
FIG. 2 is a flow chart of an example of a process for delivering treatment to a biological subject.

An example of the manner in which this is performed will now be described with reference to FIG. 2.

In particular, in this example, at step 200, the substrate is applied to the subject so that the one or more microstructures breach, and in one example, penetrate the functional barrier. For example, when applied to skin, the microstructures could penetrate the stratum corneum and enter the viable epidermis as shown in FIG. 1. This could be achieved manually and/or through the use of an actuator, to help ensure successful penetration.

At step 210, response signals within the subject are measured, with signals indicative of the measured response signals being provided to the electronic processing device 112. This may be performed following application of stimulation, although this is not essential and will vary depending on the nature of the sensing being performed.

The one or more processing devices then analyse the resulting measurement data and use results of the analysis to control the treatment delivery mechanism at step 220 and could optionally provide an output based on the measured response signals. For example, the processing device could display an indicator indicative of measured response signals and/or values derived therefrom, an indication of the therapy delivered, or the like. Alternatively, the processing device could generate a recommendation, for example to seek an intervention after the delivery of therapy, trigger an action, such as alerting a clinician, trainer or guardian, or the like, that the therapy has been performed.

The analysis can be performed in any suitable manner, and this will vary depending on nature of the measurements being performed. For example, this could involve examining measured response signal values and using these to calculate an indicator indicative of a health status, including the presence, absence, degree or prognosis of one or more medical conditions, a prognosis associated with a medical condition, a presence, absence, level or concentration of a biomarker, a presence, absence, level or concentration of an analyte, a presence, absence or grade of cancer, fluid levels in the subject, blood oxygenation, a tissue inflammation state, bioelectric activity, such as nerve, brain, muscle or heart activity, or a range of other health states. This could be achieved by monitoring changes in the values over time, and may involve comparison to values measured for reference subjects having known medical conditions. Additionally, and/or alternatively, the indicator could be indicative of measured parameters associated with the subject, such as measured, level concentrations of analytes or other biomarkers.

For example, when measuring fluid levels, this could involve examining the applied stimulatory signals and values of the measured response signals, using these to calculate a bioimpedance within the epidermis, which in turn allows an indicator indicative of fluid levels to be derived. In this regard, it will be understood that fluids within the body, such as interstitial fluid, contains ions, such as Sodium ($Na+$), Potassium ($K+$), Calcium ($Ca^{2}+$), Chloride ($Cl-$), Bicarbonate ($HCO_3-$) and Phosphate ($HPO_4{}^{2}-$). As fluid levels increase or decrease, for example as the subject's level of hydration increases or decreases, there will be a corresponding fall or rise in ion concentrations, thereby resulting in a change in conductivity of the fluid. Accordingly, measuring the impedance of the fluid can in turn be used to derive information regarding fluid conductivity, which is in turn indicative of ion concentrations and hence fluid levels. Thus, it will be appreciated that this allows changes in impedance to be used to track changes in fluid levels and hence a hydration state of the subject. Such fluid levels could include any one or more of interstitial fluid levels, a change in interstitial fluid levels, an ion concentration in interstitial fluid, a change in an ion concentration in interstitial fluid, an ion concentration, a change in an ion concentration, a total body water, intracellular fluid levels, extracellular fluid levels, plasma water levels, fluid volumes or hydration levels.

The fluid level indicator could then be used in monitoring a health status, such as hydration levels, and/or a presence, absence, degree or prognosis of one or more medical conditions, a prognosis associated with a medical condition, or the like. This could also involve monitoring changes in the values over time, for example to perform longitudinal hydration measurements, and may involve comparison to values measured for reference subjects having known hydration levels, thereby allowing an assessment to be made as to whether the subject is under or over hydrated.

In any event, it will be appreciated that the above described system operates by providing microstructures that are configured to breach a barrier, such as the stratum corneum, allowing these to be used to measure response signals within the subject, such as within the epidermis and/or dermis. These response signals can then be processed and subsequently analysed, allowing a variety of values to be derived, which could be indicative of specific measurements, or one or more aspects of subject health.

For example, the system can be configured to measure an analyte level or concentration, such as the level or concentration of a specific biomarker. Response signals could also be used to generate a visualization, a spatial mapping in 1, 2 or 3 dimensions, details of mechanical properties, forces, pressures, muscle movement, blood pulse wave, an analyte concentration such as the presence, absence, level or concentration of specific biomarkers, a blood oxygen saturation, a bioimpedance, a biocapacitance, a bioconductance or electrical signals within the body, such as ECG (Electrocardiogramhy) signals.

In one example, the system can be configured so that measurements are performed at a specific location within the subject, such as within the epidermis only, the dermis only, or the like. This allows targeted analyte detection to be performed with a high level of accuracy, providing higher quality data for more precise measures of analytes. Furthermore, constraining the location in which measurements are performed ensures these are repeatable, allowing for more accurate longitudinal monitoring. It will be appreciated that similar considerations also apply for other types of measurements, such as measurements of analyte levels, which could be performed in the epidermis and/or dermis.

In contrast to traditional approaches, breaching and/or at least partially penetrating a functional barrier, such as the stratum corneum, allows measurements to be performed from within or under the barrier, and in particular within the epidermis and/or dermis, resulting in a significant improvement in the quality and magnitude of response signals that are detected. In particular, this ensures that the response signals accurately reflect conditions within the human body, and in particular within the epidermis and/or dermis, such as the presence, absence, level or concentration of biomarkers, the impedance of interstitial fluid, or the like, as opposed to traditional external measurements, which are unduly influenced by the environment outside the barrier, such as the physical properties of the skin surface, such as the skin material properties, presence or absence of hair, sweat, mechanical movement of the applied sensor, or the like. Additionally, by penetrating the stratum corneum but not the dermis, this allows measurements to be constrained to the epidermis only, thereby avoiding interference from fluid level changes in the dermis.

For example, this allows accurate measurement of high molecular weight biomarkers to be performed, which would otherwise only pass through the skin poorly. A good example of this, is glucose, which whilst present externally, such as in sweat, is typically only present in low concentrations, and often time delayed, meaning the concentration in sweat does not necessarily reflect current glucose levels within the body. In contrast, by breaching the barrier, in this case the stratum corneum, this allows far more accurate measurements to be performed. It will be appreciated that similar considerations apply to a wide range of different biomarkers or signals, and associated barriers that otherwise prevent accurate measurement of the biomarkers or signals.

For example, in the case of impedance measurements microstructure electrodes tend to measure different impedances as opposed to standard surface electrodes, which is indicative of the fact that the microstructure electrodes do not measure skin impedance, meaning the measured impedance is more indicative of conditions within the body. As the contribution of the skin surface impedance is significant in magnitude this can result in changes in impedance within the body being masked, meaning skin based measurements are less likely to be able to detect meaningful changes.

A further issue with skin based impedance measurements is that fields generated tend to pass through the stratum corneum and dermis, and are not constrained to the epidermis. An example of this is shown in FIG. 16C.

In this example, skin based electrodes 1601, result in an electric field 1602 extending into the stratum corneum SC, the viable epidermis VEPiD and dermis D. In contrast, a microstructure patch 1603 result in fields 1604 constrained within the viable epidermis VEPiD.

An example of resulting equivalent circuits for skin based measurements and epidermal measurements are shown in FIGS. 16A and 16B, respectively. In this regard, each equivalent circuit includes three circuits for each layer, representing a contribution of current flow through the tissue in orthogonal directions. Thus, for skin based measurements shown in FIG. 16A, the impedance of the stratum corneum is represented by the circuits $C_{SC1}$, $R_{SC1}$, $C_{SC2}$, $R_{SC2}$, $C_{SC3}$, $R_{SC3}$, the epidermis is represented by the circuits $C_{VE1}$, $R_{VE1}$, $C_{VE2}$, $R_{VE2}$, $C_{VE3}$, $R_{VE3}$, and the dermis is represented by the circuits $C_{D1}$, $R_{D1}$, $C_{D2}$, $R_{D2}$, $C_{D3}$, $R_{D3}$. In this example, $R_{SC1} \gg R_{VE1}$, $R_{SC2} \gg R_{VE2}$ and $R_{SC3} \gg R_{VE3}$, meaning that the contribution of the impedance in the epidermal layer is minimal compared to the contribution of the impedance in the stratum corneum, so skin based measurements will be more reflective of the impedance in the stratum corneum.

In contrast, for epidermal sensing only, shown in FIG. 16B, the impedance is represented by the circuits $C_{VE1}$, $R_{VE1}$, $C_{VE2}$, $R_{VE2}$, $C_{VE3}$, $R_{VE3}$, only, and hence epidermal measurements are more reflective of the fluid levels in the epidermis.

Additionally, in some examples, the microstructures only penetrate the barrier a sufficient distance to allow a measurement to be made. For example, in the case of skin, the microstructures are typically configured to enter the viable epidermis and not enter the dermal layer. This results in a number of improvements over other invasive techniques, including avoiding issues associated with penetration of the dermis, such as pain caused by exposure of nerves, erythema, petechiae, or the like. Avoiding penetrating the dermal boundary also significantly reduces the risk of infection, allowing the microstructures to remain embedded for prolonged periods of time, such as several days, which in turn can be used to perform longitudinal monitoring over a prolonged time periods. However, in some instances, such as when detecting troponin or a subunit thereof, penetration of the dermal barrier may be required.

It will be appreciated that the ability of the microstructures to remain in-situ is particularly beneficial, as this ensures that measurements are made at the same site within the subject, which reduces inherent variability arising from inaccuracies of replacement of measuring equipment which can arise using traditional techniques. Despite this, it will be appreciated that the system can be used in other manners, for example to perform single time point monitoring or the like.

In one example, this allows the arrangement to be provided as part of a wearable device, enabling measurements to be performed that are significantly better than existing surface based measurement techniques, for example by providing access to signals or biomarkers that cannot otherwise pass through the barrier, but whilst allowing measurements to be performed whilst the subject is undergoing normal activities and/or over a prolonged period of time. This in turn enables measurements to be captured that are more accurately reflective of the health or other status of the subject. For example, this allows variations in a subject's condition during a course of the day to be measured, and avoids measurements being made under artificial conditions, such as within a clinic, which are not typically indicative of the actual condition of the subject. This also allows monitoring to be performed substantially continuously, which can allow conditions to be detected as they arise, for example, in the case of myocardial infarction, cardiovascular disease, vomiting, diarrhoea, or similar, which can allow more rapid intervention to be sought.

In addition to providing benefits in measuring aspects of subject health, the system incorporates a treatment delivery mechanism, allowing treatments, such as cosmetic treatments, or therapies to be delivered to the subject. Delivery of treatment is controlled based on results of the measurement, meaning treatment is only delivered as needed, thereby avoiding the delivery of unnecessary treatment. Nevertheless, this allows treatment to be delivered in a substantially real-time manner, so that interventions can be implemented even prior to any symptoms becoming apparent.

The above described system can be applied to any part of the body, and hence could be used with a wide range of different functional barriers. For example, the functional barrier could be an internal or external barrier, a skin layer, a mucosal layer, an inner barrier within an organ, an outer barrier of an organ, an epithelial layer, an endothelial layer, a melanin layer, an optical barrier, an electrical barrier, molecular weight barrier, basal layer or the stratum corneum. Thus, the microstructures could be applied to the buccal mucosa, the eye, or another epithelial layer, endothelial layer, or the like. The following examples will focus specifically on application to the skin, with the functional barrier including some or all of the stratum corneum, but it will be appreciated that this is intended to be illustrative and is not intended to be limiting.

Further variations will become apparent from the following description.

In one example, the treatment delivery mechanism system includes a signal generator operatively connected to at least one microstructure to apply stimulation, typically by applying a stimulatory signal to the microstructure. Again, the manner in which the signal generator is connected will vary depending on the preferred implementation, and this could be achieved via connections, such as wired or wireless connections and/or integrating the signal generator into the substrate and/or microstructures. Example connection types include mechanical, magnetic, thermal, electrical, electromagnetic, optical, or the like.

In one example, operation of the signal generator is controlled by the processing device, allowing the processing device to control the signal generator to thereby cause a measurement to be performed, for example by applying an electrical signal to allow an impedance measurement to be performed. Additionally, and/or alternative the processing device could control the signal generator in accordance with measured response signals, for example, allowing stimulation to be applied to the subject and/or microstructures once certain criteria are met. For example, in theranostic applications, a signal applied to microstructures can be used to release therapeutic materials. In this example, the processing device can monitor response signals and use these to assess when an intervention is required, and then control the signal generator to trigger the release.

The nature of the stimulatory signal and the manner in which this is applied will vary depending upon the preferred implementation and this could include any one or more of biochemical, chemical, mechanical, magnetic, electromagnetic, electrical, optical, thermal, or other signals.

The stimulatory signal could be used to allow the response signal to be measured and/or could be used to trigger a biological response, to thereby provide therapy or treatment. For example, this can be used to cause electroporation, to induce local mediators of inflammation, which can in turn release biomarkers, allowing concentrations of these to be measured. In this regard, electroporation, or electropermeabilization, involves applying an electrical field to cells in order to increase the permeability of the cell membrane, allowing chemicals, drugs, or DNA to be introduced into the cell.

In another example, stimulation can be used to disrupt a boundary within the subject, for example disrupting a dermal boundary allowing biomarkers within the dermal layer to be detected in the viable epidermis, without requiring penetration of the dermal layer by the microstructures. In a further example, stimulation can be used to trigger additional effects. So for example, an electrical or mechanical signal could be used to disrupt a coating on the microstructures, causing material to be released, which can in turn a chemical or other stimulation.

Stimulatory signals could also be applied to the microstructures to alter the microstructure form or function. For example, polymer microstructures could be induced to grow or shrink along their length or width with an applied electric field or temperature, whilst microstructures could be configured to move between a retracted flat position and an extended upright position, in order to penetrate and then retract from the skin or other barrier.

In a further example, one or more microstructures include a treatment material, and wherein at least one treatment delivery mechanism is provided that controls release of the treatment material. In one preferred example, release of the treatment material is controlled by applying stimulation to the microstructure(s), for example by applying light, heat or electrical stimulation to release the treatment material.

In one preferred example, the treatment material is contained in a coating on the at least one microstructure and the stimulation is used to dissolve the coating on the microstructure and thereby deliver the treatment material. It will be appreciated that this technique can be applied to any treatment material that can be incorporated into a coating, and which can be selectively released using stimulation, such as mechanical, magnetic, thermal, electrical, electromagnetic or optical stimulation.

The nature of the treatment material will vary depending on the preferred implementation and/or the nature of the treatment being performed, including whether the treatment is cosmetic or therapeutic. Example treatment materials include, but are not limited to, nanoparticles, a nucleic acid, an antigen or allergen, parasites, bacteria, viruses, or virus-like particles, metals or metallic compounds, molecules, elements or compounds, DNA, protein, RNA, siRNA, sfRNA, iRNA, synthetic biological materials, polymers, drugs, or the like.

It will be appreciated that the use of coatings is not essential however, and additionally and/or alternatively treatment materials can be incorporated into the microstructures themselves.

Irrespective of how treatment materials are provided, the substrate can include a plurality of microstructures with different microstructures having different treatment materials and/or different treatment doses. In this case, the processing devices can control the therapy delivery mechanism to release treatment material from selected microstructures, thereby allowing different treatments to be administered, and/or allowing differential dosing, depending on the results of measurements performed on the subject. In particular, as will be described in more detail below, the processing devices typically perform an analysis at least in part using the measured response signals; and, use results of the analysis to control the at least one therapy delivery mechanism, thereby allowing personalised treatment to be administered substantially in real time.

In one example, this is achieved by controlling the signal generator to thereby control stimulation that is applied to the microstructures. This this regard, stimulation can be used to control or vary a rate of release of material from microstructures, and hence thereby control a quantity of material released from microstructures. Thus, it will be appreciated that by selectively stimulating microstructures, this can be used to control a dose of material released from the microstructures. Similarly, stimulation can be used to substantially prevent or slow release of material from microstructures.

In one example, the stimulation is electrical stimulation with a change in an electrical stimulation signal applied to microstructures being used to trigger release of the material. In one particular example, a first electrical stimulation signal, such as negative or positive bias depending on the nature of the materials and microstructures, can be applied to microstructures to substantially prevent release of the material, whilst a second electrical stimulation signal, such as a signal with opposing polarity, can be applied to the microstructures to release the material.

It will be appreciated that microstructures could be differentially coated, for example by coating different microstructures with different coatings, and/or by coating different parts of the microstructures with different coatings. This could be used to allow different analytes to be detected at different depths, so that for example a different coating is used for part of the microstructure that enters the dermis as opposed to the viable epidermis. This could also be used to allow for detection of different analytes, or different concentrations of the same analyte. Additionally, at least some microstructures could remain uncoated, for example, to allow these to be used as a control, some may be partially coated, or may include a porous structure with an internal coating. It will also be appreciated that multiple coatings could be provided. For example, an outer coating could be provided that gives mechanical strength during insertion, and which dissolves once in-situ, allowing an underlying functional coating to be exposed, for example to: allow analytes to be detected.

The nature of the coating and the manner in which this is applied will vary depending on the preferred implementation and techniques such as dip coating, spray coating, jet coating or the like, could be used, as described above. The thickness of the coating will also vary depending on the circumstances and the intend functionality provided by the coating. For example, if the coating is used to provide mechanical strength, or contains a payload material to be delivered to the subject, a thicker coating could be used, whereas if the coating is used for sensing other applications, a thinner coating might be required.

In one example, stimulation, such as chemical, biochemical, electrical, optical or mechanical stimulation, can be used to release material from the coating on the microstructure, disrupt the coating, dissolve the coating or otherwise release the coating.

In another example, the microstructures can be coated with a selectively dissolvable coating. The coating could be adapted to dissolve after a defined time period, such as after the microstructures have been present within the subject for a set length of time, in response to the presence, absence, level or concentration of one or more analytes in the subject, upon breaching or penetration of the functional barrier, or in response application of a stimulatory signal, such as an electrical signal, optical signal or the like. Dissolving of the coating can be used in order to trigger a measurement process, for example by exposing a binding agent, or other functional feature, so that analytes are only detected once the coating has dissolved.

In a further example, dissolving of the coating could be detected, for example through a change in optical or electrical properties, with the measurement being performed after the coating has dissolved. Thus, dissolving of the coating could be detected based on a change in a response signal.

In one example, the coating can be used to provide mechanical properties. For example, the coating can provide a physical structure that can be used to facilitate penetration of the barrier, for example by providing a microstructure with a smooth tapered outer profile. The coating can strengthen the microstructures, to prevent microstructures breaking, fracturing, buckling or otherwise being damaged during insertion, or could be used to help anchor the microstructures in the subject. For example, the coating could include hydrogels, which expand upon exposure to moisture, so that the size of the microstructure and coating increases upon insertion into the subject, thereby it harder to remove the microstructure.

The coating can also be used to modify surface properties of the microstructures, for example to increase or decrease hydrophilicity, increase or decrease hydrophobicity and/or minimize biofouling. The coating can also be used to attract or repel at least one substance, such as analytes, cells, fluids, or the like. The coating could also dissolve to expose a microstructure, a further coating or material, allowing this to be used to control the detection process. For example, a time release coating could be used to enable a measurement to be performed a set time after the patch has been applied. This could also be used to provide stimulation to the subject, for example by releasing a treatment or therapeutic material, or the like.

Thus, in one example, the system includes a plurality of microstructures and wherein different microstructures are differentially responsive to analytes. For example, different microstructures could be responsive to different analytes, responsive to different combination of analytes, responsive to different concentrations of analytes, or the like.

In one example, at least some of the microstructures attract at least one substance to the microstructures and/or repel at least one substance from the microstructures. The nature of the substance will vary depending on the preferred implementation and may include one or more analytes, or may include other substances containing analytes, such as ISF, blood or the like. This can be used to attract or repel analytes, for example attracting analytes of interest, allowing these to be concentrated and/or sensed, or repelling analytes that are not of interest.

The ability to repel substances can also assist with preventing biofouling. For example, the microstructures could contain a material, or include a coating, such as Polyethylene glycol (PEG), which generally repels substances from the surface of the microstructure. Reduction in biofouling could also be achieved based on a choice of microstructure material, surface coatings that release to expose a sensing surface when sensing is to be performed, permeable coatings, releasable coatings that interfere with biofouling material. Physical mechanisms can also be used, including retracting the microstructures when sensing is not being performed. In this instance, whilst removed from the body, the microstructures could be cleaned, recoated or reconditioned, thereby mitigating or removing any biofouling.

As mentioned above, the signal generator and/or sensor can be connected to the microstructures via connections. The nature of the connections will vary depending on the preferred implementation and the nature of the signal. For example, if the signal is an optical or other electromagnetic signal, a waveguide, fibre optic cable, or other electromagnetic conductor can be used. In the case of electrical signals, the connections can be conductive connections, such as wires, or conductive tracks on a substrate, or could be formed by a conductive substrate. Connections could also include wireless connections, such as short-range radio frequency wireless connections, inductive connections, or the like. Connections could also be mechanical, magnetic, thermal, or the like.

In one example, inductive connections can be used to transmit signals and power, so that for example, inductive coupling could be used to power electronic circuits mounted on the substrate. This could be used to allow basic processing to be performed on board the substrate, such as amplifying and process impedance changes, using a simple integrated circuit or similar, without requiring an in-built power supply on the substrate.

In one example, the system can include response microstructures used to measure response signals and/or stimulation microstructures used to apply stimulation signals to the subject. Thus, stimulation and response could be measured via different microstructures, in which case the substrate typically incorporates response connections for allowing response signals to be measured and stimulation connections allowing stimulation signals to be applied. In some examples, multiple stimulation and response connections are provided, allowing different measurements to be performed via different connections. For example, different types of measurements could be performed via different microstructures or different parts of given microstructures, to enable multi-modal sensing. Additionally and/or alternatively, the same type of measurements could be performed at different locations and/or depths, for example to identify localised issues, such as the presence of skin cancers or similar. In other cases, stimulation and measurement could be performed via the same connections, for example when making bipolar impedance measurements.

Signals could be applied to or measured from individual microstructures and/or to different parts of microstructures, which can be useful to discern features at different locations and/or depths within the body. This can be used for example to perform mapping or tomography, for example to produce images wherein the image contrast or colour is proportional to the levels or concentrations of one or more analytes or the change in a physical property such as bioimpedance. Additionally, and/or alternatively, signals could be applied to or measured from multiple microstructures collectively, which can be used to improve signal quality, or perform measurements, such as bipolar, tetra-polar, or other multi-polar impedance measurements. Additionally and/or alternatively, microstructures might be used for both measuring and stimulation, for example applying a signal to a microstructure and then subsequently measuring a response therefrom.

In one particular example, sensors and/or signal generators can be connected to microstructures via one or more switching devices, such as multiplexers, allowing signals to be selectively communicated between the sensor or signal generator and different microstructures. The processing device is typically configured to control the switches, allowing a variety of different sensing and stimulation to be achieved under control of the processing device. In one example, this allows at least some electrodes can be used independently of at least some other electrodes. This ability to selectively interrogate different electrodes can provide benefits.

For example, this allows different electrodes to have different functionality, for example by having different electrodes functionalized with different coatings, and then interrogated or stimulated as needed, so that different measurements can be performed as required. Additionally, and/or alternatively, this allows different measurements to be performed via different microstructures, for example to perform spatial discrimination and hence mapping. For example, interrogating electrodes at different locations on a patch, this enables a map of measurements at different locations to be constructed, which can in turn be used to localise an effect, so as the presence of analytes or specific objects, such as lesions or cancer. Furthermore, this allows stimulation to be delivered to different microstructures. For example, in theranostic embodiments, different therapeutic materials or doses could be associated with different microstructures, so selectively stimulating different microstructures allows a range of different interventions to be performed. In some example, different microstructures could be used for different purposes, so that some microstructures are used for sensing, whilst others are used for delivering stimulation and/or therapy.

In one example, as described in more detail below, when electrodes are provided as pairs, this allows some pairs of electrodes to be used independently of other pairs. In one particular example, electrodes and/or pairs of electrodes, can be arranged in rows, and this can allows measurements to be performed on a row by row basis, although this is not essential and other groupings could be used.

The nature of the substrate and/or microstructures will vary depending upon the preferred implementation. For example, substrate and/or microstructures could be made from or contain fabric, woven fabric, electronic fabric, natural fibres, silk, organic materials, natural composite materials, artificial composite materials, ceramics, stainless steel, ceramics, metals, such as stainless steel, titanium or platinum, polymers, such as rigid or semi-rigid plastics, including doped polymers, silicon or other semiconductors, including doped semiconductors, organosilicates, gold, silver, carbon, carbon nano materials, or the like. The substrate and microstructures could be made from similar and/or dissimilar materials, and could be integrally formed, or made separately and bonded together. Microstructures can also be provided on one or more substrates, so for example, signals could be measured or applied between microstructures on separate substrates.

It will be appreciated that the particular material used will depend on the intended application, so for example different materials will be used if the microstructure needs to be conductive as opposed to insulative. Insulating materials, such as polymers and plastics could be doped so as to provide required conductivity, for example via doping with micro or nano sized metal particles, or conductive composite polymers could be used such as PEDOT:PSS (poly(3,4-ethylenedioxythiophene) polystyrene). If doping is used, this could involve using graphite or graphite derivates, including 2D materials such as graphene and carbon nanotubes, with these materials also being useable as stand-alone materials or as dopants in blends with polymers or plastics.

The substrate and microstructures can be manufactured using any suitable technique. For example, in the case of silicon-based structures, this could be performed using etching techniques. Polymer or plastic structures could be manufactured using additive manufacturing, such as 3D printing, or moulding. In one particular example, a mould is filled with a suitable filling material, such as a solution containing a material such as an active compound and/or sugar-based excipient, such as carboxy-methylcellulose (CMC), or one or more polymers, or the like, which is then cured and removed. It will also be appreciated that the filling material may include any required probes, reagents, or the like that are to be contained within the structures, as will be discussed in more detail below. Photosensitive polymers might be used, such as photoresists, including SU8 or polyimides, for direct patterning of electrodes on the substrate or to make microstructures. Successive layers of photosensitive resists, polymers, metals, or the like, can be deposited and/or selectively removed to produce bespoke 3D microstructure geometries.

In one example, the substrate could be at least partially flexible in order to allow the substrate to conform to the shape of a subject and thereby ensure penetration of the microstructures into the viable epidermis and/or dermis, or other functional barrier. In this example, the substrate could potentially be a textile or fabric, with electrodes and circuitry woven in, or multiple substrates could be mounted on a flexible backing, to provide a segmented substrate arrangement. Alternatively, the substrate could be shaped to conform to a shape of the subject, so that the substrate is rigid but nevertheless ensures penetration of the microstructures.

In preferred examples, the substrate and microstructures are formed from one or more of metal, polymer or silicon.

The microstructures could have a range of different shapes and could include ridges, needles, plates, blades, or similar. In this regard, the terms plates and blades are used interchangeably to refer to microstructures having a width that is of a similar order of magnitude in size to the length, but which are significantly thinner. The microstructures can be tapered to facilitate insertion into the subject, and can have different cross-sectional shapes, for example depending on the intended use. The microstructures typically have a rounded rectangular shape and may include shape changes along a length of the microstructure. For example, microstructures could include a shoulder that is configured to abut against the stratum corneum to control a depth of penetration and/or a shaft extending to the tip, with the shaft being configured to control a position of the tip in the subject and/or provide a surface for an electrode.

Other example shapes include circular, rectangular, cruciform shapes, square, rounded square, rounded rectangular, ellipsoidal, or the like, which can allow for increased surface area, which is useful when coating microstructures to maximise the coating volume and hence the amount of payload delivered per microstructure, although it will be appreciated that a range of other shapes could be used. Microstructures can have a rough or smooth surface, or may include surface features, such as pores, raised portions, serrations, or the like, which can increase surface area and/or assist in penetrating or engaging tissue, to thereby anchor the microstructures within the subject. This can also assist in reducing biofouling, for example by prohibiting the adherence and hence build-up of biofilms. The microstructures might also be hollow or porous and can include an internal structure, such as holes or similar, in which case the cross sectional shape could also be at least partially hollow. In particular embodiments, the microstructures are porous, which may increase the effective surface area of the microstructure, for example, allowing greater doses of therapeutic material to be stored thereon. The pores may be of any suitable size to allow an analyte of interest to enter the pores, but exclude one or more other analytes or substances, and thus, will depend on the size of the analyte of interest. In some embodiments, the pores may be less than about 10 μm in diameter, preferably less than about 1 μm in diameter.

In one example, the microstructures have a rounded rectangular shape when viewed in cross section through a plane extending laterally through the microstructures and parallel to but offset from the substrate. The microstructures may include shape changes along a length of the microstructure. For example, microstructures could include a shoulder that is configured to abut against the stratum corneum to control a depth of penetration and/or a shaft extending to the tip, with the shaft being configured to control a position of the tip in the subject and/or provide a surface for an electrode.

Different microstructures could be provided on a common substrate, for example providing different shapes of microstructure to achieve different functions. In one example, this could include performing different types of measurement. In other examples, microstructures could be provided on different substrates, for example, allowing sensing to be performed via microstructures on one patch and delivery of therapy to be performed via microstructures on a different patch. In this example, this could allow a therapy patch to be replaced once exhausted, whilst a sensing patch could remain in situ. Additionally, measurements could be performed between patches, for example, performing whole of body impedance measurements between patches provided at different locations on a subject.

Additionally and/or alternatively anchor microstructures could be provided, which can be used to anchor the substrate to the subject. In this regard, anchor microstructures would typically have a greater length than that of the microstructures, which can help retain the substrate in position on the subject and ensure that the substrate does not move during the measurements or is not being inadvertently removed. Anchor microstructures can include anchoring structures, such as raised portions, which can assist with engaging the tissue, and these could be formed by a shape of the micro-structure and/or a shape of a coating. Additionally, the coating could include a hydrogel or other similar material, which expands upon expose to moisture within the subject, or an applied stimulation, thereby further facilitating engagement with the subject. Similarly the microstructure could undergo a shape change, such as swelling either in response to exposure to substances, such as water or mois-ture within the subject, or in response to an applied stimu-lation. When applied to skin, the anchor microstructures can enter the dermis, and hence are longer than other micro-structures, to help retain the substrate in place, although it will be appreciated that this is not essential and will depend upon the preferred implementation. In other examples the anchor microstructures are rougher than other microstruc-tures, have a higher surface friction than other microstruc-tures, are blunter than other microstructures or are fatter than other microstructures.

In a further example, at least part of the substrate could be coated with an adhesive coating in order to allow the substrate and hence patch, to adhere to the subject.

As previously mentioned, when applied to skin, the microstructures typically enter the viable epidermis and in one example, do not enter the dermis, although in other examples, may enter the dermis. But this is not essential, and for some applications, it may be necessary for the micro-structures to enter the dermis, for example projecting shortly through the viable epidermis/dermis boundary or entering into the dermis a significant distance, largely depending on the nature of the sensing being performed. In one example, for skin, the microstructures have a length that is at least one of less than 2500 µm, less than 1000 µm, less than 750 µm, less than 600 µm, less than 500 µm, less than 400 µm, less than 300 µm, less than 250 µm, greater than 100 µm, greater than 50 µm and greater than 10 µm, but it will be appreciated that other lengths could be used. More generally, when applied to a functional barrier, the microstructures typically have a length greater than the thickness of the functional barrier, at least 10% greater than the thickness of the functional barrier, at least 20% greater than the thickness of the functional barrier, at least 50% greater than the thickness of the functional barrier, at least 75% greater than the thickness of the functional barrier and at least 100% greater than the thickness of the functional barrier.

In another example, the microstructures have a length that is no more than 2000% greater than the thickness of the functional barrier, no more than 1000% greater than the thickness of the functional barrier, no more than 500% greater than the thickness of the functional barrier, no more than 100% greater than the thickness of the functional barrier, no more than 75% greater than the thickness of the functional barrier or no more than 50% greater than the thickness of the functional barrier. This can avoid deep penetration of underlying layers within the body, which can in turn be undesirable, and it will be appreciated that the length of the microstructures used will vary depending on the intended use, and in particular the nature of the barrier to be breached, and/or signals to be applied or measured. The length of the microstructures can also be uneven, for example, allowing a blade to be taller at one end than another, which can facilitate penetration of the subject or functional barrier.

Similarly, the microstructures can have different widths depending on the preferred implementation. Typically, the widths are at least one of less than 25% of the length, less than 20% of the length, less than 15% of the length, less than 10% of the length, or less than 5% of the length. Thus, for example, when applied to the skin, the microstructures could have a width of less than 50 µm, less than 40 µm, less than 30 µm, less than 20 µm or less than 10 µm. However, alternatively, the microstructures could include blades, and could be wider than the length of the microstructures. In some example, the microstructures could have a width of less than 50000 µm, less than 40000 µm, less than 30000 µm, less than 20000 µm, less than 10000 µm, less than 5000 µm, less than 2500 µm, less than 1000 µm, less than 500 µm or less than 100 µm. In blade examples, it is also feasible to use microstructures having a width substantially up to the width of the substrate.

In general the thickness of the microstructures is signifi-cantly lower in order to facilitate penetration and is typically less than 1000 µm, less than 500 µm, less than 200 µm, less than 100 µm, less than 50 µm, less than 20 µm, less than 10 µm, at least 1 µm, at least 0.5 µm or at least 0.1 µm. In general the thickness of the microstructure is governed by mechanical requirements, and in particular the need to ensure the microstructure does not break, fracture or deform upon penetration. However, this issue can be mitigated through the use of a coating that adds additional mechanical strength to the microstructures.

In one specific example, for epidermal sensing, the micro-structures have a length that is less than 300 µm, greater than 50 µm, greater than 100 µm and about 150 µm, and, a width that is greater than or about equal to a length of the microstructure, and is typically less than 300 µm, greater than 50 µm and about 150 µm. In another example, for dermal sensing, the microstructures have a length that is less than 450 µm, greater than 100 µm, and about 250 µm, and, a width that is greater than or about equal to a length of the microstructure, and at least of a similar order of magnitude to the length, and is typically less than 450 µm, greater than 100 µm, and about 250 µm. In other examples, longer microstructures could be used, so for example for hyperd-ermal sensing, the microstructures would be of a greater length. The microstructures typically have a thickness that is less than the width, significantly less than the width and of an order of magnitude smaller than the width. In one example, the thickness is less than 50 µm, greater than 10 µm, and about 25 µm, whilst the microstructure typically includes a flared base for additional strength, and hence includes a base thickness proximate the substrate that is about three times the thickness, and typically is less than 150 µm, greater than 30 µm and about 75 µm. The microstruc-tures typically have a tip has a length that is less than 50% of a length of the microstructure, at least 10% of a length of the microstructure and more typically about 30% of a length of the microstructure. The tip further has a sharpness that is at least 0.1 µm, less than 5 µm and typically about 1 µm.

In one example, the microstructures have a relatively low density, such as less than 10000 per cm², such as less than 1000 per cm², less than 500 per cm², less than 100 per cm², less than 10 per cm² or even less than 5 per cm². The use of relatively a low density facilitates penetration of the micro-structures through the stratum corneum and in particular avoids the issues associated with penetration of the skin by high density arrays, which in turn can lead to the need for high powered actuators in order for the arrays to be correctly applied. However, this is not essential, and higher density microstructure arrangements could be used, including less than 50,000 microstructures per cm$^2$, less than 30,000 microstructures per cm$^2$, or the like. As a result, the microstructures typically have a spacing that is less than 20 mm, less than 10 mm, less than 1 mm, less than 0.1 mm or less than 10 μm. It should be noted that in some circumstances, microstructures are arranged in pairs, with the microstructures in each pair having a small spacing, such as less than 10 μm, whilst the pairs have a great spacing, such as more than 1 mm, in order to ensure a low overall density is maintained. However, it will be appreciated that this is not essential, and higher densities could be used in some circumstances.

In one specific example, the microstructures have a density that is less than 5000 per cm$^2$, greater than 100 per cm$^2$, and about 600 per cm$^2$, leading to a spacing of less than 1 mm, more than 10 μm, and about 0.5 mm, 0.2 mm or 0.1 mm.

In one example, when optical sensing is performed, the connections in the substrate include waveguides, or other electromagnetically conductive paths, such as optical fibre, which extend through the microstructures to one or more ports in the microstructure, to allow electromagnetic radiation to be emitted from or received via the ports. In one example, this is achieved by having the microstructure made from, or contain, polymer, or another similar material, which is at least partially transparent to the frequency of electromagnetic radiation being applied or received, which could include visible radiation, ultra-violet radiation, infra-red radiation, or the like, depending on the preferred application.

In one example, an at least partially electromagnetically transparent core can be surrounded by an outer electromagnetically opaque layer, with ports extending through the opaque layer, to allow electromagnetic radiation to be emitted or received via the ports. In this example, it will be appreciated that appropriate positioning of the ports, allows radiation to be delivered or received in a targeted manner, for example allowing this to be directed into a particular depth within the viable epidermis, or elsewhere. In one example, the transparent core could be made from a waveguide, such as a fibre optic cable, or part thereof. For example, the outer layer and/or reflective layer could be removed, allowing the transparent core of the microstructure to be made of the fibre optic core. In a further example, the microstructures include electromagnetically reflective layers to allow electromagnetic radiation to be conducted to and from designated ports.

Similar arrangements could be provided for electrical signalling, with the microstructures including an electrically conductive core material and optionally including an electrically insulating layer including ports to allow electrical signals to be emitted from or received by the ports, again with ports optionally being at different depths, to allow electrical signals to be measured at different locations and/or depths.

Thus, the microstructure could include an electrically conductive material covered by a non-conductive (insulating) layer, with openings providing access to the conductive material to allow conduction of electrical signals through the openings to thereby define electrodes. In one example, the insulating layer extends over part of a surface of the microstructure, including a proximal end of the microstructure adjacent the substrate. The insulating layer could extend over at least half of a length of the microstructure and/or about 60 μm, 90 μm or 150 μm of a proximal end of the microstructure, and optionally, at least part of a tip portion of the microstructure. In one specific example, this is performed so the non-insulating portion is provided in the epidermis and/or dermis, so stimulatory signals are applied to and/or response signals received from, the epidermis and/or dermis. The insulating layer could also extend over some or all of a surface of the substrate. In this regard, in some examples connections are formed on a surface of the substrate, in which case a coating could be used to isolate these from the subject. For example, electrical tracks on a surface of the substrate could be used to provide electrical connections to the electrodes, with an insulating layer being provided on top of the connections to ensure the connections do not make electrical contact with the skin of the subject, which could in turn adversely affect measured response signals.

In another example, at least some of microstructures include an electrode. The microstructures could be made from a metal or other conductive material, so that the entire microstructure constitutes the electrode, or alternatively the electrode could be coated or deposited onto the microstructure, for example by depositing a layer of gold to form the electrode. In a further example, the microstructure could include an electrically conductive core covered by a non-conductive layer, with openings providing access to the core to allow conduction of electrical signals through the openings. The electrode material could include any one or more of gold, silver, colloidal silver, colloidal gold, colloidal carbon, carbon nano materials, platinum, titanium, stainless steel, or other metals, or any other biocompatible conductive material.

The electrodes could be used to apply electrical signals to a subject, measure intrinsic or extrinsic response electrical signals, for example measuring ECG or impedances. In another example, the one or more microstructure electrodes interact with one or more analytes of interest such that a response signal is dependent on a presence, absence, level or concentration of one or more analytes of interest, thereby allowing the level or concentration of one or more analytes to be quantified.

In one example, the microstructures include plates having a substantially planar face having an electrode thereon. The use of a plate shape maximizes the surface area of the electrode, whilst minimizing the cross sectional area of the microstructure, to thereby assist with penetration of the microstructure into the subject. This also allows the electrode to act as a capacitive plate, allowing capacitive sensing to be performed. In one example, the electrodes have a surface area of at least at least 10 mm$^2$, at least 1 mm$^2$, at least 100,000 μm$^2$, 10,000 μm$^2$, at least 7,500 μm$^2$, at least 5,000 μm$^2$, at least 2,000 μm$^2$, at least 1,000 μm$^2$, at least 500 μm$^2$, at least 100 μm$^2$, or at least 10 μm$^2$. In one example, the electrodes have a width or height that is up to 2500 μm, at least 500 μm, at least 200 μm, at least 100 μm, at least 75 μm, at least 50 μm, at least 20 μm, at least 10 μm or at least 1 μm. In the case of electrodes provided on blades, the electrode width could be less than 50000 μm, less than 40000 μm, less than 30000 μm, less than 20000 μm, less than 10000 μm, or less than 1000 μm, as well as including widths outlined previously. In this regard, it will be noted that these dimensions apply to individual electrodes, and in some examples each microstructure might include multiple electrodes.

In one specific example, the electrodes have a surface area of less than 200,000 μm$^2$, at least 2,000 μm$^2$ and about 22,500 μm$^2$, with the electrodes extending over a length of a distal portion of the microstructure, optionally spaced from the tip, and optionally positioned proximate a distal end of the microstructure, again proximate the tip of the microstructure. The electrode can extend over at least 25% and less than 50% of a length of the microstructure, so that the electrode typically extends over about 60 μm 90 μm or 150 μm of the microstructure and hence is positioned in a viable epidermis and/or dermis of the subject in use.

In one example, at least some of the microstructures are arranged in groups, such as pairs, with response signals or stimulation being measured from or applied to the microstructures within the group. The microstructures within the group can have a specific configuration to allow particular measurements to be performed. For example, when arranged in pairs, a separation distance can be used to influence the nature of measurements performed. For example, when performing bioimpedance measurements, if the separation between the microstructures is greater than a few millimetres, this will tend the measure properties of interstitial fluid located between the electrodes, whereas if the distance between the microstructures is reduced, measurements will be more influenced by surface properties, such as the presence of materials bound to the surface of the microstructures. Measurements are also influenced by the nature of the applied stimulation, so that for example, current at low frequencies will tend to flow though extra-cellular fluids, whereas current at higher frequencies is more influenced by intra-cellular fluids.

In one particular example, plate microstructures are provided in pairs, with each pair including spaced apart plate microstructures having substantially planar electrodes in opposition. This can be used to generate a highly uniform field in the subject in a region between the electrodes, and/or to perform capacitive or conductivity sensing of substances between the electrodes. However, this is not essential, and other configurations, such as circumferentially spacing a plurality of electrodes around a central electrode, can be used. Typically the spacing between the electrodes in each group is typically less than 50 mm; less than 20 mm, less than 10 mm, less than 1 mm, less than 0.1 mm or less than 10 μm, although it will be appreciated that greater spacings could be used, including spacing up to dimensions of the substrate and/or greater, if microstructures are distributed across multiple substrates.

Thus, in one specific example, at least some of the microstructures are arranged in pairs, with response signals being measured between microstructures in the pair and/or stimulation being applied between microstructures in the pair. Each pair of microstructures typically includes spaced apart plate microstructures having substantially planar electrodes in opposition and/or spaced apart substantially parallel plate microstructures.

In one example, at least some pairs of microstructures are angularly offset, and in one particular example, are orthogonally arranged. Thus, in the case of plate microstructures, at least some pairs of microstructures extend in different and optionally orthogonal directions. This distributes stresses associated with insertion of the patch in different directions, and also acts to reduce sideways slippage of the patch by ensuring plates at least partially face a direction of any lateral force. Reducing slippage either during or post insertion helps reduce discomfort, erythema, or the like, and can assist in making the patch comfortable to wear for prolonged periods. Additionally, this can also help to account for any electrical anisotropy within the tissue, for example as a result of fibrin structures within the skin, cellular anisotropy, or the like.

In one specific example, adjacent pairs of microstructures are angularly offset, and/or orthogonally arranged, and additionally and/or alternatively, pairs of microstructures can be arranged in rows, with the pairs of microstructures in one row are orthogonally arranged or angularly offset relative to pairs of microstructures in other rows.

In one specific example, when pairs of microstructures are used, a spacing between the microstructures in each pair is typically less than 0.25 mm, more than 10 μm and about 0.1 mm, whilst a spacing between groups of microstructures is typically less than 1 mm, more than 0.2 mm and about 0.5 mm. Such an arrangement helps ensure electrical signals are primarily applied and measured within a pair and reduces cross talk between pairs, allowing independent measurements to be recorded for each pair of microstructures/electrodes.

To create an array of pairs of electrodes, this can be performed by manufacturing a first substrate having first microstructures and corresponding first apertures. An insulating layer is then provided on a side of the first substrate opposite the first microstructures before a second substrate is provided on the insulating layer. In this example, the second substrate has second microstructures extending through the insulating layer and the first apertures to form pairs of first and second microstructures, and an example of this will be described in more detail below. In one example, the first and second apertures are offset to reduce capacitive coupling between the first and second substrates. Alternatively, other mechanisms for capacitive coupling between the substrates could be used.

The microstructures can be configured in order to interact with, and in particular, bind with one or more analytes of interest, allowing these to be detected. Specifically, in one example, binding of one or more analytes to the microstructures can alter the charge carrying capability, in turn leading to changes in capacitance of electrode pairs, which can then be monitored, allowing analyte levels or concentrations to be derived. Binding of analytes can be achieved using a variety of techniques, including selection of mechanical properties of the microstructure, such as the presence of pores or other physical structures, the material from which the microstructures are manufactured, the use of coatings, or otherwise influencing the microstructure properties, such as by using magnetic microstructures.

Additionally, the microstructures and/or substrate can incorporate one or more materials or other additives, either within the body of the microstructure, or through addition of a coating containing the additive. The nature of the material or additive will vary depending on the preferred implementation and could include a bioactive material, a reagent for reacting with analytes in the subject, a binding agent for binding with analytes of interest, a material for binding one or more analytes of interest, a probe for selectively targeting analytes of interest, a material to reduce biofouling, a material to attract at least one substance to the microstructures, a material to repel or exclude at least one substance from the microstructures, a material to attract at least some analytes to the microstructures, or a material to repel or exclude analytes. In this regard, substances could include any one or more of cells, fluids, analytes, or the like. Example materials include polyethylene, polyethylene glycol, polyethylene oxide, zwitterions, peptides, hydrogels and self-assembled monolayers.

The material can be contained within the microstructures themselves, for example by impregnating the microstructures during manufacture, can be the material from which the microstructures are formed, or could be provided in a coating. Accordingly, it will be appreciated that at least some of the microstructures can be coated with a coating such as a material for binding one or more analytes or interest, which can be used in order to target specific analytes of interest, allowing these to bind or otherwise attach to the microstructure, so that these can then be detected in situ using a suitable detection mechanism, such as by detecting changes in optical or electrical properties.

In some embodiments, the material or additive is a material for binding one or more analytes of interest.

In particular embodiments, the material is an aptamer, especially a plurality of aptamers. In particular embodiments, the aptamer is a coating on the microstructure.

The identity of the aptamer will depend on the specific analyte of interest and the method of detection. A skilled person will readily be able to identify and use suitable aptamers for each analyte of interest and method of detection. The aptamer is one which interacts or binds with an analyte of interest, and undergoes a conformational change upon analyte binding. For example, in some embodiments, the aptamer has a first conformation in the absence of analyte binding and a second conformation upon analyte binding.

In some embodiments, the second conformation results in a portion of the aptamer (e.g. a first end of the aptamer, such as the 3' or 5' end) being closer to the microstructure (and electrode) than in the first confirmation (i.e. the spacing between the portion of the aptamer and the microstructure is decreased in the second conformation). In alternative embodiments, the second confirmation results in a portion of the aptamer being further from the microstructure (and electrode) than in the first conformation (i.e. the spacing between the portion of the aptamer and the microstructure is increased in the second confirmation). Such change in proximity between the portion of the aptamer and the microstructure may then be detected using, for example, a labelling moiety such as a redox moiety or fluorescent label attached to or close to the relevant portion of the aptamer, such as a first end. In particular embodiments, the portion of the aptamer is a first end of the aptamer (e.g. 5' end), preferably when a second end of the aptamer (e.g. the 3' end) is conjugated or otherwise attached, either directly or indirectly to the microstructure. Thus, in some embodiments, the second conformation results in a first end of the aptamer being closer to the microstructure than in the first conformation, or alternatively, results in a first end of the aptamer being further from the microstructure than in the first conformation. This may, for example, result in a first signal when the aptamer is in the first conformation and a second signal when the aptamer is in the second conformation, wherein the first signal is other than the second signals (i.e. the first and second signals are different).

While aptamers of any structure are contemplated, in particular embodiments, the aptamer comprises or consists of a stem-loop hairpin structure.

Suitable aptamers are well known in the art or may be identified using various methods well known in the art of aptamer selection.

For example, suitable aptamers may include, but are not limited to an aptamer described in Negahdary et al. (2018) *J Biomed Phys Eng*, 8(2): 167-178; Jo et al. (2015) *Anal Chem*, 87:9869-9875; US 2012/0316326 A1; CN 102703455 A; KR 20160021488 A; US 2019/0219595 A1; Pfefiffer and Mayer (2016) *Front Chem*, 4:25; WO 2017/210683 A1; CN 102660547 A; WO 2017/210683 A1; CN 105136754 A; WO 2012/130948 A1; U.S. Pat. Nos. 5,582, 981 A; 5,595,877 A; US 2018/0327746 A1; EP 2532749 B1; US 2012/0135540 A1; CN 105349545 A; US 2011/0318846 A1; CN 104745585 A; Stojanovic et al. (2000) *J Am Chem Soc*, 122:11547-11548; WO 2015/197706 A1; WO 2019/

38

094315 A1; or US 2017/0233738 A1; the entire contents of which are incorporated by reference herein.

In some embodiments, the aptamer is a troponin selective aptamer, representative examples of which include one described in Negahdary et al. (2018) *J Biomed Phys Eng*, 8(2): 167-178; Jo et al. (2015) *Anal Chem*, 87:9869-9875; US 2012/0316326 A1; CN 102703455 A; KR 20160021488 A; and US 2019/0219595 A1; the entire contents of which are incorporated herein by reference.

In some embodiments, the aptamer comprises, consists or consists essentially of a nucleotide sequence selected from the group consisting of:

```
                                          [SEQ ID NO: 1]
AGTCTCCGCTGTCCTCCCGATGCACTTGACGTATGTCTCACTTTCTTTT
CATTGACATGGGATGACGCCGTGACTG;

[SEQ ID NO: 2]
CGTGCAGTACGCCAACCTTTCTCATGCGCTGCCCCTCTTA;

[SEQ ID NO: 3]
AGTCTCCGCTGTCCTCCCGATGCACTTGACGTATGTCTCACTTTCTTTT
CATTGACATGGGATGACGCCGTGACTG;

[SEQ ID NO: 4]
CGTGCAGTACGCCAACCTTTCTCATGCGCTGCCCCTCTTA;

[SEQ ID NO: 5]
CGCATGCCAAACGTTGCCTCATAGTTCCCTCCCCGTGTCC;

[SEQ ID NO: 6]
TCACACCCTCCCTCCCACATACCGCATACACTTTCTGATT;

[SEQ ID NO: 7]
CCCGACCACGTCCCTGCCCTTTCCTAACCTGTTTGTTGAT;

[SEQ ID NO: 8]
ATGCGTTGAACCCTCCTGACCGTTTATCACATACTCCAGA;

[SEQ ID NO: 9]
CGTGCAGTACGCCAACCTTTCTCATGCGCTGCCCCTCTTA;

[SEQ ID NO: 10]
CAACTGTAATGTACCCTCCTCGATCACGCACCACTTGCAT;

[SEQ ID NO: 11]
CGCATGCCAAACGTTGCCTCATAGTTCCCTCCCCGTGTCC;
and

[SEQ ID NO: 12]
AGTCTCCGCTGTCCTCCCGATGCACTTGACGTATGTCTCACTTTCTTTT
CATTGACATGGGATGACGCCGTGACTG;

[SEQ ID NO: 13]
TCACACCCTCCCTCCCACATACCGCATACACTTTCTGATT;

[SEQ ID NO: 14]
CCCGACCACGTCCCTGCCCTTTCCTAACCTGTTTGTTGAT;

[SEQ ID NO: 15]
ATGCGTTGAACCCTCCTGACCGTTTATCACATACTCCAGA;

[SEQ ID NO: 16]
CGTGCAGTACGCCAACCTTTCTCATGCGCTGCCCCTCTTA;

[SEQ ID NO: 17]
CAACTGTAATGTACCCTCCTCGATCACGCACCACTTGCAT;

[SEQ ID NO: 18]
CGCATGCCAAACGTTGCCTCATAGTTCCCTCCCCGTGTCC;

[SEQ ID NO: 19]
TCACACCCTCCCTCCCACATACCGCATACACTTTCTGATT;

[SEQ ID NO: 20]
CCCGACCACGTCCCTGCCCTTTCCTAACCTGTTTGTTGAT;
```

-continued

[SEQ ID NO: 21]
ATGCGTTGAACCCTCCTGACCGTTTATCACATACTCCAGA;

[SEQ ID NO: 22]
CAACTGTAATGTACCCTCCTCGATCACGCACCACTTGCAT;

[SEQ ID NO: 23]
CGTGCAGTACGCCAACCTTTCTCATGCGCTGCCCCTCTTA;

[SEQ ID NO: 24]
CGCATGCCAAACGTTGCCTCATAGTTCCCTCCCCGTGTCC;

[SEQ ID NO: 25]
GGGATGGGGTGGGTGGCCAGCGATT;
and

[SEQ ID NO: 26]
TTAGGGGTGGTGTGGTTGGCAATTC; especially SEQ ID NO: 1.

The invention also contemplates variants of the sequences provided herein. Accordingly, in some embodiments, the aptamer comprises, consists or consists essentially of a nucleotide sequence which has at least about 80%, 81%, 82%, 83%, 84%, 85%, 86%, 87%, 88%, 89%, 90%, 91%, 92%, 93%, 94%, 95%, 96%, 97%, 98%, or 99% sequence identity to the nucleotide sequence of any one of SEQ ID NOs: 1-26, especially SEQ ID NO: 1.

To determine the percentage sequence identity between two nucleic acid sequences, the sequences are aligned for optimal comparison purposes (e.g. gaps can be introduced in one or both of a first and a second nucleic acid sequence for optimal alignment and non-homologous sequences can be disregarded for comparison purposes). In some embodiments, the length of a reference sequence aligned for comparison purposes is at least 40%, more usually at least 50% or 60%, and even more usually at least 70%, 80%, 90% or 100% of the length of the reference sequence. The nucleotides at corresponding nucleotide positions are then compared. When a position in the first sequence is occupied by the same nucleotide at the corresponding position in the second sequence, then the molecules are identical at that position.

The comparison of sequences and determination of percent identity between sequences can be accomplished using a mathematical algorithm. In certain embodiments, the percent identity between nucleic acid sequences is determined using the Needleman and Wünsch, (1970, *J. Mol. Biol.,* 48:444-453) algorithm which has been incorporated into the GAP program in the GCG software package (Devereaux et al. (1984) *Nucleic Acids Research,* 12:387-395), using either a Blosum 62 matrix or a PAM250 matrix, and a gap weight of 16, 14, 12, 10, 8, 6, or 4 and a length weight of 1, 2, 3, 4, 5, or 6. In some embodiments, the percent identity between nucleic acid sequences can be determined using the algorithm of Meyers and Miller (1989, Cabios, 4:11-17) which has been incorporated into the ALIGN program (version 2.0), using a PAM120 weight residue table, a gap length penalty of 12 and a gap penalty of 4.

Alternatively, a suitable aptamer may be identified and prepared using various methods known in the art of aptamer selection, including Systematic Evolution of Ligands by Exponential Enrichment (SELEX) techniques (e.g. as described in U.S. Pat. Nos. 5,475,096 A and 5,270,163 A), and the methods described in WO 2019/067383 A1, U.S. Pat. Nos. 5,582,981 A, 5,595,877 A, and 5,637,459 A, the entire contents of which are incorporated herein by reference. In particular embodiments, an aptamer may be identified and prepared using SELEX techniques. In brief, the method may comprise systematically subjecting a large random pool of oligonucleotides to negative and positive rounds of selection against a target, e.g., an analyte, such as a protein, to filter out low affinity or nonspecific binders. The remaining aptamers may be collected and propagated, e.g., PCR amplified, and used in subsequent rounds of selection.

In some embodiments, it may be desirable to improve the stability of the aptamer. Several approaches are known in the art, including capping the terminal ends of the aptamer, substituting naturally occurring nucleotides with unnatural nucleotides (e.g. 2'-F, 2'-OCH$_3$, 2'-H, 2'-OH or 2'-NH$_2$ modified nucleotides such as 2'-fluorine-substituted pyrimidines, 2'-amino pyrimidines, and 2'-O-methyl ribose purines and pyrimidines), using unnatural internucleotide linkages such as phosphorothioate, methylphosphonate or triazole linkages, using altered sugar moieties, conjugating a molecule such as biotin to the 3' end, 3' end capping with inverted thymidine (dT), conjugating protein-like side chains e.g. to the nucleotides such as the 5-position of deoxyuridine (dU) (e.g. 5-(N-benzylcarboxyamide)-2-deoxyuridine), develop "spiegelmers" which are composed entirely of unnatural L-ribonucleic acid backbone, and the like. Further approaches are discussed in, for example, Shuaijian et al. (2017) *Int J Mol Sci,* 18(8): 1683, the content of which is incorporated herein by reference in its entirety.

The aptamer may also be modified to increase the sensitivity and binding kinetics of the aptamer for the analyte of interest. It is noted that one or more of the approaches for improving the stability of the aptamer may have this result, particularly conjugating protein-like side chains e.g. to the nucleotides such as the 5-position of deoxyuridine (dU) (e.g. 5-(N-benzylcarboxyamide)-2-deoxyuridine). Additional modifications to increase the sensitivity and binding kinetics of the aptamer for the analyte of interest may be achieved using methods described in Ricci et al. (2016) *Acc Chem Res,* 49(9): 1884-1892, including population shift, allostery, matched receptor sets, sequestration and cooperativity. Further approaches contemplated by the invention may include attaching retaining structures which retain the aptamer in the second configuration to increase the aptamer recovery time, such as complementary primers attached to the ends of the aptamer, which bind together upon analyte binding to retain the aptamer in the second configuration beyond a recovery interval and at least one blocker bound to the aptamer which prevents the primers from binding together prior to analyte binding, or functional groups which interact with each other upon analyte binding to retain the aptamer in the second configuration beyond a recovery interval. Such approaches are discussed in WO 2018/031559 A1, the entire content of which is incorporated herein by reference.

In some embodiments, the aptamer comprises a moiety for attaching or immobilising the aptamer on the surface of the microstructure, such as a functional group or compound, preferably via a covalent bond. Suitable moieties for attaching or immobilising the aptamer on the surface of the microstructure include, but are not limited to, a thiol, amine, carboxylic acid, alcohol, carbodiimide, nafion, avidin, biotin, azide and the like; especially a thiol. While the moiety may be directly attached to the aptamer, in some embodiments, the moiety is attached to the aptamer via a linker, such as an alkyl chain, including a C$_1$-C$_{20}$ alkyl, especially a C$_6$ or C$_1$ alkyl, most especially a C$_0$ alkyl linker (i.e. (CH$_2$)$_6$ linker), a polymer, such as polyethylene glycol (PEG); or a nucleic acid sequence, including DNA and RNA sequences. In particular embodiments, the linker is an alkyl chain, such as a C$_1$-C$_{20}$ alkyl, especially a C$_6$ or C$_{11}$ alkyl, most especially a C$_6$ alkyl linker (i.e. (CH$_2$)$_6$ linker). Suitable linkers and synthetic routes for producing such linkers are known in the art, such as Lai et al. (2006) *Langmuir*, 22:10796-10800, the entire contents of which is incorporated herein by reference.

Aptamers may be prepared using oligonucleotide synthetic techniques standard in the art, such as chemical synthesis (refer to, e.g. Itakura et al. (1984) *Ann Rev Biochem*, 53:323-356). The aptamers may also be prepared by amplification (e.g. PCR) of aptamers prepared using SELEX techniques, as described in U.S. Pat. Nos. 5,475,096 A and 5,270,163 A, and the methods described in WO 2019/067383 A1, U.S. Pat. Nos. 5,582,981 A, 5,595,877 A, and 5,637,459 A. Aptamers are also commercially available from a number of sources including Bioneer Pacific, Biosynthesis Inc. and TriLink Biotechnologies.

The aptamer is selective for binding the one or more analytes of interest. The aptamer is preferably selective for binding the one or more analytes of interest, such as troponin or a subunit thereof, especially troponin I, over at least one other substances present in the sample, preferably the majority of other substances present in the sample.

In some embodiments, the aptamer comprises a label or labelling moiety, such as a redox moiety, a fluorescent label and the like. Such moieties are useful for detecting the conformational change of the aptamer upon analyte binding as discussed herein.

In some embodiments, the aptamer comprises a redox moiety. Suitable redox moieties include any redoxable chemical moiety that can be conjugated or otherwise attached to an aptamer. For example, suitable redox moieties include, but are not limited to, methylene blue, ferrocene, vinylferrocene, anthraquinone, nile blue, thionine, anthraquinone-C5, dabcyl, 2,6-dichlorophenal-indophenol, gallocyanine, ROX, pentamethylferrocene, ferrocene-C5, neutral red and horseradish peroxidase; especially methylene blue, ferrocene, anthraquinone or nile blue; most especially methylene blue.

The redox moiety may be attached at any suitable point on the aptamer, provided that the conformational change which occurs upon analyte binding to the aptamer results in a detectable change in the spacing between the redox moiety and the electrode of the microstructure on which the aptamer is immobilised. In some embodiments, the redox moiety is closer to the electrode of the microstructure on which the aptamer is immobilised in the second conformation (i.e. upon analyte binding) compared to the first conformation (i.e. the spacing has decreased in the second conformation). In alternative embodiments, the redox moiety is further from the electrode of the microstructure on which the aptamer is immobilised in the second conformation (i.e. upon analyte binding) compared to the first conformation (i.e. the spacing has increased in the second conformation). For example, in some embodiments, the redox moiety is attached at the 3' end or 5' end of the aptamer; especially at 3' end of the aptamer, and the aptamer is attached to the microstructure through the opposite end, such as 5' end and vice versa, preferably 5' end. Without wishing to be bound by theory, it is proposed that electron transfer from the redox moiety to the electrode of the microstructure on which the aptamer is immobilised is increased when the spacing between the redox moiety and electrode is decreased and vice versa, thereby resulting in a detectable change which may be correlated to the presence, absence, level or concentration of analyte.

In some embodiments, the aptamer comprises a fluorescent label. Suitable fluorescent labels include, but are not limited to, fluorescein, 6-carboxyflourescein (FAM), coumarins, rhodamines, 5-TMRIA (tetramethylrhodamine-5-iodoacetamide), (9-(2 (or 4)-(N-(2-maleimdylethyl)-sulfonamidyl)-4 (or 2)-sulfophenyl)-2,3,6,7,12,13,16,17-octahydro-(1-H,5H,11H,15H-xantheno (2,-3,4-ij: 5,6,7-i'j') diquinolizin-18-ium salt) (Texas Red), 2-(5-(1-(6-(N-(2-maleimdylethyl)-amino)-6-oxohexyl)-1,3-dihydro-3,3-dimethyl-5-sulfo-2H-indol-2-ylidene)-1,3-propyldienyl)-1-ethyl-3,3-dimethyl-5-sulfo-3H-indolium salt (Cy3), N,N'-dimethyl-N-(iodoacetyl)-N'-(7-nitrobenz-2-oxa-1,3-diazol-4-yl)ethylenediamine (IANBD amide), N-((2-(iodoacetoxy) ethyl)-N-methyl)amino-7-nitrobenz-2-oxa-1,3-diazole (IANBD ester), 6-acryloyl-2-dimethylaminonaphthalene (acrylodan), pyrene, 6-amino-2,3-dihydro-2-(2-((iodo-acetyl)amino)ethyl)-1,3-dioxo-1H-benz (de) isoquinoline-5, 8-disulfonic acid salt (lucifer yellow), 2-(5-(1-(6-(N-(2-maleimdylethyl)-amino)-6-oxohexyl)-1,3-dihydro-3,3-dimethyl-5-sulfo-2H-indol-2-ylidene)-1,3-pentadienyl)-1-ethyl-3,3-dimethyl-5-sulfo-3H-indolium salt (Cy5), 4-(5-(4-dimethylaminophenyl) oxazol-2-yl)phenyl-N-(2-bromoacetamidoethyl) sulfonamide (Dapoxyl® (2-bromoacetamidoethyl) sulfonamide)), (N-(4,4-difluoro-1,3,5,7-tetramethyl-4-bora-3a,4a-diaza-s-indacene-2-yl) iodoacetamide (BODIPY 507/545 IA), N-(4,4-difluoro-5,7-diphenyl-4-bora-3a,4a-diaza-s-indacene-3-propionyl)-N'-iodoacetylethylene diamine (BODIPY 530/550 LA), 5-((((2-iodoacetyl)amino)ethyl)amino) naphthalene-1-sulfonic acid (1,5-IAEDANS), carboxy-X-rhodamine, 5/6-iodoacetamide (XRIA 5,6), BODIPY-FL-hydrazide, 6-carboxytetramethyl-rhodamine (TAMRA), cyan fluorescent protein, green fluorescent protein and yellow fluorescent protein. Fluorescent quantum dots are also contemplated. Other suitable fluorescent labels include those described in ThermoFisher Scientific (2019) The Molecular Probes Handbook-A Guide to Fluorescent Probes and Labeling Technologies, accessed 29 Sep. 2019, <https://www.thermofisher.com/au/en/home/references/molecular-probes-the-handbook.html>.

The fluorescent label may be attached at any suitable point on the aptamer. For example, in some embodiments, the fluorescent label is attached at the 3' end or 5' end of the aptamer; especially at 3' end of the aptamer.

A skilled person will be well aware of suitable methods for attaching a labelling moiety to an aptamer, including chemical means, such as reduction, oxidation, conjugation, and condensation reactions. For example, a thiol-reactive group can be used to attach a labelling moiety, e.g., a fluorescent label or redox moiety, to a naturally occurring or engineered thiol group present in the aptamer. In a further example, reactive groups present in the aptamer can be labelled using succinimide ester derivatives of fluorescent labels. For example an amine may be introduced at the desired location of the aptamer for attachment of the labelling moiety, and an NHS-labelled redox moiety (e.g. NHS-labelled methylene blue) may be conjugated to the aptamer using, for example, succinimide ester coupling. Suitable methods are well known in the art, such as Liu et al. (2010) *Anal Chem*, 82(19): 8131-8136; Xiao et al. (2005) *Angew Chem Int Ed*, 44:5456-5459; and US 2016/0278638 A1, the entire contents of which are incorporated herein by reference.

The labelling moiety may also be an autofluorescent or luminescent label.

While the labelling moiety may be directed attached to the aptamer, in some embodiments, the labelling moiety is attached to the aptamer via a linker. For example, in some embodiments, the moiety is attached to the aptamer via a linker, such as an alkyl chain, including a $C_1$-$C_{20}$ alkyl, especially a $C_6$ or $C_{11}$ alkyl, most especially a $C_6$ alkyl linker (i.e. $(CH_2)_6$ linker); a polymer, such as polyethylene glycol (PEG); or a nucleic acid sequence, including DNA and RNA sequences.

In some embodiments, the fluorescent label may be the only labelling moiety attached to the aptamer. Without wishing to be bound by theory, in such embodiments, it is proposed that analyte binding results in a conformational change in the aptamer, which causes a detectable change in the fluorescence of the fluorescent label (e.g. by changing the conjugation of the fluorescent label), such as an increase in fluorescence, a wavelength shift, and/or an increase in the fluorescence lifetime. Alternatively, the fluorescent label may interact with the bound analyte, resulting in a decrease in fluorescence of the fluorescent label.

In alternative embodiments, the aptamer comprises two labelling moieties, such as two fluorescent labels. Such embodiments are particularly suitable when generating an optical output, such as Förster resonance energy transfer (FRET). Such embodiments may utilise a pair of labelling moieties (e.g. a pair of fluorescent labels) attached at different points on the aptamer, where one label acts as a donor molecule (a first labelling moiety) and the other acts as an acceptor molecule (i.e. a quencher) (a second labelling moiety), wherein the absorption spectrum of the acceptor molecule overlaps the fluorescence emission spectrum of the donor molecule. Without wishing to be bound by theory, it is proposed that analyte binding results in a conformational change in the aptamer, which causes the proximity of the first and second labelling moieties to change and, thus, the fluorescence intensity of the first labelling moiety and emission intensity of the second labelling moiety to change. In some embodiments, the first and second labelling moieties may be closer to each other in the second conformation (i.e. upon analyte binding) compared to the first conformation (i.e. the spacing has decreased in the second conformation). In such embodiments, the fluorescence intensity of the first labelling moiety will decrease, and the emission intensity of the second labelling moiety will increase in the second conformation compared to the first conformation. In alternative embodiments, the first and second labelling moieties may be further from each other in the second conformation (i.e. upon analyte binding) compared to the first conformation (i.e. the spacing has increased in the second conformation). In such embodiments, the fluorescence intensity of the first labelling moiety will increase, and the emission intensity of the second labelling moiety will decrease in the second conformation compared to the first conformation.

In particular embodiments, both labelling moieties are preferably fluorescent labels, suitable examples of which are described supra. Exemplary combinations of which include cyan fluorescent protein and yellow fluorescent protein, Cy3 and Cy5, FAM and TAMRA, and the like. In alternative embodiments, the first labelling moiety (i.e. donor molecule) is a fluorescent label and the second labelling moiety (i.e. acceptor molecule) is a non-fluorescent moiety. Non-limiting examples of suitable non-fluorescent moieties include 4-([4-(dimethylamino)phenyl]-azo)-benzoic acid (DABCYL), Iowa black RQ, 4-(4-dimethylaminophenylazo)benzenesulfonic acid (DABSYL), Iowa black FQ, IRDye QC-1, QXL quenchers, black hole quenchers including BHQ-1, BHQ-2 and BHQ-3, and the like, including the moieties described in Le Reste et al. (2012) *Biophysical Journal*, 11(6): 2658-2668, and Crisalli and Kool (2011) *Bioconj Chem*, 22(11): 2345-2354), the entire contents of which are incorporated herein by reference.

The first and second labelling moieties may be attached at any point on the aptamer, wherein the spacing between the first and second labelling moieties is different in the first and second aptamer conformations. In some embodiments, the spacing between the first and second labelling moiety is less than or equal to 10 nm in the first conformation and greater than 10 nm in the second conformation. In other embodiments, the spacing between the first and second labelling moiety is greater than 10 nm in the first conformation and less than or equal to 10 nm in the second conformation. For example, the first and second labelling moieties may be attached at or towards each end of the aptamer, e.g. at or towards 3' and 5' ends. In some embodiments, the first labelling moiety is attached at the 3' end, and the second labelling moiety is attached at the 5' end or, alternatively, the first labelling moiety is attached at the 5' end and the second labelling moiety is attached at the 3' end.

The invention also contemplates embodiments wherein the acceptor molecule is the material from which the microstructure is formed, or a coating on the microstructure, such as graphene, graphene oxide, and the like.

In preferred embodiments, the aptamer is a coating on the microstructure (also referred to herein as an aptamer coating). The number of aptamers and/or aptamer density in the coating will depend on the analyte of interest (including analyte size and expected levels or concentration to be detected), application of the system of the invention and detection method. The aptamer density in the coating should be a density which results in a measurable response upon analyte binding, such as a change in impedance or fluorescence, especially upon analyte binding at analyte concentrations or levels of interest. In some embodiments, the aptamer density in the coating is in the range of from about $1\times10^{10}$ to about $1\times10^{14}$ aptamer molecules/cm$^2$, about $5\times10^{10}$ to about $5\times10^{13}$ aptamer molecules/cm$^2$, about $1\times10^{11}$ to about $1\times10^{13}$ aptamer molecules/cm$^2$, about $5\times10^{11}$ to about $5\times10^{12}$ aptamer molecules/cm$^2$ (and all integers therebetween).

When applied as a coating on the microstructure, the aptamer may be coated using any suitable technique routine in the art, such as chemisorption, or chemical cross-linking. For example, the technique may include contacting the surface of the microstructure with the aptamer for a time period sufficient for a moiety for attaching or immobilising the aptamer on the surface of the microstructure to attach to the surface of the microstructure, such as via a covalent bond. Suitable, non-limiting methods may include chemisorption of thiolated aptamers on a gold microstructure; attachment of biotinylated aptamer to avidin-modified microstructure; immobilisation of an azide-ended aptamer to alkyne-modified microstructure; covalent immobilisation of amine-ended aptamer by amine coupling to carboxyl groups in functionalised microstructure; covalent immobilization of amine-ended aptamer to functionalized microstructure containing amine groups using glutaraldehyde, and the like. Exemplary methods are described in Xiao et al. (2007) *Nat Protocols*, 2(11): 2875-2880; Negahdary et al. (2018) *J Biomed Phys Eng*, 8(2): 167-178; and Mishra et al. (2018) *Biosensors*, 8(2): 28. The aptamer may be attached to the microstructure through any suitable point of the aptamer, especially 3' or 5' end, most especially the 5' end of the aptamer.

In other embodiments the material is a molecularly imprinted polymer.

The identity of the molecularly imprinted polymer will depend on the specific analyte of interest and the method of detection. A skilled person will readily be able to identify and use suitable molecularly imprinted polymers for each analyte of interest. For example, suitable molecularly imprinted polymers include those formed from monomers comprising one or more functional groups for binding or interacting with the analyte of interest, such as an amine, sulfide, sulfhydryl, amide, carbonyl or carboxyl group. In some embodiments, the molecularly imprinted polymer is formed from one or more monomers comprising one or more amine and/or carboxyl groups.

For example, suitable monomers include, but are not limited to, aminothiophenol (including p-aminothiophenol and o-aminothiophenol), methacrylic acid, vinyl pyridine, acrylamide, aminophenol (including o-aminophenol and p-aminophenol), 1,2-dimethylimidazole, dimetridazole, o-phenylenediamine, 4-amino-5-hydroxy-2,7-naphthalene-disulfonic acid, pyrrole, aminobenzenethiol-co-p-aminobenzoic acid, vinylpyrrolidone, vinylferrocene, bis(2,2'-bithien-5-yl) methane, pyridine, chitosan, 3,4-ethylenedioxythiophene, 1-mercapto-1-undecanol, dopamine, a methacrylate such as methylmethacrylate and dimethylmethacrylate, carboxylated pyrrole, aniline, thiophene acetic acid (e.g. 3-thiophene acetic acid) and thiophene.

The molecularly imprinted polymer may be a conductive polymer (e.g. a polymer with conjugated pi bonds along the polymer backbone) or insulating polymer.

Where the molecularly imprinted polymer is an insulating polymer, the polymer is a coating on the microstructure. Suitable insulating polymers include, but are not limited to, poly-o-phenylenediamine, poly-o-aminophenol, a polymethacrylate such as polymethylmethacrylate and polydimethylmethacrylate, polyacrylamide, non-conductive polypyrrole, polypyridine, polyvinylpyrrolidone, poly-p-aminothiophenol and polydopamine; especially non-conductive polypyrrole.

In some embodiments, the insulating polymer may be a copolymer. Thus, the polymer may be a polymer or copolymer formed from one or more monomers selected from the group consisting of pyrrole, dopamine, a methacrylate such as methylmethacrylate and dimethylmethacrylate, methacrylic acid, acrylamide, carboxylated pyrrole, o-aminophenol, phenol, p-aminothiophenol (including p-aminothiophenol and o-aminothiophenol), pyridine, vinylpyrrolidone and o-phenylenediamine. In some embodiments, the insulating polymer is a copolymer formed from a methacrylate such as methylmethacrylate or dimethylmethacrylate, and acrylamide, especially methylmethacrylate and acrylamide; or pyrrole and carboxylated pyrrole.

Where the molecularly imprinted polymer is a conductive polymer, the polymer may be a coating on the microstructure or may be the material forming the microstructure. Without wishing to be bound by theory, in some embodiments, the conductive polymer is thought to undergo a structural change upon analyte binding, leading to the polymer becoming more structurally strained. Said structural change results in a decrease in conductivity of the polymer, which can be quantified and correlated to analyte presence, absence, level or concentration. In other embodiments, analyte binding to the conductive polymer is proposed to cause a change in impedance, which can be quantified and correlated to analyte presence, absence, level or concentration.

In some embodiments, the molecularly imprinted polymer is a conductive polymer and is the material forming the microstructure. In such embodiments, the microstructure is preferably porous.

Suitable conductive polymers include, but are not limited to, polypyrrole, polyaniline, poly(3,4-ethylenedioxythiophene) and polythiophene; especially polypyrrole.

In some embodiments, the conductive polymer may be a copolymer. Thus, the polymer may be a polymer or copolymer formed from one or more monomers selected from the group consisting of pyrrole, carboxylated pyrrole, aniline, 3,4-ethylenedioxythiophene, thiophene acetic acid (e.g. 3-thiophene acetic acid) and thiophene. In some embodiments, the conductive polymer is a copolymer formed from 3,4-ethylenedioxythiophene and thiophene acetic acid, or pyrrole and carboxylated pyrrole.

While the molecularly imprinted polymer may be the sole component of the coating or forming the microstructure, in some embodiments, the polymer comprises a dopant, for example, to increase the conductivity of the polymer. Suitable dopants include, but are not limited to, sodium nitrate ($NaNO_3$), lithium perchlorate ($LiClO_4$), p-toluene sulfonate, chondroitin sulfate, dodecylbenzene sulfonate and tetrabutylammonium hexafluorophosphate (TBAPF6), preferably lithium perchlorate and dodecylbenzene sulfonate.

In some embodiments, conductivity of the polymer may be increased by varying the solvent of the polymerising solution (i.e. varying the solvent during polymerisation). Suitable solvents include, but are not limited to, water, phosphate buffered saline, acetate buffer, acetonitrile and dichlormethane; especially acetonitrile or dichloromethane.

In particular embodiments, the polymer is a conductive polypyrrole molecularly imprinted polymer, doped with $LiClO_4$, which is selective for troponin I binding.

The molecularly imprinted polymer is formed using the one or more analytes of interest or a fragment or subunit thereof as a template as discussed herein and, thus, is selective for binding the one or more analytes of interest. The molecularly imprinted polymer is preferably selective for binding the one or more analytes of interest, such as troponin or a subunit thereof, especially troponin I, over at least one other substances present in the sample, preferably the majority of other substances present in the sample.

In some embodiments, the polymer further comprises a redox moiety, particularly when the molecularly imprinted polymer is an insulating polymer. Suitable redox moieties include, but are not limited to, methylene blue, vinylferrocene and horseradish peroxidase. A skilled person will be well aware of suitable methods for incorporating a redox moiety into a polymer. For example, the redox moiety may be attached to the monomer prior to polymerisation or may be copolymerised with the monomers.

The analyte may be any compound able to be detected in the epidermis and/or dermis. In particular embodiments, the analyte is a marker of a condition, disease, disorder or a normal or pathologic process that occurs in a subject, or a compound which can be used to monitor levels of an administered substance in the subject, such as a medicament (e.g., drug, vaccine), an illicit substance (e.g. illicit drug), a non-illicit substance of abuse (e.g. alcohol or prescription drug taken for non-medical reasons), a poison or toxin, a chemical warfare agent (e.g. nerve agent, and the like) or a metabolite thereof. Suitable analytes include, but are not limited to a:

a) nucleic acid, including DNA and RNA, including short RNA species including microRNA, siRNA, snRNA, shRNA and the like;

b) antibody, or antigen-binding fragment thereof, allergen, antigen or adjuvant;

c) chemokine or cytokine;

d) hormone;

e) parasite, bacteria, virus, or virus-like particle, or a compound therefrom, such as a surface protein, an endotoxin, and the like;

f) epigenetic marker, such as the methylation state of DNA, or a chromatin modification of a specific gene/region;

g) peptide;

h) polysaccharide (glycan);

i) polypeptide;

j) protein; and k) small molecule.

In particular embodiments, the analyte of interest is selected from the group consisting of a nucleic acid, antibody, peptide, polypeptide, protein and small molecule; especially a polypeptide and protein; most especially a protein.

The analyte may be a biomarker, which is a biochemical feature or facet that can be used to measure the progress of a disease, disorder or condition or the effects of treatment of a disease, disorder or condition. The biomarker may be, for example, a virus or a compound therefrom, a bacterium or a compound therefrom, a parasite or a compound therefrom, a cancer antigen, a cardiac disease indicator, a stroke indicator, an Alzheimer's disease indicator, an antibody, a mental health indicator, and the like.

Alternatively, the analyte may be a compound which can be used to monitor levels of an administered or ingested substance in the subject, such as a medicament (e.g., drug, vaccine), an illicit substance (e.g. illicit drug), a non-illicit substance of abuse (e.g. alcohol or prescription drug taken for non-medical reasons), a poison or toxin, a chemical warfare agent (e.g. nerve agent, and the like) or a metabolite thereof.

In some embodiments, the analyte is a protein selected from the group consisting of troponin or a subunit thereof, an enzyme (e.g. amylase, creatinine kinase, lactate dehydrogenase, angiotensin II converting enzyme), a hormone (e.g. follicle-stimulating hormone or luteinising hormone), cystatin C, C-reactive protein, TNFα, IL-6, ICAM1, TLR2, TLR4, presepsin, D-dimer, a viral protein (e.g. non-structural protein 1 (NS1)), a bacterial protein, a parasitic protein (e.g. histone rich protein 2 (HRP2)), an antibody (e.g. an antibody produced in response to an infection, such as a bacterial or viral infection including an influenza infection) and botulinum toxin or a metabolite or subunit thereof; especially troponin or a subunit thereof, amylase, creatinine kinase, lactate dehydrogenase, angiotensin II converting enzyme, follicle-stimulating hormone, luteinising hormone, cystatin C, C-reactive protein, TNFα, IL-6, ICAM1, TLR2, TLR4, presepsin, D-dimer, botulinum toxin or a metabolite or subunit thereof. In particular embodiments, the analyte is troponin or a subunit thereof; especially troponin I, troponin C or troponin T; most especially troponin I.

The analyte may be a small molecule, non-limiting examples of which include a hormone (e.g. cortisol or testosterone), neurotransmitter (e.g. dopamine), amino acid, creatinine, an aminoglycoside (e.g. kanamycin, gentamicin and streptomycin), an anticonvulsant (e.g. carbamazepine and clonazepam), an illicit substance (e.g. methamphetamine, amphetamine, 3,4-methylenedioxymethamphetamine (MDMA), N-ethyl-3,4-methylenedioxyamphetamine (MDEA), 3,4-methylenedioxy-amphetamine (MDA), cannabinoids (e.g. delta-9-tetrahydrocannabinol, 11-hydroxy-delta-9-tetrahydrocannabinol, 11-nor-9-carboxydelta-9-tetrahydrocannabinol), cocaine, benzoylecgonine, ecgonine methyl ester, cocaethylene, ketamine, and the opiates (e.g. heroin, 6-monoacetylmorphine, morphine, codeine, methadone and dihydrocodeine), an anticoagulant (e.g. warfarin), a chemical warfare agent, poison or toxin such as blister agents (e.g. cantharidin, furanocoumarin, sulfur mustards (e.g. 1,2-bis(2-chloroethylthio) ethane, 1,3-bis(2-chloroethylthio)-n-propane, 1,4-bis(2-chloroethylthio)-n-butane, 1,5-bis(2-chloroethylthio)-n-pentane, 2-chloroethylchloromethylsulfide, bis(2-chloroethyl) sulfide, bis(2-chloroethylthio) methane, bis(2-chloroethylthiomethyl) ether, bis(2-chloroethylthioethyl) ether), nitrogen mustards (e.g. bis(2-chloroethyl)ethylamine, bis(2-chloroethyl)methylamine and tris(2-chloroethyl)amine) and phosgene oxime), arsenicals (e.g. ethyldichloroarsine, methyldichloroarsine, phenyldichloroarsine and 2-chlorovinyldichloroarsine) and urticants e.g. phosgene oxime), blood agents (e.g. cyanogen chloride, hydrogen cyanide and arsine), choking agents (e.g. chlorine, chloropicrin, diphosgene and phosgene), nerve agents (e.g. tabun, sarin, soman, cyclosarin, novichok agents, 2-(dimethylamino)ethyl-N,N-dimethylphosphoramidofluoridate (GV), (S)-(ethyl {[2-(diethylamino)ethyl]sulfanyl}(ethyl) phosphinate) (VE), 0,0-diethyl-S-[2-(diethylamino)ethyl] phosphorothioate (VG), S-[2-(diethylamino)ethyl]-O-ethyl methylphosphonothioate (VM), ethyl({2-[bis(propan-2-yl) amino]ethyl}sulfanyl)(methyl)phosphinate (VX), tetrodotoxin and saxitoxin), animal venom component (e.g. tetrodotoxin and saxitoxin), cyanide, arsenic, a tropane alkaloid (e.g. atropine, scopolamine and hyoscyamine), a piperidine alkaloid (e.g. coniine, N-methylconiine, conhydrine, pseudoconhydrine and gamma-coniceine), a curare alkaloid (e.g. tubocurarine), nicotine, caffeine, quinine, strychnine, brucine, aflatoxin), and the like or a metabolite thereof. In some embodiments the small molecule is selected from the group consisting of cortisol, testosterone, creatinine, dopamine, kanamycin, gentamicin, streptomycin, carbamazepine, clonazepam, methamphetamine, amphetamine, MDMA, MDEA, MDA, delta-9-tetrahydrocannabinol, 11-hydroxy-delta-9-tetrahydrocannabinol, 11-nor-9-carboxydelta-9-tetrahydrocannabinol, cocaine, benzoylecgonine, ecgonine methyl ester, cocaethylene, ketamine, heroin, 6-monoacetylmorphine, morphine, codeine, methadone, dihydrocodeine, warfarin, cantharidin, furanocoumarin, 1,2-bis(2-chloroethylthio) ethane, 1,3-bis(2-chloroethylthio)-n-propane, 1,4-bis(2-chloroethylthio)-n-butane, 1,5-bis(2-chloroethylthio)-n-pentane, 2-chloroethylchloromethylsulfide, bis(2-chloroethyl) sulfide, bis(2-chloroethylthio) methane, bis(2-chloroethylthiomethyl) ether, bis(2-chloroethylthioethyl) ether), bis(2-chloroethyl)ethylamine, bis(2-chloroethyl)methylamine and tris(2-chloroethyl)amine), phosgene oxime, ethyldichloroarsine, methyldichloroarsine, phenyldichloroarsine, 2-chlorovinyldichloroarsine, phosgene oxime, cyanogen chloride, hydrogen cyanide, arsine, chlorine, chloropicrin, diphosgene, phosgene, tabun, sarin, soman, cyclosarin, novichok agents, 2-(dimethylamino) ethyl-N,N-dimethylphosphoramidofluoridate (GV), (S)-(ethyl {[2-(diethylamino)ethyl]sulfanyl}(ethyl)phosphinate) (VE), 0,0-diethyl-S-[2-(diethylamino)ethyl]phosphorothioate (VG), S-[2-(diethylamino)ethyl]-O-ethyl methylphosphonothioate (VM), ethyl({2-[bis(propan-2-yl) amino]ethyl}sulfanyl)(methyl)phosphinate (VX), tetrodotoxin, saxitoxin, cyanide, arsenic, atropine, scopolamine, hyoscyamine, coniine, N-methylconiine, conhydrine, pseudoconhydrine, gamma-coniceine, tubocurarine, nicotine, caffeine, quinine, strychnine, brucine, aflatoxin and metabolites thereof.

In some embodiments, the analyte is a peptide, non-limiting examples of which include a hormone (e.g. oxytocin, gonadotropin-releasing hormone and adrenocorticotropic hormone), B-type natriuretic peptide, N-terminal pro B-type natriuretic peptide (NT-proBNP) and an animal venom component (e.g. a peptidic component of spider, snake, scorpion, bee, wasp, ant, tick, conesnail, octopus, fish (e.g stonefish) and jellyfish venom) or a metabolite thereof. In particular embodiments, the peptide is oxytocin, gonadotropin-releasing hormone, adrenocorticotropic hormone, B-type natriuretic peptide or NT-proBNP.

In some embodiments, the analyte is a polysaccharide (glycan), suitable non-limiting examples of which include inulin, endotoxins (lipopolysaccharides), anticoagulants (e.g. heparin) and metabolites thereof.

In some embodiments, the analyte is an illicit substance or a non-illicit substance of abuse or a metabolite thereof. Suitable illicit substances include, but are not limited to, methamphetamine, amphetamine, 3,4-methylenedioxymethamphetamine (MDMA), N-ethyl-3,4-methylenedioxyamphetamine (MDEA), 3,4-methylenedioxy-amphetamine (MDA), cannabinoids (e.g. delta-9-tetrahydrocannabinol, 11-hydroxy-delta-9-tetrahydrocannabinol, 11-nor-9-carboxydelta-9-tetrahydrocannabinol), cocaine, benzoylecgonine, ecgonine methyl ester, cocaethylene, ketamine, and the opiates (e.g. heroin, 6-monoacetylmorphine, morphine, codeine, methadone and dihydrocodeine), or metabolites thereof. Non-limiting non-illicit substances of abuse include alcohol, nicotine, prescription medicine or over the counter medicine taken for non-medical reasons, a substance taken for a medical effect, wherein the consumption has become excessive or inappropriate (e.g. pain medications such as opiates, sleep aids, anti-anxiety medication, methylphenidate, erectile-dysfunction medications), and the like, or metabolites thereof.

In some embodiments, the analyte is a medicament or a component or metabolite thereof. A wide variety of medicaments are suitable analytes, including; but not limited to, cancer therapies, vaccines, analgesics, antipsychotics, antibiotics, anticoagulants, antidepressants, antivirals, sedatives, antidiabetics, contraceptives, immunosuppressants, antifungals, antihelmintics, stimulants, biological response modifiers, non-steroidal anti-inflammatory drugs (NSAIDs), corticosteroids, disease-modifying anti-rheumatic drugs (DMARDs), anabolic steroids, antacids, antiarrhythmics, thrombolytics, anticonvulsants, antidiarrheals, antiemetics, antihistamines, antihypertensives, anti-inflammatoires, antineoplastics, antipyretics, barbiturates, β-blockers, bronchodilators, cough suppressants, cytotoxics, decongestants, diuretics, expectorants, hormones, laxatives, muscle relaxants, vasodilators, sedatives, vitamins, and metabolites thereof. Various examples of these medicaments are described herein and are well known in the art.

In some embodiments, the analyte is a poison, toxin, chemical warfare agent, or metabolite thereof. Suitable poisons, toxins and chemical warfare agents include, but are not limited to, including blister agents (e.g. cantharidin, furanocoumarin, sulfur mustards (e.g. 1,2-bis(2-chloroethylthio) ethane, 1,3-bis(2-chloroethylthio)-n-propane, 1,4-bis(2-chloroethylthio)-n-butane, 1,5-bis(2-chloroethylthio)-n-pentane, 2-chloroethylchloromethylsulfide, bis(2-chloroethyl) sulfide, bis(2-chloroethylthio) methane, bis(2- chloroethylthiomethyl) ether, bis(2-chloroethylthioethyl) ether), nitrogen mustards (e.g. bis(2-chloroethyl)ethylamine, bis(2-chloroethyl)methylamine and tris(2-chloroethyl) amine) and phosgene oxime), arsenicals (e.g. ethyldichloroarsine, methyldichloroarsine, phenyldichloroarsine and 2-chlorovinyldichloroarsine) and urticants e.g. phosgene oxime), blood agents (e.g. cyanogen chloride, hydrogen cyanide and arsine), choking agents (e.g. chlorine, chloropicrin, diphosgene and phosgene), nerve agents (e.g. tabun, sarin, soman, cyclosarin, novichok agents, 2-(dimethyl-amino)ethyl-N,N-(GV), dimethylphosphoramidofluoridate (S)-(ethyl {[2-(diethylamino)ethyl]sulfanyl}(ethyl)phosphinate) 0,0-diethyl-S-[2-(VE), (diethylamino)ethyl] phosphorothioate (VG), S-[2-(diethylamino)ethyl]-O-ethyl methylphosphonothioate (VM), ethyl({2-[bis(propan-2-yl) amino]ethyl}sulfanyl)(methyl)phosphinate (VX), tetrodotoxin, saxitoxin and botulinum toxin), animal venom component (e.g. tetrodotoxin, saxitoxin or other component of spider, snake, scorpion, bee, wasp, ant, tick, conesnail, octopus, fish (e.g stonefish) and jellyfish venom), cyanide, arsenic, a component of *Atropa Belladonna* (deadly nightshade) such as a tropane alkaloid (e.g. atropine, scopolamine and hyoscyamine), a component of hemlock such as a piperidine alkaloid (e.g. coniine, N-methylconiine, conhydrine, pseudoconhydrine and gamma-coniceine), a curare alkaloid (e.g. tubocurarine), nicotine, caffeine, alcohol, quinine, atropine, strychnine, brucine, aflatoxin and metabolites thereof. In some embodiments, the analyte is a chemical warfare agent such as a blister agent (e.g. cantharidin, furanocoumarin, a sulfur mustard (e.g. 1,2-bis(2-chloroethylthio) ethane, 1,3-bis(2-chloroethylthio)-n-propane, 1,4-bis(2-chloroethylthio)-n-butane, 1,5-bis(2-chloroethylthio)-n-pentane, 2-chloroethylchloromethylsulfide, bis(2-chloroethyl) sulfide, bis(2-chloroethylthio) methane, bis(2-chloroethylthiomethyl) ether or bis(2-chloroethylthioethyl) ether), a nitrogen mustard (e.g. bis(2-chloroethyl)ethylamine, bis(2-chloroethyl)methylamine or tris(2-chloroethyl) amine) or phosgene oxime), an arsenical (e.g. ethyldichloroarsine, methyldichloroarsine, phenyldichloroarsine or 2-chlorovinyldichloroarsine) or an urticant e.g. phosgene oxime), a blood agent (e.g. cyanogen chloride, hydrogen cyanide or arsine), a choking agent (e.g. chlorine, chloropicrin, diphosgene or phosgene), a nerve agent (e.g. tabun, sarin, soman, cyclosarin, a novichok agent, 2-(dimethyl-amino)ethyl-N,N-dimethylphosphoramidofluoridate (GV), (S)-(ethyl {[2-(diethylamino)ethyl]sulfanyl}(ethyl)phosphinate) (VE), 0,0-diethyl-S-[2-(diethylamino)ethyl]phosphorothioate (VG), S-[2-(diethylamino)ethyl]-O-ethyl methylphosphonothioate (VM), ethyl({2-[bis(propan-2-yl) amino]ethyl}sulfanyl)(methyl)phosphinate (VX), tetrodotoxin, saxitoxin or botulinum toxin) or a metabolite thereof.

Examples of suitable analytes, diseases, disorders or conditions, or applications for which they are relevant and known lowest clinically relevant serum concentration ranges are provided in Table 1.

TABLE 1

| Analyte | Relevant disease, disorder or condition, or application | Lowest clinically relevant concentration (where available) | Molecular weight |
|---|---|---|---|
| Troponin or a subunit thereof, such as troponin I, troponin C or troponin T | Cardiac damage, myocardial infarction, acute coronary syndrome | Less than 30 ng/L | 23 kDa, 18 kDa and 34 kDa, respectively for I, C and T subunits |
| Cortisol (serum) | Addison's disease, Cushing's disease, | Less than 650 nmol/L | 362 Da |

TABLE 1-continued

| Analyte | Relevant disease, disorder or condition, or application | Lowest clinically relevant concentration (where available) | Molecular weight |
|---|---|---|---|
| | adrenal and/or pituitary gland function, psychological stress (wellness applications) | | |
| Creatinine | Renal failure, creatinine clearance estimates | Less than 100 μmol/L | 113 Da |
| Dopamine | Parkinson's disease, brain cancers, depression | 0-30 pg/mL | 153 Da |
| Aminoglycosides (e.g. kanamycin, gentamicin, streptomycin) | Monitor dose of therapeutic for bacterial infection | 5-10 mg/L | Varied ~300-600 Da |
| Anticonvulsants (e.g. carbamazepine and clonazepam) | Monitor dose of therapeutic for epilepsy | 0.02-12 mg/L | Varied ~100 Da |
| Hormones such as follicle stimulating hormone, luteinising hormone, oxytocin, gonadotropin-releasing hormone and testosterone | Assisted fertility, calcium levels, substance abuse (doping) | Varied | Varied ~200-300 Da |
| Amylase | Pancreatitis, bile duct obstruction | Less than 100 U/L | 50 kDa |
| Creatinine kinase | Skeletal muscle damage, which may be indicative of rhabdomyolysis, injury and/or drug side-effects (statins) | Less than 200 U/L | 80 kDa |
| Lactate dehydrogenase | Hepatic damage | 119-229 U/L | 140 kDa |
| B-type natriuretic peptide (BNP) | Cardiac failure | 100 ng/L | 36 kDa (high molecular weight form) or 3.5 kDa low molecular weight form) |
| NT-proBNP | Cardiac failure | 300 ng/L | 8.5 kDa |
| Angiotensin II converting enzyme | Essential hypertension | 8-100 U/L | 60-170 kDa |
| Cystatin C | Renal failure | 0.6-1 mg/L | 13 kDa |
| Stress hormones e.g. adrenocorticotropic hormone (ACTH) | Adrenal insufficiency or overactivity | 2-11 pmol/L | ~4 kDa |
| Inflammatory markers (e.g. C-reactive protein (CRP), TNFα, IL-6, ICAM1, TLR2, TLR4, presepsin) | Bacterial or viral infection, autoimmune disorders, rheumatological disorders, sepsis | Less than 10 mg/L (CRP) | Varied 120 kDa (CRP) |
| Inulin | Renal failure, creatinine clearance estimates | Varied (dependent on amount administered) | Varied |
| Illicit substances (e.g. methamphetamine, amphetamine, 3,4-methylenedioxymethamphetamine (MDMA), N-ethyl-3,4-methylenedioxyamphetamine (MDEA), 3,4-methylenedioxy-amphetamine (MDA), cannabinoids (e.g. delta-9-tetrahydrocannabinol, 11-hydroxy-delta-9-tetrahydrocannabinol, 11-nor-9-carboxydelta-9-tetrahydrocannabinol), cocaine, benzoylecgonine, ecgonine methyl ester, cocaethylene, ketamine, and the opiates (e.g. heroin, 6-monoacetylmorphine, morphine, codeine, methadone and dihydrocodeine)) | Drug abuse, compliance monitoring, rehabilitation, screening | Varied (dependent on application e.g. rehabilitation compared with screening or drug abuse, and identity of substance) | Varied ~200-300 Da |
| Anticoagulants (e.g. warfarin and heparin) | Monitor dose of therapeutic for blood clotting disorders and diseases | Varied | Varied |
| Glycoproteins and glycans | Bacterial infection (i.e. bacterial endotoxins) | Varied | Varied ~10-20 kDa |
| Cellular components and breakdown products | Bacterial infection, exosome detection, cancer, platelet detection | Varied | Varied |
| D-dimer | Pulmonary embolism | 0.4 mg/mL | 180 kDa |
| Oligonucleotides and polynucleotides (e.g. DNA, RNA and fragments thereof) | Bacterial infection, viral infection, circulating tumour cell breakdown, solid tissue cancers | Varied | Varied ~200-300 Da |
| Chemical warfare agents (e.g. blister agents, blood agents, choking agents and nerve agents) | Chemical warfare, environmental contamination | Varied | Varied |

53

In some embodiments, the analyte is a metabolite of any one of the above exemplary analytes.

While the analyte preferably binds directly to the binding agent, the invention also contemplates detecting agents probative of the analyte of interest such as a specific binding pair member complementary to the analyte of interest, whose presence will be detected only when a particular analyte of interest is present in a sample. Thus, the agent probative of the analyte becomes the analyte that is detected.

In some embodiments, the microstructures are coated with a material that reduces absorption of analytes that are not of interest. Example materials include alkyl groups coated with BSA (bovine serum albumin), bifunctional polyethylene glycol (PEG) polymers, or the like. Such materials have the effect of reducing adsorption of non-specific analytes, which are effectively repelled from the microstructures.

It will be appreciated that multiple coatings could be used in conjunction, for example, to repel or exclude non-specific analytes and bind analytes of interest, thereby allowing specific analytes of interest to be selectively captured, whilst non-specific analytes remain uncaptured.

A polymer coating, including a molecularly imprinted polymer coating, may be applied using a variety of techniques routinely used in the art. For example, the microstructures can be coated with a polymer using a variety of techniques, including dip coating, spray coating, deposition coating, electropolymerisation, drop casting, electrospinning, ink jet coating, spin coating, or the like; especially electropolymerisation. In one example, a coating solution is applied to the microstructures and allowed to dry in situ, optionally using a gas jet. Where the coating is a polymer coating, the polymer may, in some embodiments, be synthesised prior to coating using, for example, bulk polymerisation. In alternative embodiments, the polymer is synthesised and coated simultaneously, such as when synthesising and coating using electropolymerisation. A skilled person will be well aware of suitable techniques.

Molecularly imprinted polymers may be prepared using a variety of techniques, non-limiting examples of which include bulk polymerisation and electropolymerisation in the presence of a template (i.e. the one or more analytes of interest or a fragment or subunit thereof); especially electropolymerisation.

For example, a molecularly imprinted polymer may be prepared by (a) preparing a polymerisation solution comprising one or more monomers of interest and a solvent (e.g. phosphate-buffered saline); (b) adding one or more template compounds (e.g. one or more analytes of interest or a fragment or subunit thereof) to the prepared polymerisation solution; (c) polymerising the template/polymerisation solution to form a molecularly imprinted polymer, optionally in the presence of one or more additives (e.g. dopant, redox moiety etc.); and (d) separating the molecularly imprinted polymer from the one or more template compounds. Molecularly imprinted polymer properties may be optimised using techniques routine in the art, such as varying the concentration of the one or more monomers and/or template compounds.

The polymer may be coated in any form suitable for detecting the one or more analytes of interest, such as a film, particle, fibre or nanotube; especially a film.

The coating may be of a suitable thickness for determining analyte presence, absence, level or concentration, such as, but not limited to, 1 nm to 100 nm; especially 10 nm to 20 nm, most especially about 15 nm.

While the polymer coating may be the only coating applied to the electrode, in some embodiments it may be desirable to increase the binding (adhesion) of the polymer coating to the electrode. Accordingly, in such embodiments, an agent which increases binding of the polymer coating to the electrode may be applied prior to adding the coating. Suitable agents include, but are not limited to, organosilanes, silicones, siloxanes, amide and amine containing compounds, organophosphorus compounds, self-assembled monolayers or other coupling agents.

To optimise coating, properties of the coating can be controlled through the addition of one or more other agents such as a viscosity enhancer, a detergent or other surfactant, and an adjuvant. These ingredients can be provided in a range of different concentrations. For example, the viscosity enhancer or surfactant can form between 0% and 90% of the coating solution.

A range of different viscosity enhancers can be used and examples include methylcellulose, carboxymethylcellulose (CMC), gelatin, agar, and agarose and any other viscosity modifying agents. The solution typically has a viscosity of between 10-3 Pa's and 10-1 Pa·s. In one example, using a coating solution containing 1-2% methylcellulose, which results in suitable uniform coatings, resulting in a viscosity within the range 0.011 (1%)-0.055 (2%) Pa·s.

Similarly, a range of different surfactants can be used to modify the surface tension of the coating solution, such as any detergent or any suitable agent that decreases surface tension, and that is biocompatible at a low concentration. The solution properties are also typically controlled through the addition of one or more other agents such as a viscosity enhancer, a detergent, other surfactant, or anything other suitable material. These ingredients can be provided in a range of different concentrations. For example, the viscosity enhancer or surfactant can form between 0% and 90% of the coating solution.

As an alternative to using a coating technique, reagents can alternatively be embedded within the microstructures. Thus, for example, in the case of moulded patches manufactured using a polymer material, the reagent can be introduced into the mould together with the polymer material so that the reagent is distributed throughout the structures. In this example, the polymer can be arranged so that pores form within the structures during the curing process.

Using affinity surface coatings on each structure also allows a reduction of non-specific adsorption of ISF and/or blood components whilst facilitating specific extraction of the molecular targets of interest.

Thus, in one example, the one or more microstructures interact with one or more analytes of interest such that a response signal is dependent on a presence, absence, level or concentration of analytes of interest. In one particular example, the analytes interact with a coating on the microstructures to change electrical and/or optical properties of the coating, thereby allowing the analytes to be detected.

For example, measurements can be performed by passing a current between electrodes, with measurements of the resulting signal between the electrodes being used to detect changes in the electrical properties and hence, the presence, absence, level or concentration of analytes. In this regard, the electrical output signal can be indicative of any one or more of a voltage, a current, a resistance, a capacitance, a conductance, or an impedance, or a change in any of these variables. Thus, signals could be potentiometic, amperometric, voltametric, impedimetric, or the like.

For example, measurements can be performed by passing a current between electrodes, with measurements of the resulting signal between the electrodes being used to detect changes in the electrical properties and hence, the presence, absence, level or concentration of analytes. In this regard, the electrical output signal can be indicative of any one or more of a voltage, a current, a resistance, a capacitance, a conductance, or an impedance, or a change in any of these variables. Thus, signals could be potentiometric, amperometric, voltametric, impedimetric, or the like.

For example, impedance measurements, such as in electrochemical impedance spectroscopy (EIS), investigate the dynamics of the bound analyte or the charge transfer in the bulk or the interfacial region of the MIP and/or aptamer. In this regard, when an MIP (especially a conductive MIP) captures a target analyte, the MIP cavities are filled, hindering the diffusion of ions in the bulk polymer. In addition, captured analyte can strain the structure of the conductive MIP causing increase in the charge transfer in the polymer. Similarly when an aptamer captures a target analyte, the captured analyte can change the structure of the aptamer changing the electrical properties. The measurement only requires ions in the samples and can be done without a redox moiety.

In this example, the electrodes can be arranged in pairs, although alternatively the system could measure impedances between different groups of electrodes, for example with one group acting as a working electrode and the other group working as a counter electrode.

In a further example, voltametric/amperometric techniques can be used, including cyclic voltammetry (CV), liner sweep voltammetry (LSV), differential pulse voltammetry (DPV), square wave voltammetry (SWV), and chronoamperometry (CA).

In this example, a current output is generated from the redox reaction of the electroactive species (redox moiety) which takes place on the conductive material (e.g gold microstructures). When analyte of interest is captured in the MIP (especially insulating MIP coating), the MIP cavities are filled thereby blocking/hindering the diffusion of the redox moieties towards the gold surface. Decrease in the penetration of the analyte in the results to decrease in the current output. Similarly, when an analyte of interest is captured in the aptamer, the structure of the aptamer changes resulting in the redox moieties moving relative to the microstructure surface, thereby altering the current output.

Since redox a reaction is required in this type of transduction, some researchers incorporate a redox moiety in the polymeric matrix.

In this example, reference electrodes might also be provided, in which case electrodes might be arranged in three groups, including working, counter and reference electrodes. The reference electrodes need only be in the vicinity of the working and counter electrodes, so that, for example, electrodes could be arranged in pairs of working and counter electrodes, with a row of pairs of electrodes being used as reference electrodes.

In a further example potentiometric measurements can be performed in which an electrical output is generated in response to binding of target analyte in the MIP and/or aptamer. Here the change in the voltage corresponding to the amount of analyte bound in the MIP and/or aptamer is measured. Potentiometric techniques can be found in sensor like ion selective electrodes (ISE) and field-effect transistors (FET).

Other measurement techniques include mass sensitive acoustic transducers such as surface-acoustic wave (SAW) oscillator, Love-wave oscillator, or quartz crystal microbalance. (QCM). In binding of analyte could be quantified via the change in the oscillation frequency resulting from the mass change at the oscillator surface.

In one example, at least some of the microstructures attract at least one substance to the microstructures and/or repel or exclude at least one substance from the microstructures. The nature of the substance will vary depending on the preferred implementation and may include one or more analytes, or may include other substances containing analytes, such as ISF, blood or the like. This can be used to attract, repel or exclude analytes, for example attracting analytes of interest, allowing these to be concentrated and/or sensed, or repelling or excluding analytes that are not of interest.

The ability to repel or exclude substances can also assist with preventing biofouling. For example, the microstructures could contain a material, or include a coating, such as polyethylene glycol (PEG), which generally repels substances from the surface of the microstructure. Reduction in biofouling could also be achieved based on a choice of microstructure material or structure of the microstructure e.g. coating the binding agent in the pores hydrogel coating such as a poly(hydroxyethyl methacrylate) or PEG coating; an isoporous silica micelle membrane; a protein membrane, such as a fibroin membrane; a polysaccharide membrane, such as a cellulose membrane or a chitosan membrane; or a diol or silane membrane; releasable coatings that interfere with biofouling material; and/or porous coatings. In particular embodiments, the microstructure is porous, and the binding agent is coated in the pores of the microstructure.

In another example, biofouling can be accounted for using a control. For example, a patch could include functionalised microstructures for analyte detection as well as un-, functionalised microstructures that act as a control. Assuming both sets of microstructures are subject to similar levels of biofouling, changes in response signals measured via the un-functionalised microstructures can be used to quantify a degree of biofouling that has occurred. This can then be accounted for when processing signals from the functionalised microstructures, for example by removing any change in response signals arising from the biofouling.

In one example, the system includes an actuator configured to apply force to the substrate, which in one example is used to help the microstructures to breach the barrier. The actuator could additionally and/or alternatively be used for other purposes.

For example, movement of the microstructures could be used to sense tissue mechanical properties. For example, a response of the actuator, such as an amount of current required to induce movement of the microstructures, could be used to sense mechanical properties, such as a degree of elasticity, or the like, which can in turn be indicative of health issues, such as diseases or similar. This could also be used in conjunction with mechanical response signals, for example measuring a stress or strain on the microstructures using a suitable sensing modality, allowing the transmission of actuator movements to be monitored. Other external mechanical stimulus could also be used, such providing a ring or other structure around the patch, which generates pressure waves within the tissue, allowing the responses to be measured.

The actuator can be used to provide mechanical stimulation, for example to trigger a biological response, such as inflammation, or to attract or repel or exclude substances.

Additionally, physical movement can be used to release material from a coating on at least some microstructures, or could be used to disrupt, dissolve, dislodge or otherwise release a coating on at least some microstructures. This can be used to trigger a measurement process, for example, releasing a coating or material to trigger a reaction with analytes, allowing the analytes to be detected. It will be appreciated that the actuator can therefore also act as the treatment delivery mechanism, allowing a coating to be disrupted and a treatment material released.

The actuator can also be used to cause the microstructures to penetrate the barrier, or retract the microstructures from the barrier and/or the subject. In one example, this allows the microstructures to be inserted and removed from the subject as needed, so that microstructures can be removed when measurements are not being performed. This can be used to comfort, to reduce the chance of infection, reduce biofouling, or the like.

As the microstructures are provided in a low-density configuration, the force required is typically minimal, in which case this could be achieved utilising an actuator that provides a small force, such as piezoelectric actuator, or a mechanical actuator, such as an offset motor, vibratory motor, or the like. Other actuators could however be used, including any one or more of an electric actuator, a magnetic actuator, a polymeric actuator, a fabric or woven actuator, a pneumatic actuator, a thermal actuator, a hydraulic actuator, a chemical actuator, or the like. For example, a chemical or biochemical reaction, including exposure to air, light, water or other substance, could trigger exothermic release of energy, which can be used for to provide a mechanical impulse to urge the substrate and hence microstructures into the subject. It will also be appreciated that actuation could also be achieved manually, by applying a force to the patch, or by using a strap or similar to urge the patch against the subject.

In one specific example, this is achieved using a biasing force, for example provided by a spring or electromagnetic actuator, together with a vibratory, periodic or repeated force, which can assist with penetration, for example by agitating the microstructures to overcome the elasticity of the stratum corneum and/or reduce friction for penetrating the epidermis and/or dermis, as well as to reduce the force required to pierce a barrier. This reduces the overall force required to penetrate the stratum corneum. However, this is not essential and single continuous or instantaneous forces could be used.

The frequency of vibration used will vary depending upon the preferred implementation and potentially the type of skin to which the microstructures are applied, and could include any one or more of at least 0.01 Hz, 0.1 Hz, 1 Hz, at least 10 Hz, at least 50 Hz, at least 100 Hz, at least 1 kHz, at least 1 kHz, or at least 100 kHz and potentially up to several MHz. In one example, a varying frequency could be used. The frequency could vary depending on a wide range of factors, such as a time of application, and in particular the length of time for which the application process has been performed, the depth or degree of penetration, a degree of resistance to insertion, or the like. In one example, the system uses response signals measured via the microstructures in order to detect when the barrier has been breached, such as when the microstructures have penetrated the stratum corneum. Thus, the frequency could be continuously varied, either increasing or decreasing, until successful penetration is achieved, or depending on a depth of penetration, which can be detected using response signals, at which point the actuator can be deactivated. In another example, the frequency starts high and progressively reduces as the microstructures penetrate the barrier, and in particular the stratum corneum.

In another example, the magnitude of the applied force can also be controlled. The force used will vary depending on a range of factors, such as the structure of the patch, the manner in which the patch is applied, the location of application, the depth of penetration, or the like. For example, patches with large numbers of microstructures typically require an overall higher force in order to ensure penetration, although for minimal numbers of microstructures, such as 10 or so, a larger force may be required to account for damping or loss from the substrate/skin. Similarly, the force required to penetrate the stratum corneum, would typically be higher than that required to penetrate the buccal mucosa. In one example, the applied force could be any one or more of at least 0.1 µN, at least 1 µN, at least 5 µN, at least 10 µN, at least 20 µN, at least 50 µN, at least 100 µN, at least 500 µN, at least 1000 µN, at least 10 mN, or at least 100 mN, per microstructure and/or collectively. For example, if there are 1000 microstructures, the force could be 100 mN in total, or 100 mN per projection, leading to an overall 100 N force.

Again, the force could vary, either increasing or decreasing, depending on a time of application, a depth or degree of penetration, which could be determined based on response signals, for examining a change in measured impedance, or an insertion resistance, or the like. In one specific example, the force is progressively increased until a point of penetration, at which point the force decreases.

As mentioned above, the force could be applied as a single continuous or instantaneous force. However, more typically the force is periodic. In this instance the nature of the periodic motion could vary, this could for example, have any waveform, including square waves, sine waves, triangular waves, variable waveforms, or the like. In this case, the force could be an absolute magnitude, or could be a peak-to-peak or Root Mean Square (RMS) force.

Similarly, a magnitude of movement of the microstructures can also be controlled. The degree of magnitude will depend on factors, such as the length of the microstructures and the degree of penetration required. The magnitude could include any one or more of greater than 0.001 times a length of the microstructure, greater than 0.01 times a length of the microstructure, greater than 0.1 times a length of the microstructure, greater than a length of the microstructure, greater than 10 times a length of the microstructure, greater than 100 times a length of the microstructure or greater than 1000 times a length of the microstructure. The magnitude may also vary, either increasing or decreasing, depending a time of application, a depth of penetration, a degree of penetration or an insertion resistance. Again, the magnitude may increase until a point of penetration and then decrease after a point of penetration.

In the above example, the system can be configured to detect aspects of the insertion process. In one example, this can be achieved by monitoring the actuator, for example, monitoring the current required by the actuator to achieve a specific movement, which can in turn be used to detect, a depth of penetration, a degree of penetration an insertion resistance, or the like, with this then being used to control the actuator.

The actuator can also be used to apply mechanical stimulation, which could be used for a variety of purposes. For example, the actuator can be configured to physically disrupt or dislodge a coating on the microstructures, physically stimulate the subject, cause the microstructures to penetrate the barrier, retract the microstructures from the barrier or retract the microstructures from the subject.

The actuator is typically operatively coupled to the substrate, which could be achieved using any suitable mechanism, such as mechanical, electromechanical, or the like.

In one specific example, the actuator includes a spring or electromagnetic actuator to provide a constant bias, and at least one of a piezoelectric actuator and vibratory motor to apply a vibratory force. The vibratory force is applied at a frequency that is at least 10 Hz, less than 1 kHz and about 100-200 Hz. The continuous force is typically greater than 1 N, less than 10 N and about 5 N, whilst the vibratory force is at least 1 mN, less than 1000 mN and about 200 mN. The actuator is typically configured to cause movement of the microstructures that is at least 10 μm, less than 300 μm and about 50 μm to 100 μm.

In one example, the system includes a housing containing at least the sensor and one or more electronic processing devices, and optionally including other components, such as a signal generator, actuator, power supply, wireless transceiver, or the like. In one particular example, the housing provides reader functionality that can be used to interrogate the microstructures, and which can be provided in an integrated device, or could be provided remote to the substrate and engaged or provided in proximity with the substrate when readings are to be performed.

In the integrated configuration, the reader is typically mechanically connected/integrated with the patch during normal use, allowing measurements to be performed automatically. For example, continual monitoring could be performed, with a reading being performed every 1 second to daily or weekly, typically every 2 to 60 minutes, and more typically every 5 to 10 minutes. The timing of readings can vary depending on the nature of the measurement being performed and the particular circumstance. So for example, an athlete might wish to undergo more frequent monitoring while competing in an event, and then less frequent monitoring during post event recovery. Similarly, for a person undergoing medical monitoring, the frequency of monitoring may vary depending on the nature and/or severity of a condition. In one example, the frequency of monitoring can be selected based on user inputs and/or could be based on a defined user profile, or the like.

In the integrated arrangement, the reader can be connected to the patch using conventional resistance bridge circuitry, with analogue to digital conversion being used to perform measurements.

Alternatively, the reader can be separate, which allows the reader to be removed when not in use, allowing the user to wear a patch without any integrated electronics, making this less intrusive. This is particularly useful for applications, such as sports, geriatric and paediatric medicine, or the like, where the presence of a bulkier device could impact on activities: In this situation, the reader is typically brought into contact or proximity with the patch allowing readings to be performed on demand. It will be appreciated that this requires a user/person to drive the interrogation. However, the reader could include alert functionality to encourage interrogation.

Readings could be performed wirelessly, optionally using inductive coupling to both power the patch and perform the reading as will be described in more detail below, although alternatively, direct physical contact could alternatively be used. In this example, the microstructures and tissue form part of a resonant circuit with discrete inductance or capacitance, allowing the frequency to be used to determine the impedance and hence fluid levels, or analyte levels or concentrations. Additionally, and/or alternatively, ohmic contacts could be used, where the reader makes electrical contact with connectors on the patch.

In either case, some analysis and interpretation of the hydration signal or analyte level or concentration may be performed in the reader, optionally allowing an indicator to be displayed on the reader using an output, such as an LED indicator, LCD screen, or the like. Additionally, and/or alternatively, audible alarms may be provided, for example providing an indication in the event that the subject is under or over hydrated or has an analyte level or concentration outside an acceptable range. The reader can also incorporate wireless connectivity, such as Bluetooth, Wi-Fi or similar, allowing reading events to be triggered remotely and/or to allow data, such as impedance values, hydration or analyte level or concentration indicators, or the like to be transmitted to remote devices, such as a client device, computer system, or cloud based computing arrangement.

In use, the housing typically couples to the substrate, allowing the housing and substrate to be attached and detached as needed. In one example, this could be achieved utilising any appropriate mechanism, such as electromagnetic coupling, mechanical coupling, adhesive coupling, magnetic coupling, or the like. This allows the housing and in particular sensing equipment to only be connected to the substrate as needed. Thus, a substrate could be applied to and secured to a subject, with a sensing system only being attached to the substrate as measurements are to be performed. However, it will be appreciated that this is not essential, and alternatively the housing and substrate could be collectively secured to the subject for example using an adhesive patch, adhesive coating on the patch/substrate, strap, anchor microstructures, or the like. In a further example, the substrate could form part of the housing, so that the substrate and microstructures are integrated into the housing.

When the housing is configured to attach to the substrate, the housing typically includes connectors that operatively connect to substrate connectors on the substrate, to thereby communicate signals between the signal generator and/or sensor, and the microstructures. The nature of the connectors and connections will vary depending upon the preferred implementation and the nature of the signal, and could include conductive contact surfaces, that engage corresponding surfaces on the substrate, or could include wireless connections, such as tuned inductive coils, wireless communication antennas, or the like.

In one example, the system is configured to perform repeated measurements over a time period, such as a few hours, days, weeks, or similar. To achieve this, the microstructures can be configured to remain in the subject during the time period, or alternatively could be removed when measurements are not being performed. In one example, the actuator can be configured to trigger insertion of the microstructures into the skin and also allow for removal of the microstructures once the measurements have been performed. The microstructures can then be inserted and retracted as needed, to enable measurements to be performed over a prolonged period of time, without ongoing penetration of the skin. However, this is not essential and alternatively short term measurements can be performed, in which case the time period can be less than 0.01 seconds, less than 0.1 seconds, less than 1 second or less than 10 seconds. It will be appreciated that other intermediate time frames could also be used.

In one example, once measurements have been performed, the one or more electronic processing devices analyse the measured response signals to determine an indicator indicative of a health and/or physiological status of the subject.

In one example, this is achieved by deriving at least one metric, which can then be used to determine an indicator. For example, the system could be configured to perform impedance measurements, with the metric corresponding to an impedance parameter, such as an impedance at a particular frequency, a phase angle, or similar. The metric can then be used to derive indicators, such as an indication of fluid levels, such as extra or intra cellular fluid levels.

The manner in which this is performed will vary depending upon the preferred implementation. For example, the electronic processing devices could apply the metric to at least one computational model to determine the indicator, with the computational model embodying the relationship between a health status or treatment requirement and the one or more metrics. In this instance, the computational model could be obtained by applying machine learning to reference metrics derived from subject data measured for one or more reference subjects having known health statuses or treatment requirement. In this instance, the health status could be indicative of organ function, tissue function or cell function, could include the presence, absence, degree or severity of a medical condition, or could include one or more measures otherwise associated with a health status, such as measurements of the presence, absence, level or concentration of one or more analytes or measurements of other biomarkers.

The nature of the model and the training performed can be of any appropriate form and could include any one or more of decision tree learning, random forest, logistic regression, association rule learning, artificial neural networks, deep learning, inductive logic programming, support vector machines, clustering, Bayesian networks, reinforcement learning, representation learning, similarity and metric learning, genetic algorithms, rule-based machine learning, learning classifier systems, or the like. As such schemes are known, these will not be described in any further detail. In one example, this can include training a single model to determine the treatment requirements using metrics from reference subjects with a combination of different health states, or the like, although this is not essential and other approaches could be used.

Measured signals can also be used in other manners. For example, changes in metrics over time can be used to track changes in a health state or medical condition for a subject, as well as the effectiveness of any delivered therapy, for example by determining if there is an improvement in a medical condition after therapy has been delivered. Measured signals can also be analysed in order to generate images or to perform mapping. For example, tomography could be used to establish a 2D or 3D image of a region of the subject based on impedance measurements or similar. The signals could also be used in contrast imaging, or the like.

In one example, the system can include a transmitter that transmits measured subject data, metrics or measurement data such as response signals or values derived from measured response signals, allowing these to be analysed remotely.

In one particular example, the system includes a wearable patch including the substrate and microstructures, and a monitoring device (also referred to as a "reader") that performs the measurements. The monitoring device could be attached or integrally formed with the patch, for example mounting any required electronics on a rear side of the substrate. Alternatively, the reader could be brought into contact with the patch when a reading is to be performed. In either case, connections between the monitoring device could be conductive contacts, but alternatively could be indicative coupling, allowing the patch to be wirelessly interrogated and/or powered by the reader.

The monitoring device can be configured to cause a measurement to be performed and/or to at least partially process and/or analyse measurements. The monitoring device can control stimulation applied to at least one microstructure, for example by controlling the signal generator and/or switches as needed. This allows the monitoring device to selectively interrogate different microstructures, allowing different measurements to be performed, and/or allowing measurements to be performed at different locations. This also allows microstructures to be selectively stimulated, for example, allowing different therapies to be applied to the subject. Thus by selectively stimulating microstructures, to thereby selectively release therapeutic materials, this could be used in order to provide dosage control, or to deliver different therapeutic materials.

The monitoring device could also be used to generate an output, such as an output indicative of the indicator or a recommendation based on the indicator and/or cause an action to be performed. Thus, the monitoring device could be configured to generate an output including a notification or an alert. This can be used to trigger an intervention, for example, indicating to a user that action is required. This could simply be an indication of an issue, such as telling a user they are dehydrated or have elevated troponin levels and/or could include a recommendation, such as telling the user to rehydrate, or seek medical attention or similar. The output could additionally and/or alternatively, include an indication of an indicator, such as a measured value, or information derived from an indicator. Thus, a hydration level or analyte level or concentration could be presented to the user.

The monitoring device could also be configured to trigger other actions,

The output could be used to alert a caregiver that an intervention is required, for example transferring a notification to a client device and/or computer of the caregiver. In another example, this could also be used to control remote equipment. For example, this could be used to trigger a drug delivery system, such as an electronically controlled syringe injection pump, allowing an intervention to be triggered automatically. In a further example, a semi-automated system could be used, for example providing a clinician with a notification including an indicator, and a recommended intervention, allowing the clinician to approve the intervention, which is then performed automatically.

In one example, the monitoring device is configured to interface with a separate processing system, such as a client device and/or computer system. In this example, this allows processing and analysis tasks to be distributed between the monitoring device and the client device and/or computer system. For example, the monitoring device could perform partial processing of measured response signals, such as filtering and/or digitising these, providing an indication of the processed signals to a remote process system for analysis. In one example, this is achieved by generating subject data including the processed response signals, and transferring this to a client device and/or computer system for analysis. Thus, this allows the monitoring device to communicate with a computer system that generates, analyses or stores subject data derived from the measurement data. This can then be used to generate an indicator at least partially indicative of a health status associated with the subject.

It will also be appreciated that this allows additional functionality to be implemented, including transferring notifications to clinicians, or other caregivers, and also allowing for remote storage of data and/or indicators. In one example, this allows recorded measurements and other information, such as derived indicators, details of applied stimulation or therapy and/or details of other resulting actions, to be directly incorporated into an electronic record, such as an electronic medical record.

In one example, this allows the system to provide the data that will underpin the growing telehealth sector empowering telehealth systems with high fidelity and accurate clinical data to enable remote clinicians to gain the information they require, and they will be highly valued both in central hospitals and in rural areas away from centralized laboratories and regional hospitals. With time to treatment a strong predictor of improved clinical outcomes with heart attack patients, decentralized populations cannot rely solely on access to conventional large-scale hospitals. Accordingly, the system can provide a low cost, robust and accurate monitoring system, capable for example of diagnosing a heart attack, and yet being provided at any local health facility and as simple as applying a patch device. In this example, resources could be dispatched quickly for patients who test positive to troponin I, with no delay for cardiac troponin laboratory blood-tests. Similarly patients determined to be low-risk could be released earlier and with fewer invasive tests, or funneled into other streams via their GP etc.

In a further example, a client device such as a smart phone, tablet, or the like, is used to receive measurement data from the wearable monitoring device, generate subject data and then transfer this to the processing system, with the processing system returning an indicator, which can then be displayed on the client device and/or monitoring device, depending on the preferred implementation.

However, this is not essential and it will be appreciated that some or all of the steps of analysing measurements, generating an indicator and/or displaying a representation of the indicator could be performed on board the monitoring device.

Again, it will be appreciated that similar outputs could also be provided to or by a remote processing system or client device, for example, alerting a clinician or trainer that a subject or athlete requires attention, that an intervention should be performed, controlling equipment, such as drug delivery devices, or the like.

The reader could be configured to perform measurements automatically when integrated into or permanently/semi permanently attached to the patch, or could perform measurements when brought into contact with the patch if the reader is separate. In this latter example, the reader can be inductively coupled to the patch.

Thus, it will be appreciated that functionality, such as processing measured response signals, analysing results, generating outputs, controlling measurement procedures and/or therapy delivery could be performed by an on-board monitoring device, and/or could be performed by remote computer systems, and that the particular distribution of tasks and resulting functionality can vary depending on the preferred implementation.

In one example, the system includes a substrate coil positioned on the substrate and operatively coupled to one or more microstructure electrodes, which could include microstructures that are electrodes, or microstructures including electrodes thereon. An excitation and receiving coil is provided, typically in a housing of a measuring device, with the excitation and receiving coil being positioned in proximity to the substrate coil in use. This is performed to inductively couple the excitation and receiving coil to the substrate coils, so that when an excitation signal is applied to the drive coil, this induces a signal in the substrate coil, which, in association with the electrodes and other reactive components on the substrate, may form a resonant circuit. As a result, the signal frequency, amplitude and damping (Q) of the resonant circuit on the substrate will be reflected in signal observed in the excitation and receive coil, which in turn alters the drive signal applied to the excitation and receiving coil, for example by changing the frequency, phase or magnitude of the signal, allowing this to act as a response signal, for example allowing a bioimpedance or biocapacitance to be measured.

This can be used in a variety of manners, but in one example, the one or more microstructure electrodes are configured to bind one or more analytes of interest, such that the response signal is dependent on a presence, absence, level or concentration of analytes of interest. This can be achieved in a variety of ways as discussed supra, such as coating the microstructures with a binding agent or forming the microstructures from material comprising a binding agent, so that analytes interact with the microstructure electrodes, hence changing their electrical properties and thereby changing the characteristics of the response signal. For example, this could include having the analytes bind to a coating or the material forming the microstructure, such as a molecularly imprinted polymer.

Detection of analytes could be performed in any manner, and this could involve examining changes in the response signal over time, for example as a level or concentration of analytes in the vicinity of the microstructure electrodes changes. Alternatively, in another example, two sets of microstructure electrodes are used, which are driven independently, with one acting as a control, and others being selectively responsive to one or more analytes so differences in measured signals are indicative of changes in analyte level or concentration.

In this example, the system typically includes a first substrate coil positioned on a substrate and operatively coupled to one or more first microstructure electrodes, a second substrate coil positioned on a substrate and operatively coupled to one or more second microstructure electrodes, the second microstructure electrodes being configured to interact with analytes of interest. At least one drive coil is positioned in proximity to at least one of the first and second substrate coils such that alteration, such as attenuation, or a phase or frequency change, of a drive signal applied acts as a response signal. In this case, the one or more electronic processing devices use the first and second response signals, and in particular difference between the first and second response signals to determine a presence, absence, level or concentration of analytes of interest.

In the case of multiple substrate coil and electrode combinations forming resonant circuits, each may be intentionally designed by selection of fixed reactive components either inductive or capacitive to possess a different resonant frequency, thereby permitting a means of frequency based multiplexing of an entire array with a single excitation and receive coil.

A further example of a system for delivering treatment to the biological subject will now be described with reference to FIGS. 3A to 3L.

In this example, the system includes a monitoring device 320, including a sensor 321 and one or more electronic processing devices 322. The system further includes a signal generator 323, which in this example acts as a treatment delivery mechanism, a memory 324, an external interface 325, such as a wireless transceiver, an actuator 326, and an input/output device 327, such as a touchscreen or display and input buttons, connected to the electronic processing device 322. The components are typically provided in a housing 330, which will be described below.

The nature of the signal generator 323 and sensor 321 will depend on the measurements being performed, and could include a current source and voltage sensor, laser or other electromagnetic radiation source, such as an LED, and a photodiode or CCD sensor, or the like. The actuator 326 is typically a spring or electromagnetic actuator in combination with a piezoelectric actuator or vibratory motor coupled to the housing, to bias and vibrate the substrate relative to an underside of the housing, to thereby urge the microstructures into the skin, whilst the transceiver is typically a short-range wireless transceiver, such as a Bluetooth system on a chip (SoC).

The processing device 322 executes software instructions stored in the memory 324 to allow various processes to be performed, including controlling the signal generator 323, receiving and interpreting signals from the sensor 321, generating measurement data and transmitting this to a client device or other processing system via the transceiver 325. Accordingly, the electronic processing device is typically a microprocessor, microcontroller, microchip processor, logic gate configuration, firmware optionally associated with implementing logic such as an FPGA (Field Programmable Gate Array), or any other electronic device, system or arrangement.

In use the monitoring device 320 is coupled to a patch 310, including a substrate 311 and microstructures 312, which are coupled to the sensor 321 and/or signal generator 323 via connections 313. The connections could include physical conductive connections, such as conductive tracks, although this is not essential and alternatively wireless connections could be provided, such inductive coupling or radio frequency wireless connections. In this example, the patch further includes anchor microstructures 314 that are configured to penetrate into the dermis and thereby assist in securing the patch to the subject.

Figure 3A:
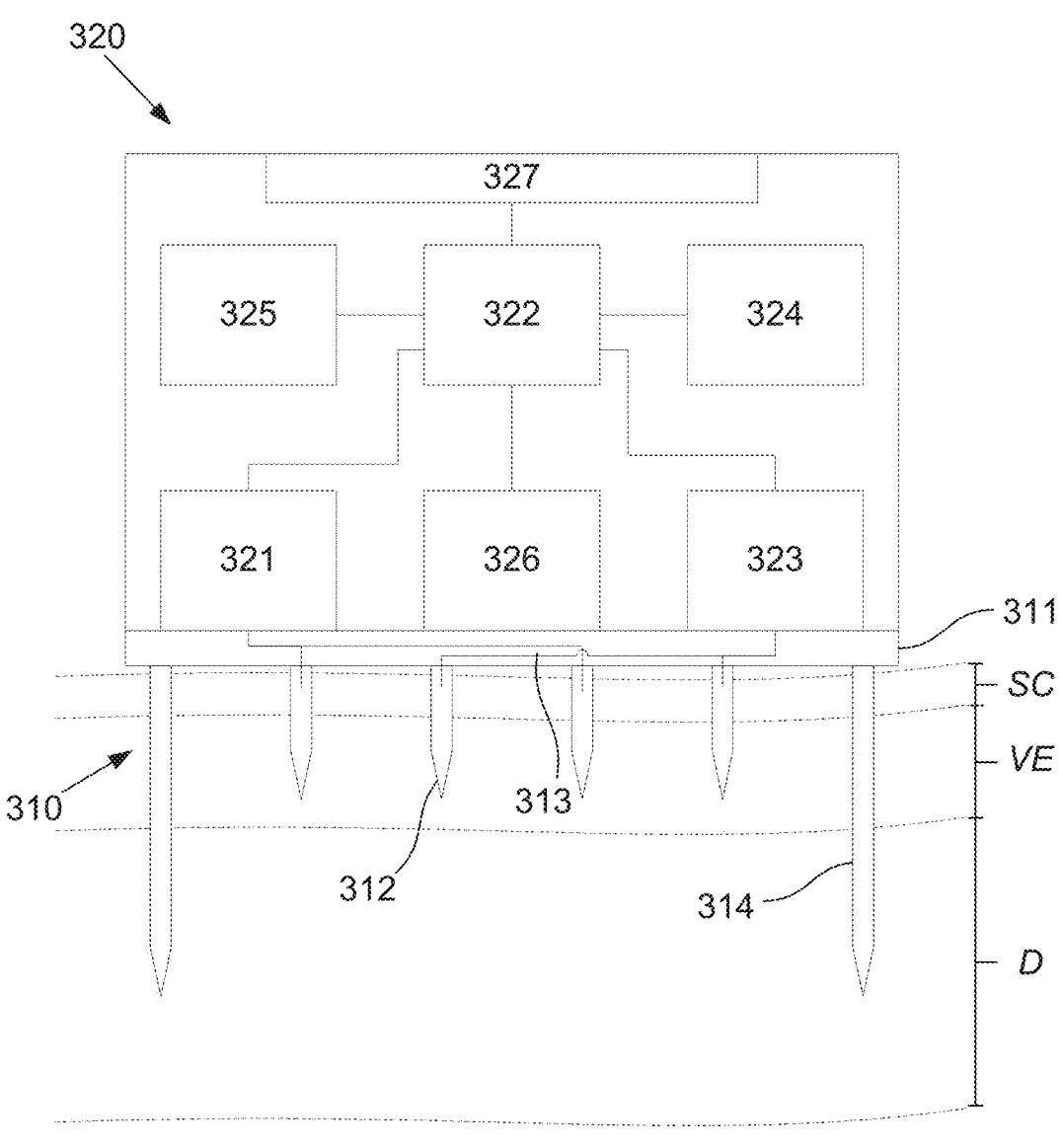
FIG. 3A is a schematic diagram of a further example of a system for delivering treatment to a biological subject.
Figure 3B:
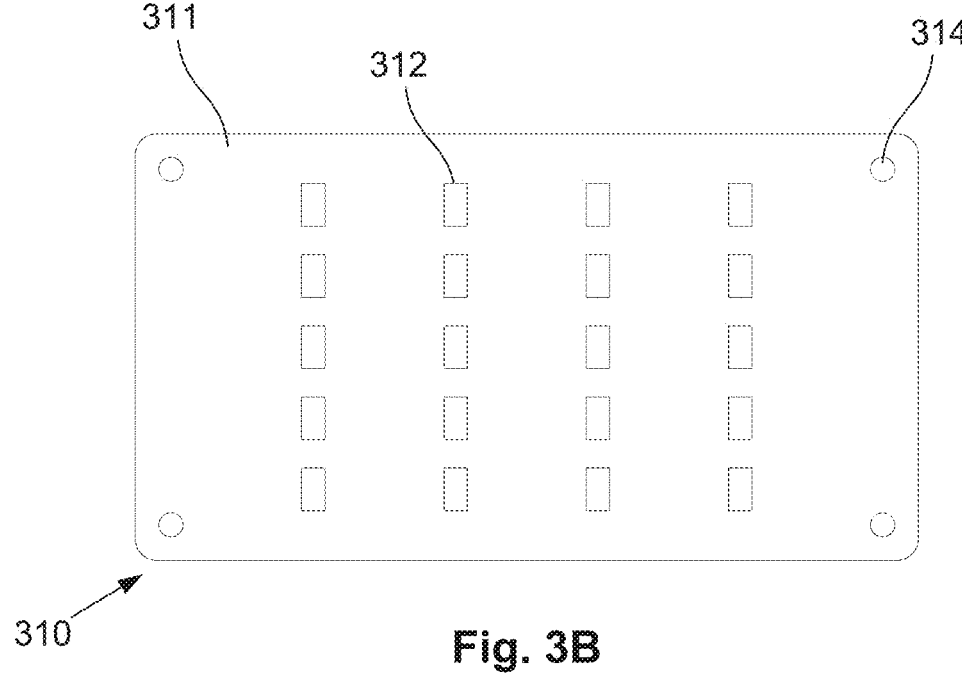
FIG. 3B is a schematic underside view of an example of a patch for the system of FIG. 3A.
Figure 3C:
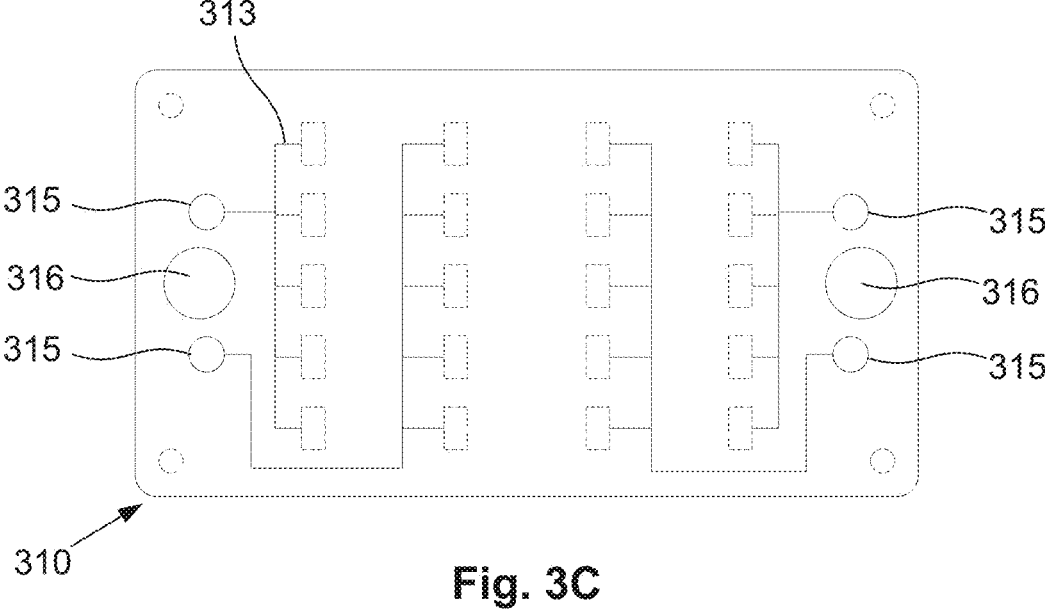
FIG. 3C is a schematic plan view of the patch of FIG. 3B.

An example of the patch 310 is shown in more detail in FIGS. 3B and 3C. In particular, in this example the substrate 311 is generally rectangular, with round corners to avoid discomfort when the substrate is applied to the subject's skin. The substrate 311 includes anchor microstructures 314 are provided proximate corners of the substrate 311 to help secure the substrate, whilst measurement microstructures 312 are arranged in an array on the substrate. In this example, the array has a regular grid formation, with the microstructures 312 being in provided in equally spaced rows and columns, but this is not essential and alternative spacing configurations could be used, as will be described in more detail below.

Figures 3D, 3E:
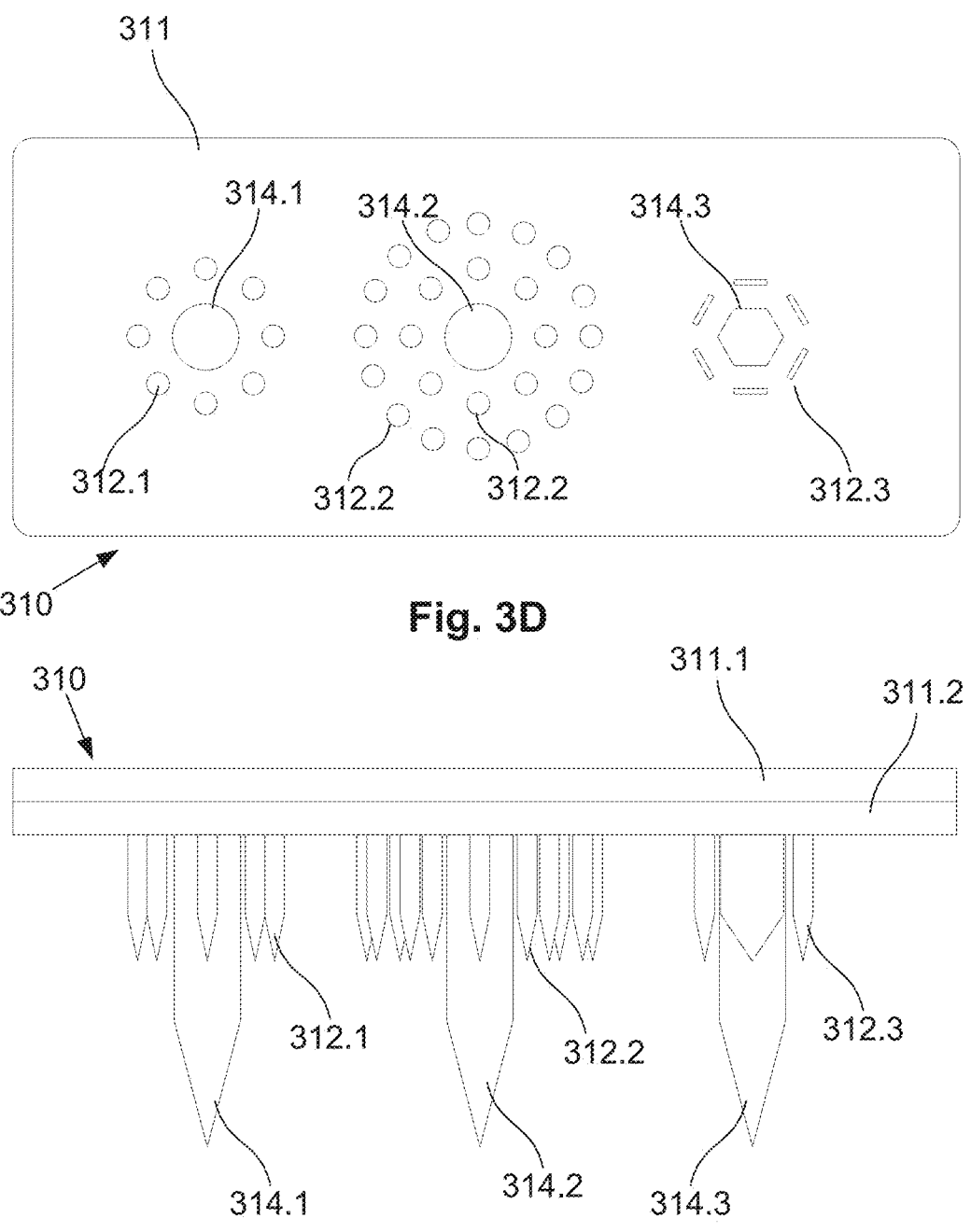
FIG. 3D is a schematic underside view of an alternative example of a patch for the system of FIG. 3A.
FIG. 3E is a schematic side view of the patch of FIG. 3D.

For example, in the arrangement of FIGS. 3D and 3E, three anchor microstructures 314.1, 341.2, 314.3 are provided, surrounded by respective circumferentially spaced microstructures 312.1, 312.2, 312.3. This can be useful to maximise the effectiveness of the anchor, specifically providing the microstructures 312 in close proximity to the anchor microstructures 314 to avoid movement of the microstructures 312 within the subject. Additionally, in this example, the anchor microstructures 314 could be used in measuring or applying signals, for example by acting as a ground connection, or similar.

In this example, the substrate is also formed from multiple substrate layers 311.1, 311.2, which can assist in creating internal structures, such as connections to the microstructures, coils, or the like, as will be described in more detail below. In a manner similar to that described below with respect to a backing, the substrate could also include different regions or layers having different material properties, or the like.

In this example, the anchor microstructure 314.1 is circular and includes a single surrounding group of circumferentially spaced microstructures 312.1. However, it will be appreciated that this is not essential, and in the case of the anchor microstructure 314.2, the anchor microstructure 314.2 is surrounded by two or more concentric groups of microstructure 312.2, with the outer group including a larger number of microstructures. This allows a greater range of measurements to be performed. It will be appreciated that other arrangements are also possible, such as providing further concentric groups, different numbers of microstructures in each group, or the like. Additionally, whilst circular groups are shown, this is not intended to be limiting, and other shapes or distributions could be used including oval shaped, square shaped, or similar.

In the case of the anchor microstructure 314.3 this is hexagonal, with six plate microstructures 312.3, each being positioned radially outwardly from a respective face of the hexagonal anchor microstructure 314.3. In this manner measurements can be performed between each face of the anchor microstructure 314.23 and a respective microstructure 312.3, which can be useful to maximise a surface area of electrodes on each face and plate, whilst maintaining equidistant separation between the anchor and surrounding microstructures.

Whilst the above configurations have been described with respect to anchor microstructures, this is not essential and it will be appreciated that similar arrangements could be used with any drive or sense microstructure. Thus, in one example, a single drive microstructure could be used with multiple surrounding sense microstructure, or a single sense microstructure could be used with multiple surrounding drive microstructures. This provides an effective master slave arrangement, in which a single master drive/sense microstructure is used with multiple sense/drive microstructures.

Such master/slave relationships can be used in wide range of applications, for example to use a single drive signal to induce responses in multiple sense microstructures. In this example, this could be used for mapping, for example to identify different responses at different locations, and hence localise an effect, so as the presence of analytes or specific objects, such as lesions or cancer. Alternatively, this could be used with sense microstructures used to detect different analytes, for example using different coatings or similar, so that a single stimulation signal can trigger detection of different analytes.

In the example of FIGS. 3B and 3C, four connectors 315 are provided which are connected to respective microstructures 312 via connections 313 to allow stimulation signals and response signals to be applied to and measured from two sets of respective microstructures. This can be used to allow for symmetric or differential application and detection of signals, as opposed to asymmetric or single-ended application or detection, which is typically performed relative to a ground reference, and which is in turn generally noisier. However, it will be appreciated that for some detection modalities, such as optical detection, or the like, this is not relevant and single connections 315 may be provided.

The substrate also includes coupling members 316, such as magnets, which can be used to attach the substrate to the housing 330.

Figure 3F:
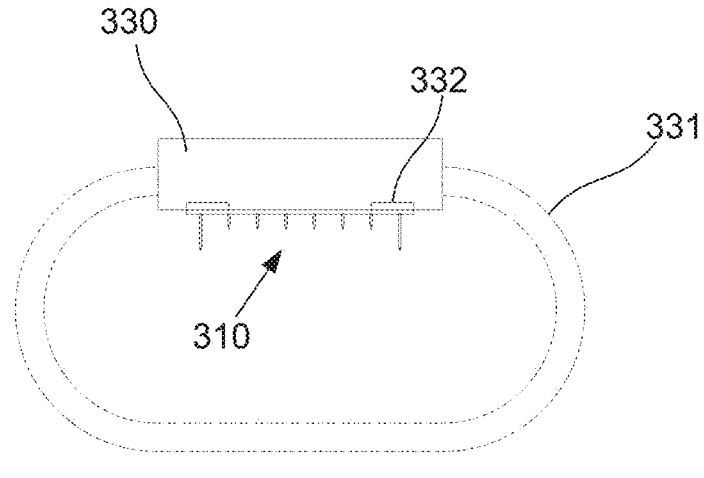
FIG. 3F is a schematic side view of an example of a housing arrangement for the system of FIG. 3A.
Figure 3G:
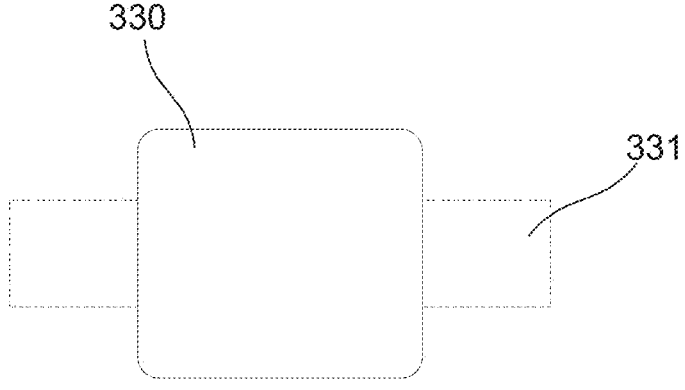
FIG. 3G is a schematic plan view of the housing arrangement of FIG. 3F.

In the example of FIGS. 3F and 3G, the housing 330 is a generally rectangular housing. The measuring device can optionally have a form factor similar to a watch, or other wearable device, in which case a strap 331 is included that allows the housing to be secured to the user. However, this is not essential and other securing mechanisms could be used. Alternatively, the housing could simply be brought into engagement with the patch and held in position each time a measurement is performed. In this example, the housing includes coupling members 332, such as magnets, or the like, which can engage with corresponding coupling members 316 on the substrate allowing the substrate to be secured to the housing. Whilst any form of coupling member could be used, the use of magnets is particularly advantageous as these can be contained within the housing 330, allowing the housing to be sealed, and can also act to ensure correct alignment of the substrate 310, for example by having polarities of the magnets guide a relative orientation of the substrate 310 and housing 330.

However, it will be appreciated that this configuration is for the purpose of illustration only, and other arrangements could be used. For example, the substrate could form part of an adhesive patch, which is applied to the subject and retained in place. Alternatively, adhesive could be provided on a surface of the substrate to adhere the substrate directly to the subject. The housing 330, could then be selectively attached to the patch, for example, using magnetic coupling, thereby allowing measurements to be performed as needed.

Figure 3H:
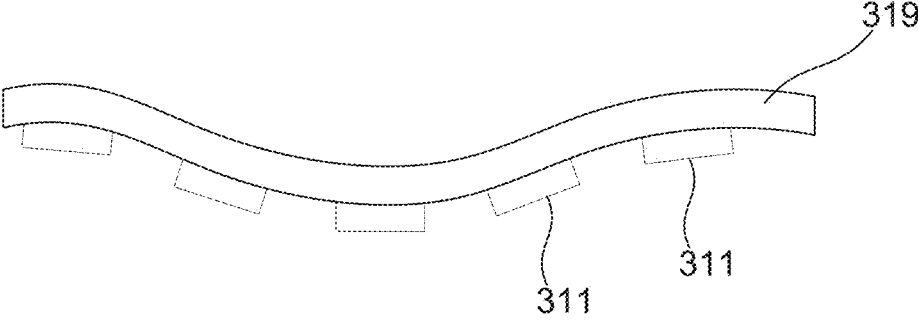
FIG. 3H is a schematic side view of an example of a flexible segmented substrate arrangement.

In this example, the substrate could be a flexible substrate, which can be achieved using a woven or non-woven fabric or other suitable material, with microstructures directly attached thereto. More typically however, flexibility is achieved using a number of individual substrates 311 mounted on a flexible backing 319, to form a segmented substrate, as shown in FIG. 3H. It will be appreciated that such arrangements can be used in a wide variety of circumstances, including having the substrates mounted to a strap or the like, for attachment to the subject.

Figure 3I:
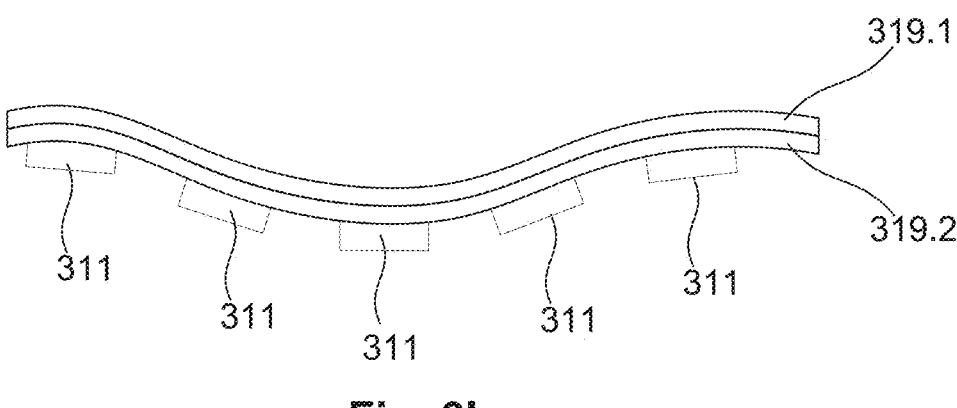
FIG. 3I is a schematic side view of a further example of a flexible segmented substrate arrangement.
Figure 3J:
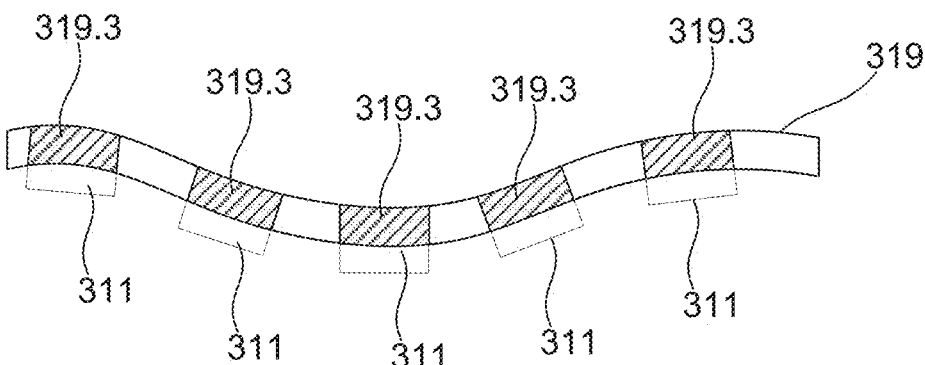
FIG. 3J is a schematic side view of a further example of a flexible segmented substrate arrangement.
Figure 3K:
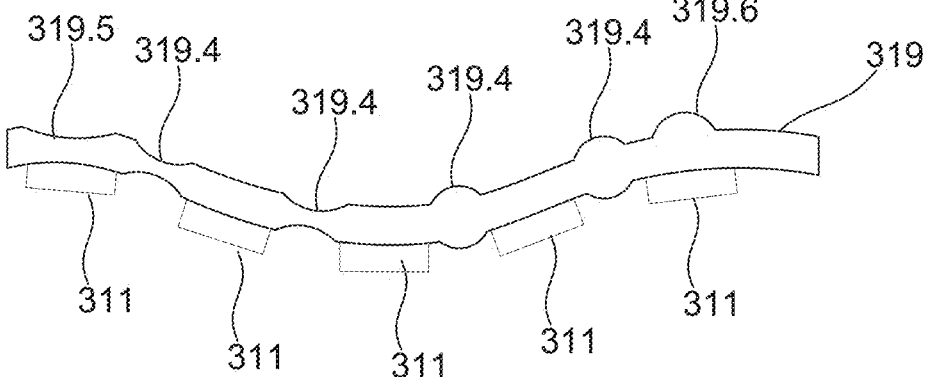
FIG. 3K is a schematic side view of a further example of a flexible segmented substrate arrangement.

A number of further variations are shown in FIGS. 3I to 3K.

Specifically in the example of FIG. 3I, the backing 319 is formed from multiple backing layers 319.1, 319.2, with two being shown in the example for the purpose of illustration only. The use of multiple layers can be beneficial in achieving desired properties, for example to provide adhesive, or waterproof layers, or the like.

In the example of FIG. 3J, the backing layer has multiple interspersed regions 319.3, which can be used for particular purposes, such as to allow for easier attachment of the substrates 311, to provide connectivity to a measuring device 320, to allow for increased flexibility between the substrates 311, or the like. In this example, interspersed regions are substantially aligned with the substrates, although it will be appreciated that this is not essential, and they could be provided at other locations.

A further example is shown in FIG. 3K, which includes a number of shape modifications, including thinner regions 319.4, located between substrates, which could be used to enhance flexibility, or thicker regions 319.5 between the substrates, which could increase strength. Similarly thinner or thicker regions 319.5, 319.6 could be provided in line with the substrates, for example to enhance strength, flexibility, connection to a measuring device, or the like.

Whilst these features have been described with reference to a backing layer, it will be appreciated that similar approaches could be used for the substrate itself.

Figure 3L:
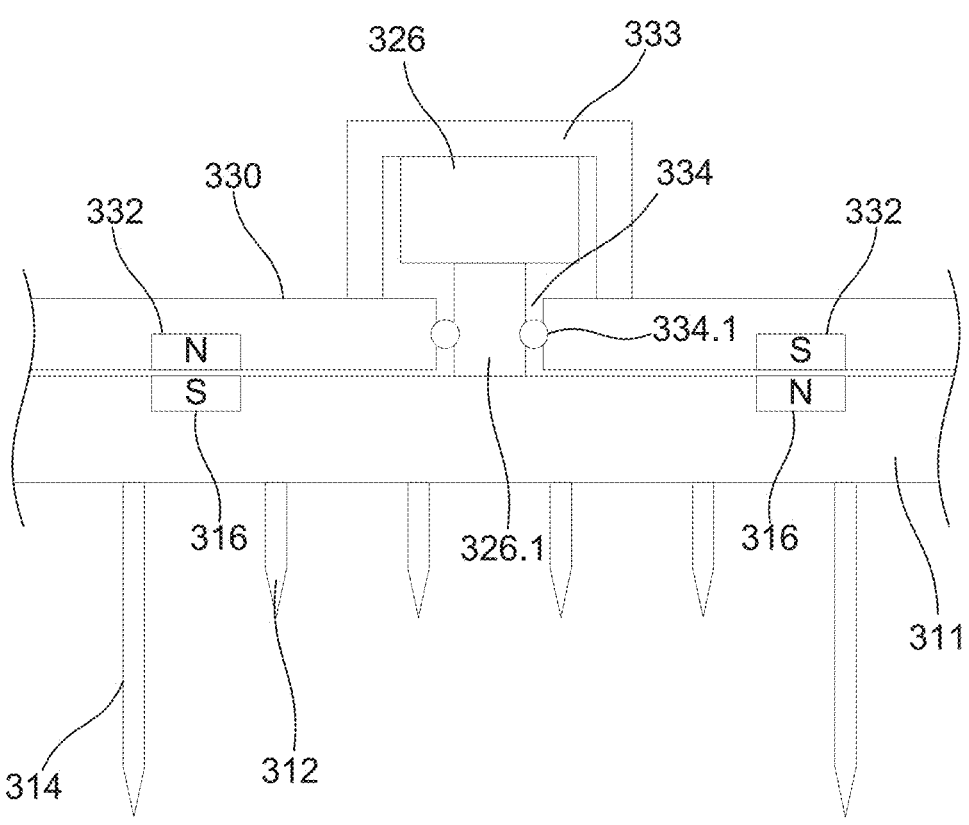
FIG. 3L is a schematic side view of an example actuator arrangement.

An example of an actuator configuration to assist with applying a patch will now be described with reference to FIG. 3L.

In this example, the housing 330 includes a mounting 333 to which the actuator 326, such as a piezoelectric actuator, or vibrating motor, is attached. The actuator 326 is typically a spring or electromagnetic actuator in combination with a piezoelectric actuator or vibratory motor coupled to the housing, to bias and vibrate the substrate relative to an underside of the housing, to thereby urge the microstructures into the skin, whilst the transceiver is typically a short-range wireless transceiver, such as a Bluetooth system on a chip (SoC).

The patch substrate 311 is positioned adjacent the underside of the housing 330, with magnets 316, 332 being arranged to urge the substrate 311 towards the housing 330. The arm 326.1 engages the substrate to thereby transmit forces from the actuator 326 to the substrate 311, allowing the substrate and hence microstructures 312, 314, to be vibrated to aid insertion of the microstructures into the subject. Specifically, this arrangement transmits forces directly to the substrate 311, allowing forces in the substrate to be maximised, whilst minimising vibration of the housing 330.

Figure 3M:
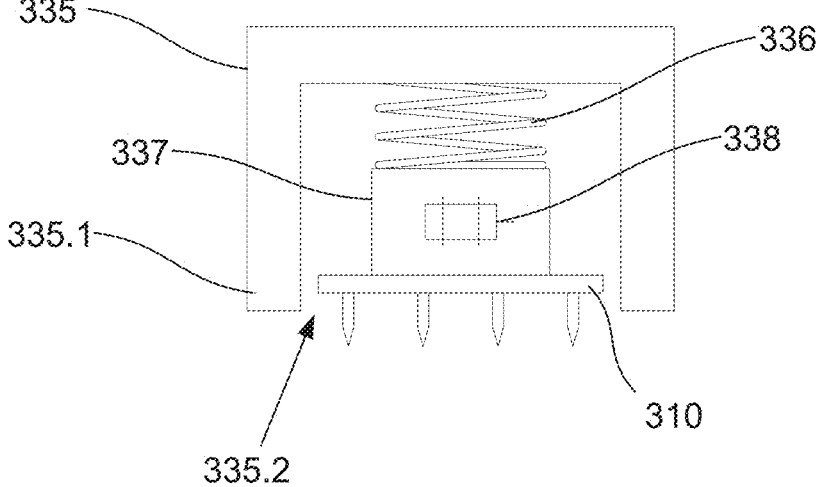
FIG. 3M is a schematic side view of a further example actuator arrangement.
Figures 4E, 4F, 4G, 4H, 4I, 4J:
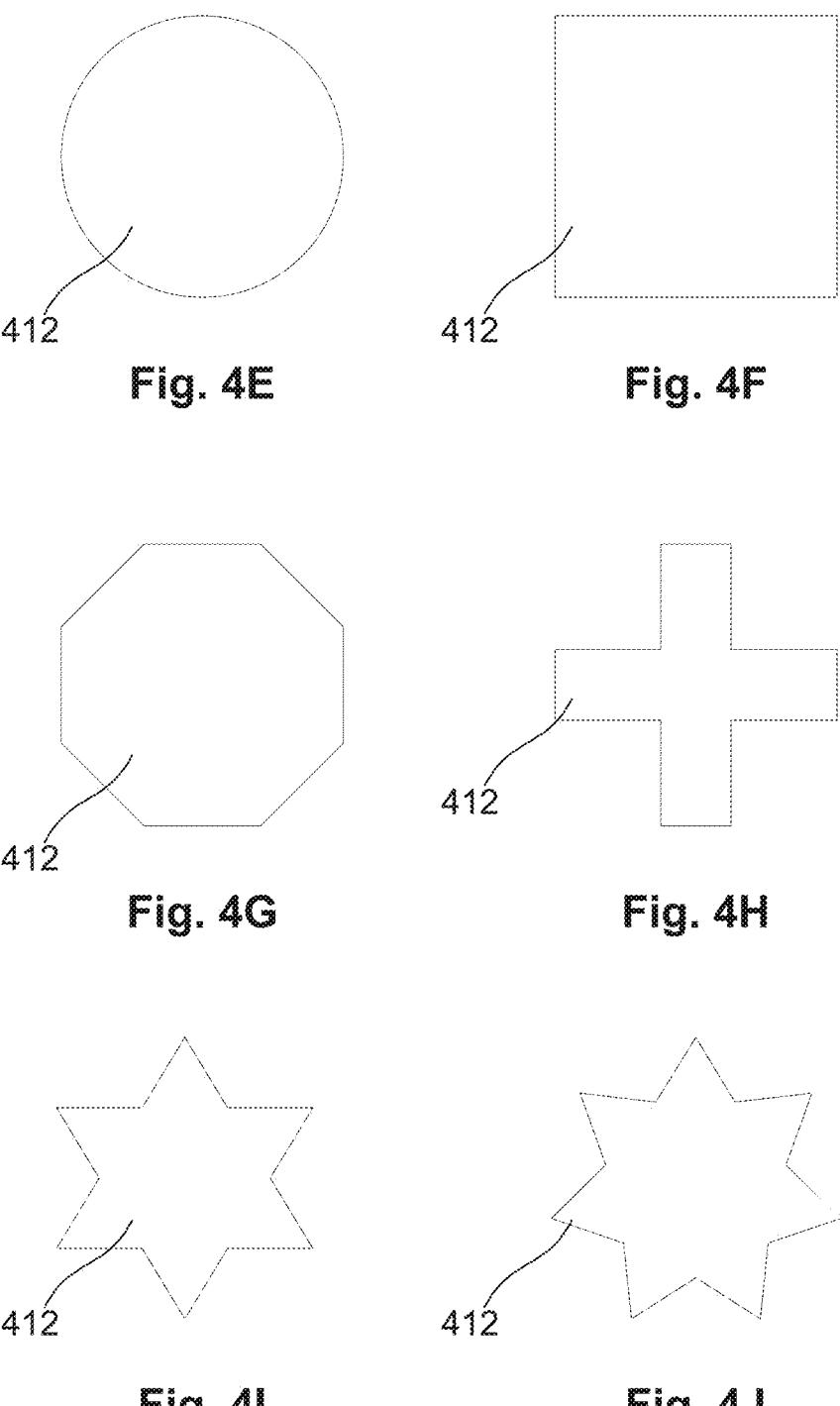
FIGS. 4E to 4J are schematic diagrams illustrating example microstructure cross sectional shapes.

A further example actuator arrangement will now be described with reference to FIG. 3M.

In this example, the actuator arrangement includes an actuator housing 335 having a base 335.1 including an opening 335.2. The housing contains a spring 336 and mounting 337, which in use supports a patch 310 (and optional integrated reader). The mounting also optionally contains a piezoelectric actuator or offset motor 338.

In use, the actuator housing 335 is positioned so that a base 335.1 of the housing 335 abuts against the subject's skin, with the patch at least partially projecting through the opening 335.2. In one example, this is achieved by having an operator hold the actuator housing. However, this is not essential and additionally and/or alternatively, the actuator housing could be integrated into and/or form part of a monitoring device as described above.

In use, the spring 336 is configured to apply a continuous biasing force to the mounting 337, so the patch 310 is urged against the subject's skin. Additionally, the piezoelectric actuator or offset motor 338 can cause the mounting 337, and hence patch 310, to vibrate, thereby facilitating piercing and/or penetration of the stratum corneum by the microstructures.

Example microstructure arrangements will now be described in more detail with reference to FIGS. 4 to 8.

In the example of FIG. 4A, different length microstructures are shown with a first microstructure 412.1 penetrating the stratum corneum and viable epidermis, but not breaching the dermis, a second microstructure 412.2 entering the dermis but only just passes the dermal boundary, whereas a third microstructure 412.3 penetrates the dermal layer at greater distance. It will be appreciated that the length of structure used will vary depending upon the intended application of the device, and specifically the nature of the barrier to be breached.

In the example of FIG. 4B, pairs of microstructures are provided with a first microstructure pair 412.4 having a closer spacing and a second microstructure pair 412.5 having a relatively large spacing, which can be used to enable different properties to be detected, or different forms of stimulation to be performed.

For example, a greater electrode spacing can be used to perform impedance measurements of interstitial fluid and other tissues and liquids between the electrodes, whereas closer spaced electrodes are more suited to performing capacitive sensing to detect different analytes present on a surface of the electrodes.

Additionally, the electrical field strength generated by applying a signal to the first and second microstructure pairs are shown in FIGS. 4C and 4D, highlighting that the field strength between the electrodes decreases as the spacing increases, which in turn impacts on the ability to perform stimulation. For example, by providing an array of closely spaced microstructures, this can be used to generate a highly uniform field within the subject, without requiring a large applied field. This can be used to allow the field to be used for stimulation, for example, to perform electroporation, or the like.

The microstructures can have a range of different shapes, and examples are shown in FIGS. 4E to 4J. Specifically, these illustrate circular, rectangular, octagonal, cruciform, and star shapes. The shapes used will vary depending on the intended application. For example, larger numbers of the microstructures can be useful to provide multiple different electrode surfaces, whilst a greater overall surface area can be useful to maximise the amount of coating. Similarly, acute angled surfaces can, such as the cruciform and star arrangements, can allow coating to be used to provide an overall circular profile, with different coating depths around the microstructure.

Figure 5C:
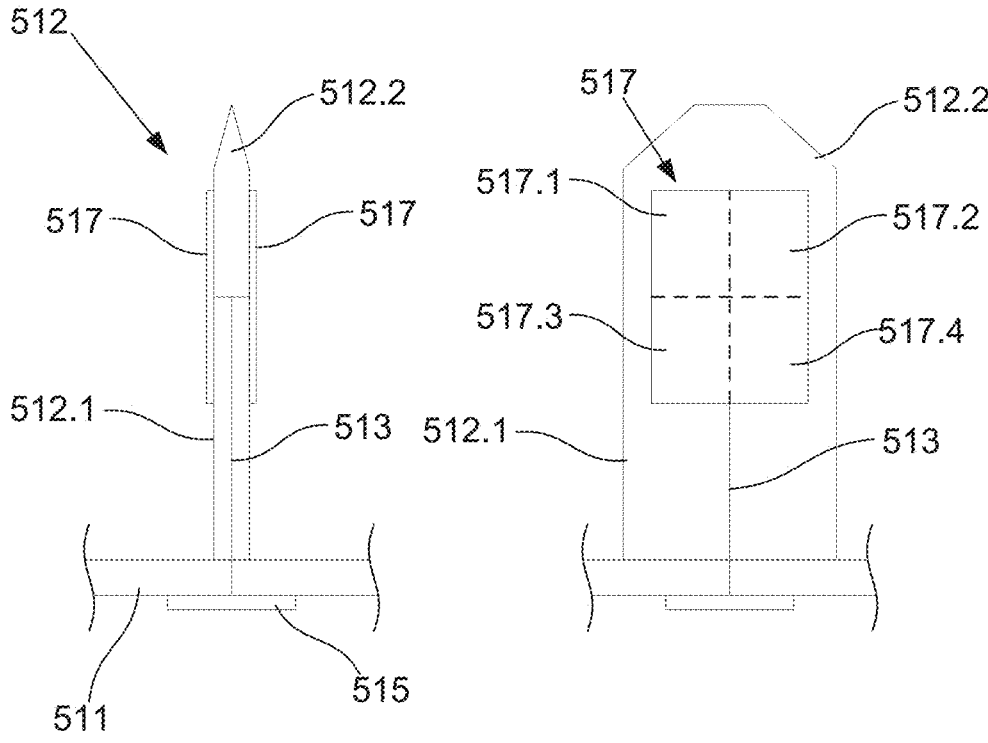
FIG. 5C is a schematic underside view of an example of a patch including the microstructure of FIG. 5A.

A specific example of a plate microstructure is shown is shown in FIGS. 5A to 5C.

In this example, the microstructure is a plate having a body 512.1 and a tip 512.2, which is tapered to facilitate penetration of the microstructure 512 into the stratum corneum. In this example, electrode plates 517 are provided on each side of the microstructure, with these being coupled via a single connection 513 to a connector 515 for onward connection to a sensor 321 and/or signal generator 323. This allows a signal to be measured from or applied to the electrode plates collectively. It will be appreciated however that this is not essential and independent connections could be provided allowing each of the electrodes to be driven or sensed independently. Additionally, each electrode 517 could be subdivided into multiple independent segments 517.1, 517.2, 517.3, 517.4, such that each face includes multiple electrodes.

Figure 5D:
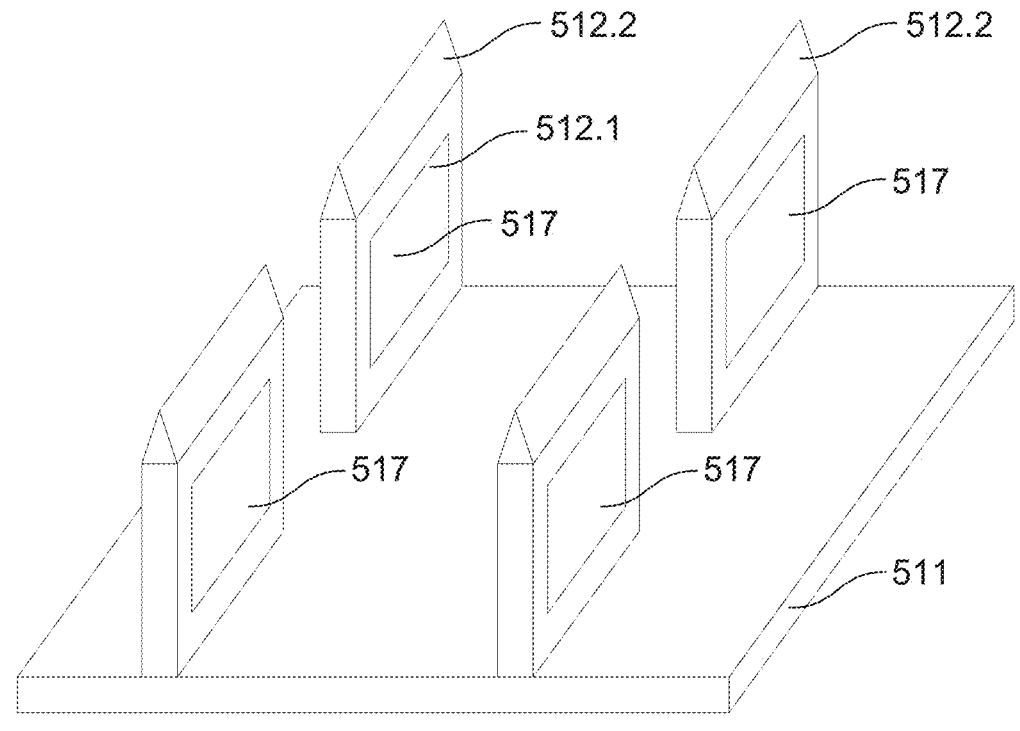
FIG. 5D is a schematic perspective topside view of an example of substrate including pairs of blade microstructures of FIGS. 5A and 5B.

As shown in FIGS. 5C and 5D, different arrangements could be used but in general, pairs of microstructures are formed with the microstructures facing each other allowing signals to be applied between the microstructures or measured between the microstructures. Again, different separations between electrodes in pairs of electrodes can be used to allow different measurements to be performed and/or to alter the profile of stimulation of the tissue between the electrodes.

Figure 5E:
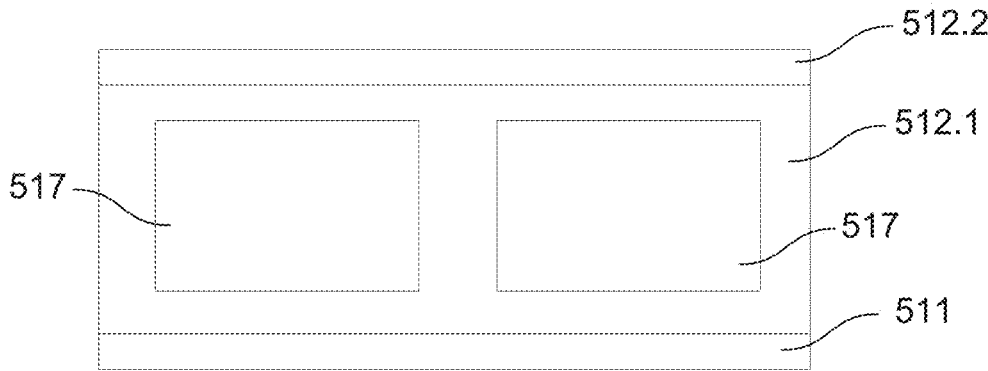
FIG. 5E is a schematic front view of an example of a blade microstructure.
Figure 5F:
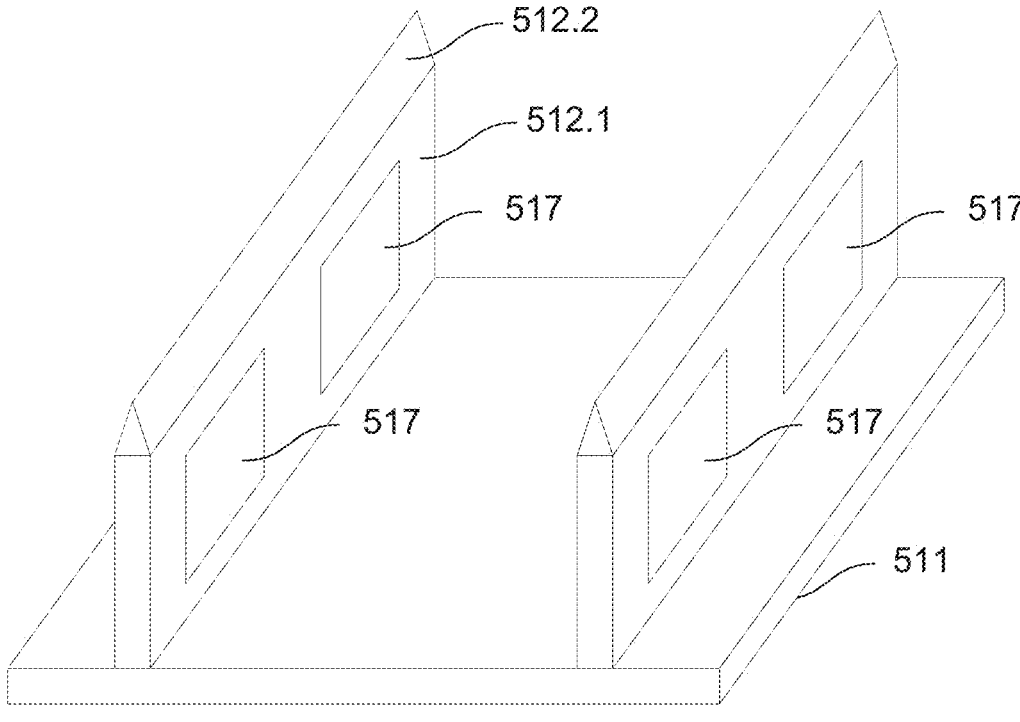
FIG. 5F is a schematic perspective topside view of an example of substrate including blade microstructures.

A further example of a blade microstructure is shown is shown in FIGS. 5E and 5F.

In this example, the microstructure is an elongate body 512.1 and tip 512.2, which is tapered to facilitate penetration of the microstructure 512. This is generally similar in profile to the plate arrangement described above, but in this example is significantly wider, and in one particular example, can extend substantially the entire distance across the substrate. In this example, the microstructures include multiple electrode plates 517 on each side of the microstructure. In this case, the substrate can include multiple spaced parallel blades, allowing signals to be applied across or measured between the electrodes on different blades. However, it will be appreciated that other configurations could be used, such as providing a single electrode, segmented electrodes, or having the entire microstructure act as an electrode.

In the example, shown the blade tip is parallel to the substrate, but this is not essential and other configurations could be used, such as having a sloped tip, so that the blade penetrates progressively along the length of the blade as it is inserted, which can in turn facilitate penetration. The tip may also include serrations, or similar, to further enhance penetration.

Figures 5G, 5H:
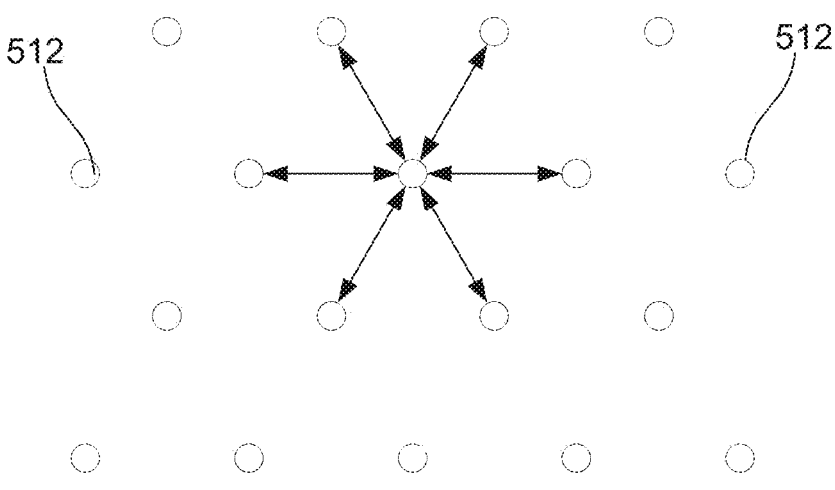
FIG. 5G is a schematic plan view of an example of a hexagonal grid microstructure array.
FIG. 5H is a schematic plan view of an alternative example of a grid of pairs of microstructures.

As mentioned above, in one example, microstructures are provided in a regular grid arrangement. However, in another example, the microstructures are provided in a hexagonal grid arrangement as shown in FIG. 5G. This is particularly advantageous as each microstructure is equally spaced to all of the nearest neighbour microstructures, as shown by the arrows, meaning measurements can be performed relative to any adjacent microstructure without requiring response or stimulation signals to be modified to account for different spacings.

Figure 5I:
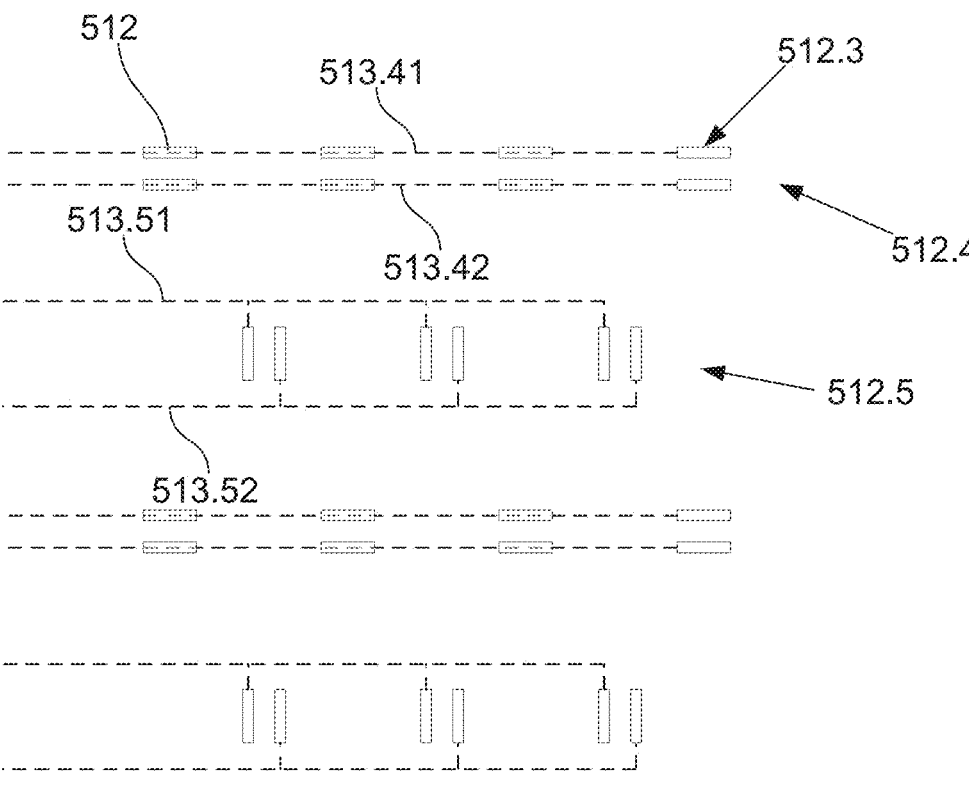
FIG. 5I is a schematic plan view of the grid of FIG. 5H showing example connections.
Figure 5J:
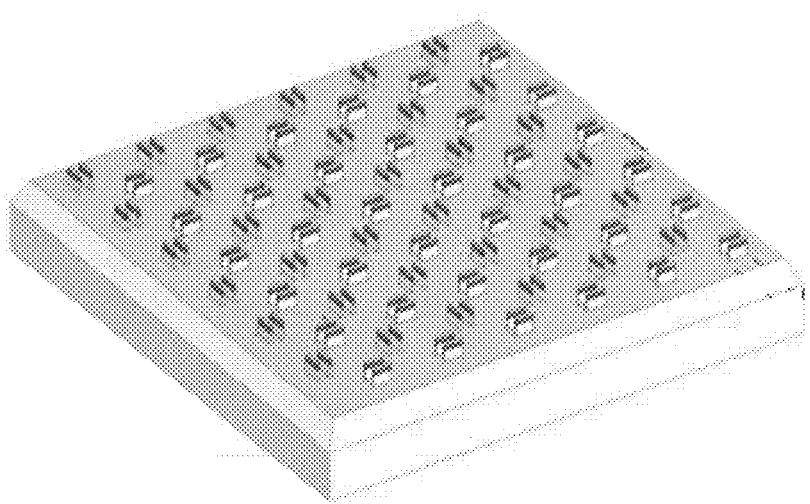
FIG. 5J is a schematic perspective view of an example of a grid of pairs of microstructures.

A further example arrangement is shown in FIGS. 5H and 5I, in which microstructures 512 are arranged in pairs 512.3, and with pairs arranged in offset rows, 512.4, 512.5. In this example, pairs in different rows are arranged orthogonally, so that the microstructures extend in different directions. This avoids all microstructures being aligned, which can in turn render a patch vulnerable to lateral slippage in a direction aligned with the microstructures. Additionally arranging the pairs orthogonally reduces interference, such as cross talk, between different pairs of electrodes, improving measurement accuracy and accounting for tissue anisotropy, particularly when measurements are being performed via multiple microstructure pairs simultaneously.

A further example arrangement is shown in FIGS. 5H to 5K, in which microstructures 512 are arranged in pairs 512.3, and with pairs arranged in offset rows, 512.4, 512.5. In this example, pairs in different rows are arranged orthogonally, so that the microstructures extend in different directions. This avoids all microstructures being aligned, which can in turn render a patch vulnerable to lateral slippage in a direction aligned with the microstructures. Additionally arranging the pairs orthogonally reduces interference, such as cross talk, between different pairs of electrodes, improving measurement accuracy and accounting for tissue anisotropy, particularly when measurements are being performed via multiple microstructure pairs simultaneously.

In one example, pairs of microstructures in each row can be provided with respective connections 513.41, 513.42; 513.51, 513.52, allowing an entire row of microstructure pairs to be interrogated and/or stimulated simultaneously, whilst allowing different rows to be interrogated and/or stimulated independently.

Figure 5K:
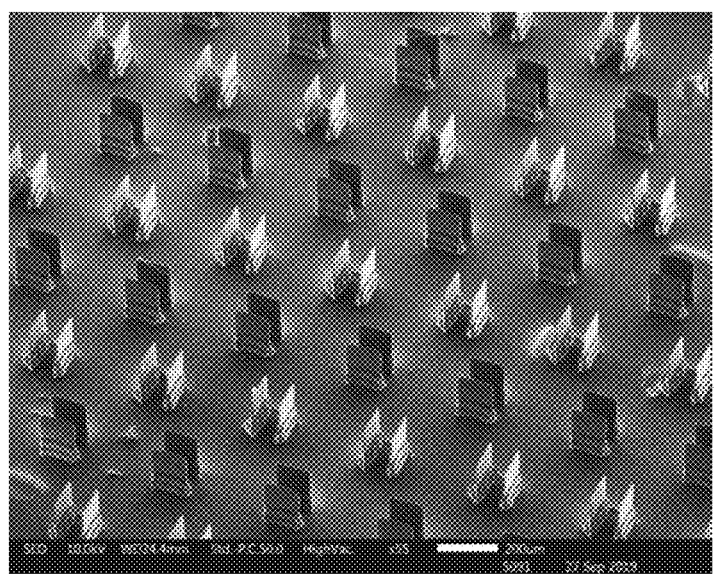
FIG. 5K is an image of an example of a patch including arrays of pairs of angularly offset plate microstructures.

A Scanning Electron Microscopy (SEM) image showing an array of pairs of offset plate microstructures is shown in FIG. 5K.

Figures 5L, 5M:
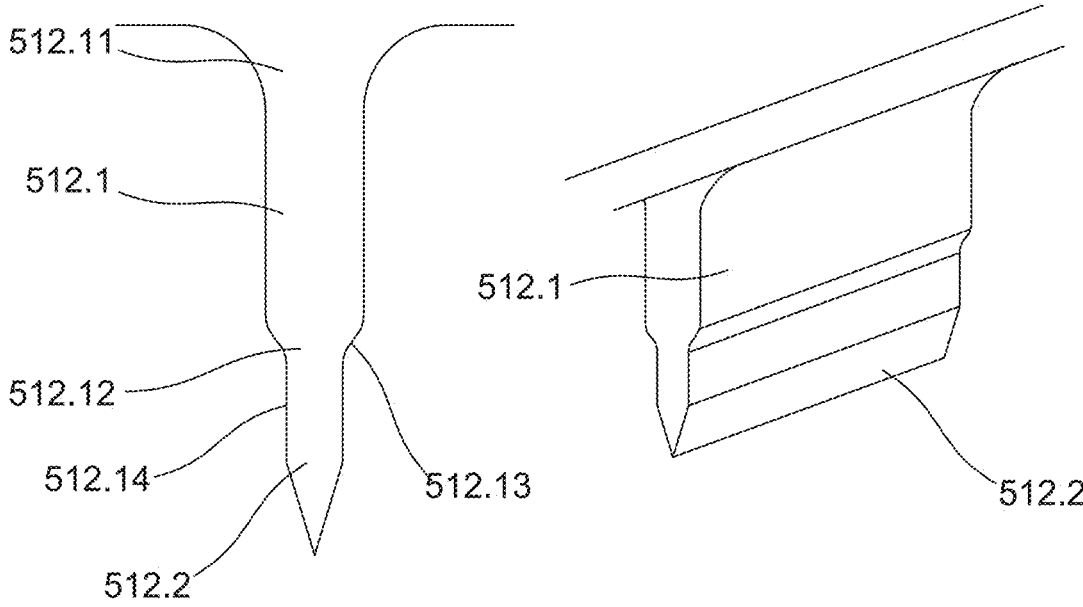
FIG. 5L is a schematic side view of a specific example of a plate microstructure.
FIG. 5M is a schematic perspective view of the plate microstructure of FIG. 5I.

Specific examples of microstructures for performing measurements in the epidermis are shown in FIGS. 5L and 5M.

In this example, the microstructures are plates or blades, having a body 512.1, with a flared base 512.11, where the body joins the substrate, to enhance the strength of the microstructure. The body narrows at a waist 512.12 to define shoulders 512.13 and then extends to a tapered tip 512.2, in this example, via an untapered shaft 512.14. Typical dimensions are shown in Table 2 below.

TABLE 2

| Parameter | Min. | Typical | Max. | Units |
|---|---|---|---|---|
| Length | 50 | 150 | 300 | microns |
| Width | 50 | 150 | 300 | microns |
| Thickness | 10 | 25 | 50 | microns |
| Density | 100 | 600 | 5000 | $cm^{-2}$ |
| Tip radius | 0.1 | 1 | 5 | microns |
| Surface area per electrode | 2,000 | 22,500 | 200,000 | $micron^2$ |
| Buttress width at base | 30 | 75 | 150 | microns |

Figure 5N:
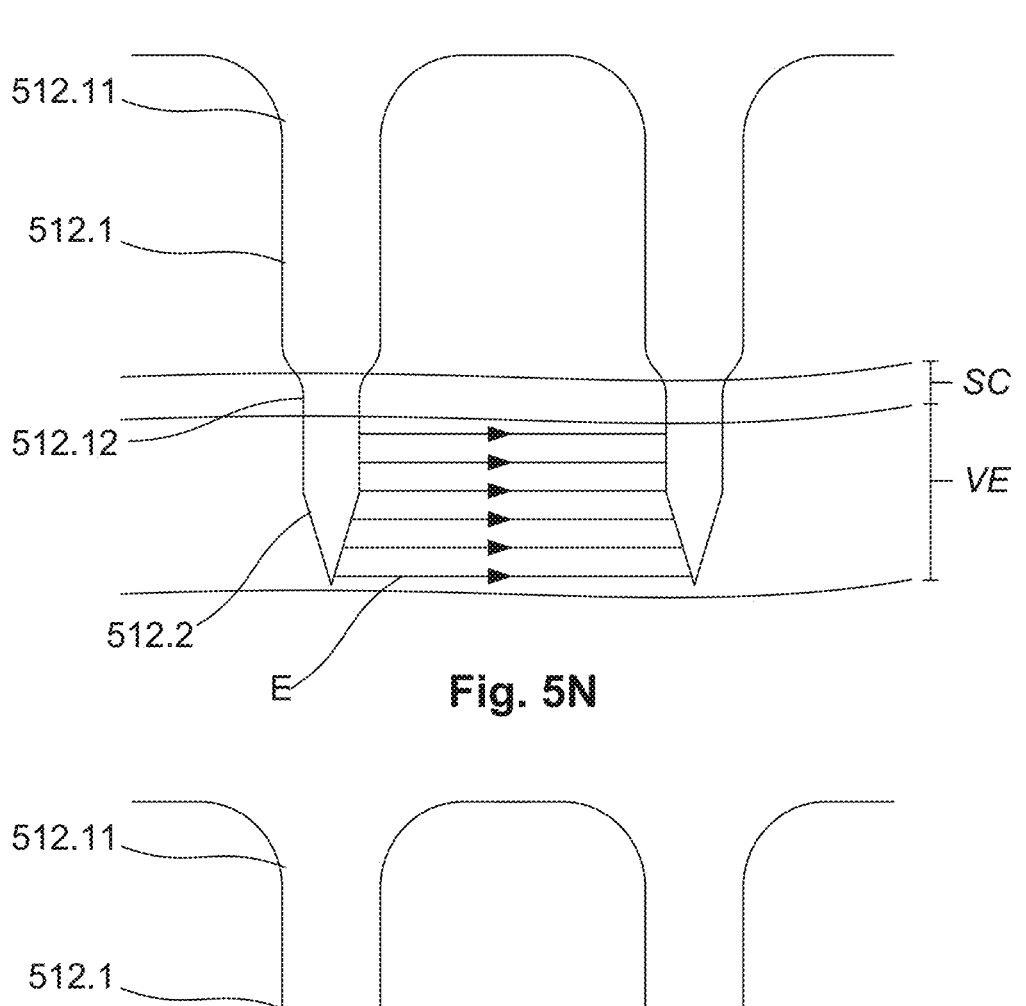
FIG. 5N is a schematic side view of an example of a pair of microstructures inserted into a subject for epidermal measurement.
Figure 5O:
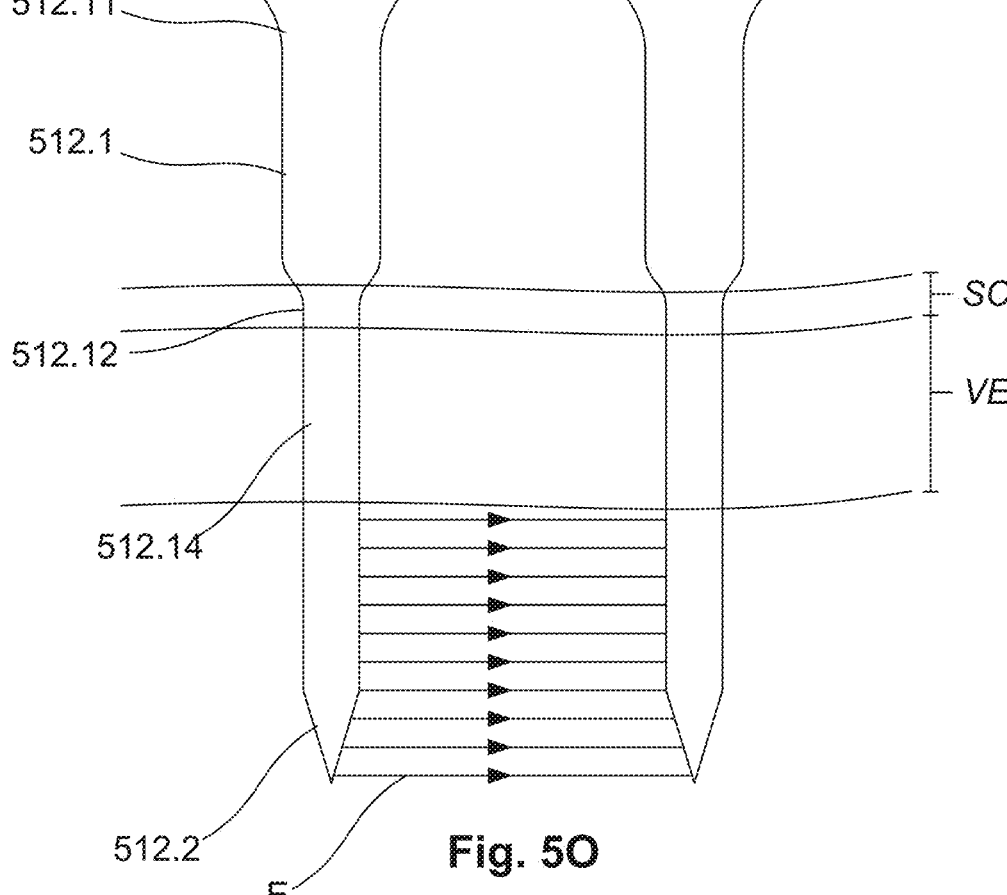
FIG. 5O is a schematic side view of an example of a pair of microstructures inserted into a subject for dermal measurement.

An example of a pair of the microstructures of FIGS. 5L and 5M on insertion into a subject is shown in FIG. 5N.

In this example, the microstructures are configured so that the tip 512.2 penetrates the stratum corneum SC and enters the viable epidermis VE. The waist 512.12, and in particular the shoulders 512.13 abut the stratum corneum SC so that the microstructure does not penetrate further into the subject, and so that the tip is prevented from entering the dermis. This helps avoid contact with nerves, which can lead to pain.

In this configuration, the body 512.1 of the microstructure can be coated with a layer of insulating material (not shown), with only the tip exposed. As a result a current signal applied between the microstructures, will generate an electric field E within the subject, and in particular within the viable epidermis VE, so that measurements reflect fluid levels in the viable epidermis VE.

However, it will be appreciated that other configurations can be used. For example, in the arrangement of FIG. 5O, the shaft 512.14 is lengthened so the tip 512.2 enters the dermis, allowing dermal (and optional epidermal) measurements to be performed.

In this example, typical dimensions are shown in Table 3 below.

TABLE 3

| Parameter | Min. | Typical | Max. | Units |
|---|---|---|---|---|
| Length | 50 | 250 | 450 | microns |
| Width | 50 | 250 | 450 | microns |
| Thickness | 10 | 30 | 50 | microns |
| Density | 100 | 600 | 5000 | $cm^{-2}$ |
| Tip radius | 0.1 | 1 | 5 | microns |
| Surface area per electrode | 10,000 | 62,500 | 427,000 | $micron^2$ |
| Buttress width at base | 30 | 75 | 150 | microns |

An example of the inter and intra pair spacing for these configurations are shown in Table 4 below.

TABLE 4

| Parameter | Min. | Typical | Max. | Units |
|---|---|---|---|---|
| Separation between microstructures in a group or pair | 10 | 100 | 1000 | microns |
| Separation between groups of microstructures | 200 | 500 | 1000 | microns |

Figures 6A, 6B, 7A, 7B:
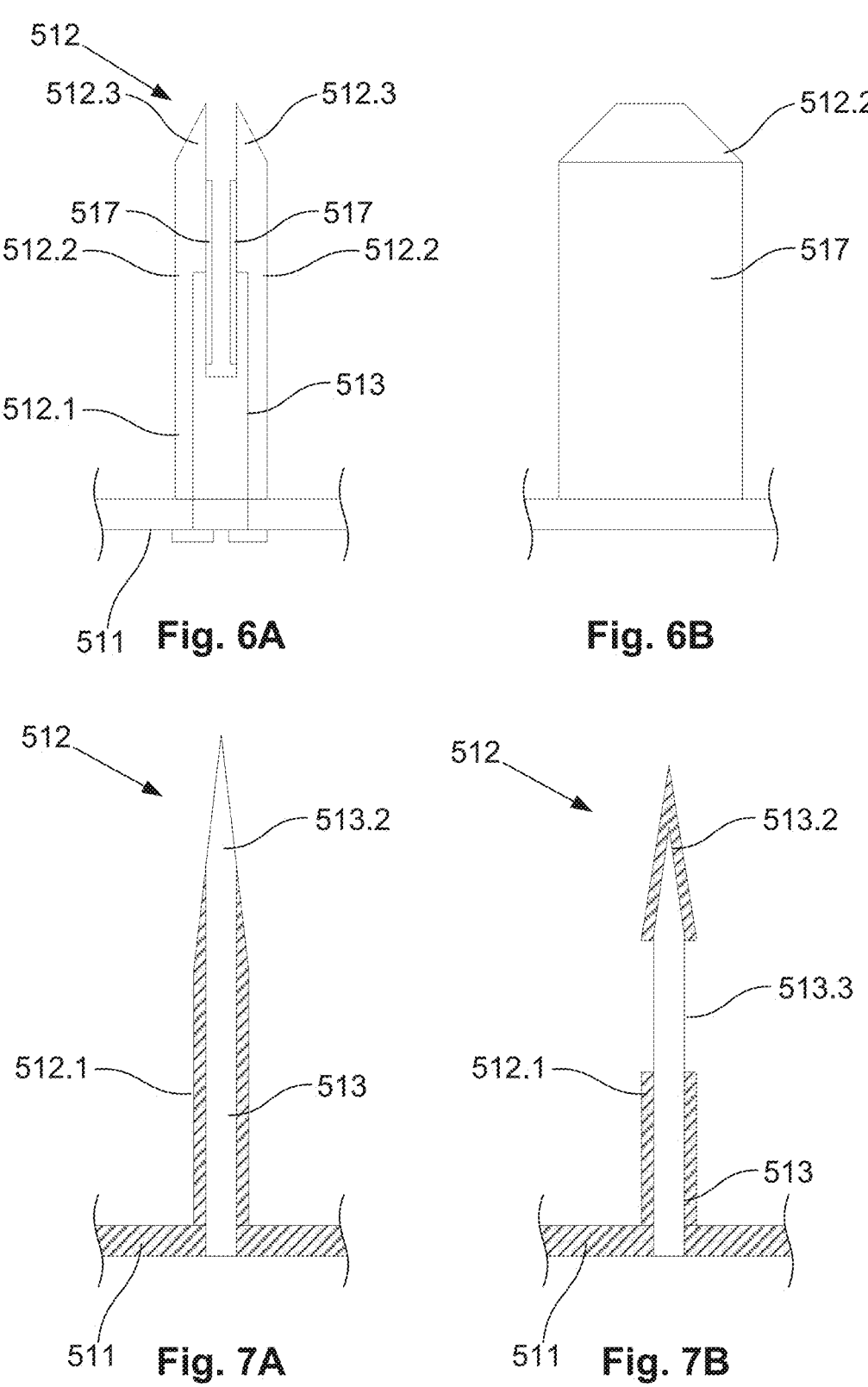
FIG. 6A is a schematic side view of a second example of a microstructure.
FIG. 6B is a schematic front view of the microstructure of FIG. 6A.
FIG. 7A is a schematic diagram of a third example of a microstructure.
FIG. 7B is a schematic diagram of a modified version of the microstructure of FIG. 7A.

A further example arrangement is shown at FIGS. 6A and 6B, with the microstructure again including a generally similar plate like arrangement, with the microstructure including spaced apart prongs 612.2, each having an electrode 617 thereon, so that the electrodes are on faces between the prongs 612.2, again allowing for the application of a highly uniform field, or to allow capacitive sensing to be performed.

A further example of a microstructure is shown at FIG. 7A and FIG. 7B, which includes a body 512.1 containing a core 513 that is conductive, covered by an insulating layer 512.1, which in one example could be a polymer or other material. In this instance, the core 513 terminates at an opening 513.2 allowing electrical signals to be communicated via the outlet. Additionally, and/or alternatively, ports 513.3 may also be provided extending through the insulating layer, allowing electrical signals to be communicated midway along the structure as shown at FIG. 7B, allowing measurements to be performed at targeted depths within the viable epidermis and/or dermis.

It will also be appreciated that when pairs of microstructures are used, electrodes could be provided on an inner face of the pair only, for example, by insulating an outer face of the pair, to thereby reduce electrical interference between different pairs of microstructures.

An alternative technique for manufacturing microstructures will now be described with reference to FIGS. 8A to 8E.

In this example, a carrier wafer 891 is provided and spin coated with a photopolymer layer 892. The photopolymer layer 892 is selectively exposed to UV illumination and crosslinked, to create structural regions 892.1, which in this example form a substrate. A second photopolymer layer 893 is spun coated onto the first layer 891, and exposed to UV illumination and cross linked to form second structural regions 893.1, which in this example form microstructures, extending from the substrate. The carrier wafer and noncrosslinked polymer are removed to create the microstructures shown in FIG. 8D.

Figures 8A, 8B, 8C, 8D, 8E:
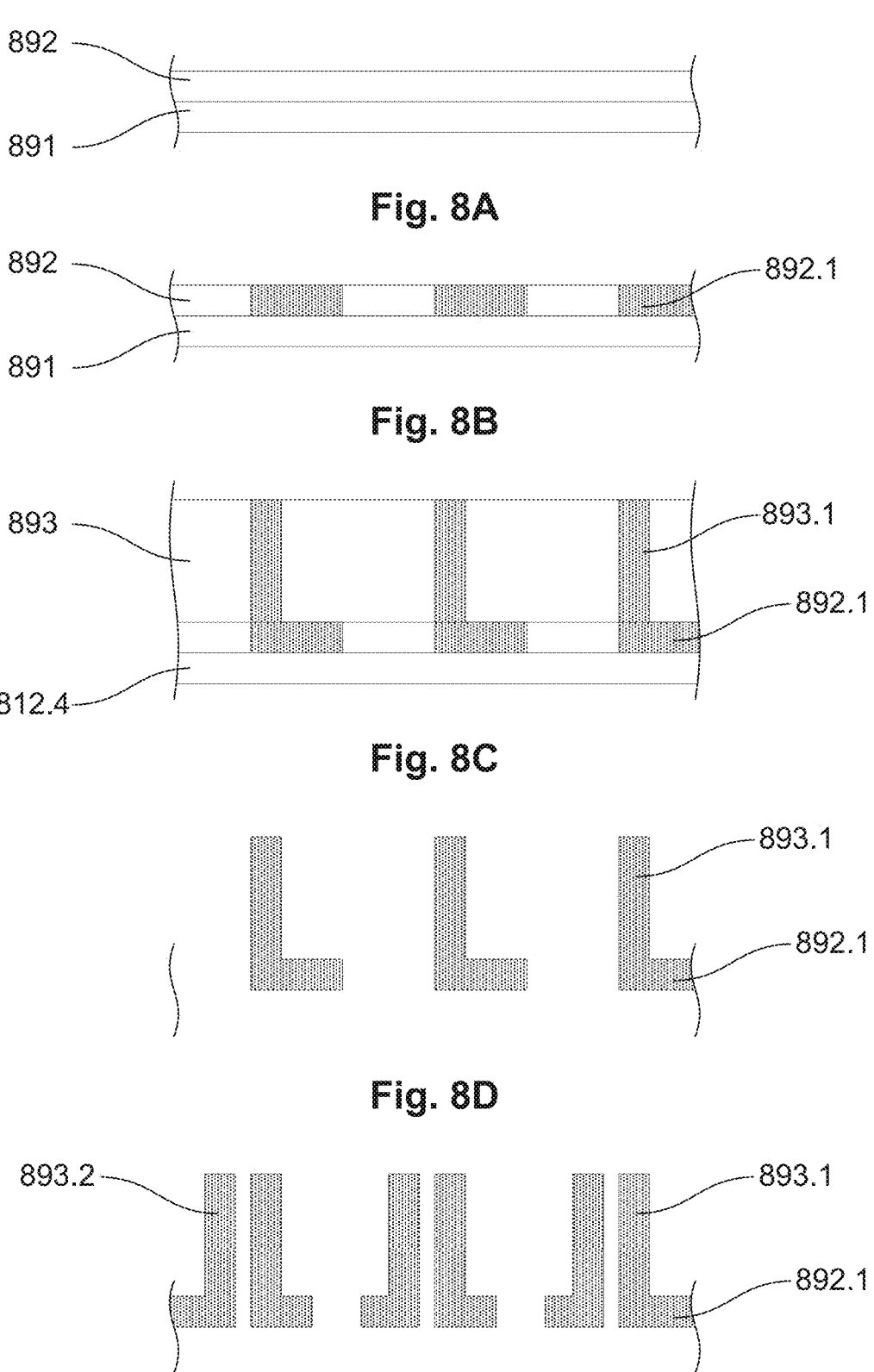
FIG. 8A is a schematic side view of an example of a first step of a microstructure construction technique.
FIG. 8B is a schematic side view of an example of a second step of a microstructure construction technique.
FIG. 8C is a schematic side view of an example of a third step of a microstructure construction technique.
FIG. 8D is a schematic side view of a first example of a microstructure configuration created using the construction technique of FIGS. 8A to 8C.
FIG. 8E is a schematic side view of a second example of a microstructure configuration created using the construction technique of FIGS. 8A to 8C.

It will be appreciated that this layering technique can be used to create a wide range of different microstructure configurations, and alternative design is shown in FIG. 8E.

Figure 9:
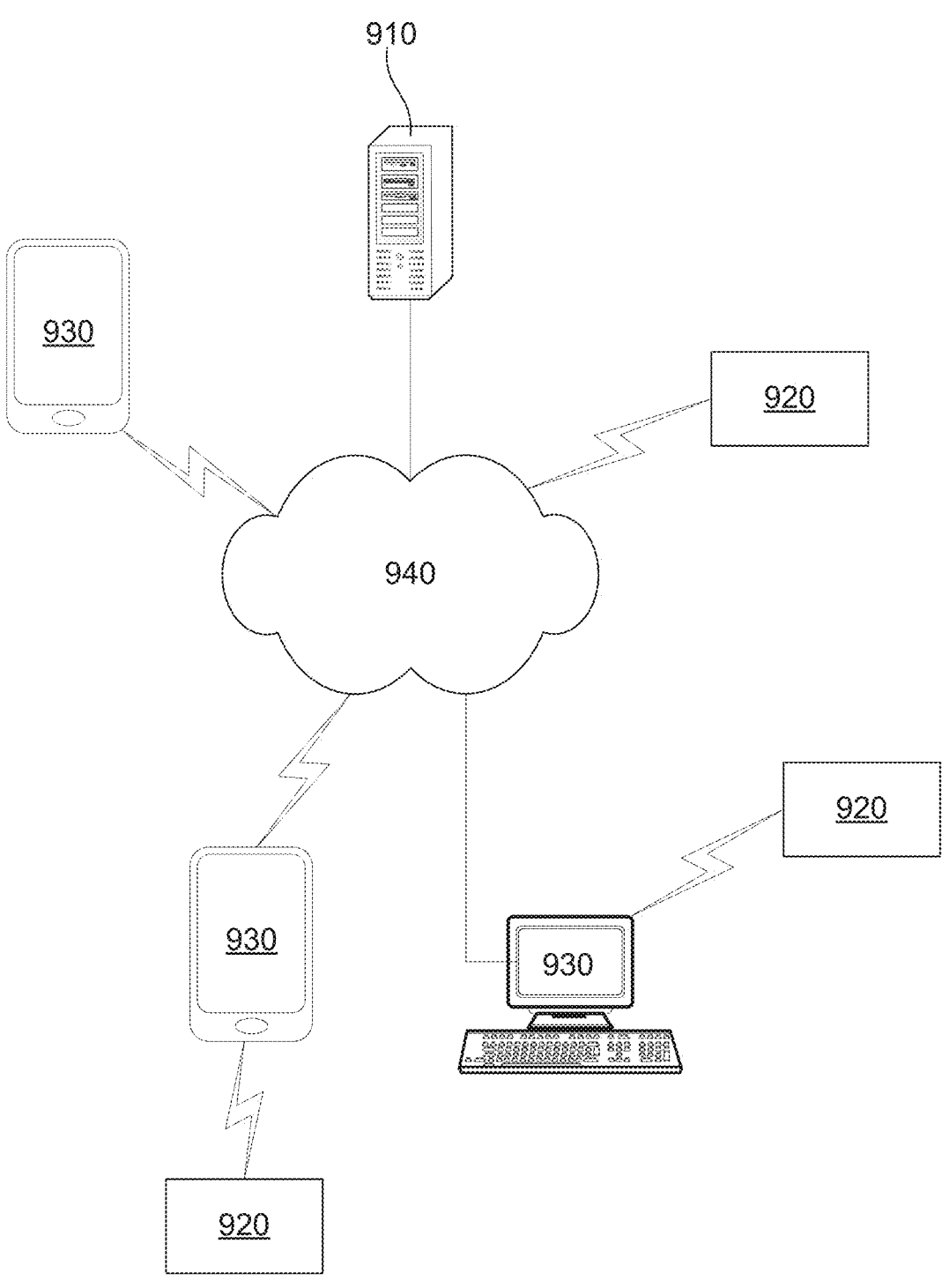
FIG. 9 is a schematic diagram of an example of a distributed computer architecture.

In one example, the monitoring device operates as part of a distributed architecture, an example of which will now be described with reference to FIG. 9.

In this example, one or more processing systems 910 are coupled via communications networks 940, and/or one or more local area networks (LANs), to a number of client devices 930 and monitoring devices 920. The monitoring devices 920 could connect direction to the networks, or could be configured to connect to a client device 930, which then provides onward connectivity to the networks 940. It will be appreciated that the configuration of the networks 940 are for the purpose of example only, and in practice the processing systems 910, client devices 930 and monitoring devices 930 can communicate via any appropriate mechanism, such as via wired or wireless connections, including, but not limited to mobile networks, private networks, such as an 802.11 networks, the Internet, LANs, WANs, or the like, as well as via direct or point-to-point connections, such as Bluetooth, or the like.

In one example, each processing system 910 is configured to receive subject data from a monitoring device 920 or client device 930, and analyse the subject data to generate one or more health status indicators, which can then be provided to a client device 930 or monitoring device 920 for display. Whilst the processing system 910 is a shown as a single entity, it will be appreciated that the processing system 910 can be distributed over a number of geographically separate locations, for example by using processing systems 910 and/or databases that are provided as part of a cloud-based environment. However, the above described arrangement is not essential and other suitable configurations could be used.

Figures 10, 11:
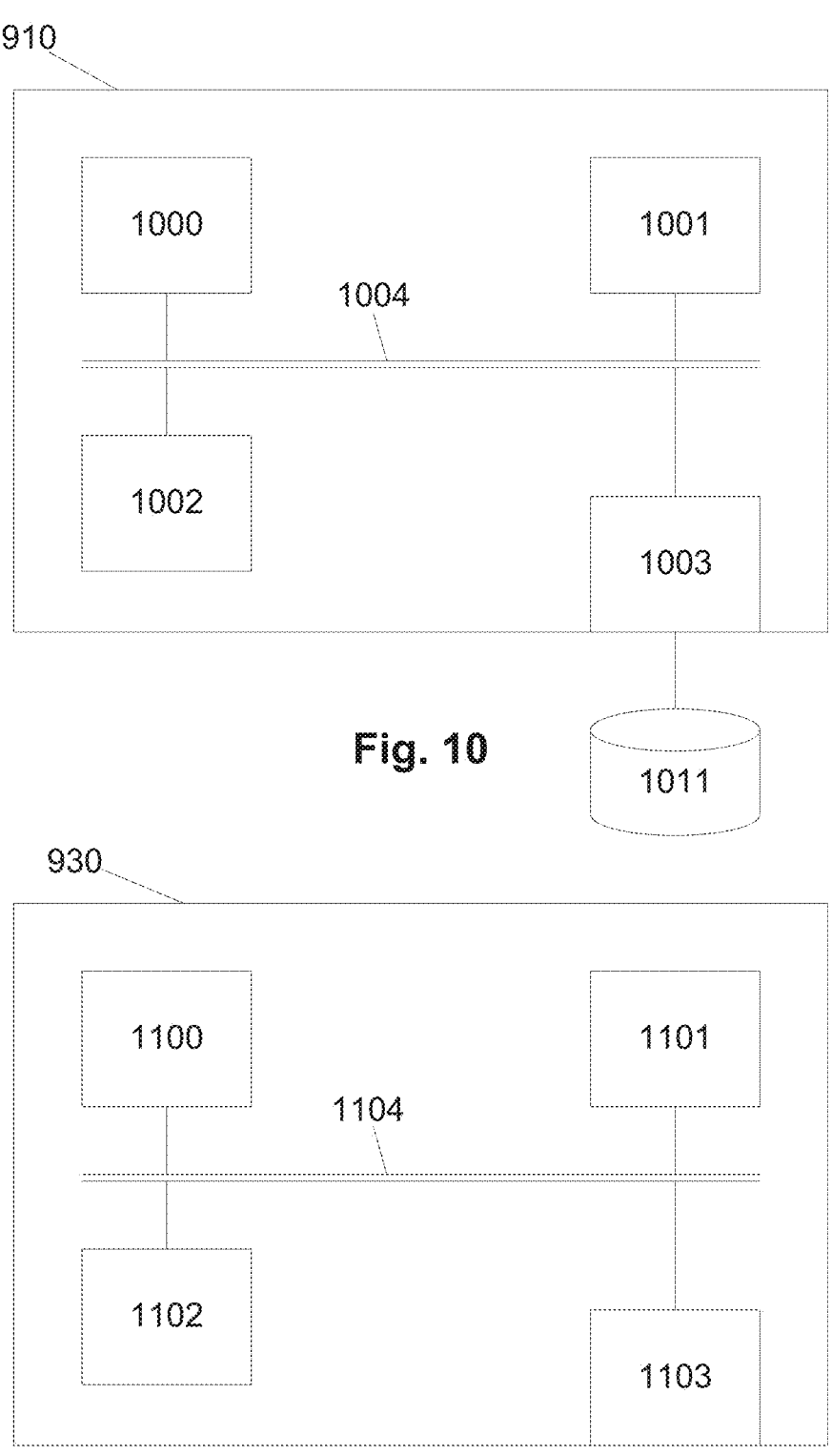
FIG. 10 is a schematic diagram of an example of a processing system.
FIG. 11 is a schematic diagram of an example of a client device.

An example of a suitable processing system 910 is shown in FIG. 10.

In this example, the processing system 910 includes at least one microprocessor 1000, a memory 1001, an optional input/output device 1002, such as a keyboard and/or display, and an external interface 1003, interconnected via a bus 1004 as shown. In this example the external interface 1003 can be utilised for connecting the processing system 910 to peripheral devices, such as the communications network 940, databases 1011, other storage devices, or the like. Although a single external interface 1003 is shown, this is for the purpose of example only, and in practice multiple interfaces using various methods (eg. ethernet, serial, USB, wireless or the like) may be provided.

In use, the microprocessor 1000 executes instructions in the form of applications software stored in the memory 1001 to allow the required processes to be performed. The applications software may include one or more software modules, and may be executed in a suitable execution environment, such as an operating system environment, or the like.

Accordingly, it will be appreciated that the processing system 910 may be formed from any suitable processing system, such as a suitably programmed client device, PC, web server, network server, or the like. In one particular example, the processing system 910 is a standard processing system such as an Intel Architecture based processing system, which executes software applications stored on non-volatile (e.g., hard disk) storage, although this is not essential. However, it will also be understood that the processing system could be any electronic processing device such as a microprocessor, microchip processor, logic gate configuration, firmware optionally associated with implementing logic such as an FPGA (Field Programmable Gate Array), or any other electronic device, system or arrangement.

An example of a suitable client device 930 is shown in FIG. 11.

In one example, the client device 930 includes at least one microprocessor 1100, a memory 1101, an input/output device 1102, such as a keyboard and/or display, and an external interface 1103, interconnected via a bus 1104 as shown. In this example the external interface 1103 can be utilised for connecting the client device 930 to peripheral devices, such as the communications networks 940, databases, other storage devices, or the like. Although a single external interface 1103 is shown, this is for the purpose of example only, and in practice multiple interfaces using various methods (eg. Ethernet, serial, USB, wireless or the like) may be provided.

In use, the microprocessor 1100 executes instructions in the form of applications software stored in the memory 1101 to allow communication with the processing system 910 and/or monitoring device 920.

Accordingly, it will be appreciated that the client devices 1130 may be formed from any suitable processing system, such as a suitably programmed PC, Internet terminal, laptop, or hand-held PC, and in one preferred example is either a tablet, or smart phone, or the like. Thus, in one example, the client device 1130 is a standard processing system such as an Intel Architecture based processing system, which executes software applications stored on non-volatile (e.g., hard disk) storage, although this is not essential. However, it will also be understood that the client devices 1130 can be any electronic processing device such as a microprocessor, microchip processor, logic gate configuration, firmware optionally associated with implementing logic such as an FPGA (Field Programmable Gate Array), or any other electronic device, system or arrangement.

Examples of the processes for performing measurements and generating indicators will now be described in further detail. For the purpose of these examples it is assumed that one or more processing systems 910 acts to analyse received subject data and generate resulting indicators. Measurements are performed by the monitoring devices 920, with subject data being transferred to the processing systems 910 via the client devices 230. In one example, to provide this in a platform agnostic manner, allowing this to be easily accessed using client devices 930 using different operating systems, and having different processing capabilities, input data and commands are received from the client devices 930 using via a webpage, with resulting visualisations being rendered locally by a browser application, or other similar application executed by the client device 930. The processing system 910 is therefore typically a server (and will hereinafter be referred to as a server) which communicates with the client device 930 and/or monitoring device 920, via a communications network 940, or the like, depending on the particular network infrastructure available.

To achieve this the server 910 typically executes applications software for hosting webpages, as well as performing other required tasks including storing, searching and processing of data, with actions performed by the processing system 910 being performed by the processor 1000 in accordance with instructions stored as applications software in the memory 1001 and/or input commands received from a user via the I/O device 1002, or commands received from the client device 1030.

It will also be assumed that the user interacts with the server 910 via a GUI (Graphical User Interface), or the like presented on the client device 930, and in one particular example via a browser application that displays webpages hosted by the server 910, or an App that displays data supplied by the server 910. Actions performed by the client device 930 are performed by the processor 1100 in accordance with instructions stored as applications software in the memory 1101 and/or input commands received from a user via the I/O device 1102.

However, it will be appreciated that the above described configuration assumed for the purpose of the following examples is not essential, and numerous other configurations may be used. It will also be appreciated that the partitioning of functionality between the monitoring devices 920, client devices 930, and the server 910 may vary, depending on the particular implementation.

Figure 12A:
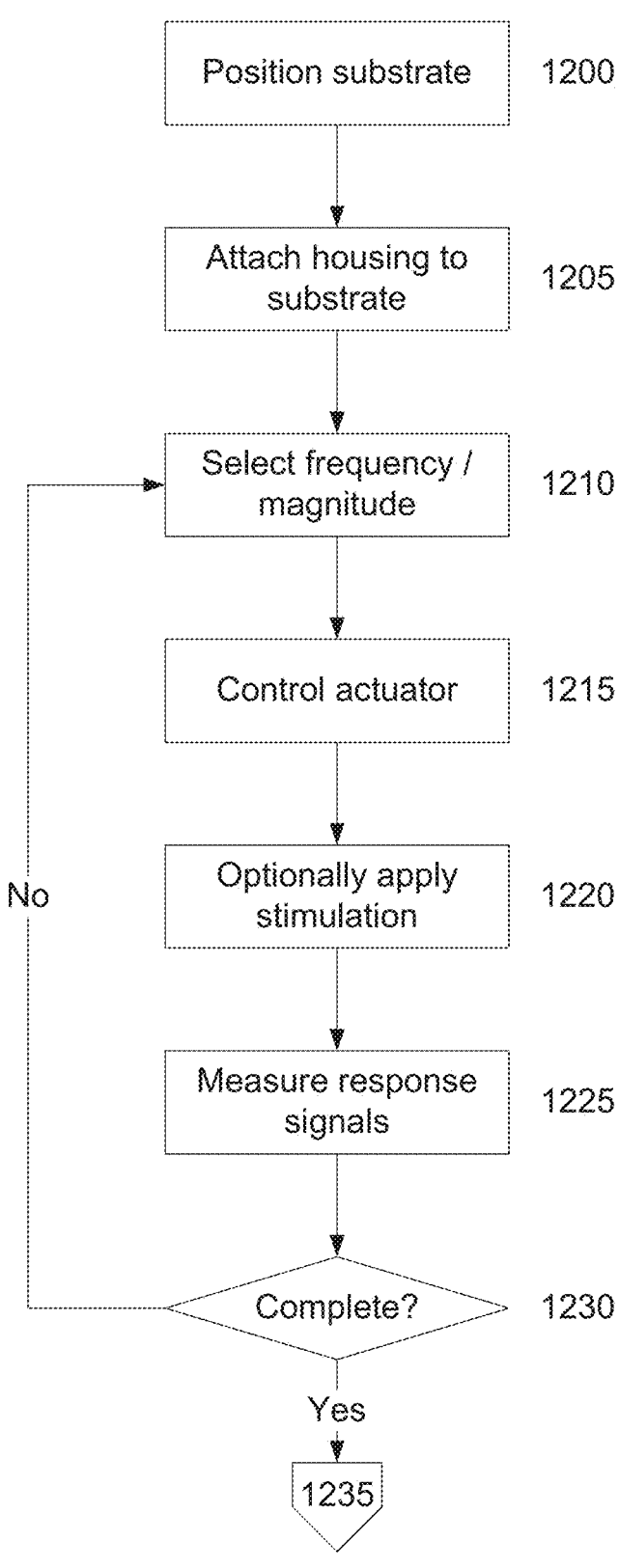
FIGS. 12A and 12B are a flow chart of an example of a process for delivering treatment to a biological subject.
Figure 12B:
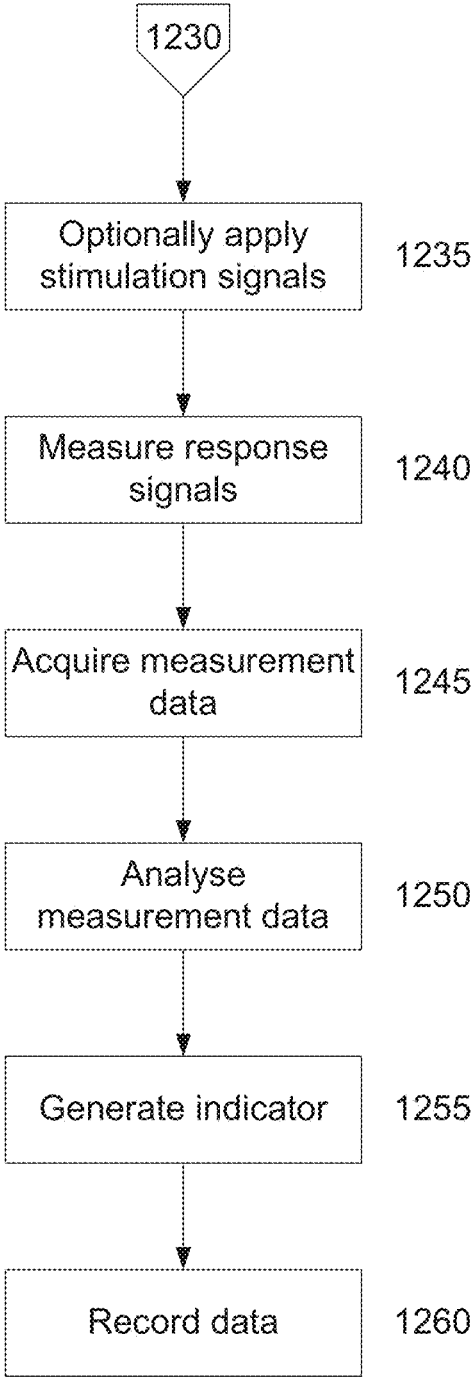

An example of process for performing measurements on a subject will now be described in more detail with reference to FIGS. 12A and 12B.

In this example, a process for applying a patch including the substrate and microstructures is shown in steps 1200 to 1230, whilst a measurement process is shown in steps 1235 to 1260. In this regard, it will be appreciated that for patches that are used for performing multiple measurements over a period of time, steps 1200 to 1230 would only be performed a single time, with steps 1235 to 1260 being repeated as needed.

Furthermore, for the purpose of this example, it is assumed that the system includes a reader formed by the housing 330 and associated signal generator, sensor and processing electronics. The reader could be integral with the patch 310 and/or separate from the patch 310 depending on the preferred implementation.

At step 1200, the substrate is provided in a desired position, with the substrate and microstructures in place against the subject. At step 1205, assuming the reader is not integrated into the patch 310, the housing 330 is attached to the substrate 311, for example, by magnetically or otherwise coupling the housing and substrate, or by holding the housing in contact with the patch 310.

At step 1210, the processing device 322 selects a frequency/magnitude for the actuator. This can be a standard value and/or might depend on the barrier to be breached, so that different values might be selected for different sites on a subject, and/or for different subjects.

At step 1215, the actuator 326 is controlled, to thereby begin vibration of the microstructures, and hence facilitate movement of the microstructures within the subject.

At step 1220 stimulation is optionally applied, with response signals being measured at step 1225, allowing the processing device 322 to monitor breaching of the functional barrier and/or a depth of penetration. The mechanism for achieving this will depend on the nature of the response signals and optional stimulation. For example, the stimulation and response could be used to derive an impedance, with the impedance value altering as the microstructures penetrate the stratum corneum and enter the viable epidermis.

At step 1230, the processing device 322 optionally determines if breaching or penetration are complete and if not the process returns to step 1210 to select a different frequency and/or magnitude. Thus, this process allows the frequency and/or magnitude of any applied force to be adjusted continuously as the substrate and microstructures are applied, and in particular as the microstructures breach and optionally penetrate the functional barrier. In one example, this is used to allow the frequency to decrease during insertion, whilst the force progressively increases until the barrier is breached, at which point the force decreases. In this regard, it has been found that this can facilitate penetration of the barrier.

Once the patch is applied, measurements can commence. In this regard, if the reader is integrated into the patch, measurements can be performed as needed. Alternatively, if the reader is separate, this may require the reader be brought into proximity and/or contact with the patch, to allow a measurement to be performed.

In this example, at step 1235 the monitoring device 920 applies one or more stimulatory signals to the subject, and then measures response signal at step 1240. The response signals are measured by the sensor 321, which generates measurement data that is provided to the processing device 322 at step 1245. In this example, the monitoring device 920 then transfer the measurement data to a client device 930 for further processing. In particular, the client device 930 might perform preliminary pre-processing of data and may append additional information, for example derived from onboard sensors, such as GPS or other like, to thereby add time or location information, or the like. This information can be useful in circumstances, such as tracking spread of infectious diseases or similar.

The resulting data is collated, for example by creating subject data, which can then be transferred to a server 910 allowing this to be analysed at step 1250. However, it will also be appreciated that the analysis could be performed on board the reader, and an indicator derived by performing the analysis could be displayed on the reader.

The nature of the analysis will vary depending on the preferred implementation and a wide range of options are envisaged.

When performing fluid level measurements, alternating electrical current signals are applied to the subject via a pair of microstructures, with resulting voltage signals being measured via the same microstructures. The magnitude and phase of the applied current and resulting voltage can then be used to calculate an impedance value, which depends on fluid levels within the subject. Accordingly, the measured impedance value can be correlated with a fluid level, allowing a subject hydration to be determined, and an example of this will be described in more detail below.

It will further be appreciated that different information can be derived depending on the frequency at which measurements are performed. For example, the system can use Bioimpedance Analysis (BIA) in which a single low frequency signal is injected into the subject S, with the measured impedance being used directly in the determination of biological parameters. In one example, the applied signal has a relatively low frequency, such as below 100 kHz, more typically below 50 kHz and more preferably below 10 kHz. In this instance, such low frequency signals can be used as an estimate of the impedance at zero applied frequency, which are indicative of extracellular fluid levels.

Alternatively, the applied signal can have a relatively high frequency, such as above 200 kHz, and more typically above 500 kHz, or 1000 kHz. In this instance, such high frequency signals can be used as an estimate of the impedance at infinite applied frequency, which is in turn indicative of a combination of the extracellular and intracellular fluid levels.

Alternatively, and/or additionally, the system can use Bioimpedance Spectroscopy (BIS) in which impedance measurements are performed at multiple frequencies, which can then be used to derive information regarding both intracellular and extracellular fluid levels, for example by fitting measured impedance values to a Cole model.

When performing analyte level or concentration measurements, alternating electrical current signals are applied to the subject via a pair of microstructures, with resulting voltage signals being measured via the same microstructures. The magnitude and phase of the applied current and resulting voltage can then be used to calculate an impedance or capacitance value, which depends on analyte level or concentration within the subject. Accordingly, the measured impedance value can be correlated with an analyte level or concentration, allowing the progression of a disease, disorder or condition to be monitored or a disease, disorder or condition to be diagnosed, or the presence, absence, level or concentration of a medicament, illicit substance or non-illicit substance of abuse, or chemical warfare agent, poison or toxin to be determined.

For example, the subject data could be used in conjunction with previously collected subject data in order to perform a longitudinal analysis, examining changes in measured values over time. Additionally, and/or alternatively, the subject data could be analysed using a machine learning model or similar.

At step 1255, the treatment delivery mechanism is controlled to allow treatment to be delivered to the user. In a preferred example, the microstructures include a coating that dissolves on application of stimulation, allowing treatment material to be delivered to the subject. Typically different microstructures have different doses of treatment material and/or different treatment material doses, so that the monitoring device 920 can apply stimulation selectively to different microstructures, to allow different treatments or different doses to be delivered.

One or more indicators may be generated at step 1260, with the nature of the indicators and the manner in which these are generated varying depending upon the preferred implementation and the nature of the analysis being performed.

At step 1265 data, such as the subject data, the indicators, or the measurement data, are recorded allowing this to be subsequently accessed as needed. The indicator may also be provided to the client device 930 and/or monitoring device 920, allowing this to be displayed.

Figure 13:
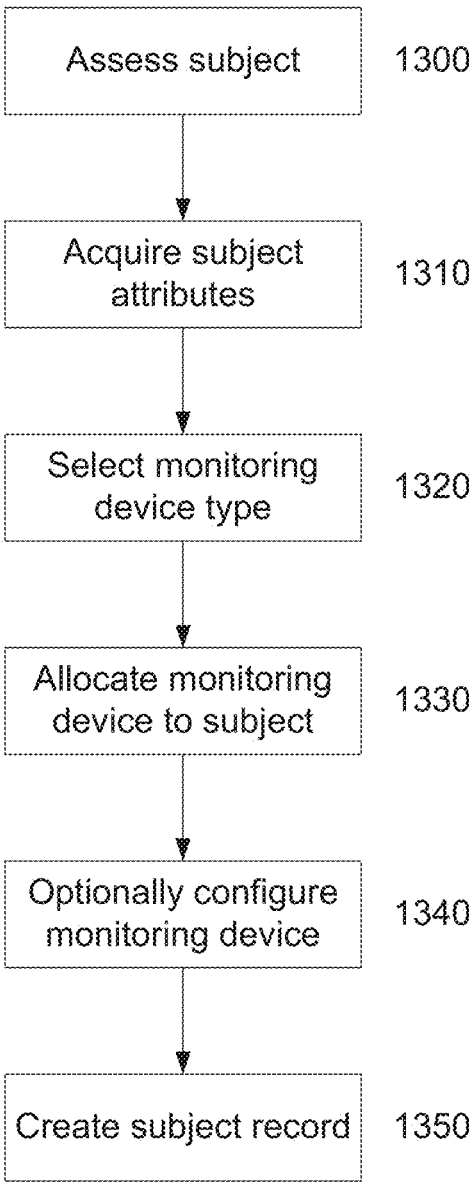
FIG. 13 is a flow chart of an example of a process for creating a subject record.

In one example, monitoring devices are allocated to respective users, with this allocation being used to track measurements for the subject. An example of a process for allocating a monitoring device 920 to a subject will now be described with reference to FIG. 13.

In this example, the subject initially undergoes an assessment at step 1300, with this process being performed by a clinician. The clinician will use the assessment to guide the type of monitoring that needs to be performed, for example to identify particular biomarkers that are to be measured, which in turn may depend on any symptoms or medical diseases, disorders or conditions suffered by the subject. As part of this process, the clinician will typically acquire subject attributes at step 1310, such as measurement of weight, height, age, sex, details of medical interventions, or the like. This can be performed using a combination or techniques, such as querying a medical record, asking questions, performing measurements or the like.

Once the assessment has been completed, a monitoring device type can be selected at 1320, with this being performed based on the measurements that are required. In this regard, it will be appreciated that different combinations of microstructure arrangement and sensing modalities can be used in order to allow a range of different measurements to be performed, and it is therefore important that the correct selection is made to enable the measurements to be collected. A specific monitoring device 920 is then allocated to the subject at step 1330. In this regard, in each device will typically include a unique identifier, such as a MAC (Media Access Control) address or other identifier, which can be used to uniquely associate the monitoring device with the subject.

At step 1340 the monitoring device 920 can optionally be configured, for example to update firmware or the instruction set needed to perform the respective measurements. At step 1350, a subject record is created, which is used to store details associated with the subject, including subject attributes, subject data, indicators, or any other relevant information. Additionally, the subject record will also typically include an indication of the monitoring device identifier, thereby associating the monitoring device with the subject.

Figure 14A:
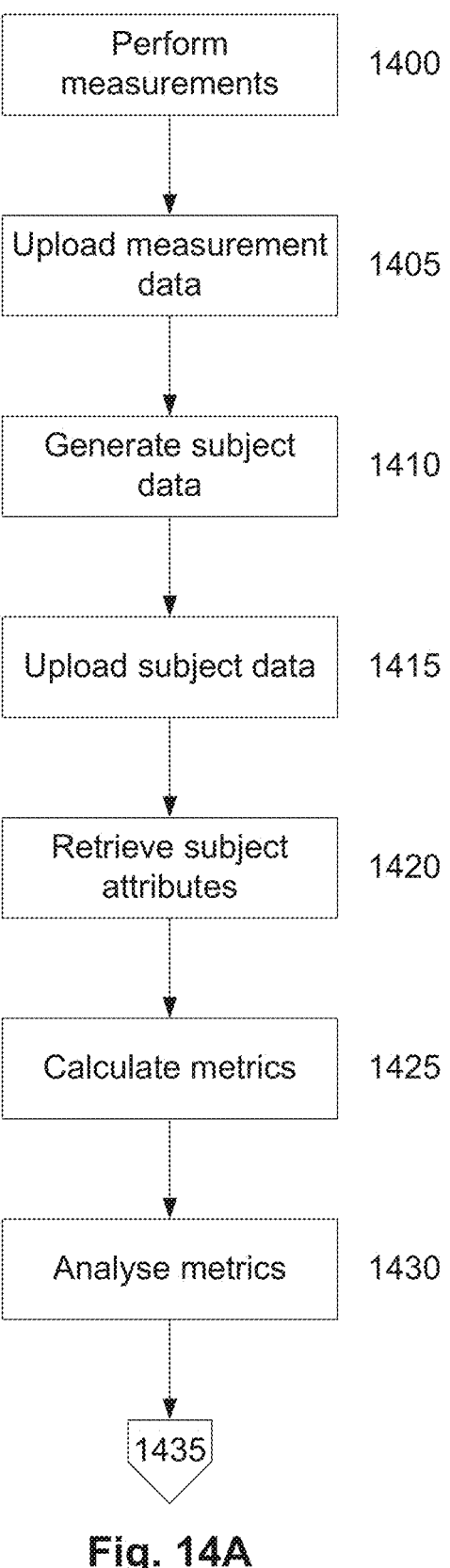
FIGS. 14A and 14B are a flow chart of a specific example of a process for delivering treatment to a biological subject.
Figure 14B:
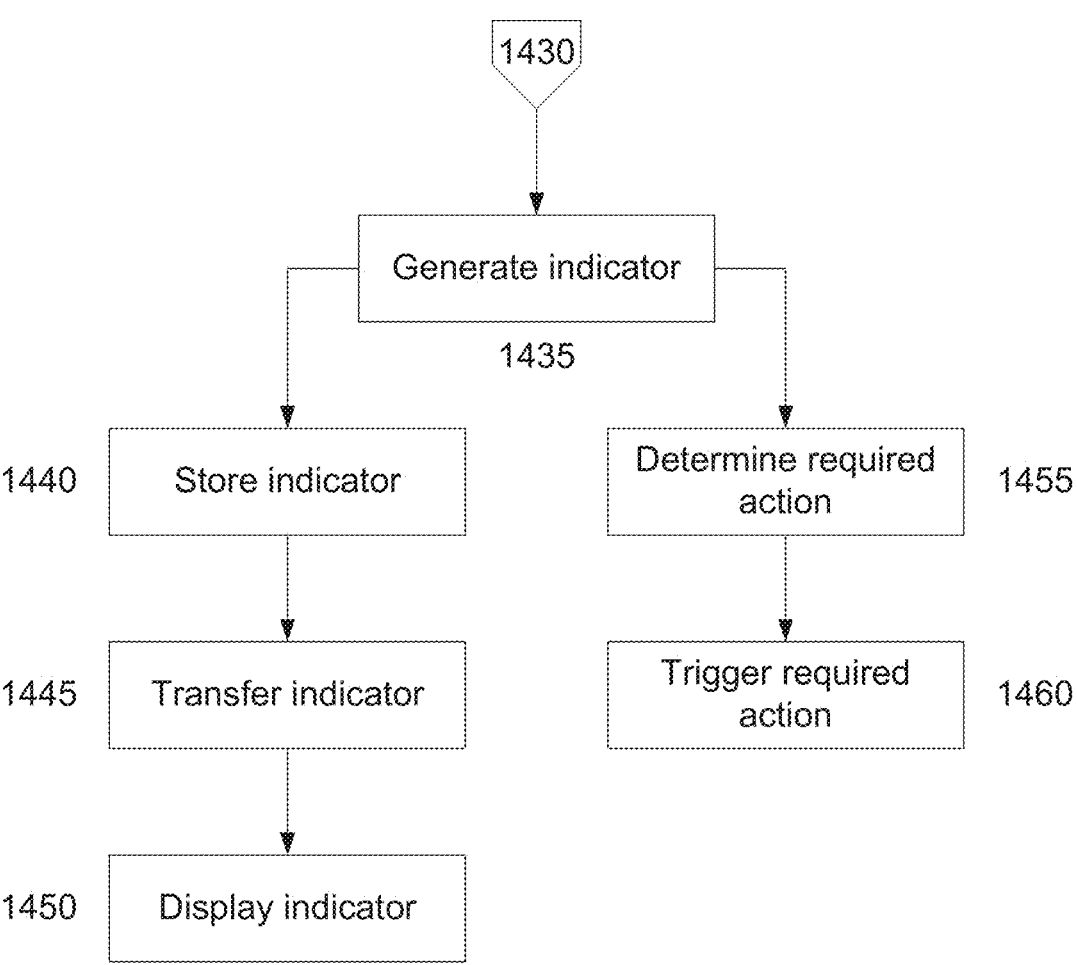

An example of the process of using the device to perform treatment will now be described with reference to FIGS. 14A and 14B.

In this example, at step 1400 one or more measurements are performed. The measurements are performed by utilising the process described above, for example by having the monitoring device apply stimulatory signals and measure response signals. Measurement data is recorded based on the response signals with this being uploaded to the client device 930 at step 1405, allowing the client device 930 to generate subject data at step 1410. The subject data could simply be the measurement data, but may also include additional information provided by the client device 930. This allows user inputs to be provided via the client device 930, for example providing details of symptoms, changes in attributes or the like. The subject data is then uploaded to the server 910 at step 1415. The server 910 then retrieves one more subject attributes at step 1420, for example from the subject record, with the server 910 then calculating one or more metrics at step 1425.

At step 1430, the server 910 analyses the metrics. The manner in which this is performed will vary depending on the preferred implementation. For example, this could be achieved by applying the metrics to a computational model that embodies a relationship between a relevant health status and the one or more metrics. Alternatively, the metrics could be compared to defined thresholds, which can be established from a population of reference subjects, and which are used to represent certain diseases, disorders or conditions, such as the presence or absence of a medical condition. As a further option, the metrics could be compared to previous metrics for the subject, for example to examine changes in the metrics, which could in turn represent a change in health status. The results of the analysis can be used to generate one or more indicators at step 1435. In one example, the indicator can be in the form of a score representing a health status, or could be indicative of a presence, absence or degree of condition.

At step 1440 the indicator can be stored, with an indication of the indicator being transferred to the client device 930 at step 1445, allowing the indicator to be displayed, either by the client device 930 or the monitoring device 920 at step 1450.

Additionally, and/or alternatively, at step 1455 the indicator can be used to determine if an action is required, for example if an intervention should be performed. The assessment of whether an action is required could be performed in any one of a number of manners, but typically involves comparing the indicator to assessment criteria defining a predetermined threshold or range of acceptable indicator values. For example, comparing a hydration indicator to a range indicative of normal hydration, or comparing an analyte indicator indicative of a normal level or concentration of analytes.

The assessment criteria can also specify the action required if the indicator falls outside of the acceptable range, and any steps required to perform the action, allowing the action to be performed at step 1460. For example, in a theranostic application, this could involve causing the applying monitoring device to apply a stimulation signal to electrodes, thereby allowing one or more therapeutic agents to be released. Alternatively, if the subject is dehydrated, the action could include having the monitoring device provide a recommendation to the user to hydrate, whereas if certain analytes are detected, this could be indicative of a medical situation, in which the processing system or monitoring device could generate a notification which is provided to a clinician, or other nominated person or system, allowing them to be alerted. The notification could include any determined indicator and/or measured response signals, allowing the clinician to rapidly identify any interventions needed. In a theranostic application, the action could involve causing the applying monitoring device to apply a stimulation signal to electrodes, thereby allowing one or more therapeutic agents to be released. This could be performed in accordance with a dosing regime, which could be specified as part of the assessment criteria or defined manually by a clinician, for example in response to a notification provided as described above. Alternatively, the action could involve notifying the user, so for example, if the subject is dehydrated, the action could include having the monitoring device provide a recommendation to the user to hydrate.

It will be therefore be appreciated that this enables actions to be triggered as needed.

In one example, this allows the treatment delivery mechanism can be controlled, in order to allow treatment to be delivered. Specifically, this will be performed by applying stimulation to respective microstructures, allowing a desired dose of a treatment material to be delivered.

The above described processes describe transfer of data to remote systems for analysis, which can have a number of benefits. For example, this allows more complex analysis to be performed than would otherwise be the case with existing processing capabilities. This also allows remote oversight, for example, allowing a clinician to access records associated with multiple patients, in real-time, enabling the clinician to respond rapidly as needed. For example, in the event that measured data shows an indication of a deleterious health state, the clinician could be alerted or notified, allowing an intervention to be triggered. Similarly, in a case where a treatment material is to be delivered, this can be used to provide oversight, and specifically to allow a clinician to approve the treatment prior to administration. Additionally, collective monitoring provides public health benefits, for example to allow tracking of infectious diseases or similar. Furthermore, central analysis allows data mining to be used in order refine analysis processes, making this more accurate as more data is collected.

However, it will be appreciated that the distributed implementation is not essential, and additionally or alternatively, analysis could be performed in situ, for example, by having the monitoring device 920 and/or client device 930 perform steps 1425 to 1460 with resulting information being displayed locally, for example, using the client device 930 or a in-built display.

A further example of a microstructure arrangement and analysis technique will now be described with reference to FIGS. 15A to 15F.

In this example, a patch 1510 is provided, including a substrate 1511 having a number of microstructures 512 thereon. The form and configuration of the microstructures is not critical for the purpose of this example, and it will be appreciated that a range of different configurations could be used, as described above.

In this example, the substrate 1511 includes a substrate coil 1515, positioned on the substrate 1511, typically on a rear surface. The coil is operatively coupled to the one or more microstructure electrodes, which could be electrodes provided on microstructures, or conductive microstructures themselves. Typically the substrate coil includes two ends, with each end being coupled to different microstructure electrodes, as shown by the dotted lines, so that a signal in the substrate coil 1511 is applied between the microstructure electrodes. An excitation and receiving coil (not shown) is provided, typically in a housing of a measuring device, so that the excitation and receiving coil is aligned with and placed in proximity to the substrate coil when a measurement is to be performed, for example, when the housing is attached to the substrate. This is performed to inductively couple the excitation and receiving coil to the substrate coil, so that when an excitation signal is applied to the excitation and receiving coil by the signal generator, this induces a corresponding signal in the substrate coil 1515, which is then applied across the microstructure electrodes.

Figure 15A:
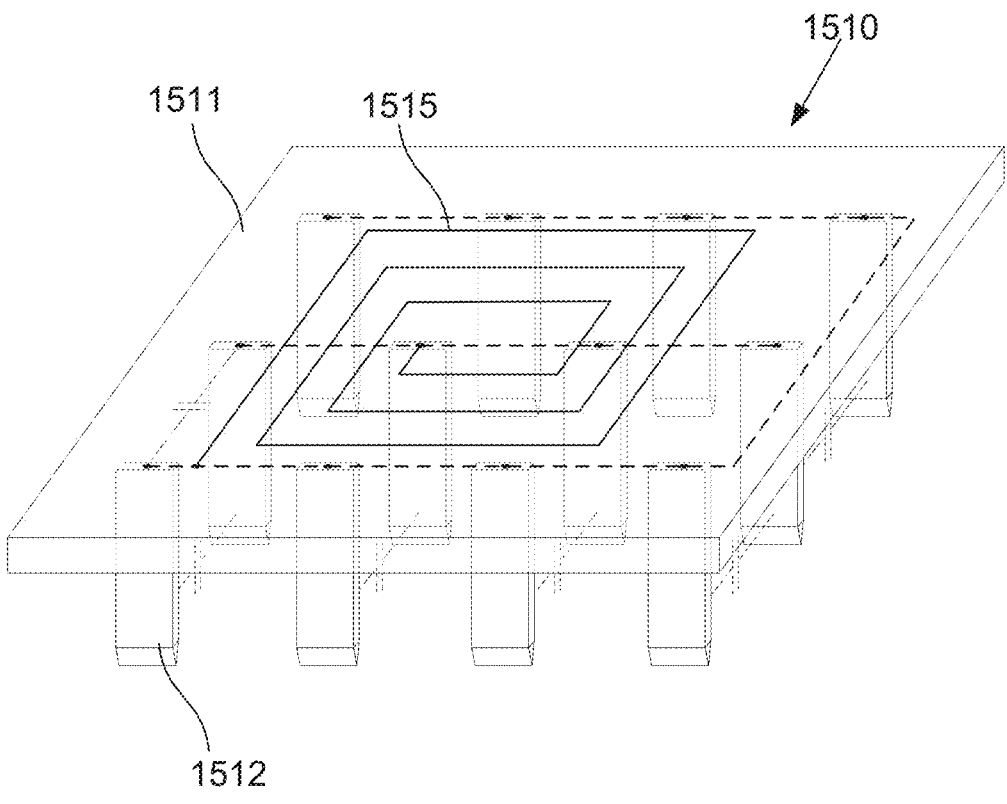
FIG. 15A is a schematic perspective topside view of an example of a patch including a substrate incorporating microstructure electrodes and a substrate coil.
Figure 15B:
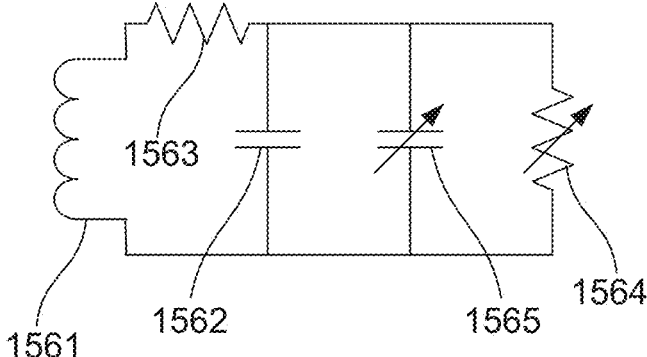
FIG. 15B is a schematic diagram of an equivalent circuit representing the electrical response of the patch of FIG. 15A.

The tissue and/or fluid surrounding the microstructure electrodes, and the electrodes, act as capacitors, as shown. As a result, the excitation and receiving coil and the substrate coil act as a tuned circuit, and an example circuit configuration is shown in FIG. 15B. This includes a fixed inductance 1561 and capacitance 1562 and resistance 1563, representing the inherent responsiveness of the excitation and substrate coils. The circuit also includes a variable capacitance and variable resistance 1565, 1564, representing the responsiveness of the microstructure electrodes, and the tissue or other materials between the electrodes. Thus, it will be appreciated that the frequency response and damping (Q) of the tuned circuit will vary depending on the values of the variable capacitance and resistance, which in turn depends on the environment within which the microstructure electrodes are present.

Figure 15C:
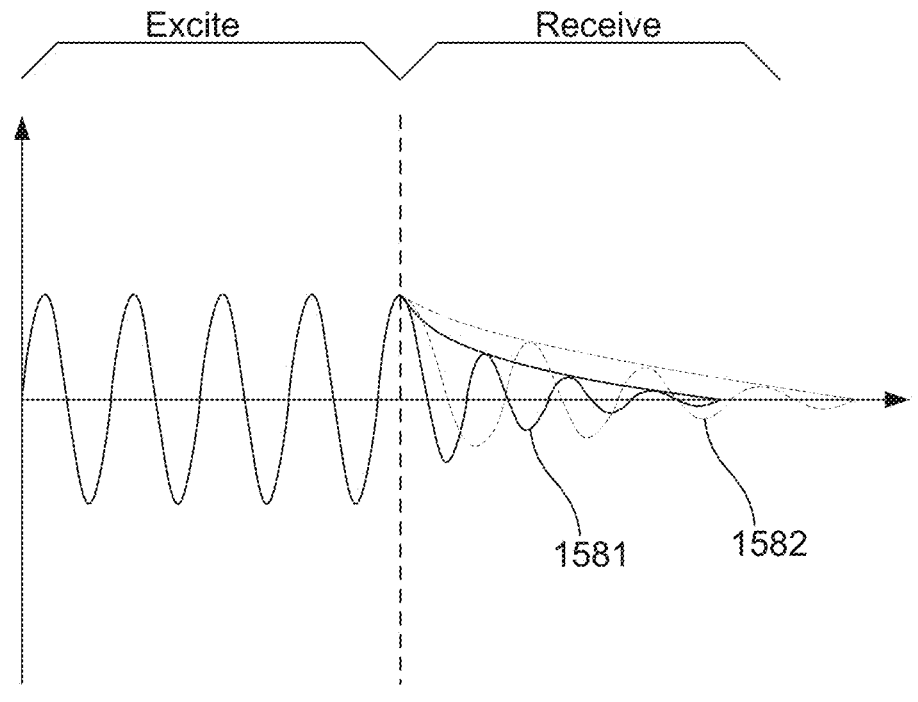
FIG. 15C is a graph illustrating the response to a drive signal for the patch of FIG. 15A.

In general, when a signal is applied to the excitation and receiving coil, the overall response will be a constant amplitude signal in the excitation and receiving coil, as shown in FIG. 15C. When the drive signal is halted, the circuit will continue to resonant, with the resulting signal decaying over time as shown to the right of the dotted line. The rate and/or frequency of the decay depends on the values of the variable capacitance and resistance, so different responses 1581, 1582 will arise depending on conditions within the subject, which in turn allows information regarding conditions within the subject to be derived. For example, this can be influenced by binding of analytes to the microstructure electrode, fluid levels, or the like, so examining changes in the decay rate and frequency can be used to derive information regarding the presence of analytes, fluid levels, or the like.

Figure 15D:
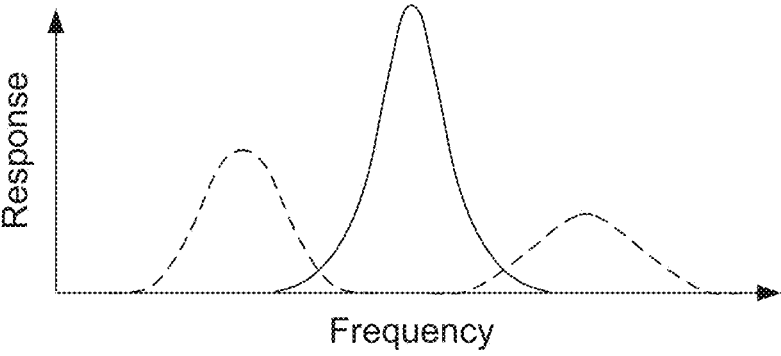
FIG. 15D is a graph illustrating the resonance response of the patch of FIG. 15A.

However, as decay signals are transient, in another example the circuit's response at different frequencies is analysed and used to determine the resonant frequency and Q factor of the tuned circuit, which are in turn indicative of the resistance and capacitance values. In this regard, a change in electrical conditions within the subject will result in a change in the frequency response, as shown in FIG. 15D. For example, a response in absence of analytes might be as shown in solid lines, whereas the presence of analytes might result in an increase or decrease in the resonant frequency and/or Q factor, as shown in dotted lines.

Figure 15E:
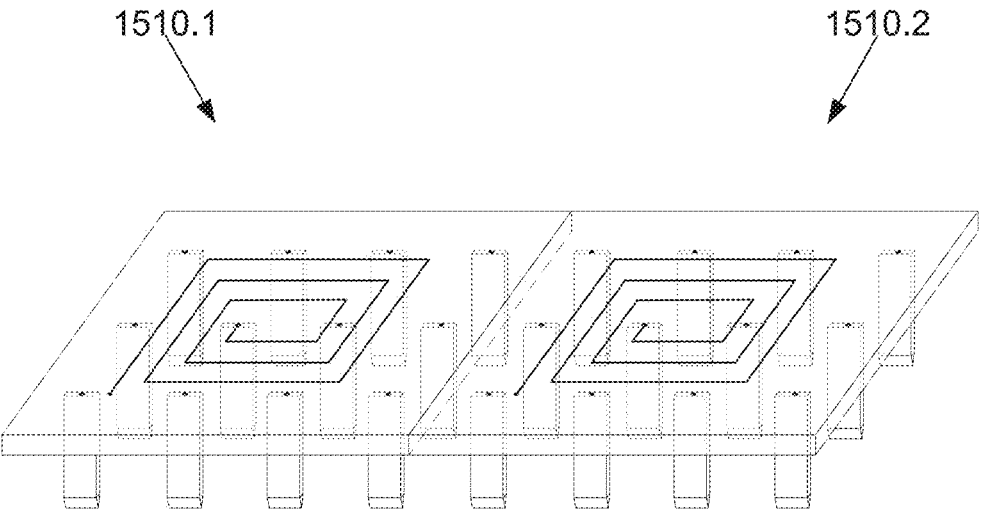
FIG. 15E is a schematic perspective topside view of an example of a dual patch arrangement.

In one particular example, in order to be able to more accurately interpret the response, it is preferable to provide a control reference. An example of this is shown in FIG. 15E, in which two patches 1510.1, 1510.2, are provided, each having a respective substrate 1511 microstructures 1512 and substrate coils 1515. In this example, the patch 1510.2 is coated with a binding agent to attract analytes of interest, whilst the patch 1510.1 is uncoated and acts as a control.

Figure 15F:
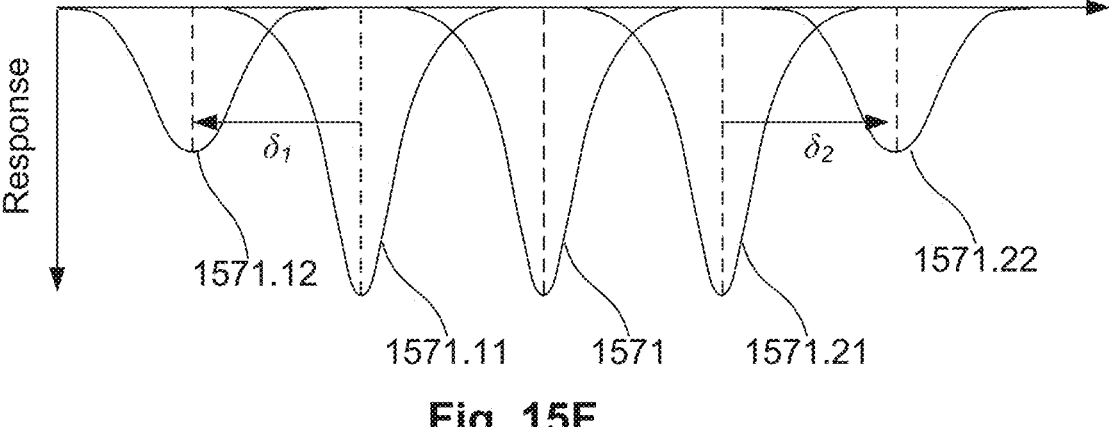
FIG. 15F is a graph illustrating an example of drive signal attenuation for the dual patch configuration of FIG. 15E.

In this case, each substrate coil is driven and alterations, including attenuation and/or frequency or phase changes of the signal are measured, which will depend on the resonant frequency and Q factor. Example altered drive signals are shown in FIG. 15F, with the signals 1571 representing a control obtain for the patch 1510.2, and the signals 1571.11, 1571.12 and 1571.21, 1571.22 representing different response obtained for the patch 1510.2, respectively. In this regard, the signals 1571.11, 1571.21 represent applied signals with no analytes, highlighting how different patches can have different tuned frequency responses, and with the signals 1571.12, 1571.22, showing changes in frequency 81, 82, which highlight how different responses can be measured, which can in turn be used to derive information regarding the level or concentration of analytes in the vicinity of the microstructures of the second patch 1510.2.

The measurement of the changes in frequency occurring in response to different analyte levels or concentrations may also be performed in the frequency domain by use of a return-loss-bridge circuit in the excitation coil. In this manner, the absorption of rf electromagnetic signal while being swept over a range of frequencies will show a signal loss in decibels (dB) at the resonant frequency of the substrate coil. The frequency and depth of this absorption will be indicative of the analyte level or concentration.

It will be appreciated that this technique employs a patch with no electronically active sensing elements, whilst allowing measurements to be made regarding conditions within the subject, such as the presence, absence, level or concentration of analytes to be easily determined. It will also be appreciated that suitably adapting the coating allows a range of different analytes to be sensed and that this can also be adapted for performing other suitable measurements.

Further details exemplifying the above described arrangements will now be described.

Manufacture

Example process for manufacturing a substrate including microstructures will now be described in more detail.

Figures 17A, 17B, 17C, 17D, 17E, 17F, 17G:
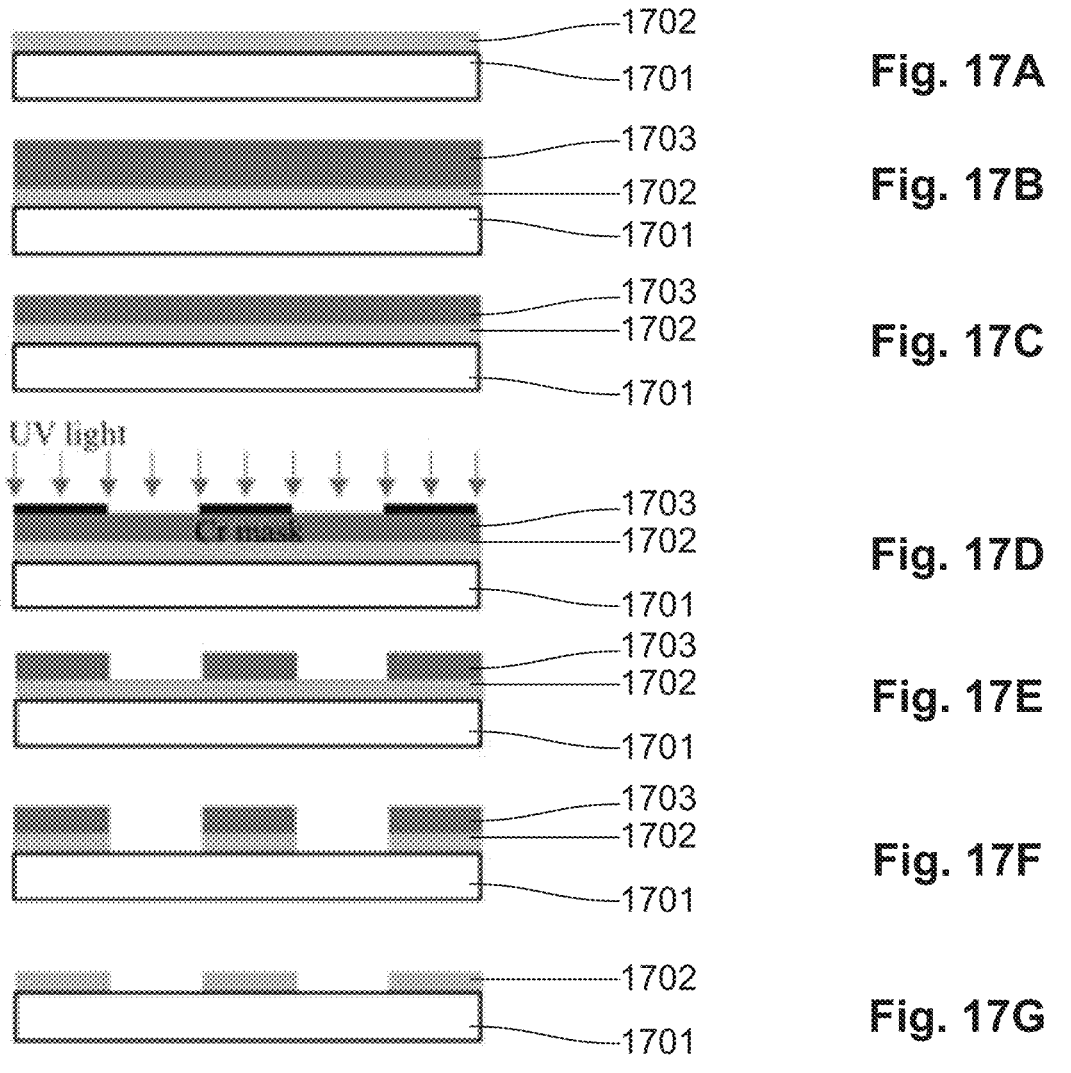
FIGS. 17A to 17P are schematic diagrams illustrating steps in an example manufacturing process.
Figures 17H, 17I, 17J, 17K, 17L, 17M, 17N, 17O, 17P:
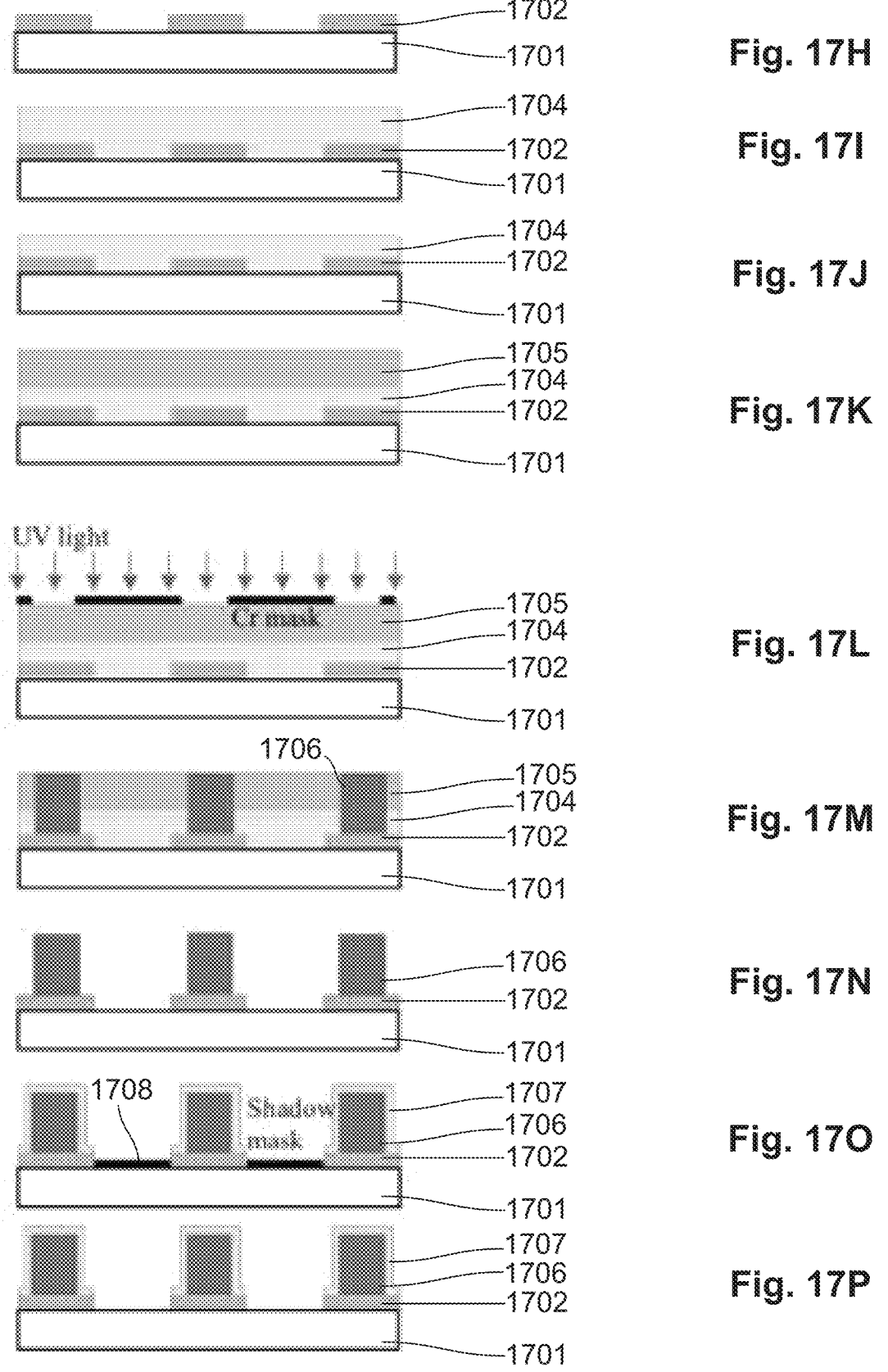
Figure 18A:
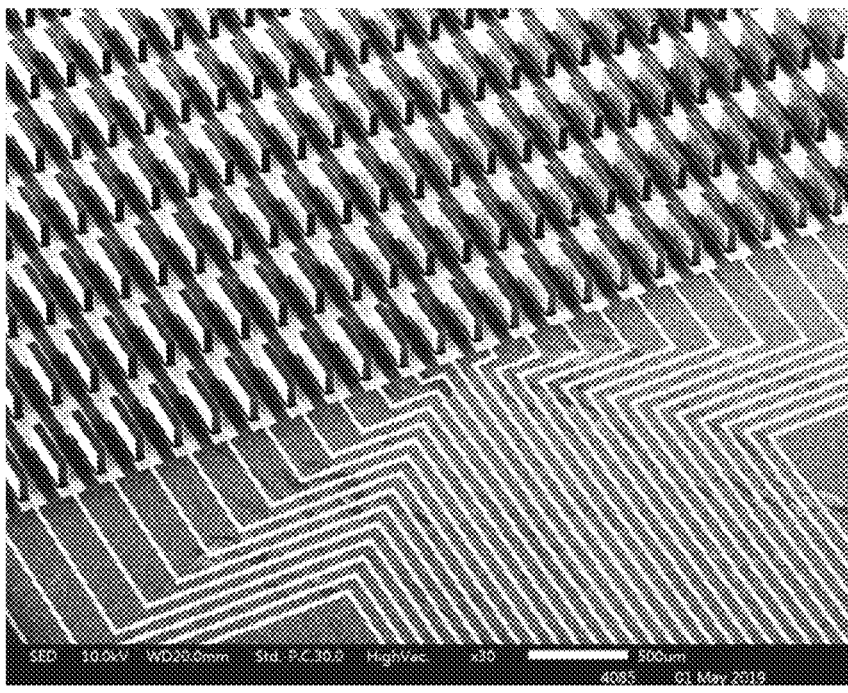
FIGS. 18A to 18D are micrograph images of examples of microstructures manufactured using the approach of FIGS. 17A to 17P.
Figure 18B:
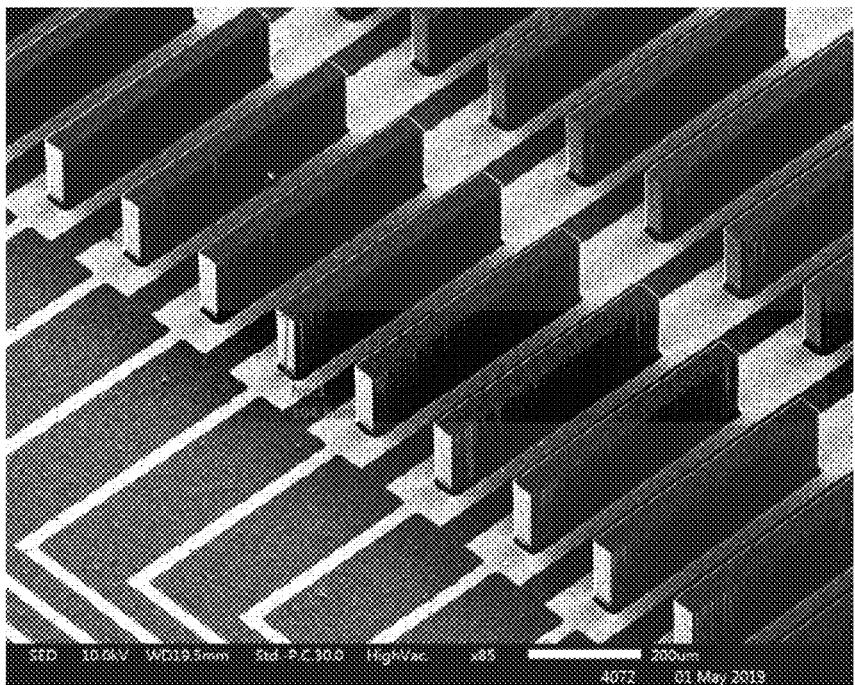
Figure 18C:
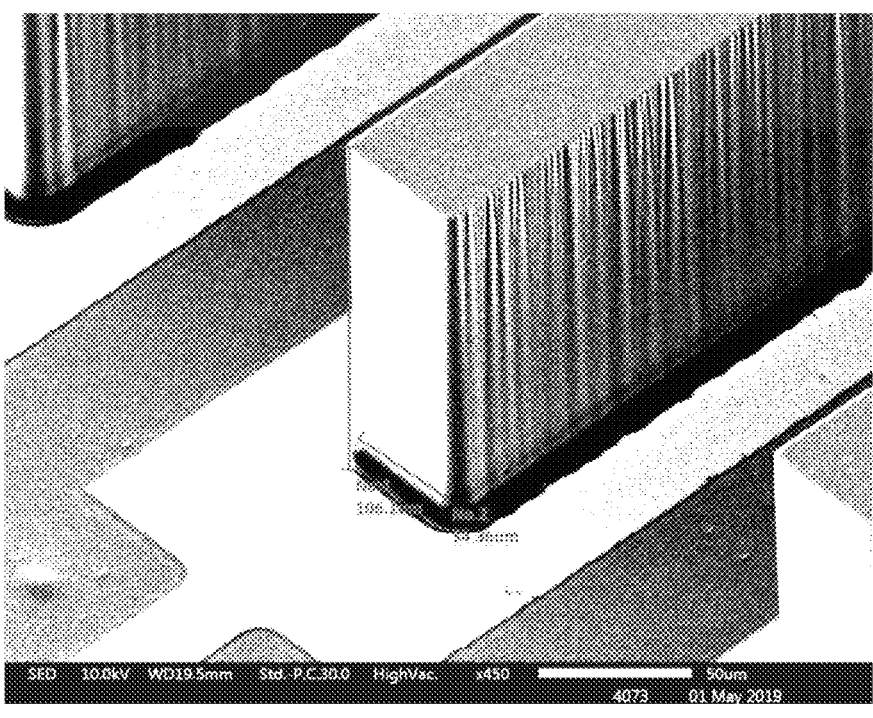
Figure 18D:
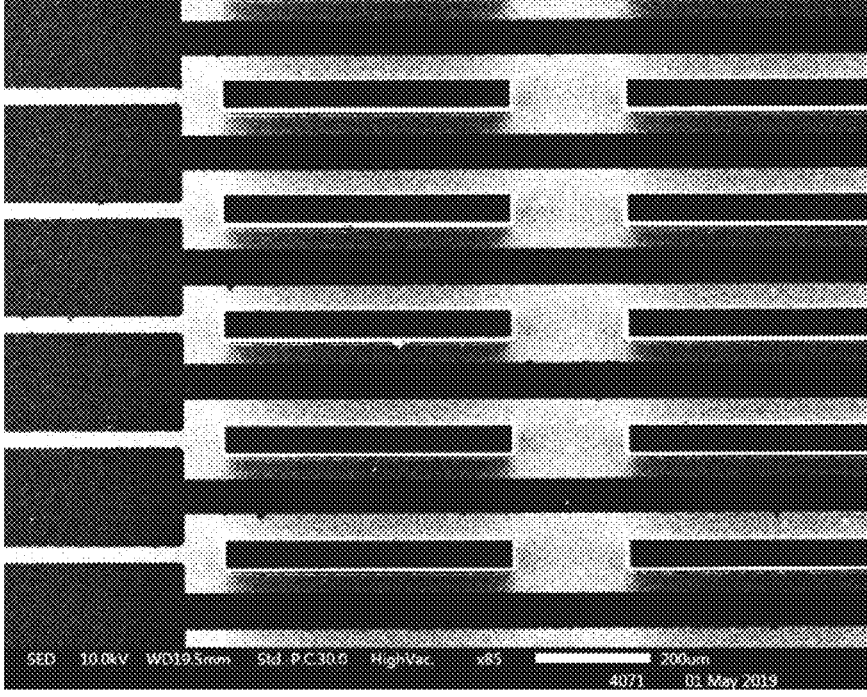

In a first example, shown in FIGS. 17A to 17P, microstructures are made from an insulating polymer applied to a substrate, with electrodes patterned on the substrate through selective etching to act acting as electrical connections for the polymer microstructures. It will be also be appreciated that conductive polymers could be used, for example through suitable doping of an insulating polymer.

In this example, a first step shown in FIGS. 17A to 17G is to selectively pattern an electrode architecture onto a flexible polyethylene terephthalate (PET) substrate 1701. An electrode design, upon which microstructures were to be defined, was patterned on the PET; in this case Indium Tin Oxide (ITO) 1702. layer deposited atop flexible PET substrate, and the electrode pattern selectively etched from the ITO layer. The substrate was prepared (FIG. 17A), before a positive photoresist, AZ1518 (MicroChemicals), was patterned on top of the ITO via photolithography (FIG. 17B), and soft baked (FIG. 17C). The photoresist is selectively exposed to UV (FIG. 17D) to define an electrode pattern, before the photoresist is baked and developed using a developer AZ 726MIF (MicroChemicals) (FIG. 17E) and the exposed ITO regions wet acid etched (FIG. 17F). The photoresist was removed to reveal the final etched ITO pattern that provides the conductive electrodes for the device (FIG. 17G).

In a second step, shown in FIGS. 17H to 17P, 3D microstructures were fabricated from photosensitive polymers onto the ITO electrodes. The patterned PET substrate with ITO electrodes was treated with an oxygen plasma (FIG. 17H), to improve wetting and resist adhesion, and a seed adhesion layer of SU-8 3005 (MicroChemicals) 1704 was spin-coated on to the ITO-PET substrate (FIG. 17I). After baking of the seed SU-8 layer lamination (FIG. 17J) an SUEX SU-8 film resist 1705 (DJ MicroLaminates) was bonded to the substrate (FIG. 17K) through thermal lamination. After alignment and exposure to UV through a mask aligner (FIG. 17L), the exposed SU-8 areas crosslinked to form rows of rectangular microstructures 1706 with vertical wall profile along the conductive ITO fingers 1702 (FIG. 17M). The structures are baked, with the SU-8 1704 and SUEX 1705 before being developed in PGMEA (Propylene glycol monomethyl ether acetate) (Sigma Aldrich), and then hard baked (FIG. 17N). A shadow mask 1708 is applied to the substrate 1701 with the microstructures 1706 being coated with gold 1707 (FIG. 17O) through selective deposition, before the mask is removed (FIG. 17P), leaving selectively metallized microstructures that act as electrodes.

In this example the microstructures have flat tips, but it will be appreciated that other UV lithography techniques such as greyscale lithography, backside diffraction lithography, 2 photon lithography etc. could be employed to define tapered microstructures.

Resulting microstructures are shown in FIGS. 18A to 18D.

In a second example, shown in FIGS. 19A to 19L, microstructures are made by molding.

Figures 19A, 19B, 19C, 19D, 19E, 19F, 19G:
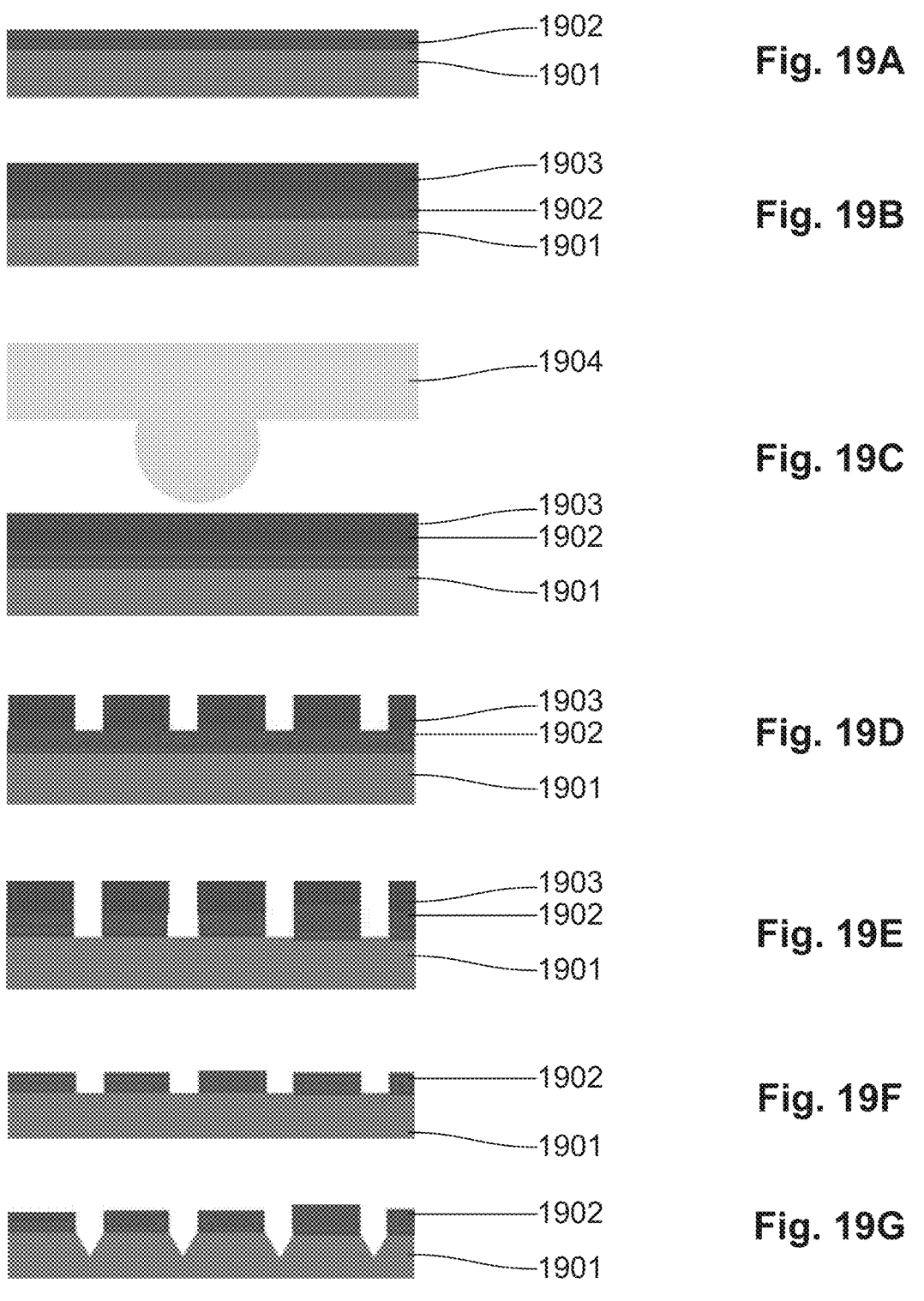
FIGS. 19A to 19L are schematic diagrams illustrating steps in an example manufacturing process.

In this example, a silicon wafer 1901 was deposited with a 90 nm layer 1902 of Nitride (FIG. 19A). AZ1505 (MicroChemicals) positive resist 1903 was then spun on at 4000 rpm (FIG. 19B). Rectangular pattern to define the blade outline was directly written using a mask writer 1904 (FIG. 19C). The written pattern was developed using AZ 726 MIF (MicroChemicals) for 30 secs (FIG. 19D). Reactive ion etching is used to remove the nitride layer 1902 (FIG. 19F), before the photoresist 1913 is removed (FIG. 1919E). The wafer is then held vertically in a bath of Potassium Hydroxide at 80° C. for 40 mins, to etch the silicon wafer along the crystal axis of the wafer (FIG. 19G). The etching stops at the axis 111 thus defining the sharp tips needed, this then acts as a mold for the devices that are fabricated.

Figures 19H, 19I, 19J, 19K, 19L:
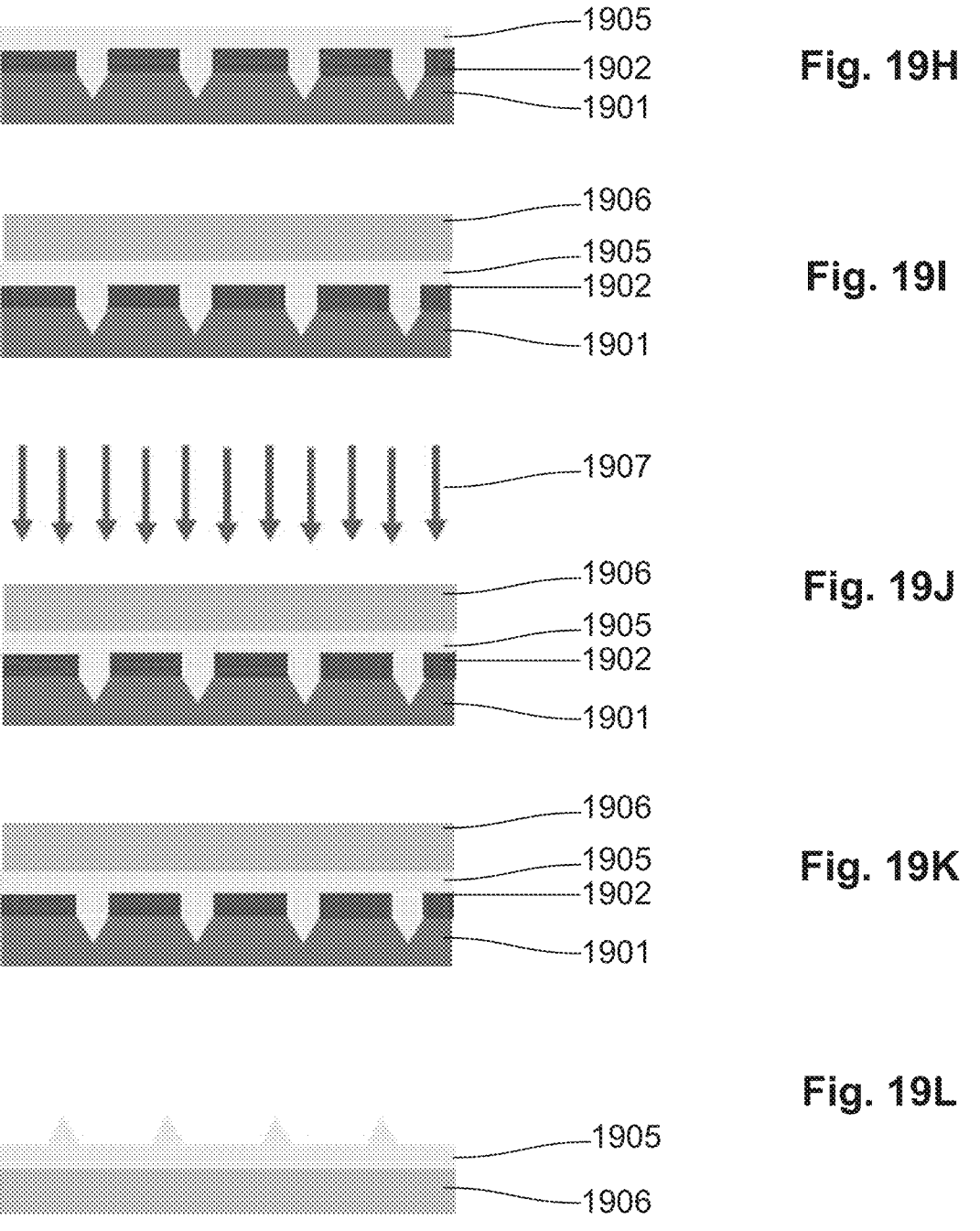
Figure 20A:
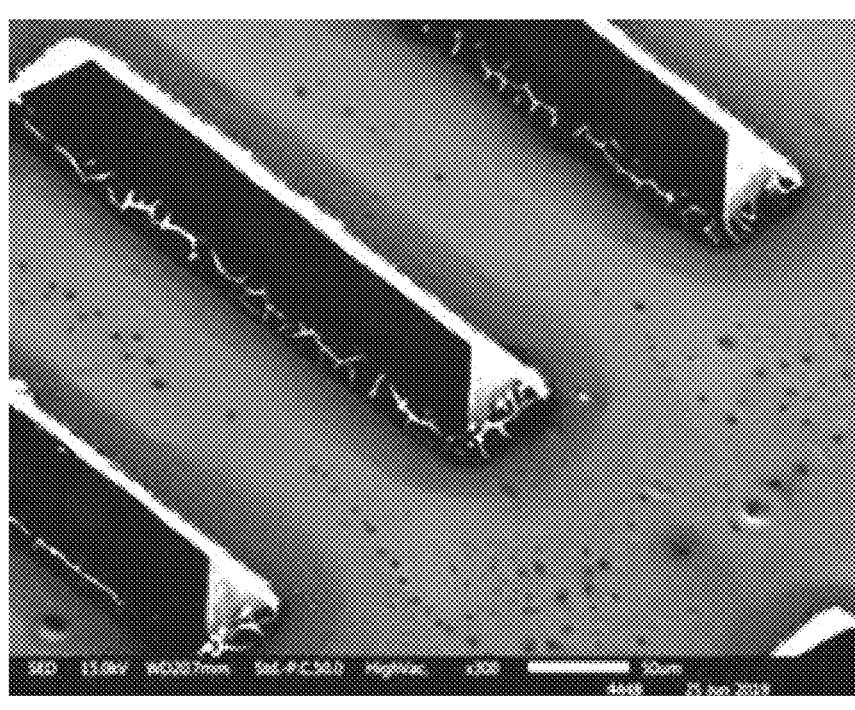
FIGS. 20A and 20B are micrograph images of examples of microstructures manufactured using the approach of FIGS. 19A to 19L.
Figure 20B:
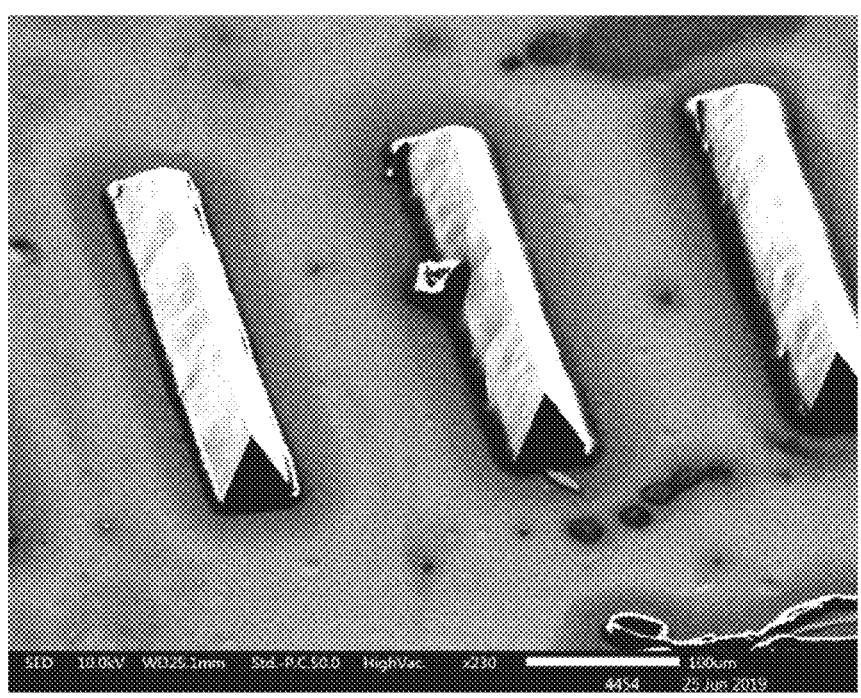
Figure 20C:
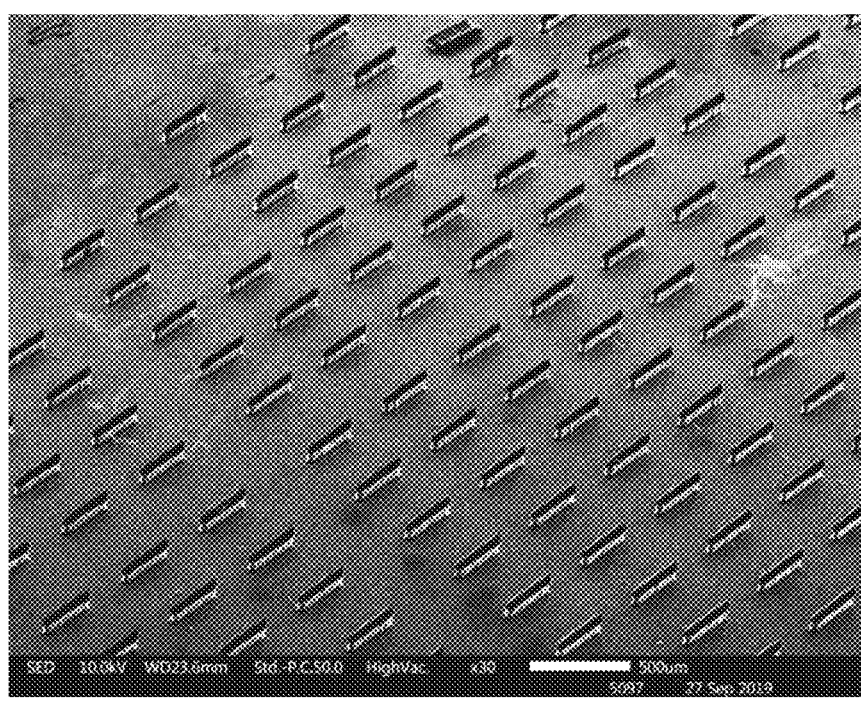
FIGS. 20C and 20D are micrograph images of further examples of microstructures manufactured using the approach of FIGS. 19A to 19L.
Figure 20D:
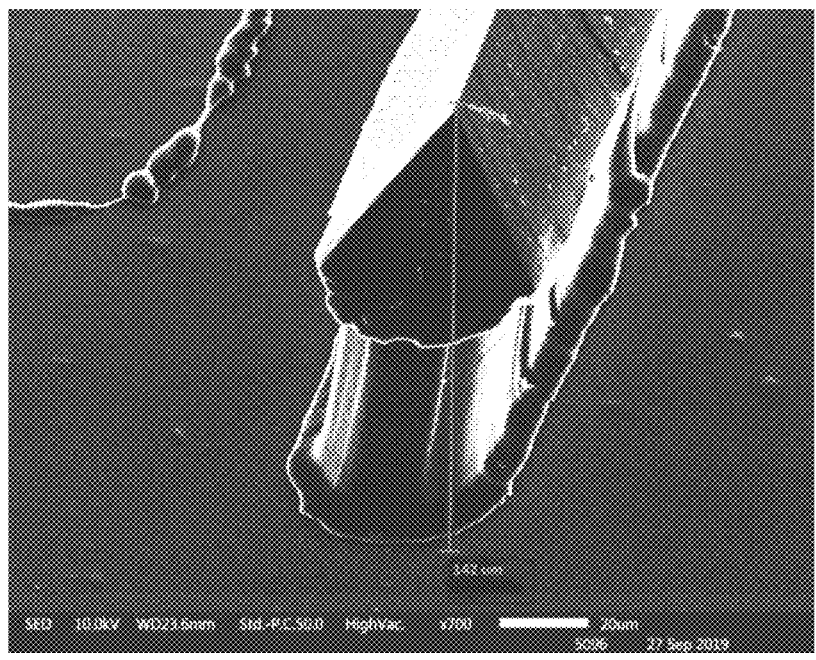

Omni-Coat is used as a lift off resist and is coated onto the wafer to a thickness of about 20 nm, using a spin recipe of 3000 RPM for 1 min and then baking at 200° C. for 1 min. Following this a 5 micron layer 1905 of SU8 3005 is spun on to the wafer at 3000 RPM following by baking at 65° C. for 1 min, then at 95° C. for 20 secs followed by 65° C. again for 1 min (FIG. 19H). The thinner formulation of the SU8 3005 would allow it to flow more easily into the sharp triangular crevices etched into the silicon wafer mold. A layer 2016 of SU8 1900 is then spun on top of this layer to a thickness of 200 microns using a spin recipe of 2000 RPM for 60 secs (FIG. 19I). Following this the wafer was baked at 65° C. for 5 mins, then at 95° C. for 35 mins and then again at 65° C. for 5 mins. This layer of SU8 1900 would allow the sharp tips to stand on a solid layer.

Finally the wafer is flood exposed using an Ultra Violet source 1907 delivering 15 mW/cm² of Power for 40 secs (FIG. 19J). The structures are released by soaking the wafer in an AZ 726 developer solution overnight (FIG. 19K) and exposed the wafer to a thermal shock of 120° C. for 15 secs. The structures are removed from the mold flipped and dried using Nitrogen gas (FIG. 19L).

Resulting microstructures are shown in FIGS. 20A and 20B and 20C and 20D.

Figure 21A:
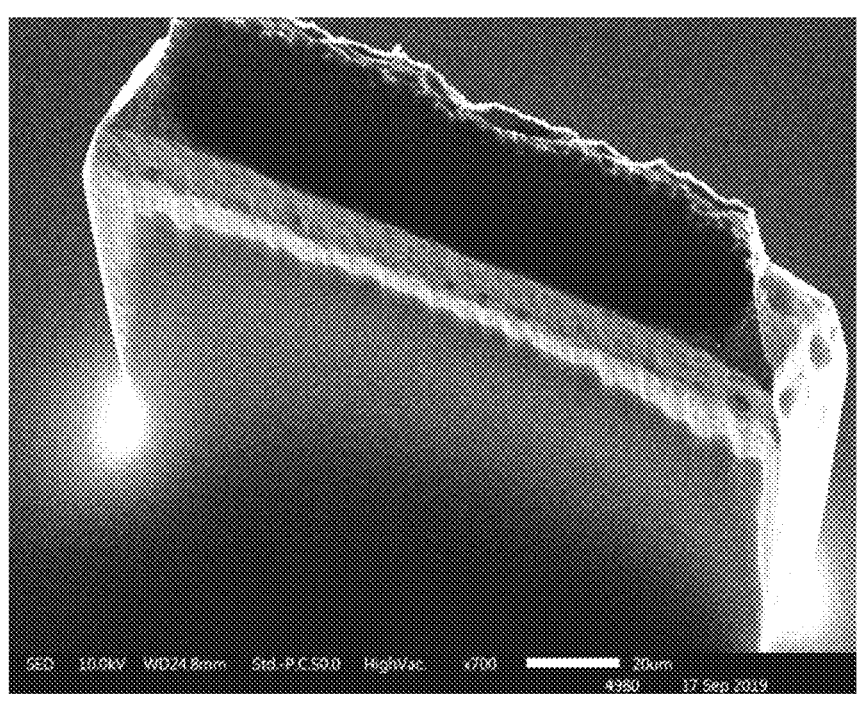
FIGS. 21A and 21B are micrograph images of examples of partially coated microstructures.
Figure 21B:
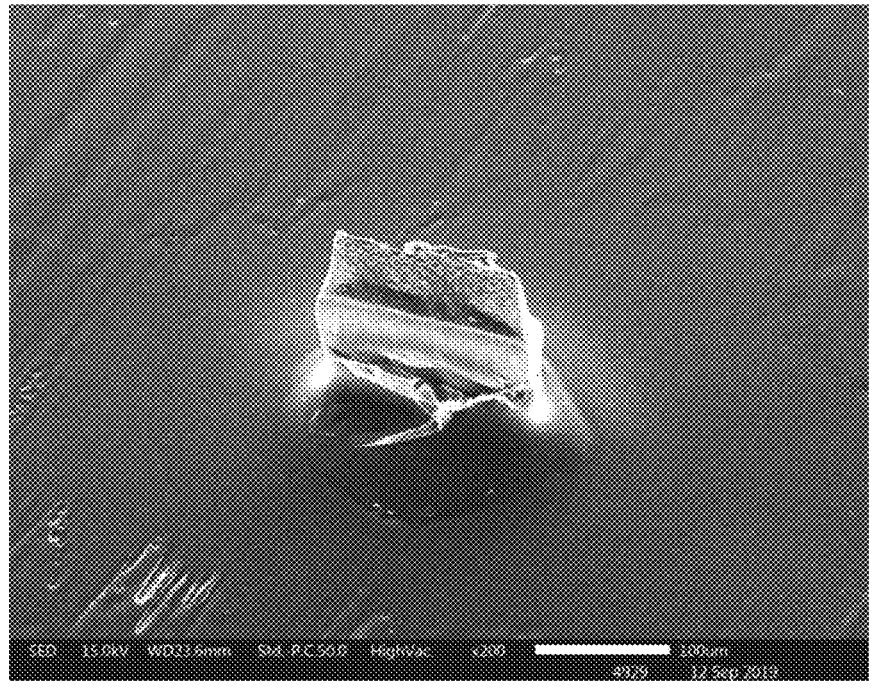

FIGS. 21A and 21B show silicon blades fabricated via etching. FIG. 21A shows the blade coated with a nearly 1 micron thick layer of SU8 3005 which has been diluted in a ratio of 3:2 using SU8 thinner and spun at 5000 RPM for 40 secs. FIG. 21B gives a depiction of the blade selectively coated at its base with the polymer coating. While the tip of the blade is bare and available for detection purposes only at this area. This selective coating is achieved by pressing and removing the coated blade in FIG. 21A into a thin layer of Aluminium foil which mechanically removes the resist from the tip of the blade. This allows the blade to be partially covered with an insulative coating, so that only the tip portion acts as an electrode, thereby allowing measurements to be performed in the epidermis and/or dermis, as described above with respect to FIGS. 5L and 5M.

Application

Vibration applied to a patch, can result in a temporary change to the mechanical properties of the skin surrounding the patch, resulting in reduced friction between the microstructures and skin, increased crack propagation and an decrease in application force due to a modulation effect caused by the vibration. As a result of these changing properties a patch applied with the addition of vibration will penetrate deeper than a patch without vibration for the same applied force.

Experiments were conducted to validate this, with forces ranging from 1.25N to 40N being used to apply a patch into porcine ear at a quasi-static velocity of 0.83 mm/s. Each force was tested with and without vibration, with the patch being applied to the tissue for 10 seconds under load, before then being removed in each case. The mechanism of vibration was a z-axis vibration motor run at 6.6Vpp and 180 Hz resulting in a vibration amplitude of 30 μm. Once testing was complete each test site was removed from the ear and examined via H&E staining.

Observing the results below for the penetration of a patch at 2.5N with and without vibration there is evidence to suggest an increase in penetration depth with the addition of vibration. Of the 6 penetration sites extracted from one row of microarray structures without vibration, all 6 blades were able to penetrate the stratum corneum while only 1 microstructure was able to penetrate the epidermis. In contrast, of the 5 penetration sites extracted from the sample with vibration, there is clear and significant penetration for 3 of the microstructures. Considering this, there is evidence to suggest that the addition of vibration will increase penetration depth of the patch for the same forces than for patch without.

Figure 22A:
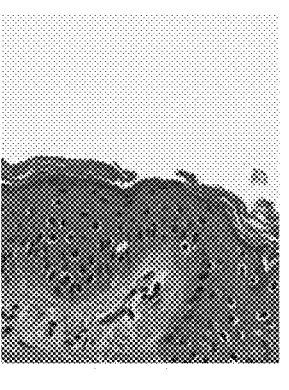
FIGS. 22A to 22F are images illustrating an example of penetration of porcine ear by a microstructure without vibration.
Figure 22B:
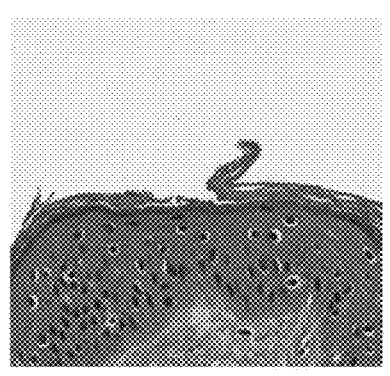
Figure 22C:
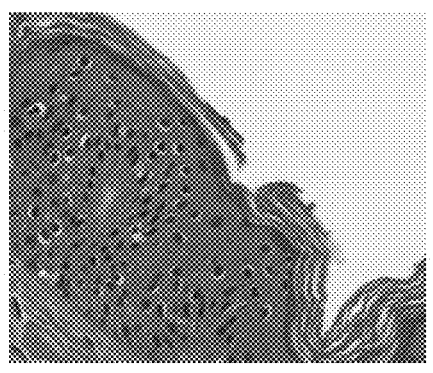
Figure 22D:
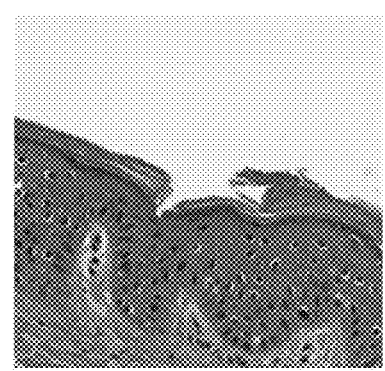
Figure 22E:
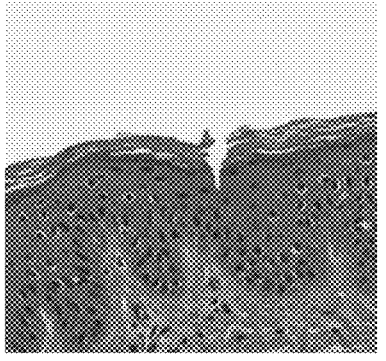
Figure 22F:
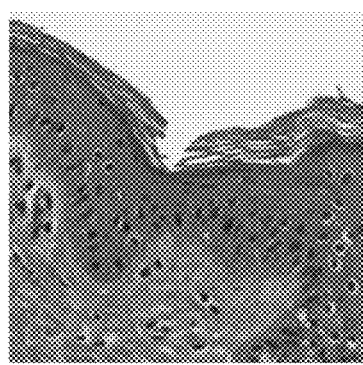
Figure 22G:
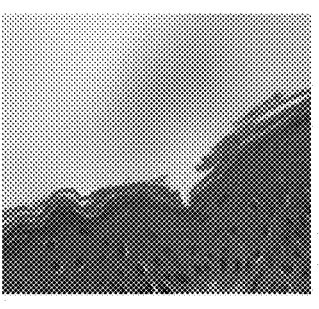
FIGS. 22G to 22K are images illustrating an example of penetration of porcine ear by a microstructure with vibration.
Figure 22H:
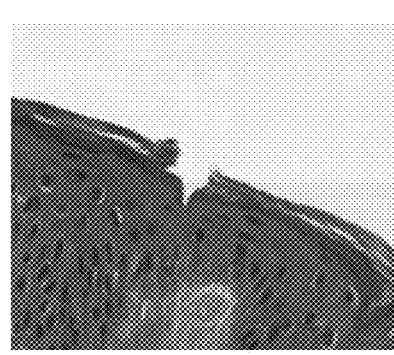
Figure 22I:
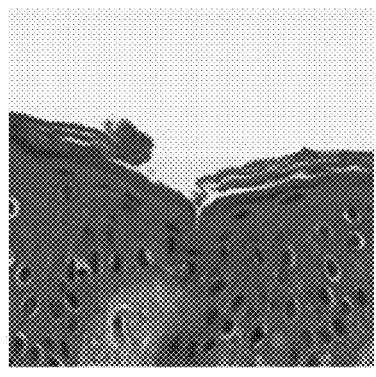
Figure 22J:
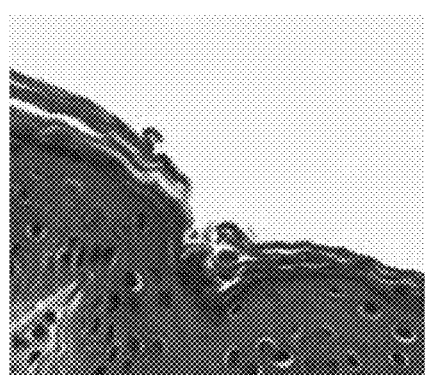
Figure 22K:
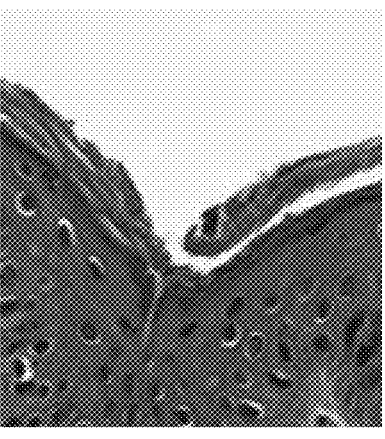

FIG. 22A to 22F are images demonstrating penetration of porcine ear by a microstructure using a 2.5 N force without vibration for 10 seconds, with only FIG. 22E demonstrating penetration of the epidermis, whereas FIG. 22G to 22K are images demonstrating penetration of porcine ear by a microstructure using a 2.5 N force with about 175 Hz vibration for 10 seconds, with FIGS. 22H, 22I, 22K demonstrating penetration of the epidermis.

Figure 23A:
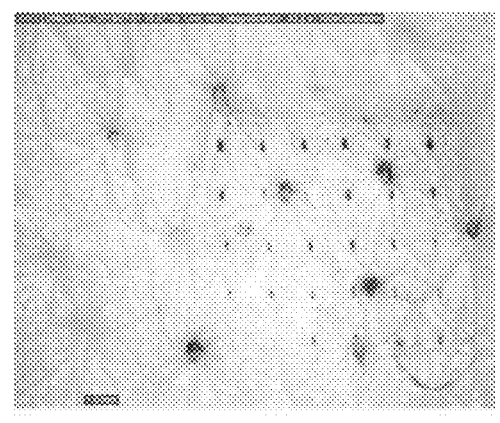
FIGS. 23A to 23C are images illustrating examples of penetration of the stratum corneum for patches having a microstructure density of 188 per $cm^2$, 300 per $cm^2$, 550 per $cm^2$, respectively.
Figure 23B:
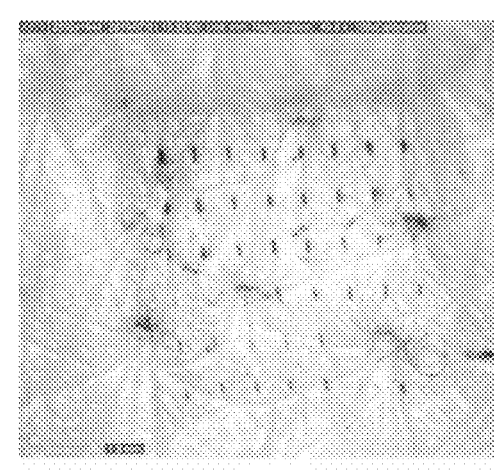
Figure 23C:
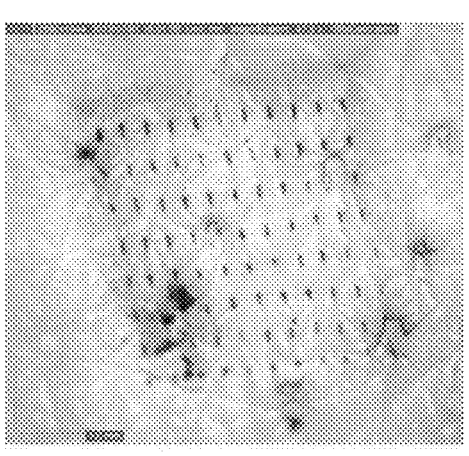
Figure 23D:
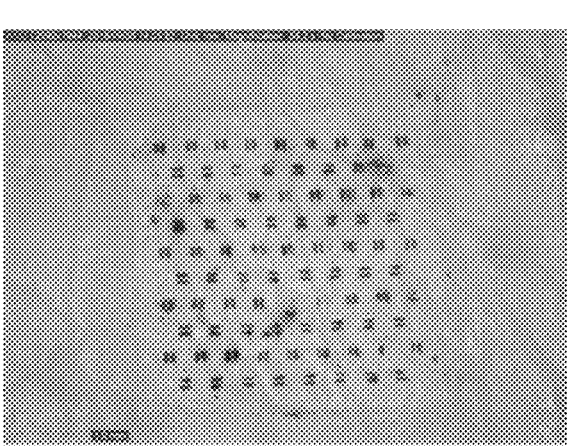
FIG. 23D is an image illustrating examples of penetration of the stratum corneum for the patch of FIG. 5K.
Figure 24A:
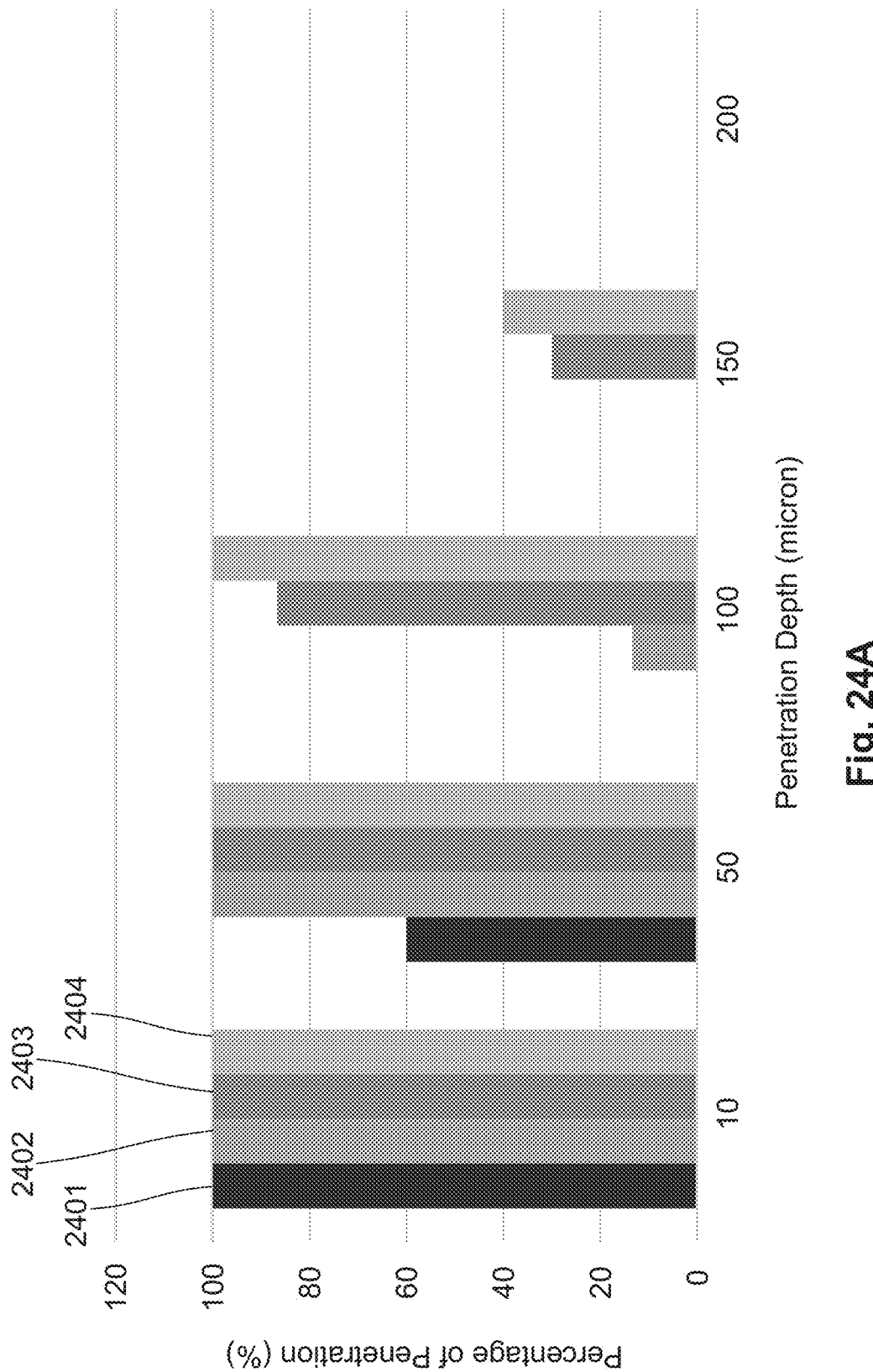
FIG. 24A is a graph showing a depth of penetration for different microstructure and force configurations.

In further experiment, immediately after a patch is applied to tissue, and then removed, an aqueous solution of Methylene Blue (1% v/v) was applied to the site and removed. As shown in FIG. 23A to 23C, which shows results for patches having a microstructure density of 188 per cm², 300 per cm², 550 per cm², the blue die selectively stains the sites at which the stratum corneum is penetrated and demonstrates microstructures penetration across the patch. FIG. 23D is an image illustrating examples of penetration of the stratum corneum for the patch of FIG. 5K;

In a further example, a penetration test was performed for microstructures with different configurations and different application forces. In this example, a microstructure density was 188 per cm². The force is applied with a handheld force gauge, no vibration, with the patch being applied for 10 seconds under load, before then being removed. For this example, microstructures in the form of plates were used that included vertical side walls, similar to those shown in FIGS. 5A and 5B, as well as plates including shoulders, similar to those shown in FIGS. 5L and 5M. Results shown in FIG. 24A include microstructures with shoulders at 5N applied force 2401, microstructures with shoulders at 10N applied force 2402, microstructures with no shoulders at 5N applied force 2403, microstructures with no shoulders at 10N applied force 2404.

As shown, all blades are shown to penetrate to a depth of 10 μm at forces of 5N or 10N. With an application force of 5N 60% of the blades with shoulders penetrate to 50 μm, and zero blades with shoulders penetrate to 100 μm, compared to 100% and 90% for blades with vertical sidewalls at 50 μm and 100 μm respectively.

With an application force of 10N 100% of the blades penetrate to 50 μm for both geometries, but only 15% of blades with shoulders penetrate to 100 μm, compared to 100% for blades with vertical sidewalls.

This demonstrates both that only relative low force is required to apply the microstructures and that the presence of shoulders can be used to control the extent of penetration into the epidermis.

Figure 24B:
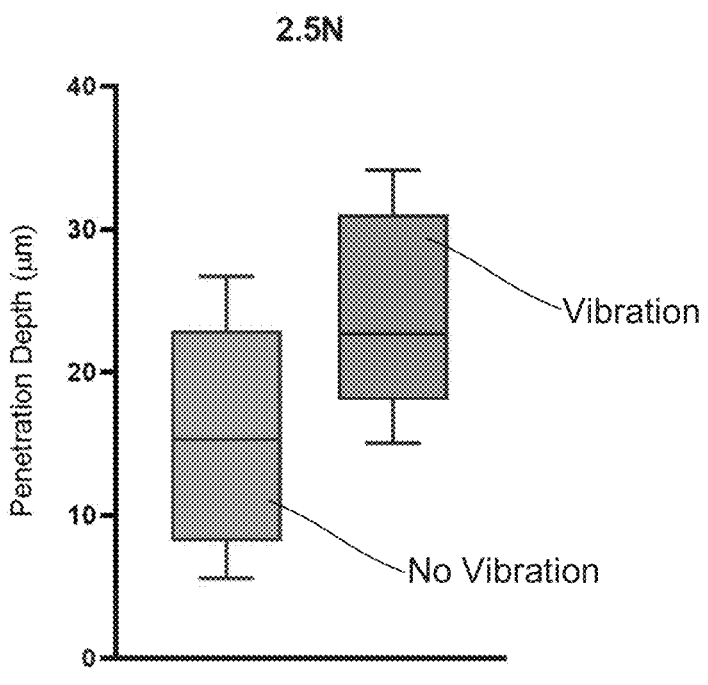
FIG. 24B is a graph showing a depth of penetration for application with or without vibration.

In another experiment, microstructure penetration with application at a constant force (2.5N), with or without vibration was compared. Results shown in FIG. 24B demonstrate vibration helps increase penetration depth.

Hydration

An example of use of the microstructures in measuring hydration will now be described.

In this regard studies have suggested that there is a strong correlation between level of performance and hypohydration measured as % Δ in body mass, with significant hypohydration occurring when body mass loss is >2%. Evidence suggests that hypohydration detrimentally effects high-intensity muscular endurance, strength and power. Furthermore, there is a relationship between decrease in muscular strength and power and the likelihood of injury occurrence, which suggests that the ability to accurately measure hydration could be valuable for athletes, particularly in high risk sports.

An experiment was performed to measure pig skin hydration using a microstructure impedance based approach. In this example, tissue was measured at a nominal 'fresh' hydration point and dehydrated by application to a warming plate with a set point of 38° C. Tissue block volume was measured by a displacement method at the commencement, and end of the experiment. It was assumed that all mass change was due to water loss due to evaporation from the excised tissue.

Figure 25A:
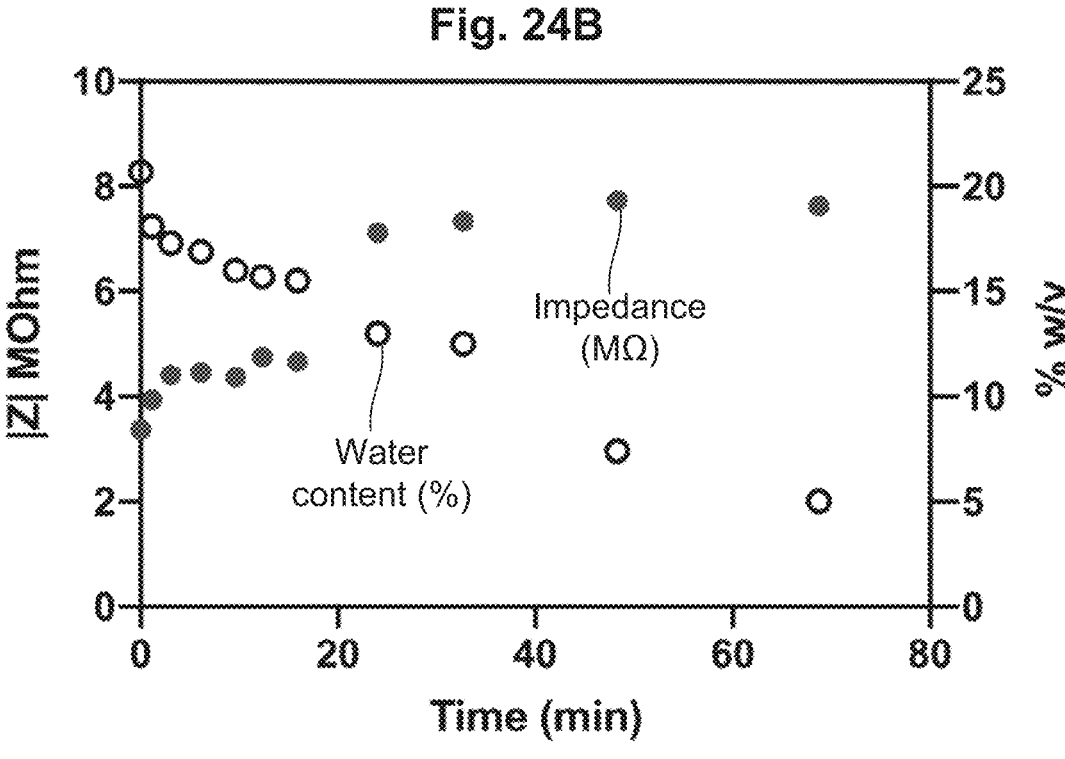
FIG. 25A is a graph illustrating an example of changes in epidermal impedance versus changing hydration in pig skin.

Time-series data of impedance measured at 200 Hz is shown in FIG. 25A, with the second axis representing concurrent water content estimates derived from measured mass and volume measures. The inverse relationship between impedance and water content is as expected and the first-order water loss rate is mirrored in the impedance changes measured.

This demonstrates a microstructure patch can successfully engage and allow measurement of the specimen water loss to a satisfactory level of precision. This architecture is thereby a firm basis for development of the electrically interfacing microstructure patch as demonstrated in hydration sensing.

A human water loss and rehydration experiment was conducted to examine the ability of the above described arrangements, to assess body water loss (and gain) through interrogation of the interstitial fluid in the viable epidermis layers of the human anterior forearm. A 4×4 mm gold-coated patch was applied and multi-frequency impedance measures were made with bench instrument (Keysight E4990A). The 4×4 mm device was electrically divided into two 2×4 mm regions with 15 blade microstructure electrodes of 150 μm depth and 260 μm wide, which are expected to have penetrated to around 80 μm deep into the human tissue an in in vivo experiment.

Dehydration was controlled over a three-hour period and a reference or 'ground truth' measure of plasma water loss was performed by serial hematocrit (Hct) measures. Normal red cell mass accounts for approximately 43% of the plasma volume at normal hydration levels in the adult male. Increases in the Hct in the absence of blood loss are therefore due to water loss.

Figure 25B:
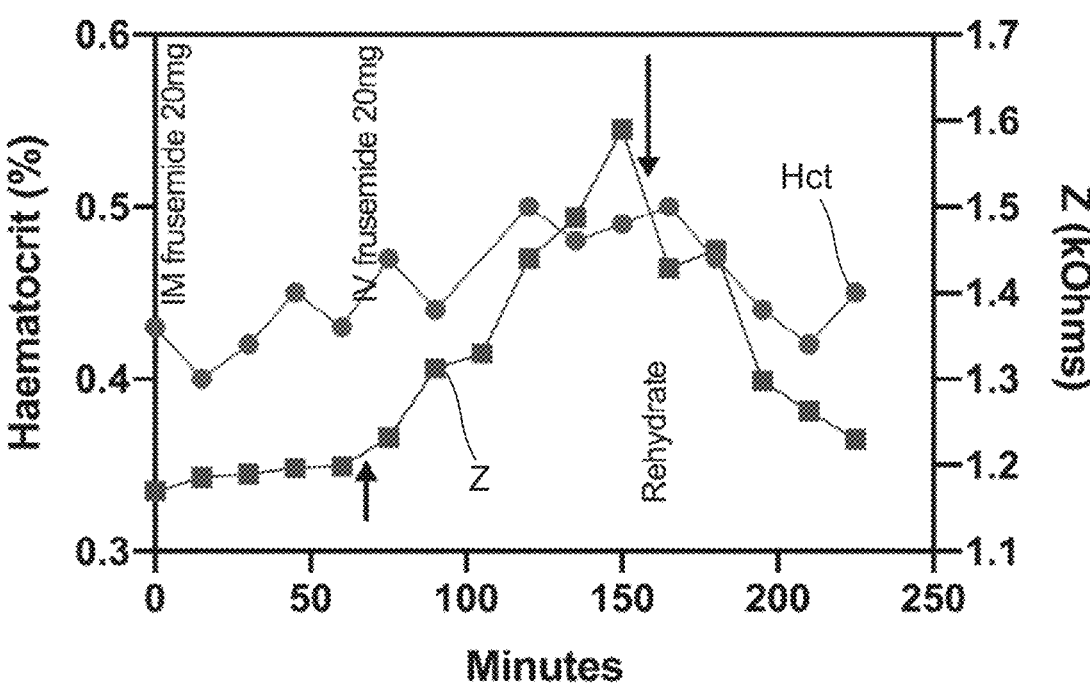
FIG. 25B is a graph illustrating an example of changes in epidermal impedance and Hematocrit versus changing in hydration.

FIG. 25B is a graph showing resulting measured impedance (Z) and hematocrit (Hct) vs. time as total body water loss approaches 1.7%. Impedance trend follows dehydration as measured by Hct and follows restoration with a response time of minutes.

Recording Hct and impedance of the viable epidermis over time shows good association with dehydration. At the rehydration point the measure also follows the restoration of total body water levels. Body weight and urine analysis were used to quantify total body water loss and gain over the study period.

Notably at a total body water loss of less than 1.7%, electrical correlates were able to be detected. This level is below the threshold of detection of dehydration by trained clinicians and would conventionally require plasma osmolarity measures by blood sampling and laboratory assay. Restoration of body water was rapid and the sensor was able to detect this change in the ISF in less than 15 minutes.

The two-electrode measurement and range of impedance changes seen on a bench instrument is easily miniaturized into a wearable device and the minimally invasive nature of the sensor resulted in only extremely mild local erythema post removal of the device.

It is also notable that total body water loss induces physiological responses which may be categorized depending on the resultant osmolarity of plasma. For example, loss of water through sweat and restriction of oral fluids results predominantly in hypertonic hypovolaemia i.e. reduced plasma volume with disproportionately higher salt ($Na^+$, $Cl^-$, $K^+$) concentration. By contrast, water loss induced by diuretics, vomiting, cold and altitude induces isotonic or hypotonic hypovolaemia. Plasma osmolarity is reduced due to the disproportionate loss of salt with respect to water. Conductivity of interstitial fluid (ISF) is intimately related to the concentration of conductive ions, and therefore these different modes of hydration change can be discerned based on changes in impedance.

Figure 25C:
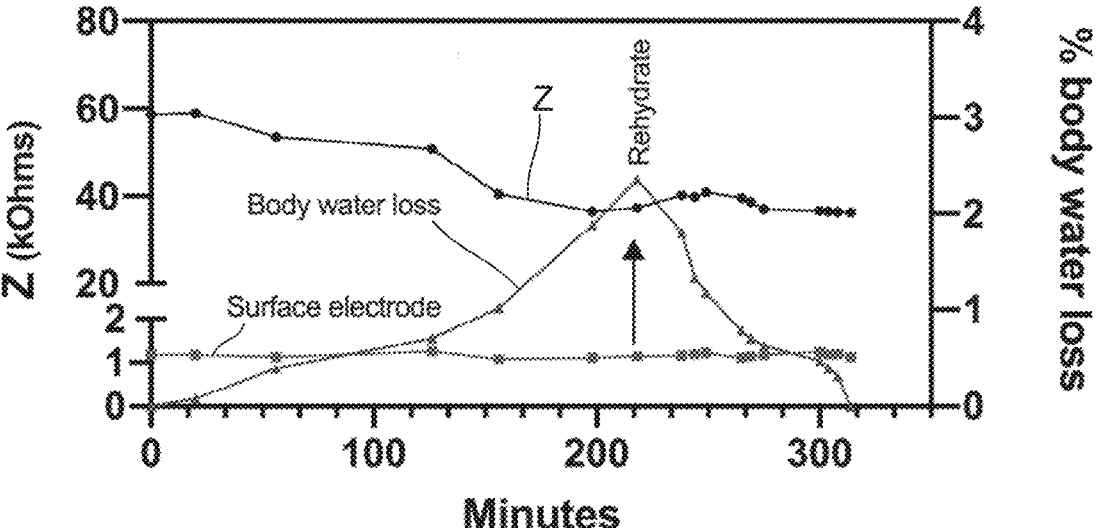
FIG. 25C is a graph illustrating an example of changes in epidermal and skin impedance versus changing in hydration.

An example of this is shown in FIG. 25C, which illustrates changes in impedance as a result of exercise induced water loss, which causes a hypertonic response whereby conductivity is increased (impedance declines). This is contrasted to the results in FIG. 25B of diuretic induced hypovolaemia shows an increase in impedance consistent with a loss of ions disproportionate to the water excreted through the kidneys.

It will therefore be appreciated that not only can changes in impedance be indicative of hydration changes, but that additionally monitoring a direction of impedance change can be used to indicate the nature of the water loss, and specifically, whether this is hypertonic or isotonic, with the magnitude of any change reflecting the amount of fluid lost. Similarly, if a hydration level is maintained or approximately constant then a change in impedance is indicative of a change in ion concentrations Theranostics In one example, as outlined above, the above described arrangements can be used to deliver therapy to a subject. In one preferred example, the delivery of therapy is achieved by selectively releasing a therapeutic into the skin from one or more microstructures.

In one preferred example, the system is designed to provide for a controlled release of a therapeutic into the skin in response to a stimulus, such as an electrical stimulus, although as previously described other stimulus could be used. In any event, this allows the system to operate as a 'closed loop' theranostic, whereby detection of a biochemical parameter/diagnostic biomarker will initiate and direct the rate of therapeutic release.

To achieve this, an electrically-responsive material is required that can encapsulate drugs and swell upon hydration (i.e. when inserted into the skin interstitial fluid environment) and to de-swell upon application of a positive bias thereby actively releasing therapeutic molecules from the hydrogel 'lattice' into the aqueous environment down a concentration gradient. Many hydrogel compounds have been described for tunable electro-responsive drug delivery, such as xanthan gum and sodium alginate. Methyl cellulose and sucrose has also been used for bulk delivery of therapeutics into the skin, when coated onto microstructures.

Accordingly, hydrogel formulations including Xanthan gum and methyl cellulose/sucrose were assessed to ascertain their ability to direct the delivery of a proxy drug methylene blue (300 Da) from a 2D gold coated electrode (area 1×1 cm) into solution. Methylene blue is an ionic blue dye that absorbs light at a wavelength of 665 nm and therefore can be detected and quantified by UV vis spectrometry. It can be used therapeutically to treat rare blood disorders with a clinical dose is in the range of 1 mg/kg (1%).

For in vitro experiments, the following steps were performed:

Plate electrodes were prepared with polyamide insulating tape so that a 1×1 cm area was exposed.

Electrodes were cleaned by sonicating 5 min in acetone, and then isopropanol, followed by drying using N2.

Xanthan gum 2% was prepared by mixing in deionised water, 0.8 mg/mL methylene blue was added to this and the formulation was magnetically stirred overnight.

Electrodes were treated with 200 µL 0.01% w/v poly-l-lysine for 30 mins at RT, this was removed, then electrodes were dried with N2.

Electrodes were dipped into the formulation multiple times so that the 1×1 cm area was covered with a film thickness of 1-2 mm and were dried under vacuum in desiccator overnight.

Experimental set up consisted of a plastic tube containing 5 mL phosphate buffered saline (PBS) into which the dip-coated working electrode was inserted, with an Ag/AgCl reference electrode.

Fresh tubes were replaced each 2-5 min throughout the period and the concentration of methylene blue that had been released into solution was ascertained by reading absorbance at 665 nm.

Cumulative release over time (ng), and release rate (ng/hr) were calculated

A first experiment tested the application of a negative bias to prevent passive release of proxy drug (methylene blue).

Figure 26A:
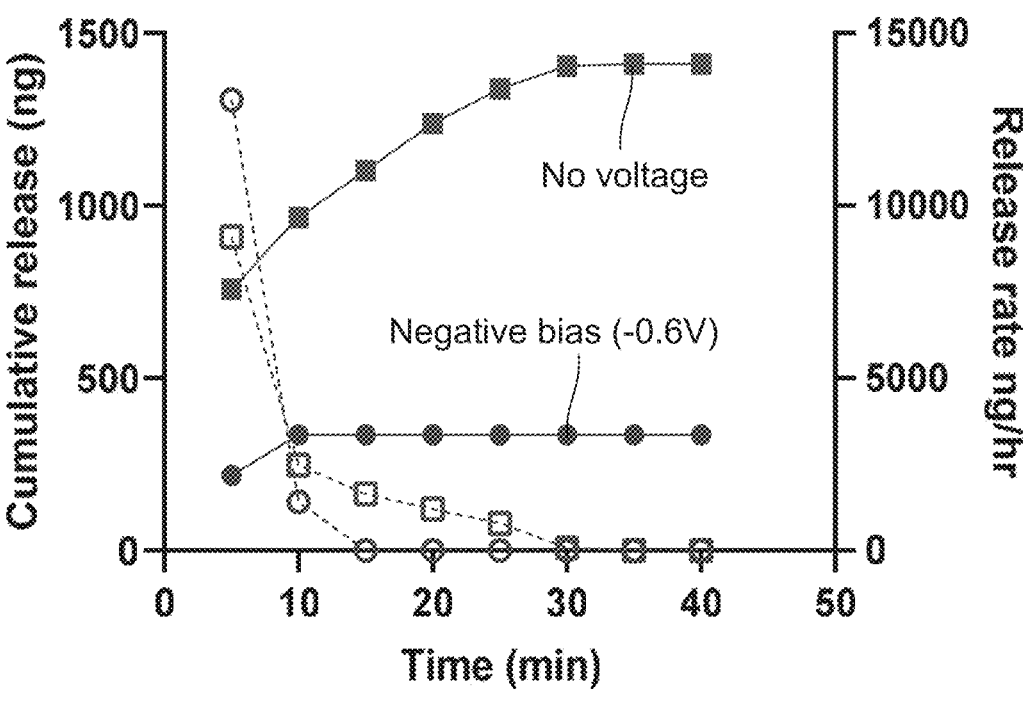
FIG. 26A is a graph illustrating results of a first experiment to test the application of a negative electrical bias to prevent passive release of proxy drug (methylene blue)
Figure 26B:
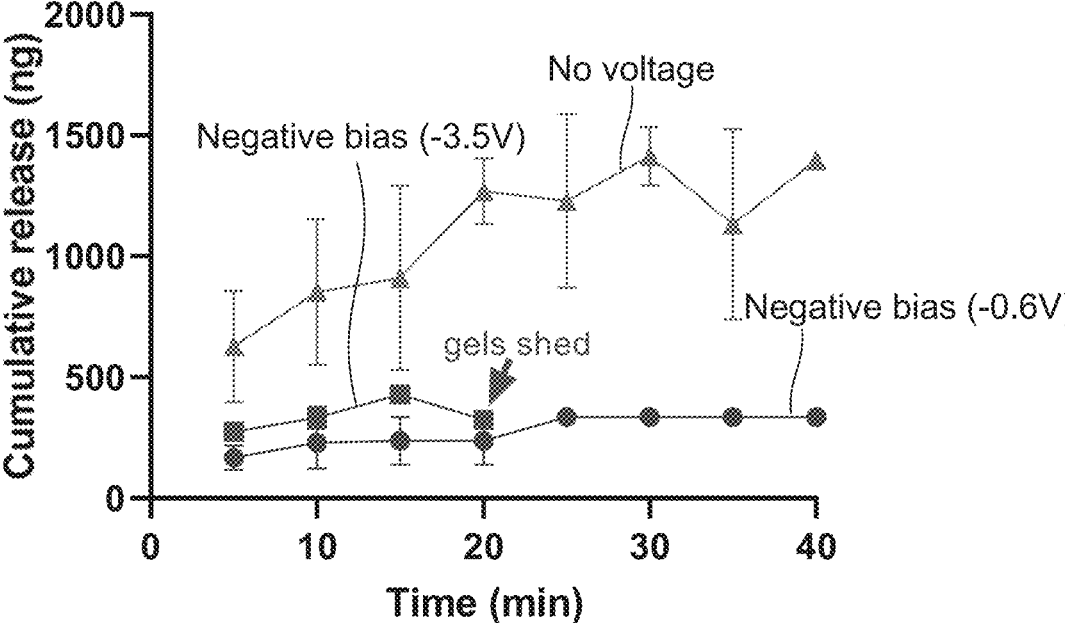
FIG. 26B is a graph illustrating further results of an experiment to test the application of a negative electrical bias to prevent passive release of proxy drug (methylene blue)

Literature suggests that passive release of encapsulated drug occurs during the hydrogel swelling phase, and that this can be impeded by the application of a negative voltage. FIG. 26A shows that-0.6V applied at the time of immersion into the PBS reduces this passive release to zero within 15-20 mins. The compilation of data shown in FIG. 26B demonstrates this effect over 5 experiments (no voltage) and 2 experiments (−0.6V, −3.5V). Both voltages tested were effective in impeding the passive release of proxy drug over time, but −3.5V was found to strip hydrogel from the electrode. This was mitigated by 1) reducing the magnitude of the voltage and 2) pre-coating electrodes with 0.01% poly-l-lysine to anchor hydrogel to electrode.

A second experiment tested the pulsatile release of proxy drug tunable with alternating polarity.

Figure 27A:
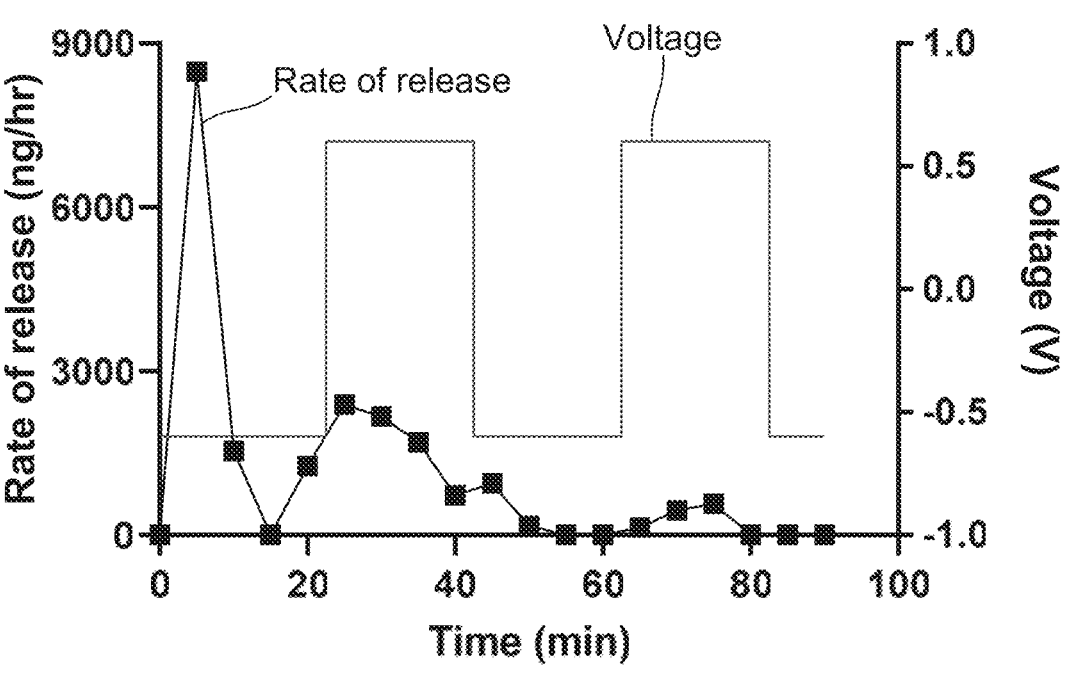
FIG. 27A is a graph illustrating results of an experiment to test the pulsatile release of proxy drug tunable with alternating polarity electrical bias.
Figure 27B:
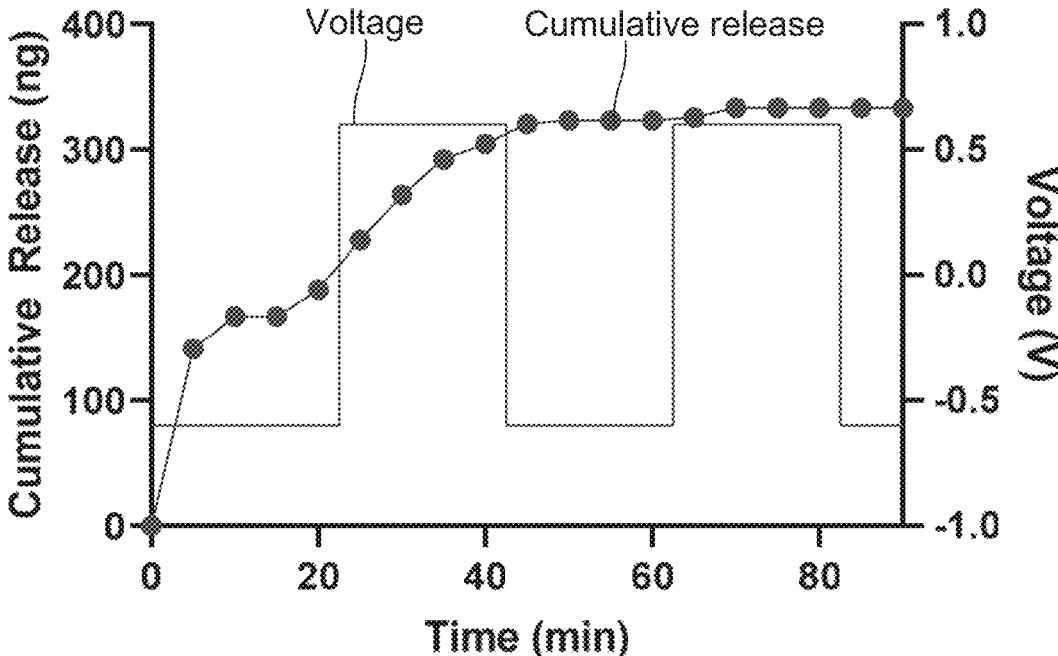
FIG. 27B is a graph illustrating further results of an experiment to test the pulsatile release of proxy drug tunable with alternating polarity electrical bias.
Figure 27C:
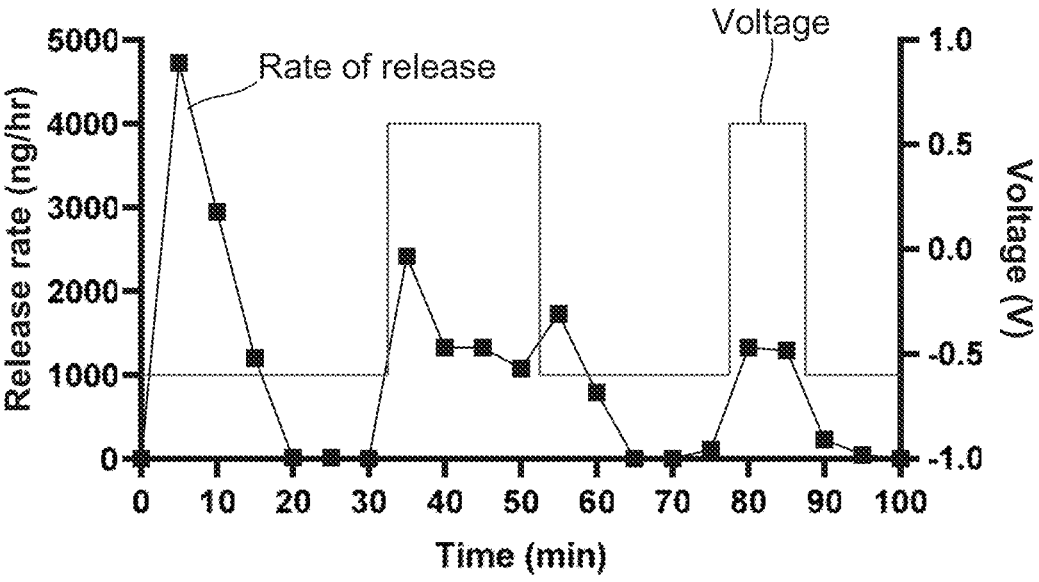
FIG. 27C is a graph illustrating results of a further experiment to test the pulsatile release of proxy drug tunable with alternating polarity electrical bias.
Figure 27D:
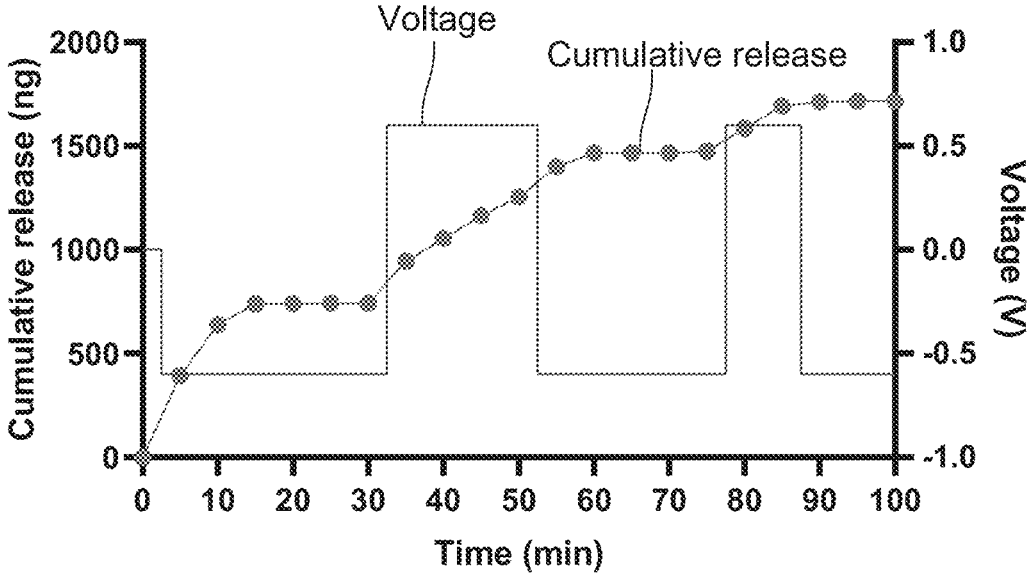
FIG. 27D is a graph illustrating further results of the further second experiment to test the pulsatile release of proxy drug tunable with alternating polarity electrical bias.

In this example, two experiments with xanthan gum-encapsulated methylene blue coated plate electrodes were performed. Application of a negative voltage (−0.6V) reduced the passive release during hydrogel swelling to zero within 20 mins. Application of +0.6V resulted in an increase in the rate of release, as shown in FIGS. 27A and 27C, and corresponding increase in the cumulative release FIGS. 27B and 27D. A return to −0.6V reduced the release rate dramatically, returning to zero. A second pulse of +0.6V increased the rate again (though less so than the first pulse). This data demonstrates the electrically tunable release of methylene blue from xanthan gum hydrogels coated onto electrodes.

Figure 28:
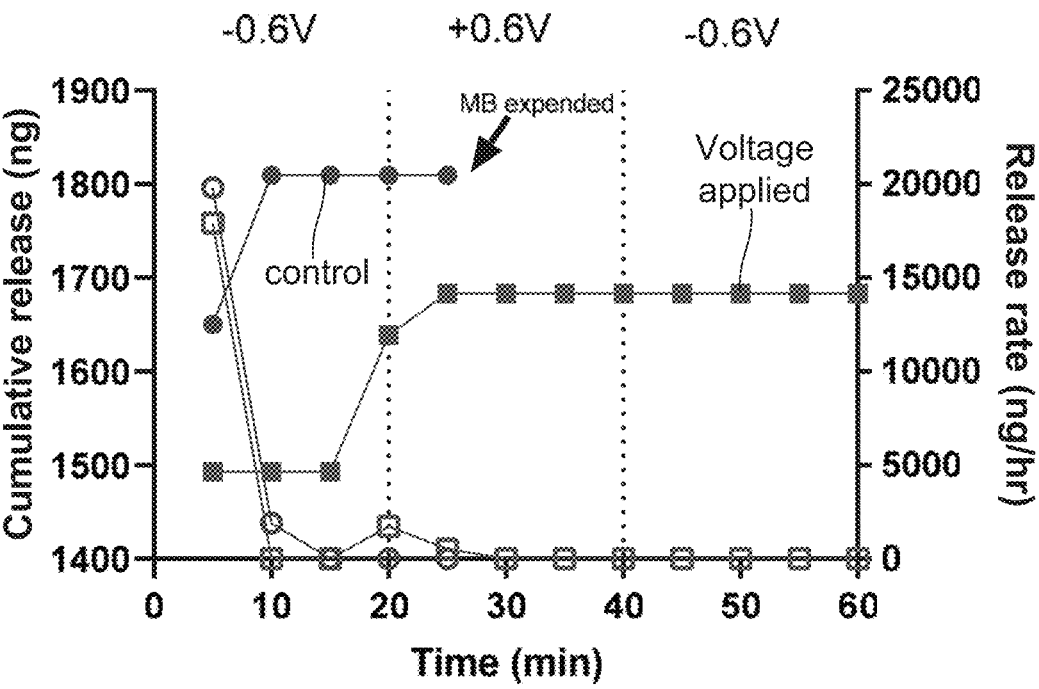
FIG. 28 is a graph illustrating results of a third experiment to test methyl cellulose/sucrose suitability for therapeutic delivery.

A second experiment tested methyl cellulose/sucrose suitability for bulk delivery of therapeutic, and results are shown in FIG. 28.

Methyl cellulose/sucrose formulation was tested for its ability to release methylene blue. There was a rapid release of dye within the first 10 minutes of immersion into the PBS. This was reduced to zero by 15 mins (perhaps more due to the ionic nature of methylene blue rather than the properties of controllable hydrogel swelling as was seen with xanthan gum). No pulsatile release was observed, no change in either the rate or released amount occurred after 20 minutes, suggesting that the coating was dissolving off the electrode at a constant rate. This demonstrates that this formulation is suitable for bulk delivery of therapeutic where controlled delivery is not a requirement.

Following this, Xanthan gum was chosen to move forward into ex vivo pig skin experiments. The ex vivo pig skin experiments were performed using the following steps:

Gold coated microstructure patches were fabricated and connected to electrical connections.

Patches were cleaned using acetone, then isopropanol and dried using N2.

Patches were treated with 20 uL 0.01% w/v poly-l-lysine for 30 mins, removed, then dried under N2.

Patches were dip coated in 2% w/v xanthan gum 0.8 mg/mL methylene blue, then dried upside down under vacuum in a desiccator overnight.

Pig skin was acquired and stored at minus 20° C. until used. Hair was clipped and shaved, and the ear pinna removed.

A silver/silver chloride reference electrode was inserted just underneath the surface of the skin.

Patches (either unconnected, no voltage controls, or wired patches connected to a DC power supply) were applied to the skin with a force of 40N for 10 seconds.

Polyacrylamide tape-insulated reverse forceps/metal pegs were used to keep patches in place throughout experiment.

Skin was kept hydrated by applying Krebs Heinseleit perfusate soaked paper towels in between experiments, and by adding 2 drops of perfusate on top of each patches at the beginning of each experiment to aid swelling in the ex vivo tissue.

Monitoring period was 60 minutes in total during which time −0.6V or +0.6V was applied, or −0.6V for 20 mins followed by +0.6V for 40 mins. After this period patches were removed and placed in 5 mL PBS on the vortex shaker for 2 hours to remove all remaining methylene blue on the surface of the patch. Photographs were taken of the skin site for visual assessment of engagement and delivery.

Absorbance was measured at 665 nm and released amount calculated. To gain a 'delivered amount' 9× dip-coated and immediately eluted patches gave an 'average coating amount' which was used to calculate delivered amount and percentage.

A fourth experiment tested the electrically tunable release of proxy drug into pig skin.

The results show amounts of methyleneblue eluted from microstructure patches immediately after removal from the skin surface, when either no voltage was applied (red), −0.6V was applied for 20 min, then +0.6V was applied for 40 min (green), +0.6V was applied for 60 min (orange) or a voltage of −0.6V was applied for 60 mins (purple).

Figure 29A:
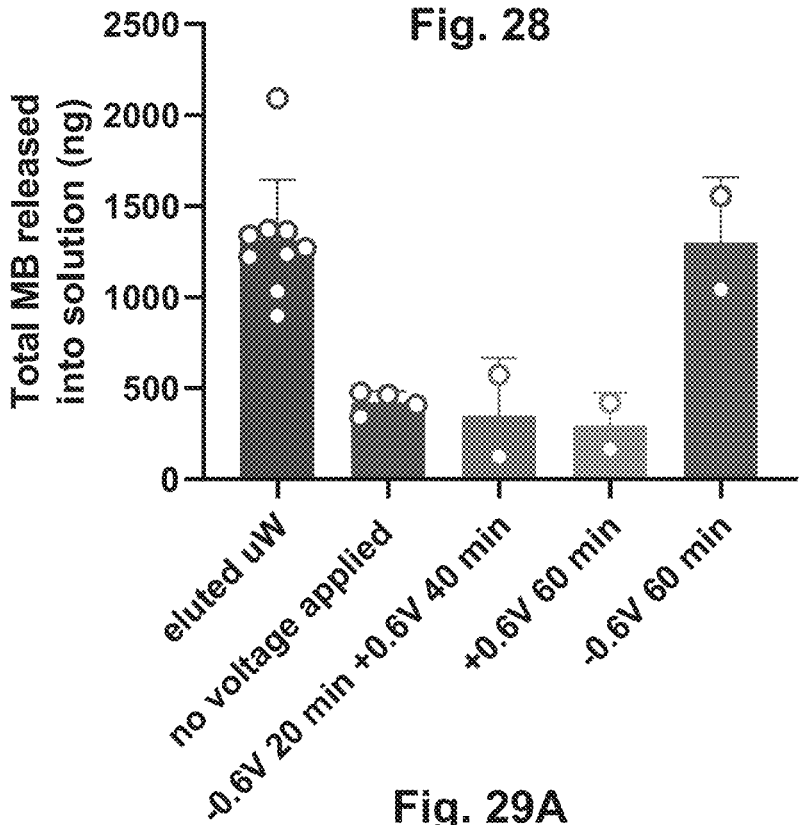
FIG. 29A is a graph illustrating a total amount of methylene blue retained on a patch for a fourth experiment to test electrically tunable release of proxy drug into pig skin.
Figures 29B, 29C:
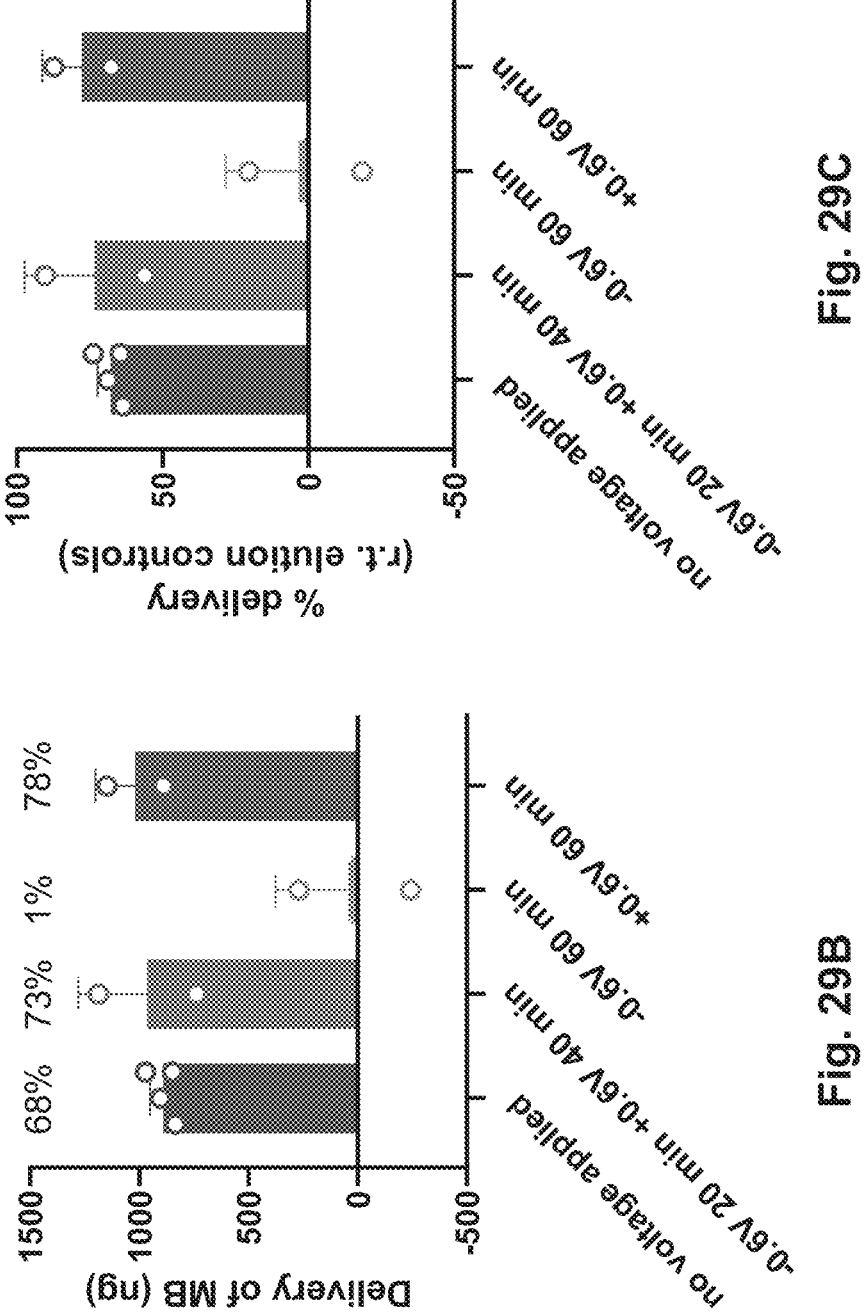
FIG. 29B is a graph illustrating a delivered amount of methylene blue for the fourth experiment.
FIG. 29C is a graph illustrating a percentage amount of methylene blue delivered for the fourth experiment.

Results in FIGS. 29A to 29C show a slightly increased delivery when +0.6V is applied compared to when no voltage is applied, with similar levels of delivery between the +0.6V 60 min and −0.6V followed by +0.6V programs (73% and 78% compared to 68%). Delivery into the skin was dramatically reduced when a negative bias was applied, with an average delivery of only 1% (relative to the average reading from nine control patches that coated and then were immediately eluted). This suggests a tight control over the timing of delivery of a therapeutic, such that a negative bias can be applied when drug should NOT be delivered, and removed/switched to a positive bias when a signal is received to initiate therapeutic release.

Optical Sensing

As mentioned above, in some examples, optical sensing can be performed. In this regard, Resazurin is a widely used colorimetric and fluorometric indicator of the metabolic capacity of live cells. At physiological pH resazurin is a deep blue colour, however in the presence of small molecules, like NADH from the mitochondria, resazurin can be reduced to resorufin, which is pink and fluorescent. This assay is quantifiable, inexpensive, and highly sensitive to cellular activity.

To produce optically clear flat-topped microstructures for this proof of concept an etched ITO circuit on a PET Substrate was bonded to an SU8 laminate, which is then patterned using photolithography. There were then coated these structures with biocompatible alginate hydrogel as a vehicle to contain the resazurin.

The alginate hydrogel was prepared by coating bare SU8 microstructures via drop casting: first a poly-l-lysine solution to increase adhesion, then a resazurin/alginate/sucrose hydrogel solution, then a calcium chloride crosslinking solution.

The cells used to reduce the resazurin were dried yeast in a phosphate buffered saline with glucose, which was pipetted on to the microstructures and held at a temperature of 37° C. for 30 minutes. The solution was then pipetted off and the microstructures rinsed and dried before UV-vis measurements.

The resazurin-coated clear microstructures reacted with the cell broth and changed appreciably to a pink colour. UV-vis measurements were taken through the microstructures from 900-300 nm. Photos were taken of representative hydrogel-coated microstructures directly on as well as at a slight angle so that the coating on the sides of the microstructures is visible.

Figure 30A:
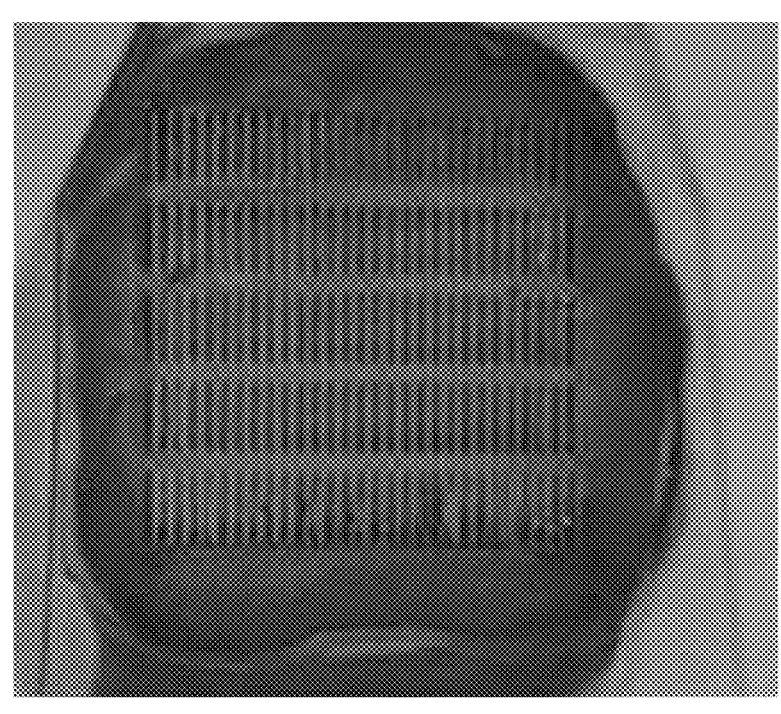
FIG. 30A is an image of a resazurin-coated clear microstructure patch.
Figure 30B:
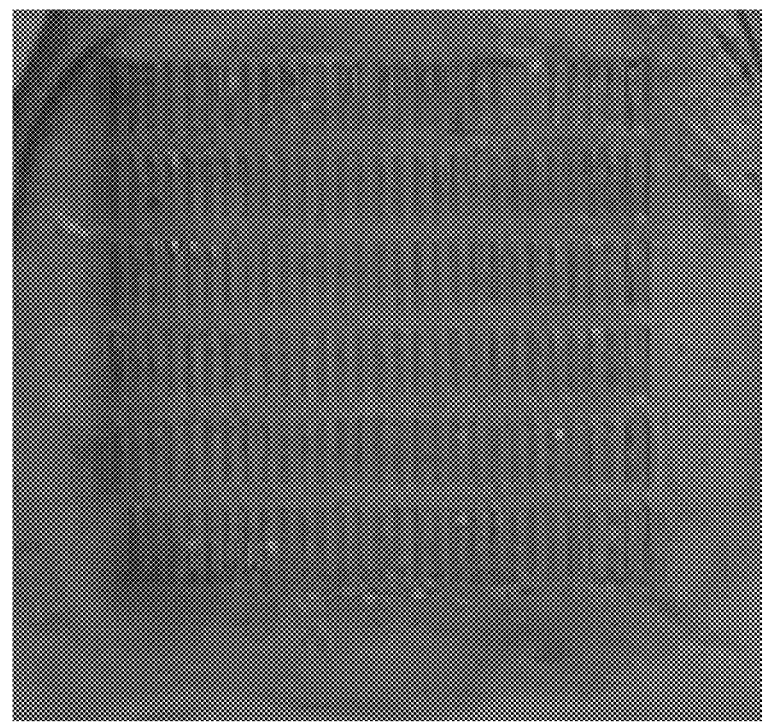
FIG. 30B is an image of the patch of FIG. 30A after exposure to a cell broth.
Figure 30C:
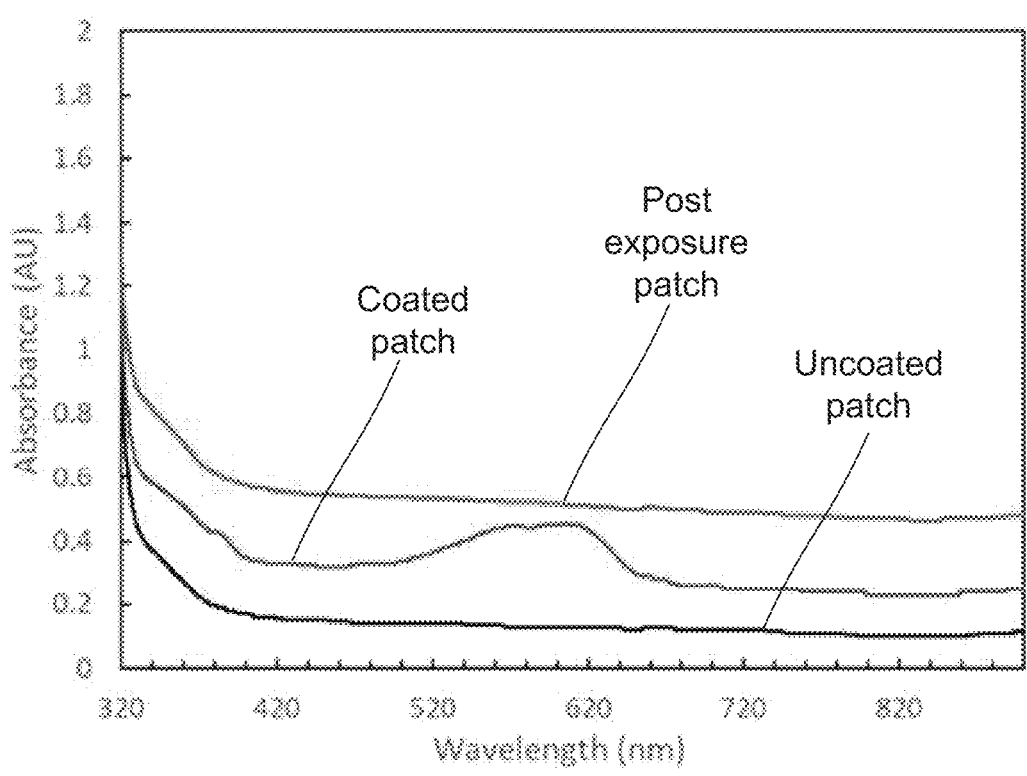
FIG. 30C is a graph of UV-vis measurements taken through the microstructures of the patch of FIG. 30A, prior to coating, after coating and following exposure.

FIG. 30A shows as-deposited resazurin hydrogel on SU8 microstructures, showing the vivid blue colour and distribution of the hydrogel on the sides of the flat-topped plates. FIG. 30B demonstrates the colour change after 30 mins of exposure to the yeast broth. Each microstructure is approximately 200 μm long. The graph in FIG. 30C shows the UV-vis spectra of the blank patch, resazurin-coated patch, and the resazurin-patch post exposure with the lower wavelengths excluded due to high absorption from the SU8. Disappearance of the peaks at 570 nm and 610 nm in the UV-vis spectrum also indicate the reaction with metabolites.

These results demonstrate the ability to detect colour changes in a coating on the patch either using suitable sensing, such as a CCD sensor, photodiode, or similar, or by way of visual inspection.

A further experiment on optical detection of biological analytes was demonstrated by the color changes of electropolymerized polyaniline in the presence of iron (III). Almost 70 percent of Iron in the body is found in the red blood cells. Presence of iron in the ISF may suggest occurrence of hemorrhaging.

In this example, polyaniline changes color when exposed to acids or bases as a result from the changes in its structure when protonated to deprotonate. The structure of PANI also changes when reduced (Leucoemeraldine structure) or oxidized (Emeraldine structure), and so a biologically relevant analyte that can cause redox reaction may be detected from the changes in the color of polyaniline. In this example, Iron (III) ions are deficient of electrons which can be supplemented by another species in the reaction. This transfer of electrons causes oxidation of another reactant which in this case is the polyaniline.

Polyaniline was prepared by electropolymerisation on Gold plated glass substrate. The polymerizing solution contained: 0.1M Aniline in 0.1M HCl. Polyaniline was formed by applying voltage sweep from −0.2 to 1V, at 50 mV/s for 5 and 10 cycles. 5 cycles made a yellow (Leucoemeraldine) polyaniline coating, while 10 cycles made a green (Emeraldine) polyaniline coating.

Optical sensing experiment using acid (0.1 M HCl), base (0.1 M NaOH), and $Fe^{3+}$ (0.1 M $FeCl_3$) were performed which demonstrated colour changes in Polyaniline. The polyaniline was yellow in acid and was dark blue in base. This color change was reversible. When introduced to Fe3+, the polyaniline turned from greenish to dark blue which was irreversible. The change of color indicated the detection of Fe3+.

Analyte Detection—Molecularly Imprinted Polymers

Analyte detection has been demonstrated using molecularly imprinted polymers (MIPs). All chemicals and reagents used are commercially available from, for example, Sigma-Aldrich Co. LLC, unless otherwise specified.

A microstructure coated with the conductive MIP, molecularly imprinted conductive polypyrrole (MICP), doped with $LiClO_4$ was prepared by electropolymerisation on gold coated microstructures. A polymerising solution was prepared by dissolving the monomer (0.01 M pyrrole), the template (which is the target analyte; 1.2 µg/mL recombinant troponin I), and the supporting electrolyte/dopant (0.005 M $LiClO_4$) in 0.15 M phosphate-buffered saline (PBS). Electropolymerisation was performed using a 3-electrode system where the microstructure was the working electrode, commercial Ag/AgCl was the reference electrode, and platinum coil was the counter electrode. Cyclic voltammetry was performed between −0.8 to 1.2 V at 50 mV/s for 20 cycles. The template was then separated from the polymer by soaking in 0.005 M oxalic acid overnight at 4° C. to produce the MICP-coated microstructure.

To demonstrate the effectiveness of MICP for analyte detection, experiments were performed to detect troponin using the MICP-coated microstructure prepared using the method described above.

An in vitro experiment was performed using the following steps:

The experiment was done in a well plate.

The binding of the target analyte (recombinant troponin I) in the MICP was measured from the change in the impedance of the system.

Impedance analysis was performed using a 2-electrode system at open circuit potential (OCP). The impedance was measured from 100 kHz to 0.1 Hz with an oscillation potential amplitude of 10 mV.

The interdigitated electrode (1 part coated with MICP, which was the working electrode; and the other part bare Gold (AU), which was the reference/counter electrode) was soaked in 0.15 M PBS solution.

Impedance was measured every 5 min for 30 min.

After 30 min, a volume of recombinant troponin I was added to the PBS solution to simulate a myocardial infarction.

The impedance was then measured every 5 min for 30 min.

After 30 min, a volume of recombinant troponin I was again added into the solution, and the impedance was monitored every 5 min.

Recombinant troponin I addition and impedance measurements were repeated until the concentration of troponin I in the solution reached 100 ng/ml.

Figure 31:
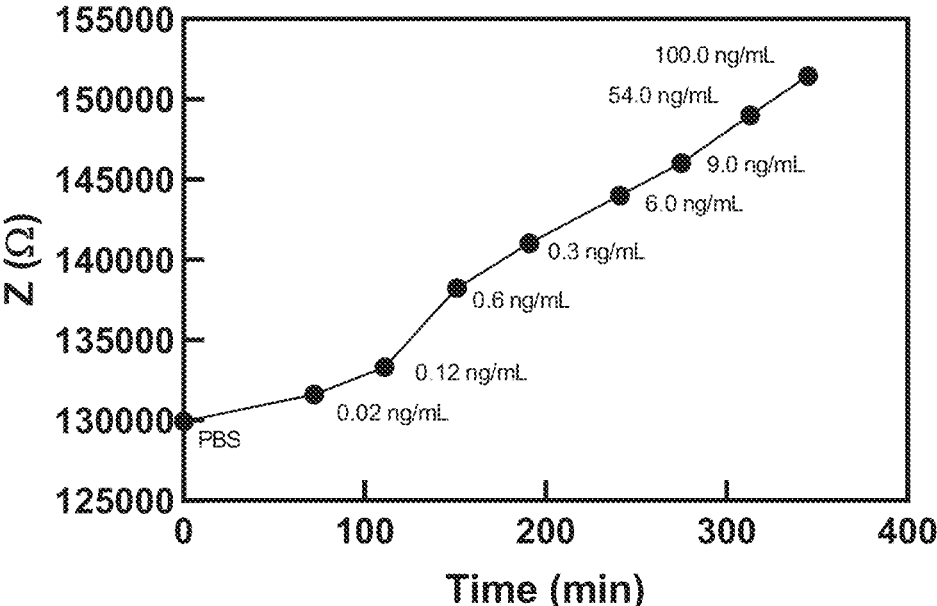
FIG. 31 is a graph of change in impedance of a molecularly imprinted polymer on exposure to troponin-I.

The measured impedance is shown in FIG. 31. After 10 min in PBS, the impedance had equilibrated. Upon addition of increasing amounts of recombinant troponin I, the impedance correspondingly increased. The change in the impedance suggests the binding of recombinant troponin I to the imprints of the polymer. The filled imprints cause hindered diffusion of ions into the polymer and also promote strain in the structure causing increase in the resistance in the system.

The effectiveness of MIP for analyte detection ex vivo was determined using soaked pig skin using the following steps:

~8 mm×16 mm skin tissues were sampled from pig ear.

The skin tissues were soaked in PBS solutions of recombinant troponin I (0, 300, 600, and 1000 ng/mL) overnight at 4° C. Note that troponin concentration in the skin tissue may not be the same as the troponin concentration in the solution.

Before measurement, the skin tissues were pat dry.

Microstructures were engaged on the skin by applying ~40N forces on them. The microstructures were held in place using clips.

Figure 32A:
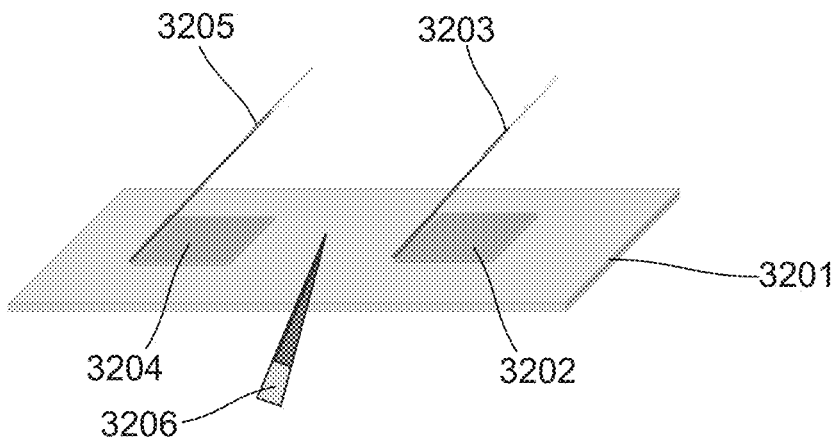
FIG. 32A is a schematic diagram of an example of an experimental configuration for ex-vivo detection of troponin-I in pig skin.

The impedance measurement was performed using 2-electrode set-up as shown in FIG. 32A, including the pig skin 3201, patches 3202, 3204 and respective connections 3203, 3205 and a reference electrode 3206. The patch 3202 was coated with non-imprinted conductive polypyrrole (NICP) (using the method described above, in the absence of the template) whilst patch 3204 was coated with molecularly imprinted conductive polypyrrole (MICP) (using the method described above).

Impedance was measured within 100 kHz to 0.1 Hz.

Figure 32B:
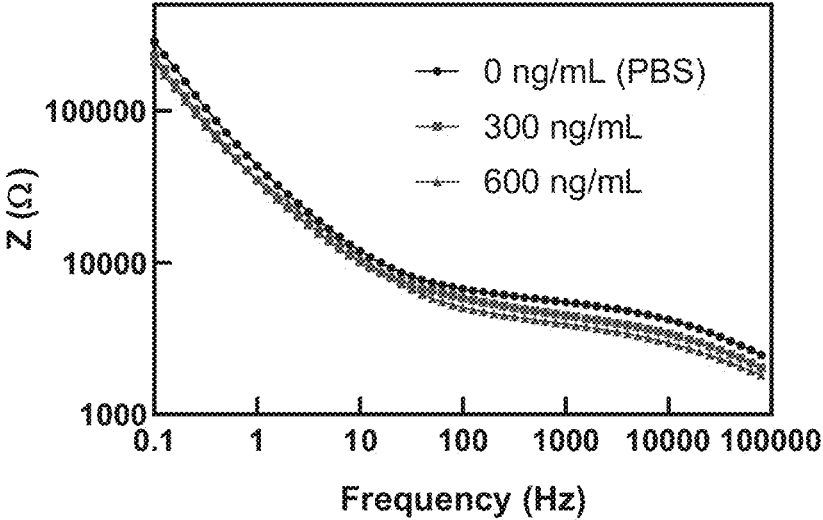
FIG. 32B is a graph illustrating changes in impedance for different concentrations of troponin-I for a molecularly imprinted conductive polypyrrole (MICP) coated patch.
Figure 32C:
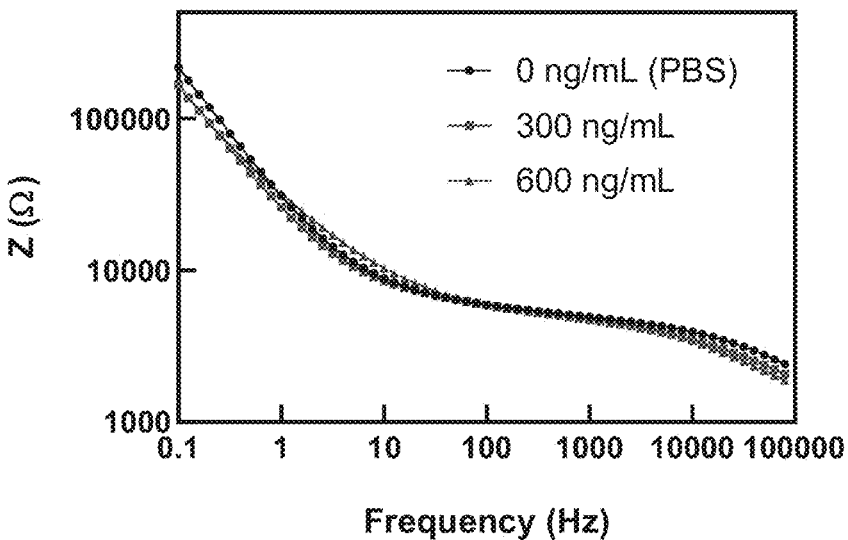
FIG. 32C is a graph illustrating changes in impedance for different concentrations of troponin-I for a non-imprinted conductive polypyrrole (NICP) coated patch.

FIGS. 32B and 32C display the raw impedance readings for MICP and NICP-coated microstructures, respectively, in the presence of varying concentrations of troponin I and highlight that a change in impedance arises for different concentrations of troponin, and that similar raw impedance profiles are detected for MICP and NICP. This also highlights that compared to the in vitro experiment above, the ex vivo impedance readings are generally lower as the skin contains more ions than what is in PBS, resulting in greater conductivity (lower resistance).

Figure 32D:
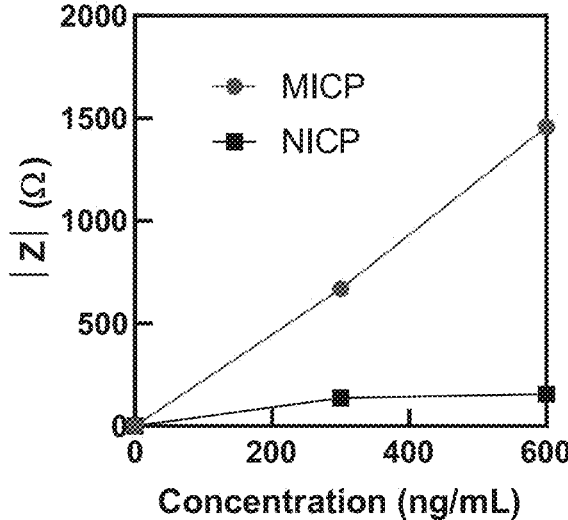
FIG. 32D is a graph illustrating a comparison of changes in impedance for MICP and NICP patches.

A comparison of the change in impedance at 100 Hz for MICP and NICP-coated microstructures in the presence of varying concentrations of troponin I is shown in FIG. 32D. This data shows that there is a greater change in impedance readings with increasing concentrations of troponin I for the MICP-coated microstructure, with there being little to no change in impedance readings for the NICP-coated microstructure with increasing troponin I concentration.

This is in alignment with predicted results, as the NICP-coated microstructure is expected to have a lower response than the MICP-coated microstructure to troponin as it does not contain troponin-specific cavities. Accordingly, the presence of troponin will not have a high effect on the structure of the NICP. This demonstrates the efficacy of MIPs for detecting analytes.

The effectiveness of MIP for analyte detection in a perfused ex vivo system was determined using perfused pig skin using the following steps:

A whole fresh pig ear was first perfused.

The areas for electrodes were shaved to remove the hairs.

The MICP-coated microstructures (prepared using the method described above) were engaged on the skin by applying ~40N force on it. The microstructure was held in place using forceps.

A sharp Ag/AgCl reference electrode was inserted close to the microstructure.

0.5 mL Krebs-Henseleit perfusate was injected to the veins every minute to avoid dehydration of the skin.

Recombinant troponin I was introduced to the skin by injecting 5 mL of 600 ng/ml recombinant troponin I in 0.15M PBS into the pig ear veins after 5 mins.

Figure 33A:
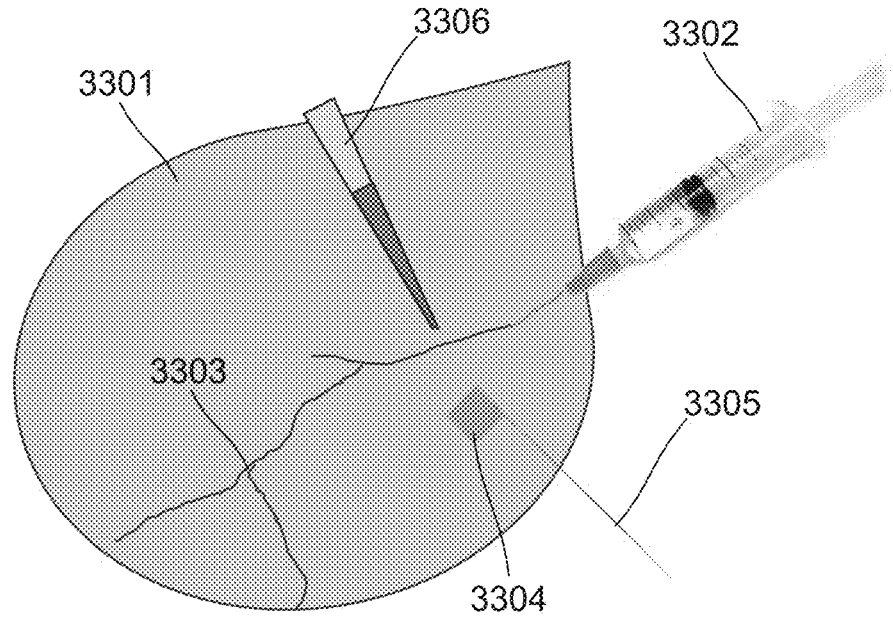
FIG. 33A is a schematic diagram of an example of an experimental configuration for ex-vivo detection of troponin-I in pig skin.

The impedance measurement was performed using a 2-electrode set-up shown in FIG. 33A, including pig skin 3301, perfused using a syringe 3302 to inject perfusate into veins 3303. A patch 3304 is positioned proximate the veins and coupled to an electrical connection 3305, with an Ag/AgCl reference electrode 3306 being provided proximate to the vein.

The impedance was measured every 30 seconds at 1 Hz.

Figure 33B:
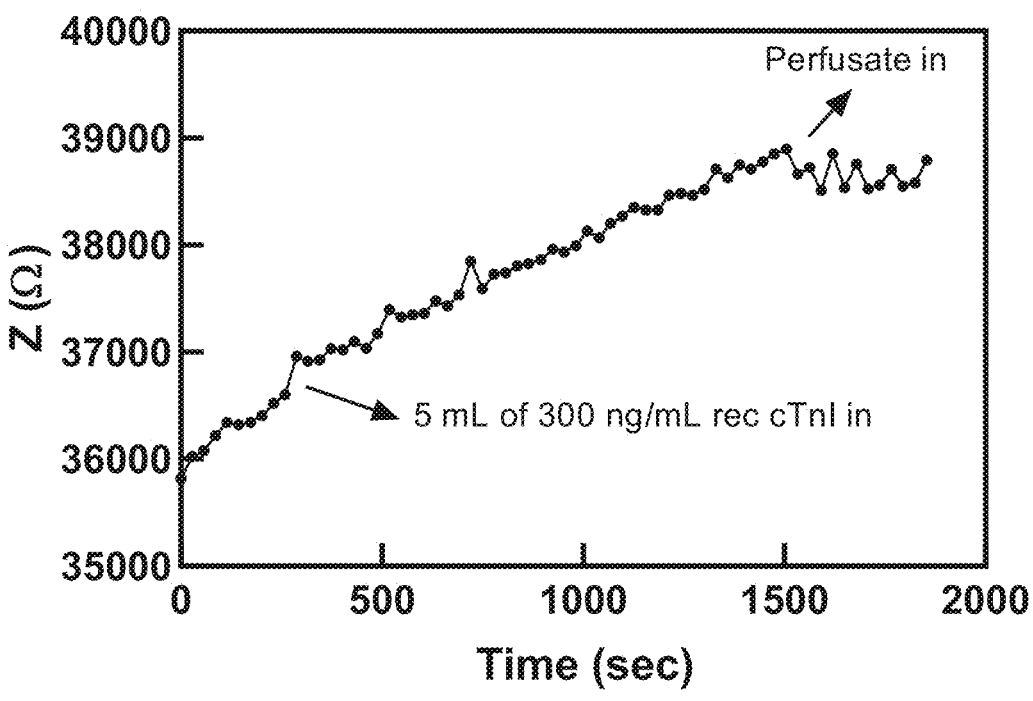
FIG. 33B is a graph illustrating example raw impedance values over time as the pig skin of FIG. 33A is perfused.
Figure 33C:
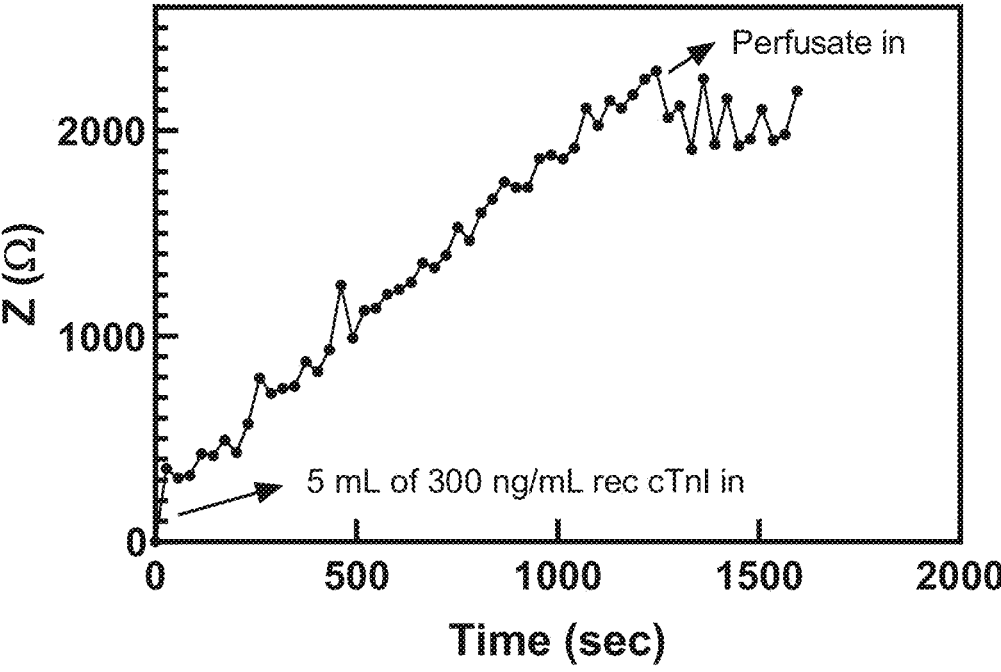
FIG. 33C is a graph illustrating example changes in impedance values over time as the pig skin of FIG. 33A is perfused.

Results shown in FIGS. 33B and 33C highlight that there is a gradual increase in the impedance over time even before troponin I was injected, highlighting that perfusing to maintain hydration causes a change in impedance. Nevertheless, after injection of troponin I there is a jump in impedance. Furthermore, after 30 min, the troponin was washed out with perfusate, leading to a leveling off of impedance. This demonstrates an increase in the impedance when troponin I was introduced, with this ceasing when the troponin I was washed out with perfusate.

Analyte Detection—Aptamers

Analyte detection has been demonstrated using aptamers.

To demonstrate the effectiveness of aptamers experiments were performed to detect troponin. All chemicals and reagents used are commercially available from, for example, Sigma-Aldrich Co. LLC, unless otherwise specified.

An aptamer with the following sequence was obtaineded (Bioneer Pacific): 5'-(SH)-(CH$_2$)$_6$-AGT CTC CGC TGT CCT CCC GAT GCA CTT GAC GTA TGT CTC ACT TTC TTT TCA TTG ACA TGG GAT GAC GCC GTG ACT G-[Methylene blue]-3' as previously described in Negahdary et al. (2018) *J. Biomed. Phys. Eng.*, 8(2): 167. The methylene blue (MB) and the thiol group were covalently attached to the 5' and 3' ends of the aptamer using standard techniques, such as those described in Liu et al. (2010) *Anal Chem*, 82(19): 8131-8136, the contents of which is incorporated herein by reference. The aptamers were immobilised to the gold electrode, to form thiol self-assembled monolayers. This is achieved by immersing the electrode in a 10 µM aptamer 150 mM PBS solution for 80 minutes, drop casting, waiting 80 minutes and removing excess solution. The electrode was washed with deionised water and dried with nitrogen, before the process was repeated with a 1 mM 6-mercaptohexanol 150 mM PBS solution for 40 minutes, before rinsing and drying as above and then storing the electrode in a cooled PBS solution in dark conditions for 7 days.

Figure 34B:
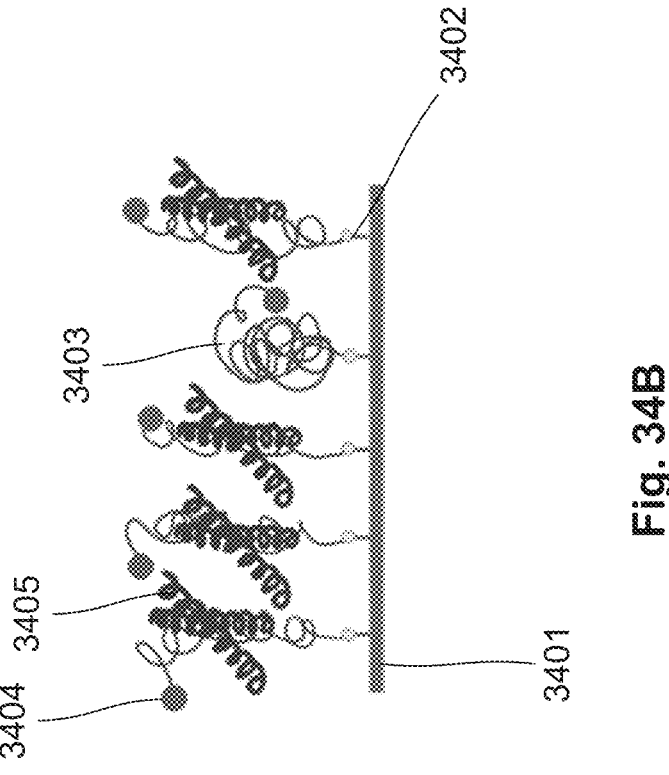
FIG. 34B is a schematic diagram illustrating an example of an aptamer configuration after reaction with an analyte.
Figure 34A:
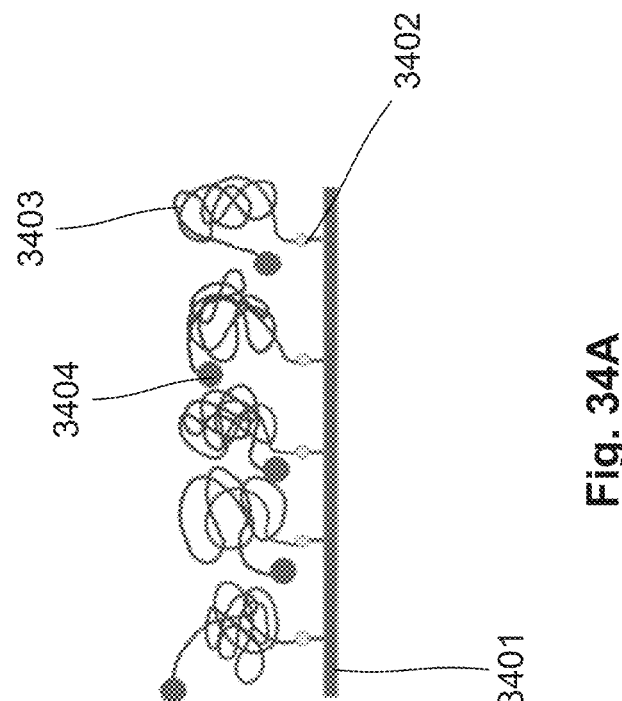
FIG. 34A is a schematic diagram illustrating an example of an aptamer configuration.

This aptamer is composed of three distinct elements as shown in FIGS. 34A and 34B. In this example, the aptamers include a thiol group 3402 for adhesion to gold electrodes 3401, a DNA section 3403 in the middle that interacts to specifically bind troponin I 3405, and a methylene blue (MB) moiety 3404 attached to the 3' end. The MB is electrochemically active, thus when it comes into proximity of the electrode at a certain potential it will oxidize or reduce, producing a measurable current. When in the presence of troponin I, as shown in FIG. 34B, the aptamers adopt a significantly different spatial conformation to unbound aptamers shown in FIG. 34A, with the result being the MB moieties are less able to interact with the electrode and the measurable redox current is therefore smaller.

An experiment was performed using cyclic voltammetry to detect electrical changes in aptamer-coated microstructures provided in perfused pig skin. The following steps were used:

Microstructures were coated with gold on the front (protrusion side) and on one of the patch edges, with the protrusion side further coated in a layer of aptamers as described above.

Copper wire was soldered to the gold covered edge to provide an electrical contact. Silver foil coated in AgCl was used as a pseudo-reference/counter electrode and was placed under the skin near the microstructure.

40 N of pressure was used to push the microstructures into the skin, which were held in place with surgical clamps during the measurements.

Data was measured with alternating current voltammetry to boost the signal obtained from the redox of the MB groups.

Starting at 25 minutes, 5 mL of perfusate containing 600 ng recombinant troponin I/mL was introduced over the course of 10 minutes, with massaging the vein in between measurements to help diffusion into the surrounding tissue.

Figure 35:
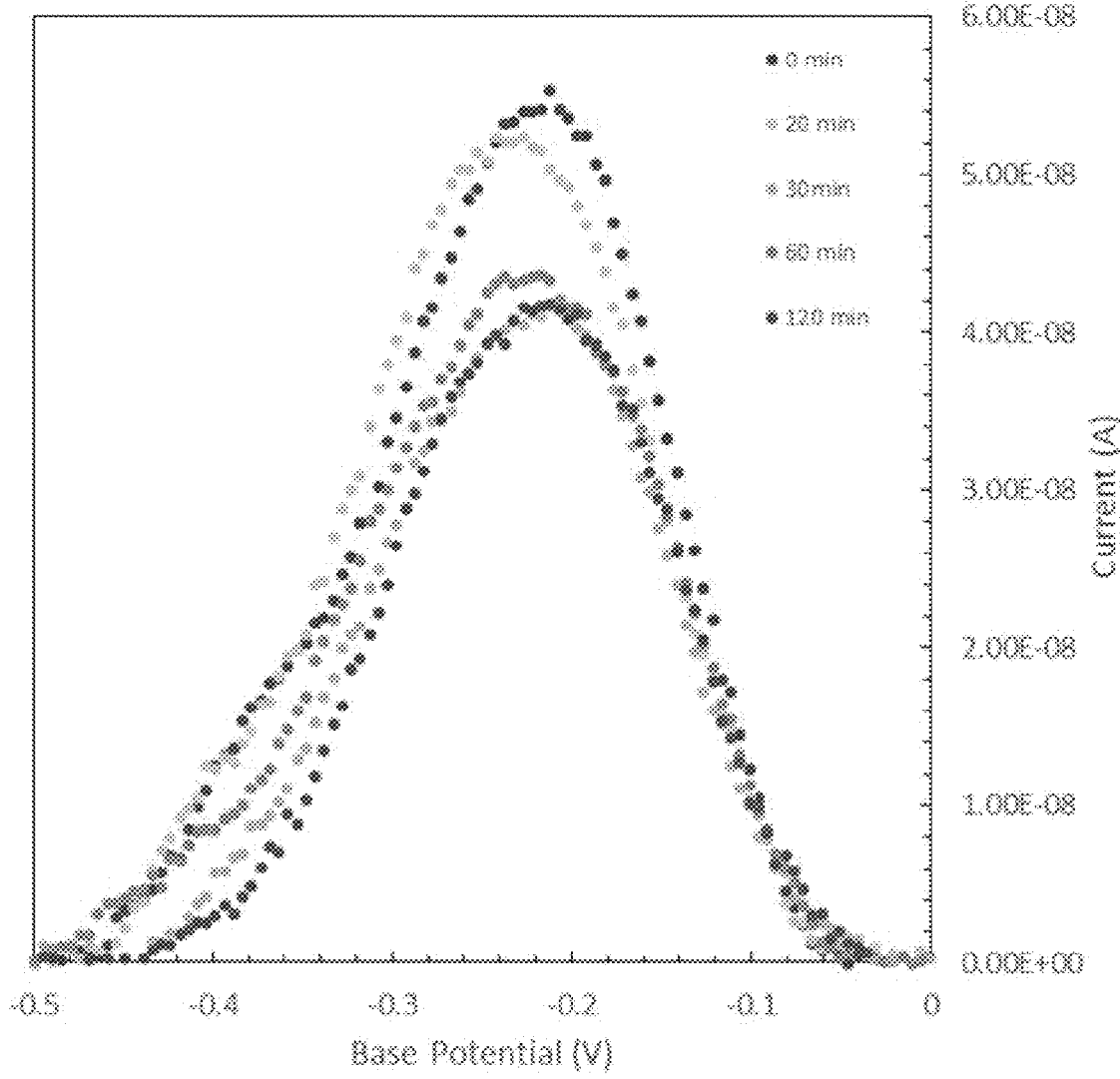
FIG. 35 is a graph illustrating changes in cyclic voltammetry readings following exposure of aptamer functionalised microstructures to an analyte.

Results in FIG. 35 show the effect on an aptamer-functionalized microstructure of adding troponin I in perfusate to a vein in a pig ear. The 0 min and 20 min curves establish a baseline for the size of the MB redox peak, then at 25 minutes troponin I was introduced into the vein. Voltammograms measured at 30 mins, 60 mins, and 120 mins show the decreased current response of MB with troponin I exposure, indicating that the patch quickly responds to the analyte and maintains a constant signal.

It is possible that this consistency of the signal over the course of the experiment is due to saturation of the aptamer layer with troponin I, and therefore does not show the changing levels of troponin in the system as more perfusate is injected.

A further experiment was performed using aptamer-functionalized disk electrodes to establish specificity of the aptamer-functionalized electrodes to troponin I over a non-specific protein. These data were measured in vitro, measuring the current response of aptamer-functionalized gold disk electrode in phosphate buffered saline (PBS) with increasing amounts of recombinant troponin I added to the solution. The following steps were performed:

Gold disk electrodes (4 mm diameter) were coated in a layer of aptamers (prepared as described above). A coiled platinum wire was used as a counter electrode, and an Ag/AgCl wire was used as a pseudo reference electrode.

Data was measured with alternating current voltammetry to boost the signal obtained from the redox of the MB groups.

150 mM PBS was used (pH 7.4) as a proxy for interstitial fluid.

Figure 36A:
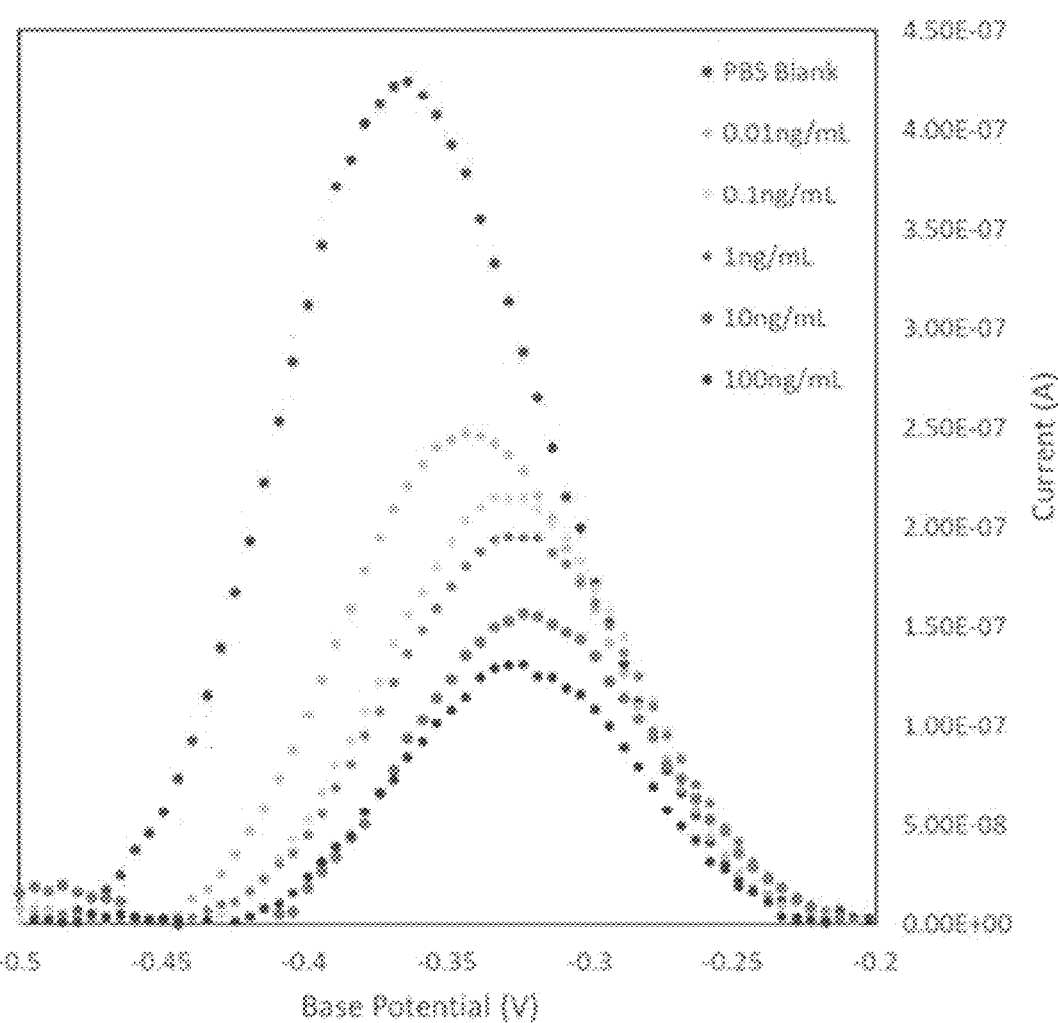
FIG. 36A is a graph illustrating changes in cyclic voltammetry readings following exposure of aptamer functionalised microstructures to an analyte.
Figure 36B:
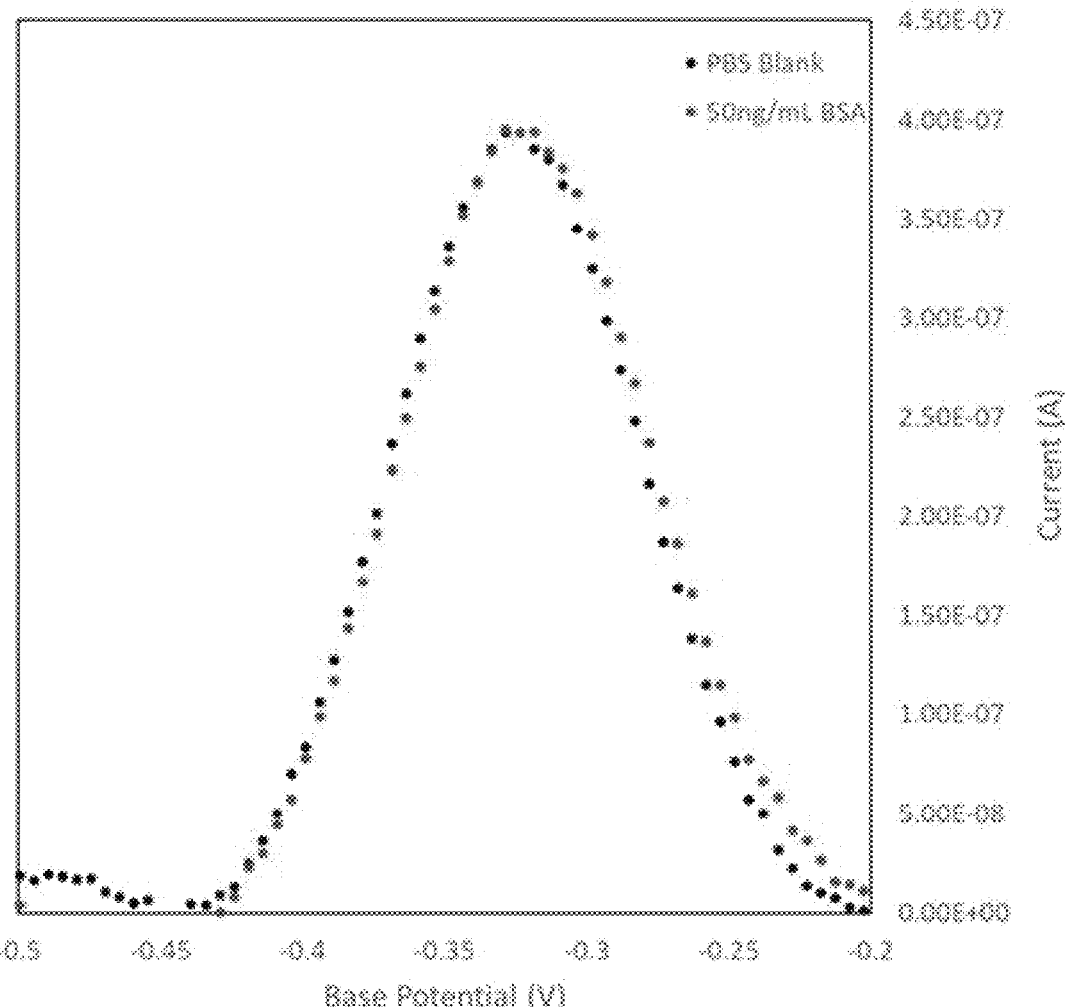
FIG. 36B is a graph illustrating changes in cyclic voltammetry readings following exposure of aptamer functionalised microstructures to control solution.

Results are shown in FIGS. 36A and 36B. FIG. 36A shows current response of the MB in PBS as a baseline measurement, with this decreasing with increasing concentrations of troponin I. The range of concentrations covers the 0.03-50 ng/mL clinically relevant range of troponin I in solution and are differentiable. Concentration curve data were measured once 5, 10 and 15 minutes had passed after spiking the solution with troponin I, then were averaged. It was assumed that an apatamer-troponin I equilibrium was established in the first few minutes because there were no systematic changes in the voltammagrams between 5, 10, and 15 min.

The graph in FIG. 36B shows the current response of a similarly-functionalized disk electrode in PBS and after being spiked with 50 ng/ml bovine serum albumin to test the selectivity of the aptamer response to troponin I. The similarity of the two spectra indicate little interaction, demonstrating the ability of the aptamer to target a specific analyte.

Analyte Detection—Antibodies

Antibody-capture of proteins of interest is a widely established technique. An interdigitate gold substrate is functionalized and the capture antibody is then attached. All chemicals, antibodies and reagents used are commercially available from, for example, Sigma-Aldrich Co. LLC, or Abcam unless otherwise specified.

Figure 37B:
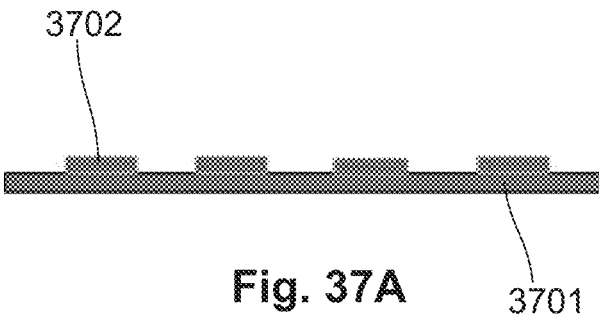
Figure 37B:
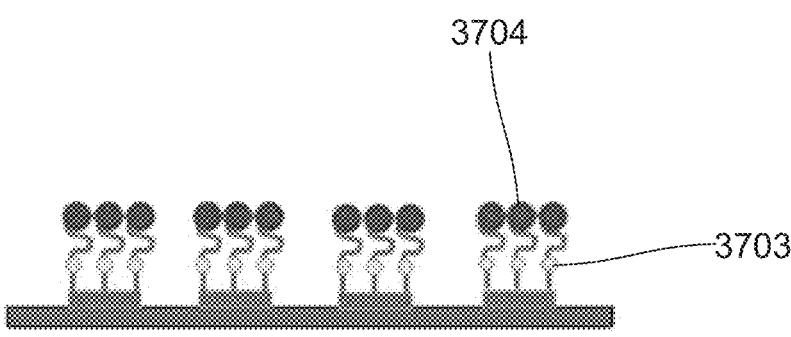
Figure 37C:
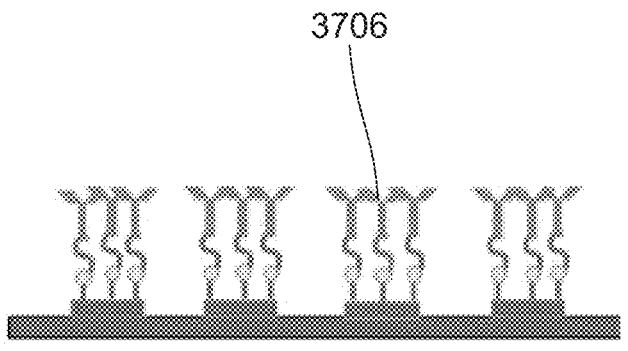

An example of this is shown in FIGS. 37A to 37C, in which a substrate 3701 having electrodes 3702 is functionalised with dithiobis(succinimidyl propionate) (DSP) 3704 attached to the electrodes via a thiol group 3603. An antibody 3705 is then bound to the DSP as shown in FIG. 37C.

Electrochemical methods such as electrochemical impedance spectroscopy (EIS) quantify the antibody-analyte capturing interactions when the functionalized electrode is exposed to the desired analyte. Without wishing to be bound by theory, analyte capture should result in thicker films with increased film capacitances as well as higher system impedances.

An experiment was performed using rabbit monoclonal anti-troponin I antibodies (Abcam) using the following steps:

An interdigitate gold substrate was functionalized by creating a self-assembled monolayer (SAM) out of DSP, and a monoclonal anti-troponin I antibody was attached.

Measurements were made on 100 μm wide gold interdigitate arrays with 100 μm gaps between working and counter electrodes. The reference electrode used was a 3 M Ag/AgCl reference electrode. The electrolyte used was 0.150 M PBS with a 5 mM ferrous/ferric cyanide redox probe. Samples were allowed to equilibrate in solution for 30 minutes before measurements.

Electrodes were exposed to increasing concentrations of recombinant troponin I and impedance and film capacitance (CPE) were measured over time.

Selectivity tests with 50 ng/mL BSA vs PBS have shown an average film impedance increase of 104 ohm±59.3 ohm.

Figure 38A:
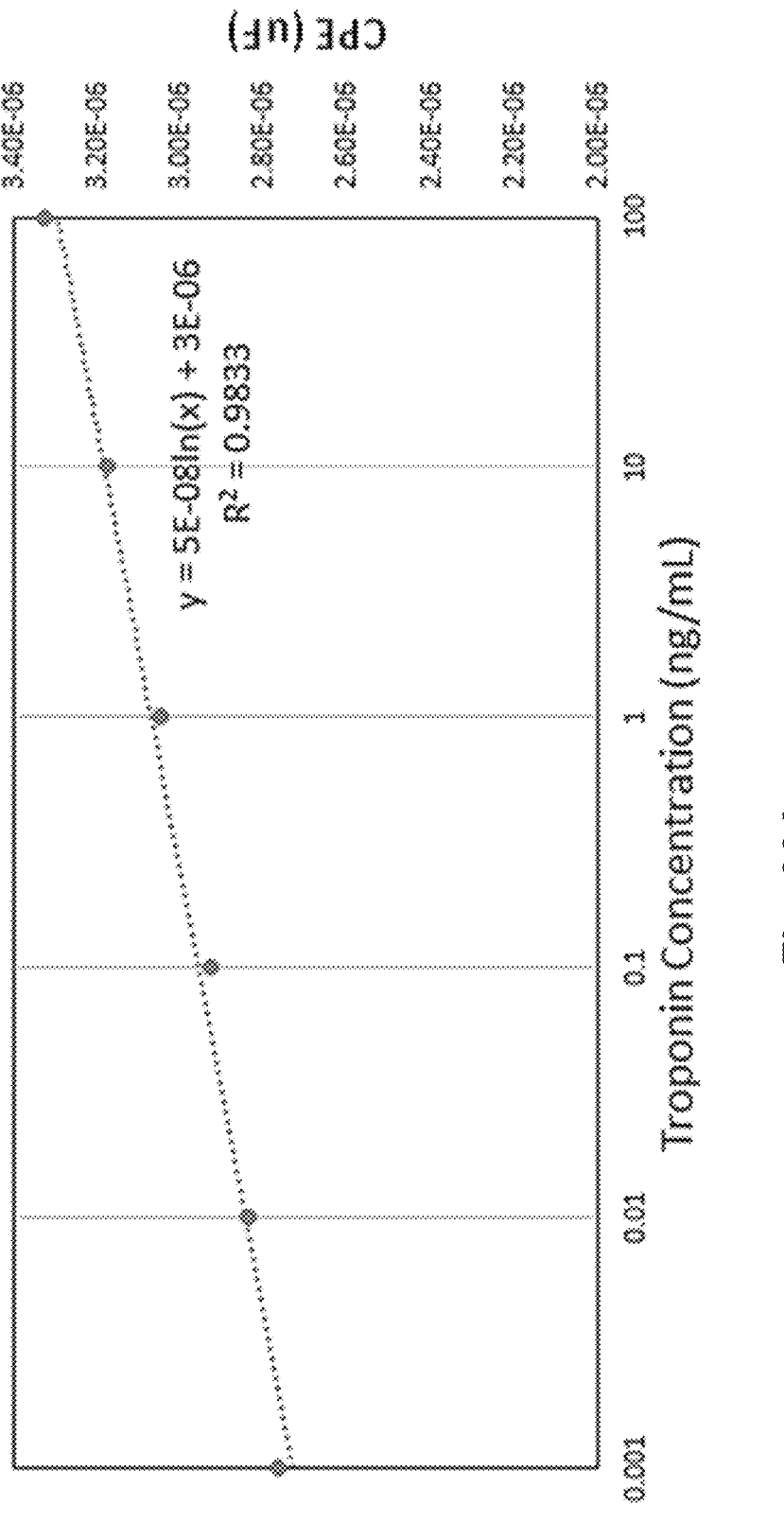
FIG. 38A is a graph showing a change in capacitance on exposure to analytes.
Figure 38B:
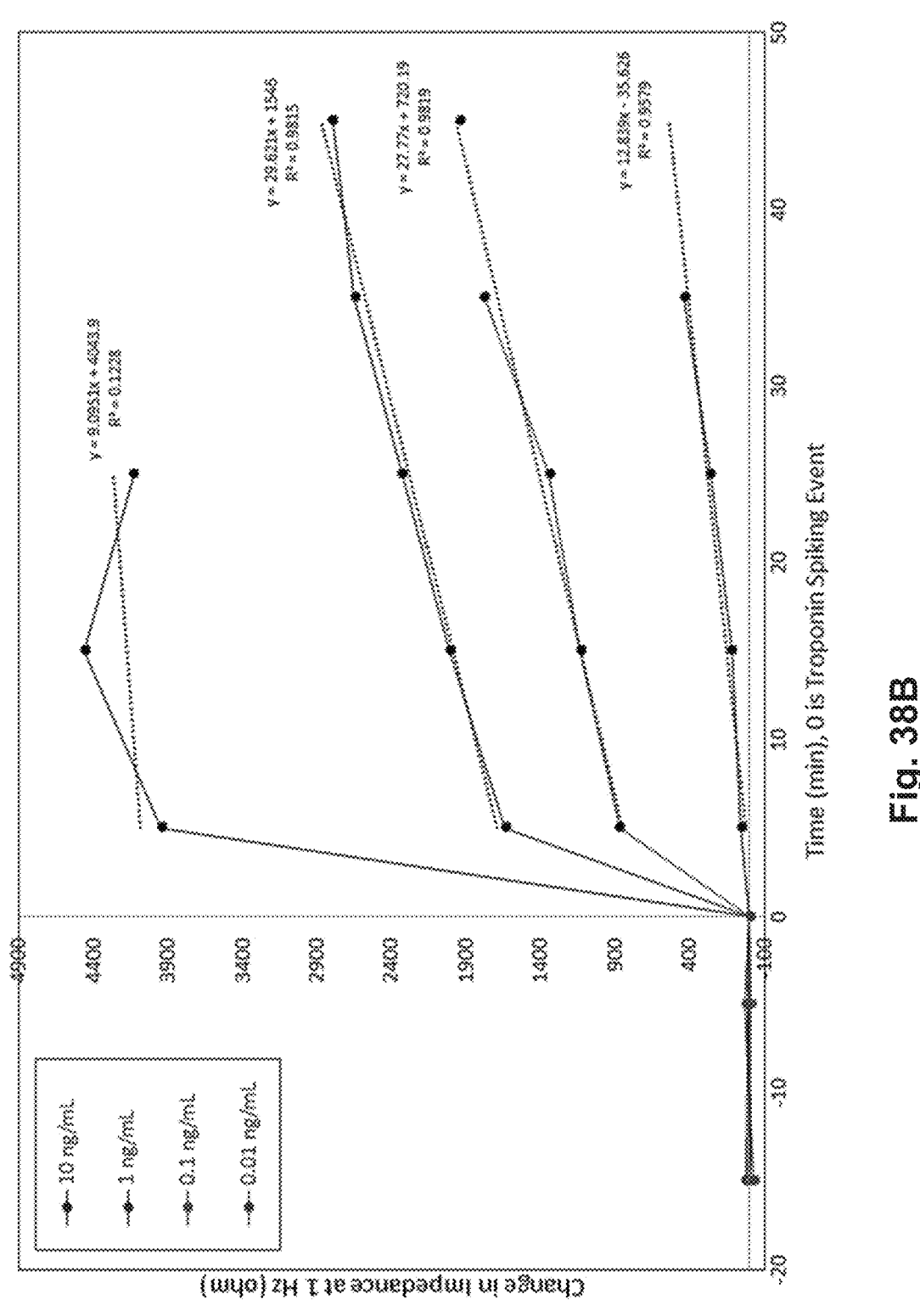
FIG. 38B is a graph showing a change in impedance on exposure to troponin-I.

Results are shown in FIGS. 38A and 38B. FIG. 38A shows a measure of film capacitance (CPE) of an electrode as it is exposed to progressively higher concentrations of troponin I in solution. The same electrode is used and placed in increasingly concentrated solutions, resulting in the expected capacitance increase.

FIG. 38B demonstrates changes in impedance in response to simulated heart attacks (myocardial infarction). In this example, an electrode is measured in PBS until it reaches equilibrium, then a spike of recombinant troponin I is added to bring the solution up to a desired concentration of troponin I. This graph shows the responses of five electrodes to troponin spikes that cover clinically relevant concentrations, and demonstrates that the change in impedance increases with increasing troponin I concentrations.

Erythema

Studies have been performed to evaluate the tolerability and functionality of microstructure patches in humans.

Figure 39A:
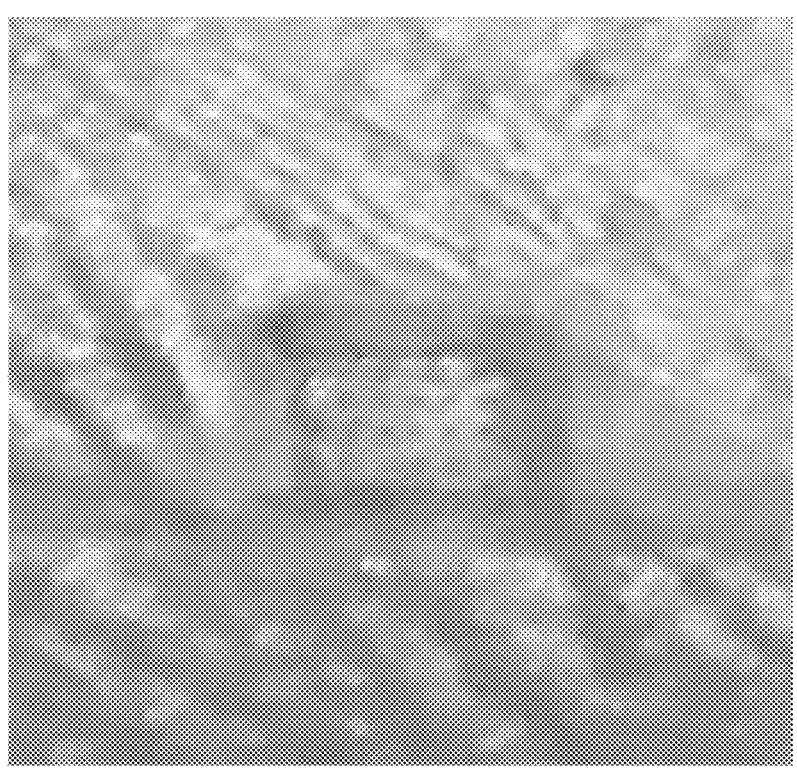
FIG. 39A is an image of a microstructure patch application site on a human forearm skin immediately post-removal.

In one example, a qualitative tolerability assessment was performed following microstructure patches application which noted a very mild local response at the application site immediately post-removal. This was characterized by slight indentation with no overt erythema or oedema, which was resolved within 15 minutes of removal. This is shown in FIG. 39A. This shows the indentation was most prominent around the edges and corners of the microstructure patch, with very mild redness at these locations, and with no redness associated with the microstructures themselves.

Figure 39B:
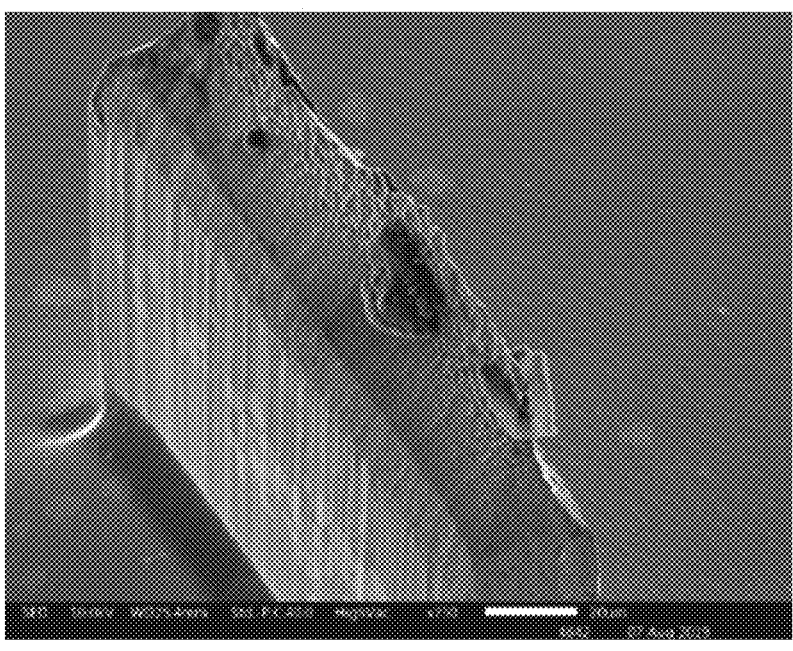
FIG. 39B is a Scanning Electron Micrograph of a microstructure after application to human skin.

Scanning Electron Microscopy (SEM) was performed to confirm that the microstructures had, in fact, penetrated the skin, showing cellular debris remaining on the removed microstructures, as shown in FIG. 39B, confirming successful microstructure penetration despite the absence of overt erythema.

To investigate this observation further, we two dedicated erythema studies were performed with multiple subjects. These studies investigated the local skin response to microstructure patch application to the skin of the anterior forearm over a time period of 2 hours. Microstructure patches were applied using a guided load cell mechanism, at a force of either 5N remaining in place for 30 minutes (Study 1) or 3N and remaining in place for 10 minutes (Study 2).

The first human erythema study was on five volunteers. In some cases, hair was removed from the skin using depilatory cream and a paper mask was fixed to the application area to avoid any effect due to sensitivity to surgical adhesives in tapes. Three separate non-functionalised microstructure patches were applied to skin exposed by windows in the paper mask, and a fourth window was untreated and used as a control for comparison.

Observations were made for local erythema and a scoring rubric was used as given in Table 5 below.

TABLE 5

| eScore | Observation |
|--------|-------------|
| 0 | No discernable difference relative to control |
| 1 | Very mild redness |
| 2 | Mild redness |
| 3 | Red region extending beyond 4 $mm^2$ application area |
| 4 | Extensive redness and/or capillary rupture |
| 5 | Frank blood and/or oedema superficially |

Figure 40A:
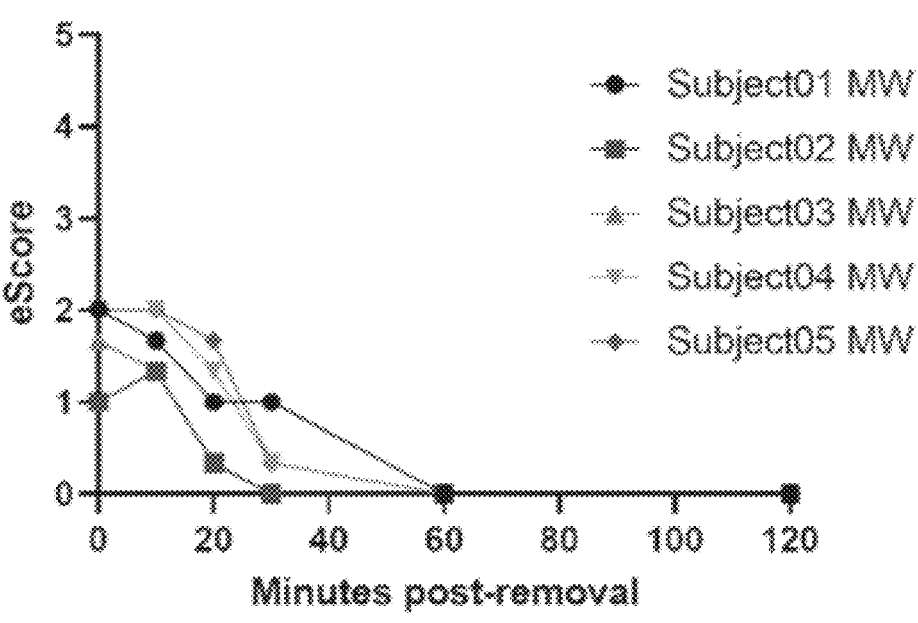
FIG. 40A is a graph of example qualitative scores of erythema at microstructure patch application sites on human forearm skin from a first study.

Results from the first study are shown in FIG. 40A, which shows the eScores for Subjects 01-05 in this study, which were independently assessed at 10, 20, 30, 60 and 120 minutes post-application. Data points represent the average eScore from three Microwearables per subject per timepoint.

Results show that all volunteers experienced some mild or very mild erythema at the site of Microwearable application as observed immediately after removal, which quickly resolved within 60 minutes. No erythema was noted after this time point. Similar to the earlier single subject observation, the indentation/redness was localised around the edges of the Microwearable, with little or no effect seem from the microstructures themselves.

Figure 40B:
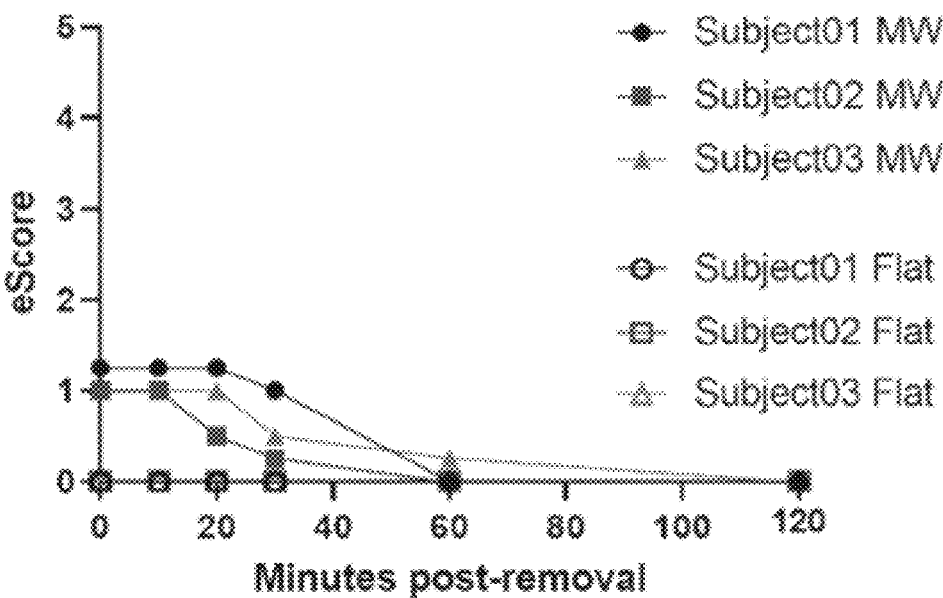
FIG. 40B is a graph of example qualitative scores of erythema at microstructure patch application sites on human forearm skin from a second study.

The second erythema study was performed on three volunteers. Two Microwearable devices were applied at 3N and were removed after 10 minutes of wearing. To investigate further the 'edge effect' observed in a first-in-human trial and in Study 1, a flat patch (i.e. without microstructures) was applied on the third skin site, for comparison. The fourth window remained untreated as a control. Results are shown in FIG. 40B, which shows the eScore observations (data points are an average of 2 separate observations per subject per time point) over 120 minutes post-removal.

Results are similar to Study 1 in that no subject experienced erythema more extensive than 'mild redness' at the site immediately prior to removal of the Microwearable. This mild erythema resolved quickly within 60 minutes, with one subject with a score of 0.5 at 60 minutes, which subsequently resolved completely by 120 minutes. No erythema was observed following application of flat patches, which may suggest that the very mild/mild erythema observed following microstructure patch application is associated with skin barrier penetration (i.e. by the presence of microstructures).

Microstructure patch eScores were, in general, lower in Study 2 than Study 1, suggesting that lowering the application force of application reduces the extent of the mild erythema that occurs. As the erythema was observed immediately after the microstructure patches were removed and did not increase over time, it appears erythema is caused by the application event itself—driven by the corners and edges of the microstructure patches—and is not exacerbated by continuous wearing. Future-generation microstructure patch can use different edges and corner configurations leading to negligible erythema.

As no local erythema was observed within the area covered by microstructures, SEM was performed to confirm that the structures had successfully penetrated the skin of the subjects in Study 1. Example images of individual or row of microstructures after application to two subjects are shown in FIGS. 41, including images of individual microstructures prior to application to the skin (FIGS. 41A and 41D) and images post application (FIGS. 41B, 41C and 41E, 41F).

Images from all subjects confirmed successful penetration of the skin, from the presence of biological material located on the upper portion of the microstructures (FIGS. 41B and 41E), with arrows indicating examples of cellular debris extracted by the microstructures on removal.

Figures 41A, 41B, 41C, 41D, 41E, 41F:
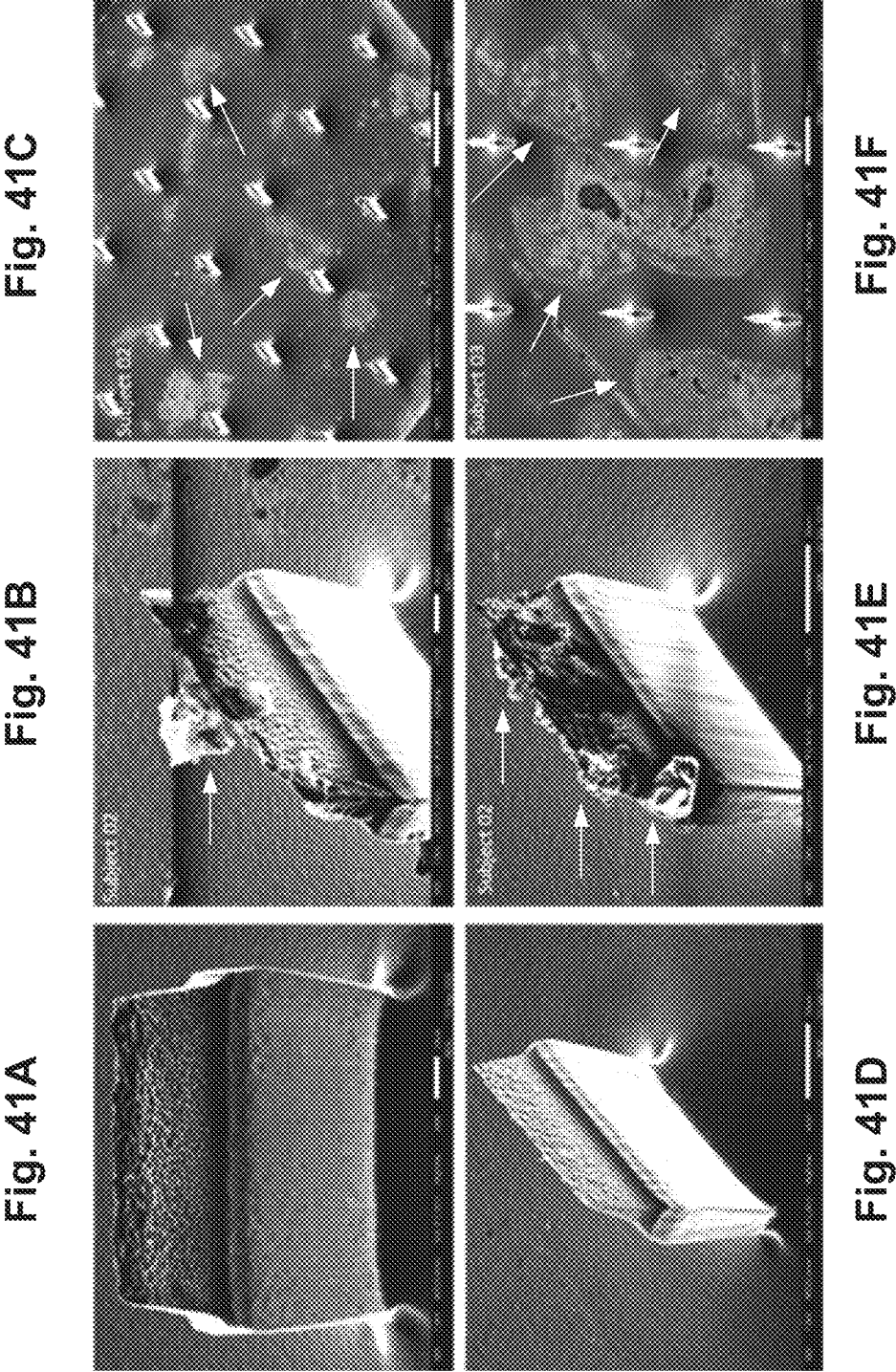
FIG. 41A is a Scanning Electron Micrographs of microstructure prior to application into human forearm skin.
FIG. 41B is a Scanning Electron Micrographs of the microstructure of FIG. 41A post application into human forearm skin.
FIG. 41C is a Scanning Electron Micrographs of a microstructure patch post application into human forearm skin.
FIG. 41D is a Scanning Electron Micrographs of microstructure prior to application into human forearm skin.
FIG. 41E is a Scanning Electron Micrographs of the microstructure of FIG. 41D post application into human forearm skin; and, FIG. 41F is a Scanning Electron Micrographs of a microstructure patch post application into human forearm skin.

FIGS. 41C and 41F show rows of microstructures, and exhibit areas with dried interstitial fluid as indicated by the arrows. These observations confirm that the microstructures have successfully breached the outermost stratum corneum layer of the skin and are able to access cellular environments beneath to gain access to the interstitial fluid, which is the source of bio-signals including biomarkers of disease.

It is therefore apparent that microstructure patches are at worst only associated with very mild/mild erythema at the site of application. This mild local response is transient, and is completely resolved within 60-120 mins post-application.

Any redness immediately occurs after application, and is not associated with continuous wearing of the microstructure patch.

Any erythema is focused around the edges and corners of the microstructure patch, with little/no erythema noted in the area covered by microstructures, but the observation that a flat patch had no effect suggests that the erythema after microstructure patch application is associated with a physical breach of the skin barrier.

Despite the observation that microstructures did not cause overt erythema, it was we confirmed that microstructure penetration was successful, with visible breaching of the stratum corneum and with confirmed access to skin compartments rich in interstitial fluid.

Use of the System

The system of the invention may be used to determine the presence, absence, level or concentration of one or more analytes in a wide range of applications as discussed herein, including, diagnosing or monitoring the progression of a disease, disorder or condition in a subject; the presence, absence, level or concentration of an illicit substance or non-illicit substance, or a chemical warfare agent, poison or toxin, or the level or concentration of a medicament.

Accordingly, in a further aspect, there is provided a method for diagnosing or monitoring the progression of a disease, disorder or condition in a subject, comprising determining the presence, absence, level or concentration of one or more analytes in the viable epidermis and/or dermis of the subject using the system of the invention, and determining the presence, absence and/or progression of the disease, disorder or condition based on whether the one or more analytes is present or absent, or whether the level or concentration of the one or more analytes is above or below a corresponding predetermined threshold that correlates with the presence, absence or progression of the disease, disorder or condition.

The invention also provides the use of the system of the invention for diagnosing or monitoring the progression of a disease, disorder or condition in a subject. There is further provided the system of the invention for use in diagnosing or monitoring the progression of a disease, disorder or condition in a subject. In particular embodiments of any one of the above aspects, the system determines the presence, absence, level or concentration of one or more analytes in the viable epidermis and/or dermis of the subject and the presence, absence and/or progression of the disease, disorder or condition is determined based on whether the one or more analytes is present or absent, or whether the level or concentration of the one or more analytes is above or below a corresponding predetermined threshold that correlates with the presence, absence or progression of the disease, disorder or condition.

Suitable diseases, disorders or conditions, analytes and exemplary concentration levels are discussed supra.

In some embodiments, the disease, disorder or condition is selected from cardiac damage, myocardial infarction and acute coronary syndrome, and the one or more analytes is troponin or a subunit thereof. In particular embodiments, the one or more analytes is troponin I.

In another aspect, there is provided a method of treating a disease, disorder or condition in a subject comprising determining the presence, absence, level or concentration of one or more analytes in the viable epidermis and/or dermis of the subject using the system of the invention, determining the presence or progression of the disease, disorder or condition based on whether the one or more analytes is present, or whether the level or concentration of the one or more analytes is above or below a corresponding predetermined threshold that correlates with the presence or progression of the disease, disorder or condition, and administering a treatment for the disease, disorder or condition.

In a further aspect, there is provided a method of treating a disease, disorder or condition in a subject comprising exposing the subject to a treatment regimen for treating the disease, disorder or condition based on an indicator obtained from an indicator-determining method, said indicator-determining method comprising determining the presence, absence, level or concentration of one or more analytes in the viable epidermis and/or dermis of the subject using the system of the invention, and determining the presence or progression of the disease, disorder or condition based on whether the one or more analytes is present, or whether the level or concentration of the one or more analytes is above or below a corresponding predetermined threshold that correlates with the presence or progression of the disease, disorder or condition.

In a related aspect, the present invention provides a method for managing a disease, disorder or condition in a subject comprising exposing the subject to a treatment regimen for treating the disease, disorder or condition based on an indicator obtained from an indicator-determining method, said indicator-determining method comprising determining the presence, absence, level or concentration of one or more analytes in the viable epidermis and/or dermis of the subject using the system of the invention, and determining the presence or progression of the disease, disorder or condition based on whether the one or more analytes is present, or whether the level or concentration of the one or more analytes is above or below a corresponding predetermined threshold that correlates with the presence or progression of the disease, disorder or condition.

In any one of the above aspects, the predetermined threshold represents a level or concentration of the analyte in a corresponding sample from a control subject (e.g. in the viable epidermis and/or dermis of the control subject), or represents a level or concentration above or below the level or concentration of the analyte in a corresponding sample from a control subject, and levels or concentrations above or below said threshold indicates the presence, absence or progression of a disease, disorder or condition. The control subject may be a subject who does not have the disease, disorder or condition; a subject who does have the disease, disorder or condition; or a subject who has a particular stage or severity of the disease, disorder or condition. When progression of the disease, disorder or condition is being monitored, the predetermined threshold may be a level or concentration of the analyte in a sample from the same subject taken at an earlier time (e.g. several minutes, hours, days, weeks or months earlier), and an increase or decrease in the analyte level or concentration may indicate the progression or regression of the disease, disorder or condition.

Suitable treatments for the disease, disorders or conditions discussed supra are well known in the art, and a skilled person will readily be able to select an appropriate treatment. For example, suitable disorders and exemplary treatments include, but are not limited to, renal failure and treatment with dialysis, a kidney transplant, an angiotensin-converting enzyme inhibitor (e.g. benazepril, zofenopril, perindopril, trandolapril, captopril, enalapril, lisinopril or ramipril), an angiotensin II receptor blocker (e.g. losartan, irbesartan, valsartan, candesartan, telmisartan or fimasartan), a diuretic (e.g. furosemide, bumetanide, ethacrynic acid, torsemide, chlorothiazide, hydrochlorothiazide, bendroflumethiazide or trichlormethiazide), a statin (e.g. atorvastatin, fluvastatin, lovastatin, mevastatin, pitavastatin, pravastatin, rosuvastatin or simvastatin), calcium, glucose or sodium polystyrene sulfonate, and/or a calcium infusion; cardiac failure and treatment with an angiotensin-converting enzyme inhibitor (e.g. benazepril, zofenopril, perindopril, trandolapril, captopril, enalapril, lisinopril or ramipril), an angiotensin II receptor blocker (e.g. losartan, irbesartan, valsartan, candesartan, telmisartan or fimasartan), a diuretic (e.g. furosemide, bumetanide, ethacrynic acid, torsemide, chlorothiazide, hydrochlorothiazide, bendroflumethiazide or trichlormethiazide), a beta blocker (e.g. carvedilol, metoprolol or bisoprolol), an aldosterone antagonist (e.g. spironolactone or eplerenone), and/or an inotrope (e.g. digoxin, berberine, levosimendan, calcium, dopamine, dobutamine, dopexamine, epinephrine, isoprenaline, norepinephrine, angiotensin II, enoximone, milrinone, amrinone, theophylline, glucagon or insulin); essential hypertension and treatment with a beta blocker (e.g. carvedilol, metoprolol or bisoprolol), a calcium channel blocker (e.g. amlodipine, felodipine, isradipine, nicardipine, nifedipine, nimodipine or nitrendipine), a diuretic (e.g. furosemide, bumetanide, ethacrynic acid, torsemide, chlorothiazide, hydrochlorothiazide, bendroflumethiazide or trichlormethiazide), angiotensin-converting enzyme inhibitor (e.g. benazepril, zofenopril, perindopril, trandolapril, captopril, enalapril, lisinopril or ramipril), an angiotensin II receptor blocker (e.g. losartan, irbesartan, valsartan, candesartan, telmisartan or fimasartan), and/or a renin inhibitor (e.g. aliskiren); bacterial infection and treatment with antibiotics (e.g. quinolones (e.g. amifloxacin, cinoxacin, ciprofloxacin, enoxacin, fleroxacin, flumequine, lomefloxacin, nalidixic acid, norfloxacin, ofloxacin, levofloxacin, lomefloxacin, oxolinic acid, pefloxacin, rosoxacin, temafloxacin, tosufloxacin, sparfloxacin, clinafloxacin, gatifloxacin, moxifloxacin, gemifloxacin, or garenoxacin), tetracyclines, glycylcyclines or oxazolidinones (e.g. chlortetracycline, demeclocycline, doxycycline, lymecycline, methacycline, minocycline, oxytetracycline, tetracycline, tigecycline, linezolide or eperezolid), aminoglycosides (e.g. amikacin, arbekacin, butirosin, dibekacin, fortimicins, gentamicin, kanamycin, menomycin, netilmicin, ribostamycin, sisomicin, spectinomycin, streptomycin or tobramycin), β-lactams (e.g. imipenem, meropenem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephacetrile, cephalexin, cephaloglycin, cephaloridine, cephalothin, cephapirin, cephradine, cefinetazole, cefoxitin, cefotetan, azthreonam, carumonam, flomoxef, moxalactam, amdinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, cefdinir, ceftibuten or cefozopran), rifamycins, macrolides (e.g. azithromycin, clarithromycin, erythromycin, oleandomycin, rokitamycin, rosaramicin, roxithromycin or troleandomycin), ketolides (e.g. telithromycin or cethromycin), coumermycins, lincosamides (e.g. clindamycin or lincomycin) or chloramphenicol); viral infection and treatment with antivirals (e.g. abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir or zidovudine); autoimmune disorders and treatment with immunosuppressants (e.g. prednisone, dexamethasone, hydrocortisone, budesonide, prednisolone, tofacitinib, cyclosporine, cyclophosphamide, nitrosoureas, platinum compounds, methotrexate, azathioprine, mercaptopurine, fluorouracil, dactinomycin, anthracyclines, mitomycin C, bleomycin, mithramycin, antithymocyte globulin, thymoglobulin, Muromonab-CD3, basiliximab, daclizumab, tacrolimus, sirolimus, everolimus, infliximab, etanercept, IFN-β, mycophenolic acid or mycophenolate, fingolimod, azathioprine, leflunomide, abatacept, adalimumab, anakinra, certolizumab, golimumab, ixekizumab, natalizumab, rituximab, secukinumab, toclizumab, ustekinumab, vedolizumab, or myriocin) and/or NSAIDs (e.g. acetylsalicylic acid (aspirin), diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin, zomepirac, celecoxib, deracoxib, etoricoxib, mavacoxib or parecoxib); rheumatological disorders and treatment with NSAIDs as described supra, DMARDs (e.g. methotrexate, hydroxychloroquinone or penicillamine), prednisone, dexamethasone, hydrocortisone, budesonide, prednisolone, etanercept, golimumab, infliximab, adalimumab, anakinra, rituximab, abatacept, and/or other immunosuppressants described supra; sepsis and antibiotics as described supra, immunosuppressants as described supra and/or an antihypotensive agent (e.g. vasopressin, norepinephrine, dopamine or epinephrine); and pulmonary embolism and treatment with an anticoagulant (e.g. heparin, warfarin, bivalirudin, dalteparin, enoxaparin, dabigatran, edoxaban, rivaroxaban, apixaban or fondaparinux) and/or a thrombolytic/fibrinolytic (e.g. tissue plasminogen activator, reteplase, streptokinase or tenecteplase).

In some embodiments, the disease, disorder or condition is cardiac damage, myocardial infarction or acute coronary syndrome, the one or more analytes is troponin or a subunit thereof. Suitable treatments for cardiac damage, myocardial infarction or acute coronary syndrome may include, but are not limited to, aspirin, an anticoagulant (e.g. heparin, warfarin, bivalirudin, dalteparin, enoxaparin dabigatran, edoxaban, rivaroxaban, apixaban or fondaparinux), a beta-blocker (e.g. carvedilol or metoprolol), a thrombolytic/fibrinolytic (e.g. tissue plasminogen activator, reteplase, streptokinase or tenecteplase), an angiotensin-converting enzyme inhibitor (e.g. benazepril, zofenopril, perindopril, trandolapril, captopril, enalapril, lisinopril or ramipril), an angiotensin II receptor blocker (e.g. losartan, irbesartan, valsartan, candesartan, telmisartan or fimasartan), a statin (e.g. atorvastatin, fluvastatin, lovastatin, mevastatin, pitavastatin, pravastatin, rosuvastatin or simvastatin), an analgesic (e.g. morphine, etc.), nitroglycerin, and the like, or combinations thereof.

The invention further contemplates the use of the system of the invention for determining the presence, absence, level or concentration of an illicit substance or non-illicit substance of abuse in a subject. Accordingly, in another aspect, there is provided a method of determining the presence, absence, level or concentration of an illicit substance or non-illicit substance of abuse in a subject, comprising determining the presence, absence, level or concentration of the illicit substance, non-illicit substance of abuse or a metabolite thereof in the viable epidermis and/or dermis of the subject using the system of the invention.

There is also provided the use of the system of the invention for determining the presence, absence, level or concentration of an illicit substance or non-illicit substance of abuse in a subject, and the system of the invention for use in determining the presence, absence, level or concentration of an illicit substance or non-illicit substance of abuse in a subject. In particular embodiments of any one of these aspects, the system determines the presence, absence, level or concentration of the illicit substance, non-illicit substance of abuse or metabolite thereof in the viable epidermis and/or dermis of the subject.

Suitable illicit substances are discussed supra and include, but are not limited to, methamphetamine, amphetamine, 3,4-methylenedioxymethamphetamine (MDMA), N-ethyl-3,4-methylenedioxyamphetamine (MDEA), 3,4-methylene-dioxy-amphetamine (MDA), cannabinoids (e.g. delta-9-tetrahydrocannabinol, 11-hydroxy-delta-9-tetrahydrocannabinol, 11-nor-9-carboxydelta-9-tetrahydrocannabinol), cocaine, benzoylecgonine, ecgonine methyl ester, cocaethylene, ketamine, and the opiates (e.g. heroin, 6-monoacetylmorphine, morphine, codeine, methadone and dihydrocodeine). Non-limiting non-illicit substances of abuse include alcohol, nicotine, prescription medicine or over the counter medicine taken for non-medical reasons, a substance taken for a medical effect, wherein the consumption has become excessive or inappropriate (e.g. pain medications, sleep aids, anti-anxiety medication, methylphenidate, erectile-dysfunction medications), and the like.

The invention further contemplates the use of the system of the invention for determining the presence, absence, level or concentration of a chemical warfare agent, poison and/or toxin in a subject. Accordingly, in another aspect, there is provided a method of determining the presence, absence, level or concentration of a chemical warfare agent, poison and/or toxin in a subject, comprising determining the presence, absence, level or concentration of the chemical warfare agent, poison and/or toxin or a metabolite thereof in the viable epidermis and/or dermis of the subject using the system of the invention. In particular embodiments, the method is for determining the presence, absence, level or concentration of a chemical warfare agent.

There is also provided the use of the system of the invention for determining the presence, absence, level or concentration of a chemical warfare agent, poison and/or toxin in a subject, and the system of the invention for use in determining the presence, absence, level or concentration of a chemical warfare agent, poison and/or toxin in a subject; especially a chemical warfare agent. In particular embodiments of any one of these aspects, the system determines the presence, absence, level or concentration of the chemical warfare agent, poison and/or toxin or a metabolite thereof in the viable epidermis and/or dermis of the subject.

Suitable chemical warfare agents, poisons and/or toxins are discussed supra.

The system of the invention may also be used to determine and/or monitor the level or concentration of a medicament administered to a subject, for example, to optimise and/or adjust the dose of the medicament. The invention provides a method for determining and/or monitoring the level or concentration of a medicament administered to a subject, comprising determining the level or concentration of the medicament or a component or metabolite thereof in the viable epidermis and/or dermis of the subject using the system of the invention.

There is further provided the use of the system of the invention for determining and/or monitoring the level or concentration of a medicament administered to a subject, and the system of the invention for use in determining and/or monitoring the level or concentration of a medicament administered to a subject. In particular embodiments, the system of the invention determines the level or concentration of the medicament or a component or metabolite thereof in the viable epidermis and/or dermis of the subject.

In some embodiments, the dose of the medicament is increased or decreased following determination of the level or concentration of the medicament or a component or metabolite thereof.

In a further aspect, there is provided a method of monitoring the efficacy of a treatment regimen in a subject with a disease, disorder or condition, wherein the treatment regimen is monitored for efficacy towards a desired health state (e.g. absence of the disease, disorder or condition. Such method generally comprises determining the presence, absence, level or concentration of one or more analytes indicative of the efficacy of the treatment regimen in the viable epidermis and/or dermis of the subject using the system of the invention after treatment of the subject with the treatment regimen, and comparing the level or concentration of the one or more analytes to a reference level or concentration of the one or more analytes which is correlated with a presence, absence or stage of the disease, disorder or condition to thereby determine whether the treatment regimen is effective for changing the health status of the subject to a desired health state. In some embodiments, the one or more analytes is a medicament administered during the treatment regimen, or a component or metabolite thereof.

In a related aspect, there is provided a method of monitoring the efficacy of a treatment regimen in a subject with a disease, disorder or condition, wherein the treatment regimen is monitored for efficacy towards a desired health state (e.g. absence of the disease, disorder or condition). Such method generally comprises determining an indicator according to an indicator-determining method, said indicator-determining method comprising determining the presence, absence, level or concentration of one or more analytes in the viable epidermis and/or dermis of the subject using the system of the invention after treatment of the subject with the treatment regimen, and assessing the likelihood of the subject having a presence, absence or stage of a disease, disorder or condition based on whether the one or more analytes is present, or whether the level or concentration of the one or more analytes is above or below a corresponding predetermined threshold that correlates with the presence, absence or stage of the disease, disorder or condition, using the indicator to thereby determine whether the treatment regimen is effective for changing the health status of the subject to a desired health state. In some embodiments, the one or more analytes is a medicament administered during the treatment regimen, or a component or metabolite thereof.

In some embodiments of any one of the above aspects, the treatment regimen is adjusted following such methods. Suitable predetermined thresholds for such aspects are discussed supra.

The invention also provides the system of the invention for use in such methods, and the use of the system for such methods.

A skilled person will readily appreciate that the system of the invention may be used to determine and monitor the level or concentration of a wide range of medicaments and treatment regimens and will readily be able to use and select suitable medicaments and treatment regimens. For example, suitable medicaments include, but are not limited to, cancer therapies, vaccines, analgesics, antipsychotics, antibiotics, anticoagulants, antidepressants, antivirals, sedatives, antidiabetics, contraceptives, immunosuppressants, antifungals, antihelmintics, stimulants, biological response modifiers, NSAIDs, corticosteroids, DMARDs, anabolic steroids, antacids, antiarrhythmics, thrombolytics, anticonvulsants, antidiarrheals, antiemetics, antihistamines, antihypertensives, anti-inflammatoires, antineoplastics, antipyretics, antivirals, barbiturates, β-blockers, bronchodilators, cough suppressants, cytotoxics, decongestants, diuretics, expectorants, hormones, laxatives, muscle relaxants, vasodilators, tranquilizers and vitamins.

In particular embodiments, the medicament is one which has a narrow therapeutic window, such as particular antibiotics (e.g. aminoglycosides including kanamycin, gentamycin and streptomycin), anticonvulsants (e.g. carbamazepine and clonazepam), vasodilators, anticoagulants including heparin and warfarin, digoxin, and the like. In such embodiments, the methods and uses may further comprise increasing or decreasing the dose of the medicament administered to the subject.

In any one of the above aspects, the methods and uses further comprise attaching the system of the invention to the skin of the subject prior to determining the presence, absence, level or concentration of the one or more analytes. In such embodiments, the system of the invention breaches a stratum corneum of the subject.

The above described patches may also be used to test other forms of subjects, such as food stuffs, or the like. In this example, the patch could be used to test for the presence of unwanted contaminants, such as pathogens, such as bacteria, exotoxins, mycotoxins, viruses, parasites, or the like, as well as natural toxins. Additionally contaminants could include agrochemicals, environmental contaminants, pesticides, carcinogens, bacteria, or the like.

Accordingly, it will be appreciated that the term subject can include living subjects, such as humans, animals, or plants, as well as non-living materials, such as foodstuffs, packaging, or the like.

Accordingly, the above described arrangement provides a wearable monitoring device that uses microstructures that breach a barrier, such as penetrating into the stratum corneum in order to perform measurements on a subject. The measurements can be of any appropriate form, and can include measuring the presence of biomarkers or other analytes within the subject, measuring electrical signals within the subject, or the like. Measurements can then be analysed and used to generate an indicator indicative of a health status of the subject.

In one example, the above described system allows analytes to be detected in specific tissue sites in the skin, in situ. The microstructures can be coated with a material for binding one or more analytes of interest or may be formed by a binding agent as described supra, allowing analytes within the subject to bind to the microstructures in turn allowing these to be detected using suitable optical or electrical measurement techniques. The coatings and/or microstructures can be specifically designed to capture analytes with extremely high specificity. Such specificity allows specific analytes of interest to be detected without the need for purification or complex chemical analysis.

The length of the structures can be controlled during manufacture to enable targeting of specific layers in the target tissue. In one example, this is performed to target analytes in the epidermal and/or dermal layers, although analytes in capillary blood can also be targeted.

Specific probes can be localized to individual structures or areas of structures, so that multiple targets can be analysed in a single assay simply by their location in a 2-dimensional array. This could facilitate the analysis of disease-specific analyte panels to increase the sensitivity/specificity of the diagnostic results.

The patches can therefore provide a measurement device which overcomes the need for traditional blood or ISF samples to be taken for diagnostic purposes representing an opportunity for a clinician to diagnose and avoid time and processing costs at centralised testing facilities. It may also open new markets since diagnostic equipment and blood sampling expertise is not needed e.g. in developing countries, 'in-field' military applications, medical countermeasures, emergency and triage.

This allows patches to be used as a non-invasive, pain-free measurement platform that can measure analytes in situ. The type of material detected by the patch may be controlled by the length of the structures, such that different regions can be targeted specifically. This embodiment does not include a specific analysis type; a number of established techniques can be used for fluid analysis including, but not limited to, mass spectrometry, microarrays, DNA/protein sequencing, HPLC, ELISA, Western Blots and other gel methods, etc.

Using affinity surface coatings on each structure allows a reduction of non-specific adsorption of substances whilst facilitating specific extraction of the molecular targets of interest.

By arranging the structures in a two-dimensional format, multiple probes can be attached to the same patch, with the results from the sandwich assay decoded based on the 2-D array position of the individual structures. This essentially allows array-style processing without the need for sample extraction, purification, labelling, etc.

Accordingly, in one example, the above described system provides a minimally-invasive and pain-free way to access blood-borne biomarkers of disease: by accessing the outer skin layers with devices applied to the skin that are also pain-free. Currently, blood is accessed by a needle/lancet which is often painful and laborious. Alternatively, blood is accessed directly in the body by surgically implanting a sensor. Surgical implants are not likely to be used widely, as implanting is an invasive procedure, with limited choice of materials suitable for implantation.

The system can provide rapid "on the spot" disease detection on the person, rather than the delays of sending blood samples to pathology laboratories for processing. This is also an advance over the current point-of-care devices, which usually still require a blood sample (e.g. by a needle) to be analysed away from the body.

The system can provide high-fidelity, low power, low cost body signal (e.g. biopotential, optical) sensing for practical disease/health diagnostics. As one example, pre-clinical animal skin testing of microstructure patches show a 100 fold reduction of bioimpedance, compared to standard, approaches applied to the surface of skin, leading to improved signal to noise ratio.

The system can provide simple, semi-continuous or continuous monitoring: a low cost-device micro wearable would be applied to the skin and potentially be worn for days (or longer), and then simply replaced by another micro wearable component. Thus, micro wearables provide a route for monitoring over time—which can be particularly important in detecting sudden events (e.g. cardiac biomarkers for a heart attack)—without surgically implanting a sensor into the body.

In one example, the above described approach can allow wearables to provide widespread, low-cost healthcare monitoring for a multitude of health conditions that cannot be assayed by current devices, which are placed on the skin.

In one example, the microstructure patches penetrate the skin barrier and so unlike today's wearables, access blood-borne biomarkers of disease for rapid "on the spot" disease detection on the person. Contrast this to the current method of sending blood samples to pathology laboratories for processing. This is also an advance over the current point-of-care devices, which usually still require a blood sample (e.g. by a needle) to be analysed away from the body.

In one example, the system can provide a low-cost microstructure patches would be applied to the skin and potentially be worn for days (or longer) for simple and pain free semi-continuous or continuous monitoring, and then simply replaced by another microstructure patch component. Thus, microstructure patches provide a route for monitoring over time-which can be particularly important in detecting sudden events (e.g. cardiac biomarkers for a heart attack)-without surgically-implanting a sensor into the body.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers. As used herein and unless otherwise stated, the term "approximately" means±20%.

Embodiment 1. A system for delivering treatment to a biological subject, the system including: at least one substrate including one or more microstructures configured to breach a functional barrier of the subject; at least one sensor operatively connected to at least one microstructure, the at least one sensor being configured to measure response signals from the at least one microstructure; at least one treatment delivery mechanism operatively coupled to at least one microstructure to deliver treatment via at least one microstructure; and, one or more electronic processing devices that control the at least one treatment delivery mechanism to thereby deliver treatment to the subject at least partially in accordance with the measured response signals.

Embodiment 2. A system according to embodiment 1, wherein the functional barrier is at least one of: multiple layers; a mechanical discontinuity; a tissue discontinuity; a cellular discontinuity; a neural barrier; a sensor barrier; a cellular layer; a skin layer; a mucosal layer; an internal barrier; an external barrier; an inner barrier within an organ; an outer barrier of an organ; an epithelial layer; an endothelial layer; a melanin layer; an optical barrier; an electrical barrier; molecular weight barrier; basal layer; and, a stratum corneum.

Embodiment 3. A system according to embodiment 1 or embodiment 2, wherein at least one treatment delivery mechanism includes a signal generator operatively connected to at least one microstructure to apply stimulation.

Embodiment 4. A system according to any one of the embodiments 1 to 3, wherein the system applies stimulation to at least one of microstructures and the subject, and wherein the stimulation is at least one of: biochemical; chemical; mechanical; magnetic; thermal; electrical; electromagnetic; and, optical.

Embodiment 5. A system according to any one of the embodiments 1 to 4, wherein at least one microstructure includes a material, and wherein at least one treatment delivery mechanism controls release of the material.

Embodiment 6. A system according to embodiment 5, wherein release of the material is controlled by applying stimulation to the at least one microstructure.

Embodiment 7. A system according to embodiment 5 or embodiment 6, wherein the material is contained in a coating on the at least one microstructure.

Embodiment 8. A system according to embodiment 7, wherein the stimulation is used to at least one of: release material from the coating on the microstructure; disrupt the coating; dissolve the coating; and, release the coating.

Embodiment 9. A system according to embodiment 7 or embodiment 8, wherein at least one of: at least some microstructures are uncoated; at least some microstructures are porous with an internal coating; at least some microstructures are partially coated; different microstructures have different coatings; different parts of microstructures include different coatings; and, at least some microstructures include multiple coatings.

Embodiment 10. A system according to any one of the embodiments 7 to 9, wherein stimulation is used to at least one of: release material from the coating on the microstructure; disrupt the coating; dissolve the coating; and, release the coating.

Embodiment 11. A system according to any one of the embodiments 7 to 10, wherein at least some of the microstructures are coated with a selectively dissolvable coating.

Embodiment 12. A system according to embodiment 11, wherein the selectively dissolvable coating dissolves at least one of: after a defined time period; in response to breaching or penetration of the functional barrier; in response to application of a stimulatory signal; in response to a presence, absence, level or concentration of analytes; and, upon breaching or penetration of the functional barrier.

Embodiment 13. A system according to embodiment 12, wherein the system is configured to: detect the coating dissolving; and, at least one of: perform at least one measurement after the coating has dissolved; and, apply treatment after the coating has dissolved.

Embodiment 14. A system according to embodiment 13, wherein the system is configured to detect the coating dissolving based on a change in a response signal.

Embodiment 15. A system according to any one of the embodiments 7 to 14, wherein the coating at least one of: undergoes a shape change to selectively anchor microstructures; modifies surface properties to at least one of: increase hydrophilicity; increase hydrophobicity; and, minimize biofouling; attracts at least one substance to the microstructures; repels at least one substance from the microstructures; provides a physical structure to at least one of: facilitate penetration of the barrier; strengthen the microstructures; and, anchor the microstructures in the subject; dissolves to at least one of: expose a microstructure; expose a further coating; and, expose a material; provides stimulation to the subject; contains a material; and, selectively releases a material.

Embodiment 16. A system according to any one of the embodiments 5 to 15, wherein the substrate includes a plurality of microstructures and wherein different microstructures include at least one of: different materials; and, different doses.

Embodiment 17. A system according to embodiment 16, wherein the one or more processing devices control at least one treatment delivery mechanism to release material from selected microstructures.

Embodiment 18. A system according to any one of the embodiments 5 to 17, wherein the material includes at least one of: antivirals; antibacterials; anti-inflammatoires or inflammatories; agonists or antagonists; adjuvants; vaccines; nanoparticles; a nucleic acid; an antigen or allergen; parasites, bacteria, viruses, or virus-like particles; metals or metallic compounds; molecules, elements or compounds; DNA; protein; RNA, siRNA, sfRNA, iRNA; synthetic biological materials; polymers; drugs; hormones; and, neurotransmitters.

Embodiment 19. A system according to any one of the embodiments 1 to 18, wherein the one or more processing devices: perform an analysis, at least in part, using the measured response signals; and, use results of the analysis to control the at least one treatment delivery mechanism.

Embodiment 20. A system according to any one of the embodiments 1 to 19, wherein the one or more electronic processing devices: analyse measured response signals to determine at least one metric; and, use at least one metric to determine treatment requirements.

Embodiment 21. A system according to embodiment 20, wherein the one or more electronic devices apply at least one metric to at least one algorithm to determine the treatment requirements, the at least one algorithm embodying a relationship between treatment requirements and the at least one metric.

Embodiment 22. A system according to embodiment 21, wherein the at least one computational model is obtained by applying machine learning to reference metrics derived from subject data measured for one or more reference subjects.

Embodiment 23. A system according to any one of the embodiments 1 to 22, wherein the system includes a transmitter that transmits at least one of: measured response signals;

subject data derived from the measured response signals; and, at least one metric derived from the measured response signals.

Embodiment 24. A system according to any one of the embodiments 1 to 23, wherein the one or more electronic processing devices: generate subject data indicative of the measured response signals; and, at least one of: at least partially analyse the subject data; or, store an indication of the subject data; or, display an indication of subject data.

Embodiment 25. A system according to any one of the embodiments 1 to 24, wherein the system includes: a wearable device that performs the measurements; and, a processing system that: receives subject data derived from the measured response signals; and, analyses the subject data to at least one of: generate at least one indicator, the at least one indicator being at least partially indicative of a health status associated with the subject; and, determine treatment requirements.

Embodiment 26. A system according to embodiment 25, wherein the health status is indicative of at least one of: organ function; tissue function; cell function; a presence, absence or degree of a medical condition; a prognosis associated with a medical condition; a presence, absence, level or concentration of a biomarker; a presence, absence, level or concentration of an analyte; a presence, absence or grade of cancer; fluid levels in the subject; tissue inflammation; blood oxygenation; and, bioelectric activity.

Embodiment 27. A system according to embodiment 25 or embodiment 26, wherein the system includes a client device that: receives measurement data from the wearable monitoring device; generates subject data using the measurement data; transfers the subject data to the processing system; stores a representation of the indicator; receives an indicator from the processing system; and, displays a representation of the indicator.

Embodiment 28. A system according to any one of the embodiments 1 to 27, wherein the microstructures include at least one of: response microstructures used to measure response signals; and, stimulation microstructures used to apply stimulation signals to the subject.

Embodiment 29. A system according to any one of the embodiments 1 to 28, wherein the substrate includes connections to allow signals to be communicated with respective microstructures.

Embodiment 30. A system according to embodiment 29, wherein the connections are at least one of: mechanical; magnetic; thermal; electrical; electromagnetic; optical; conductive; inductive; and wireless.

Embodiment 31. A system according to embodiment 29 or embodiment 30, wherein the substrate includes at least one of: response connections allowing response signals to be received from one or more respective microstructures; and, stimulation connections allowing stimulation signals to be applied to one or more respective microstructures.

Embodiment 32. A system according to any one of the embodiments 1 to 31, wherein the system includes one or more multiplexers for selectively connecting at least one of the at least one sensor and at least one signal generator to one or more of the microstructures.

Embodiment 33. A system according to any one of the embodiments 1 to 32, wherein the response signals are at least one of: mechanical; magnetic; thermal; electrical; electromagnetic; and, optical.

Embodiment 34. A system according to any one of the embodiments 1 to 33, wherein the response signals are indicative of at least one of: a visualization; a mapping; mechanical properties; forces; pressures; muscle movement; blood pulse wave; an analyte concentration; a blood oxygen saturation; a tissue inflammation state; a bioimpedance; a biocapacitance; a bioconductance; and, electrical signals within the body.

Embodiment 35. A system according to any one of the embodiments 1 to 34, wherein at least one of the substrate and the microstructures include at least one of: fabric; woven fabric; electronic fabric; natural fibres; silk; organic materials; natural composite materials; artificial composite materials; ceramics; stainless steel; metal; polymer; silicon; semiconductor; organosilicates; gold; silver; carbon; carbon nano materials; platinum; and, titanium.

Embodiment 36. A system according to any one of the embodiments 1 to 35, wherein the substrate and microstructures include at least one of: the same material; and, different materials.

Embodiment 37. A system according to any one of the embodiments 1 to 36, wherein the substrate is at least one of: at least partially flexible; configured to conform to an outer surface of the functional barrier; and, configured to conform to a shape of at least part of a subject.

Embodiment 38. A system according to any one of the embodiments 1 to 37, wherein at least some of the microstructures are at least one of: blades; ridges; needles; and, plates.

Embodiment 39. A system according to any one of the embodiments 1 to 38, wherein at least some of the microstructures at least one of: are at least partially tapered; have a cross sectional shape that is at least one of: circular; rectangular; cruciform; square; rounded square; rounded rectangular; ellipsoidal; and, at least partially hollow; have a surface that is at least partially at least one of: smooth; serrated; includes one or more pores; includes one or more raised portions; and, rough; are at least partially hollow; are porous; and, include an internal structure.

Embodiment 40. A system according to any one of the embodiments 1 to 39, wherein the microstructures include anchor microstructures used to anchor the substrate to the subject.

Embodiment 41. A system according to embodiment 40, wherein the anchor microstructures at least one of: undergo a shape change; undergo a shape change in response to at least one of substances in the subject and applied stimulation; swell; swell in response to at least one of substances in the subject and applied stimulation; include anchoring structures; have a length greater than that of other microstructures; and, enter the dermis.

Embodiment 42. A system according to any one of the embodiments 1 to 41, wherein the microstructures have a length that is at least one of: greater than the thickness of the functional barrier; at least 10% greater than the thickness of the functional barrier; at least 20% greater than the thickness of the functional barrier; at least 50% greater than the thickness of the functional barrier; at least 75% greater than the thickness of the functional barrier; at least 100% greater than the thickness of the functional barrier; no more than 2000% greater than the thickness of the functional barrier; no more than 1000% greater than the thickness of the functional barrier; no more than 500% greater than the thickness of the functional barrier; no more than 100% greater than the thickness of the functional barrier; no more than 75% greater than the thickness of the functional barrier; and, no more than 50% greater than the thickness of the functional barrier.

Embodiment 43. A system according to any one of the embodiments 1 to 42, wherein the microstructures are applied to skin of the subject, and wherein at least some of the microstructures at least one of: penetrate the stratum corneum; enter the viable epidermis but not the dermis; and, enter the dermis.

Embodiment 44. A system according to any one of the embodiments 1 to 43, wherein at least some of the microstructures have a length that is at least one of: less than 2500 μm; less than 1000 μm; less than 750 μm; less than 600 μm; less than 500 μm; less than 400 μm; less than 300 μm; less than 250 μm; greater than 50 μm; and, greater than 100 μm.

Embodiment 45. A system according to any one of the embodiments 1 to 44, wherein at least some of the microstructures have a maximum width that is at least one of: less than 50000 μm; less than 40000 μm; less than 30000 μm; less than 20000 μm; less than 10000 μm; less than 1000 μm; less than 500 μm; less than 100 μm; less than 50 μm; less than 40 μm; less than 30 μm; less than 20 μm; and, less than 10 μm.

Embodiment 46. A system according to any one of the embodiments 1 to 45, wherein at least some of the microstructures have a maximum thickness that is at least one of: less than 1000 μm; less than 500 μm; less than 200 μm; less than 100 μm; less than 50 μm; less than 20 μm; less than 10 μm; at least 1 μm; at least 0.5 μm; and, at least 0.1 μm.

Embodiment 47. A system according to any one of the embodiments 1 to 46, wherein the microstructures have a density that is at least one of: less than 50,000 per cm$^2$; less than 30,000 per cm$^2$; less than 10,000 per cm$^2$; less than 1,000 per cm$^2$; less than 500 per cm$^2$; less than 100 per cm$^2$; less than 10 per cm$^2$; and, less than 5 per cm$^2$.

Embodiment 48. A system according to any one of the embodiments 1 to 47, wherein the microstructures have a spacing that is at least one of: less than 20 mm; less than 10 mm; less than 1 mm; less than 0.1 mm; and, less than 10 μm.

Embodiment 49. A system according to any one of the embodiments 1 to 48, wherein microstructures include an at least partially electromagnetically transparent material.

Embodiment 50. A system according to embodiment 49, wherein microstructures include an electromagnetically opaque layer including ports to allow electromagnetic radiation to be emitted from or received by the ports.

Embodiment 51. A system according to embodiment 50, wherein microstructures include electromagnetically reflective layers to allow electromagnetic radiation to be conducted to and from designated ports.

Embodiment 52. A system according to any one of the embodiments 1 to 51, wherein at least some of microstructures include at least part of an active sensor.

Embodiment 53. A system according to any one of the embodiments 1 to 52, wherein microstructures include an electrically conductive core material.

Embodiment 54. A system according to embodiment 53, wherein microstructures include an electrically insulating layer including ports to allow electrical signals to be emitted from or received by the ports.

Embodiment 55. A system according to embodiment 51 or embodiment 54, wherein the ports are provided at different depths.

Embodiment 56. A system according to any one of the embodiments 1 to 55, wherein at least some of microstructures include an electrode.

Embodiment 57. A system according to any one of the embodiments 1 to 56, wherein the microstructures include plates having a substantially planar face including at least one electrode.

Embodiment 58. A system according to embodiment 56 or embodiment 57, wherein at least one electrode has a surface area of at least one of: at least 10 mm$^2$; at least 1 mm$^2$; at least 100,000 μm$^2$; at least 10,000 μm$^2$; at least 7,500 μm$^2$; at least 5,000 μm$^2$; at least 2,000 μm$^2$; at least 1,000 μm$^2$; at least 500 μm$^2$; at least 100 μm$^2$; and, at least 10 μm$^2$.

Embodiment 59. A system according to any one of the embodiments 56 to 58, wherein at least one electrode has a width that is at least one of: less than 50000 μm; less than 40000 μm; less than 30000 μm; less than 20000 μm; less than 10000 μm; less than 1000 μm; at least 500 μm; at least 200 μm; at least 100 μm; at least 75 μm; at least 50 μm; at least 20 μm; at least 10 μm; and, at least 1 μm.

Embodiment 60. A system according to any one of the embodiments 56 to 59, wherein at least one electrode has a height that is at least one of: up to 2500 μm at least 500 μm; at least 200 μm; at least 100 μm; at least 75 μm; at least 50 μm; at least 20 μm; at least 10 μm; and, at least 1 μm.

Embodiment 61. An system according to any one of the embodiments 56 to 60, wherein the one or more microstructure electrodes interact with one or more analytes of interest such that a response signal is dependent on a presence, absence, level or concentration of analytes of interest.

Embodiment 62. A system according to any one of the embodiments 1 to 61, wherein at least some of the microstructures are arranged in groups, and wherein at least one of: response signals are measured between microstructures in a group; and, stimulation is applied between microstructures in a group.

Embodiment 63. A system according to embodiment 62, wherein the group is a pair of microstructures including spaced apart plate microstructures having substantially planar electrodes in opposition.

Embodiment 64. A system according to embodiment 62 or embodiment 63, wherein the spacing between the electrodes in each group are at least one of: less than 50 mm; less than 20 mm; less than 10 mm; less than 1 mm; less than 0.1 mm; and, less than 10 μm.

Embodiment 65. A system according to any one of the embodiments 1 to 64, wherein the system includes: a first substrate having first microstructures and corresponding first apertures; an insulating layer provided on a side of the first substrate opposite the first microstructures; a second substrate provided on the insulating layer, the second substrate having second microstructures extending through the insulating layer and the first apertures to form pairs of first and second microstructures.

Embodiment 66. A system according to embodiment 65, wherein the second substrate includes second apertures and wherein the first and second apertures are at least partially offset to control capacitive coupling between the first and second substrates.

Embodiment 67. A system according to any one of the embodiments 1 to 66, wherein the microstructures include a material including at least one of: a bioactive material; a reagent for reacting with analytes in the subject; a binding agent for binding with analytes of interest; a probe for selectively targeting analytes of interest; a material to reduce biofouling; a material to attract at least one substance to the microstructures; a material to repel at least one substance from the microstructures; a material to attract at least some analytes to the projections; and, a material to repel at least some analytes from the projections.

Embodiment 68. A system according to any one of the embodiments 1 to 67, wherein the substrate includes a plurality of microstructures and wherein different microstructures are at least one of: differentially responsive to analytes; responsive to different analytes; responsive to different combination of analytes; and, responsive to different concentrations of analytes.

Embodiment 69. A system according to any one of the embodiments 1 to 68, wherein at least some of the microstructures at least one of: attracts at least one substance to the microstructures; repels at least one substance from the microstructures; attracts at least one analyte to the microstructures; and, repels at least one analyte from the microstructures.

Embodiment 70. A system according to any one of the embodiments 1 to 69, wherein the microstructures are configured to deliver stimulation including at least one of: chemical stimulation; mechanical stimulation; magnetic stimulation; thermal stimulation; electrical stimulation; electromagnetic stimulation; optical stimulation; and, stimulation to trigger a biological response in the subject.

Embodiment 71. A system according to any one of the embodiments 1 to 70, wherein the one or more microstructure electrodes interact with one or more analytes of interest such that a response signal is dependent on a presence, absence, level or concentration of analytes of interest.

Embodiment 72. A system according to any one of the embodiments 1 to 71, wherein the system includes an actuator configured to apply a force to the substrate to at least one of: sense tissue mechanical properties; provide mechanical stimulation; attract or repel substances; trigger a biological response; release material from a coating on at least some microstructures; disrupt a coating on at least some microstructures; dissolve a coating on at least some microstructures; dislodge a coating on the microstructures; release a coating on at least some microstructures; cause the microstructures to penetrate the barrier; cause the microstructures to breach the barrier; retract the microstructures from the barrier; and, retract the microstructures from the subject.

Embodiment 73. A system according to embodiment 72, wherein the actuator is at least one of: an electric actuator; a magnetic actuator; a polymeric actuator; a fabric or woven actuator; a pneumatic actuator; a thermal actuator; a hydraulic actuator; a chemical actuator; a piezoelectric actuator; and, a mechanical actuator.

Embodiment 74. A system according to embodiment 72 or embodiment 73, wherein the actuator is configured to apply at least one of: a vibratory force; a periodic force; a repeated force; a single continuous force; and, a single instantaneous force.

Embodiment 75. A system according to embodiment 74, wherein the force is applied at a frequency that is at least one of: at least 0.01 Hz; at least 0.1 Hz; at least 1 Hz; at least 10 Hz; at least 50 Hz; at least 100 Hz; at least 1 kHz; at least 10 kHz; at least 100 kHz; varying; varying depending on at least one of: a time of application; a depth of penetration; a degree of penetration; and, an insertion resistance; and, increasing with an increasing depth of penetration; decreasing with an increasing depth of penetration; increasing until a point of penetration; and decreasing after a point of penetration.

Embodiment 76. A system according to any one of the embodiments 72 to 75, wherein the force is at least one of: at least 0.1 μN; at least 1 μN; at least 5 μN; at least 10 μN; at least 20 μN; at least 50 μN; at least 100 μN; at least 500 μN; at least 1000 μN; at least 10 mN; at least 100 mN; varying depending on at least one of: a time of application; a depth of penetration; a degree of penetration; and, an insertion resistance; increasing with an increasing depth of penetration; decreasing with an increasing depth of penetration; increasing until a point of penetration; and decreasing after a point of penetration.

Embodiment 77. A system according to any one of the embodiments 72 to 76, wherein the actuator is configured to cause movement of the microstructures that is at least one of: greater than 0.001 times a length of the microstructure; greater than 0.01 times a length of the microstructure; greater than 0.1 times a length of the microstructure; greater than a length of the microstructure; greater than 10 times a length of the microstructure; greater than 100 times a length of the microstructure; greater than 1000 times a length of the microstructure; varying depending on at least one of: a time of application; a depth of penetration; a degree of penetration; and, an insertion resistance; increasing with an increasing depth of penetration; decreasing with an increasing depth of penetration; increasing until a point of penetration; and decreasing after a point of penetration.

Embodiment 78. A system according to any one of the embodiments 72 to 77, wherein the system: detects, using response of the actuator, at least one of: a depth of penetration; a degree of penetration; and, an insertion resistance; controls the actuator in accordance with the detection.

Embodiment 79. A system according to any one of the embodiments 72 to 78, wherein the system: detects, using measured response signals, at least one of: breaching of the barrier by the microstructures; and, a depth of penetration by the microstructures; controls the actuator in accordance with the detection.

Embodiment 80. A system according to any one of the embodiments 1 to 79, wherein the at least one treatment delivery mechanism includes an actuator configured to cause at least some of the microstructures to breach the functional barrier and deliver a treatment to the subject.

Embodiment 81. A system according to any one of the embodiments 1 to 80, wherein the system includes a housing containing the at least one sensor and at least one electronic processing device.

Embodiment 82. A system according to embodiment 81, wherein the housing selectively couples to the substrate.

Embodiment 83. A system according to embodiment 82, wherein the housing couples to the substrate using at least one of: mechanical coupling; adhesive coupling; and, magnetic coupling.

Embodiment 84. A system according to any one of the embodiments 81 to 83, wherein at least one of the housing and substrate are at least one of: secured to the subject; secured to the subject using anchor microstructures; secured to the subject using an adhesive patch; and, secured to the subject using a strap.

Embodiment 85. A system according to any one of the embodiments 81 to 84, wherein the housing includes housing connectors that operatively connect to substrate connectors on the substrate to communicate signals with the microstructures.

Embodiment 86. A system according to any one of the embodiments 1 to 85, wherein the system is configured to perform repeated measurements over a time period.

Embodiment 87. A system according to embodiment 86, wherein the time period is at least one of: less than 0.01 seconds; less than 0.1 seconds; less than 1 second; less than 10 seconds; at least one hour; at least one day; and, at least one week.

Embodiment 88. A system according to embodiment 86 or embodiment 87, wherein the microstructures are configured to remain in the subject during the time period.

Embodiment 89. A system according to embodiment 86 or embodiment 87, wherein the microstructures are configured to be removed when measurements are not being performed.

Embodiment 90. A system according to any one of the embodiments 1 to 89, wherein system includes: a substrate coil positioned on the substrate and operatively coupled to one or more microstructure electrodes; and, an excitation and receiving coil positioned in proximity to the substrate coil such that attenuation of a drive signal applied to the excitation and receiving coil acts as a response signal.

Embodiment 91. A system according to embodiment 90, wherein the one or more microstructure electrodes interact with one or more analytes of interest such that the response signal is dependent on a presence, absence, level or concentration of analytes of interest.

Embodiment 92. A system according to embodiment 90 or embodiment 91, wherein system includes: a first substrate coil positioned on a substrate and operatively coupled to one or more first microstructure electrodes; a second substrate coil positioned on a substrate and operatively coupled to one or more second microstructure electrodes, the second microstructure electrodes being configured to interact with analytes of interest; at least one excitation and receiving coil alteration in proximity to at least one of the first and second substrate coils such that attenuation of a drive signal applied to the at least one excitation and receiving coil acts as a response signal, and wherein the one or more electronic processing devices use the first and second response signals to a presence, absence, level or concentration of analytes of interest.

Embodiment 93. A system according to embodiment 92, wherein first and second excitation and receiving coils positioned in proximity to respective ones of the first and second substrate coils such that alteration of a drive signal applied to each excitation and receiving coil acts as a respective response signal.

Embodiment 94. A system according to any one of the embodiments 1 to 93, wherein the system is at least partially wearable.

Embodiment 95. A method for delivering treatment to a biological subject, the method including: using at least one substrate including one or more microstructures to breach a functional barrier of the subject; using at least one sensor operatively connected to at least one microstructure to measure response signals from the at least one microstructure; using at least one treatment delivery mechanism operatively coupled to at least one microstructure to deliver treatment via at least one microstructure; and, in one or more electronic processing devices, controlling the at least one treatment delivery mechanism to thereby deliver treatment to the subject at least partially in accordance with the measured response signals.

Embodiment 96. A method according to embodiment 95, wherein the treatment is at least one of: therapeutic; and, cosmetic.

Persons skilled in the art will appreciate that numerous variations and modifications will become apparent. All such variations and modifications which become apparent to persons skilled in the art, should be considered to fall within the spirit and scope that the invention broadly appearing before described.

---

The claims defining the invention are as follows:

1. A system for delivering treatment to a biological subject, the system including:
   a) at least one substrate including a plurality of microstructures configured to breach a stratum corneum of the subject;
   b) at least one sensor operatively connected to at least one microstructure of the plurality of microstructures, the at least one sensor being configured to measure response signals from the at least one microstructure of the plurality of microstructures;
   c) at least one treatment delivery mechanism operatively coupled to at least one microstructure of the plurality of microstructures to deliver treatment via at least one microstructure of the plurality of microstructures, wherein the at least one treatment delivery mechanism includes a signal generator operatively connected to the at least one microstructure of the plurality of microstructures to send an electrical stimulation signal to the at least one microstructure of the plurality of microstructures, and thereby deliver the treatment; and, wherein the electrical stimulation signal is used to at least one of:
      i) release material from a coating on the at least one microstructure of the plurality of microstructures;
      ii) disrupt the coating on the at least one microstructure of the plurality of microstructures;
      iii) dissolve the coating on the at least one microstructure of the plurality of microstructures; and
      iv) release the coating on the at least one microstructure of the plurality of microstructures; and,
   d) one or more electronic processing devices that are configured to control the at least one treatment delivery mechanism to thereby deliver treatment to the subject at least partially in accordance with the measured response signals.

2. A system according to claim 1, wherein at least one microstructure of the plurality of microstructures includes a material, and wherein the at least one treatment delivery mechanism controls release of the material.

3. A system according to claim 2, wherein at least one of:
   a) release of the material is controlled by applying at least one of optical and electrical stimulation to the at least one microstructure of the plurality of microstructures;

b) stimulation is used to at least one of:
      i) control a rate of release of material from the at least one microstructure of the plurality of microstructures;
      ii) vary a rate of release of material from the at least one microstructure of the plurality of microstructures;
      iii) control a quantity of material released from the at least one microstructure of the plurality of microstructures;
      iv) control a dose of material released from the at least one microstructure of the plurality of microstructures;
      v) substantially prevent release of material from the at least one microstructure of the plurality of microstructures;
      vi) substantially slow release of material from the at least one microstructure of the plurality of microstructures; and,
      vii) release material from the at least one microstructure of the plurality of microstructures;
   c) a change in an electrical stimulation signal applied to the at least one microstructure of the plurality of microstructures is used to trigger release of the material;
   d) a first electrical stimulation signal is applied to the at least one microstructure of the plurality of microstructures to substantially prevent release of the material; and,
   e) a second electrical stimulation signal is applied to the at least one microstructure of the plurality of microstructures to release the material.

4. A system according to claim 2, wherein the material is contained in at least one of:
   a) a coating on the at least one microstructure of the plurality of microstructures; and,
   b) a selectively dissolvable coating on the at least one microstructure of the plurality of microstructures and wherein at least one of:
      i) at least some microstructures of the plurality of microstructures are uncoated;
      ii) at least some microstructures of the plurality of microstructures are porous with an internal coating;
      iii) at least some microstructures of the plurality of microstructures are partially coated;
      iv) different microstructures of the plurality of microstructures have different coatings;

v) different parts of microstructures of the plurality of microstructures include different coatings; and, vi) at least some microstructures of the plurality of microstructures include multiple coatings.

5. A system according to claim 1, wherein at least one microstructure of the plurality of microstructures includes a selectively dissolvable coating and wherein the selectively dissolvable coating dissolves at least one of:

a) after a defined time period;

b) in response to breaching or penetration of a functional barrier;

c) in response to application of a stimulatory signal;

d) in response to a presence, absence, level or concentration of analytes; and, e) upon breaching or penetration of a functional barrier.

6. A system according to claim 5, wherein the system is configured to:

a) detect the selectively dissolvable coating dissolving based on a change in a response signal; and, b) at least one of:

i) perform at least one measurement after the selectively dissolvable coating has dissolved; and, ii) deliver treatment after the selectively dissolvable coating has dissolved.

7. A system according to claim 1, wherein at least some microstructures of the plurality of microstructures include a coating that at least one of:

a) undergoes a shape change to selectively anchor the at least some microstructures of the plurality of microstructures;

b) modifies surface properties to at least one of:

i) increase hydrophilicity;

ii) increase hydrophobicity; and, iii) minimize biofouling;

c) attracts at least one substance to the at least some microstructures of the plurality of microstructures;

d) repels at least one substance from the at least some microstructures of the plurality of microstructures;

e) attracts at least one analyte to the microstructures of the plurality of microstructures;

f) repels at least one analyte from the at least some microstructures of the plurality of microstructures;

g) provides a physical structure to at least one of:

i) facilitate penetration of the barrier;

ii) strengthen the at least some microstructures of the plurality of microstructures; and, iii) anchor the at least some microstructures of the plurality of microstructures in the subject;

h) dissolves to at least one of:

i) expose the at least some microstructure of the plurality of microstructures;

ii) expose a further coating; and, iii) expose a material;

i) provides stimulation to the subject;

j) contains a material;

k) selectively releases a material;

l) Acts as a barrier to preclude at least one substance from the at least some microstructures of the plurality of microstructures; and, m) includes at least one of:

i) polyethylene;

ii) polyethylene glycol;

iii) polyethylene oxide;

iv) zwitterions;

v) peptides;

vi) hydrogels; and, vii) self-assembled monolayer.

8. A system according to claim 1, wherein at least some microstructures of the plurality of microstructures include the material and wherein at least one of:

a) different microstructures of the at least some microstructures of the plurality of microstructures include at least one of:

i) different materials; and, ii) different doses of the therapeutic material;

b) the one or more electronic processing devices are configured to control the at least one treatment delivery mechanism to release the material from selected microstructures of the at least some microstructures of the plurality of microstructures; and, c) the material includes at least one of:

i) a bioactive material;

ii) a reagent for reacting with analytes in the subject;

iii) a binding agent for binding with analytes of interest;

iv) a material for binding one or more analytes of interest;

v) a probe for selectively targeting analytes of interest;

vi) an insulator;

vii) a material to reduce biofouling;

viii) a material to attract at least one substance to the at least some microstructures of the plurality of microstructures;

ix) a material to repel at least one substance from the at least some microstructures of the plurality of microstructures;

x) a material to attract at least some analytes to the at least some microstructures of the plurality of microstructures;

xi) a material to repel at least some analytes from the at least some microstructures of the plurality of microstructures;

xii) antivirals;

xiii) antibacterials;

xiv) anti-inflammatoires or inflammatories;

xv) agonists or antagonists;

xvi) adjuvants;

xvii) vaccines;

xviii) nanoparticles;

xix) a nucleic acid;

xx) an antigen or allergen;

xxi) parasites, bacteria, viruses, or virus-like particles;

xxii) metals or metallic compounds;

xxiii) molecules, elements or compounds;

xxiv) DNA;

XXV) protein;

xxvi) RNA, siRNA, sfRNA, iRNA;

xxvii) synthetic biological materials;

xxviii) polymers;

xxix) drugs;

xxx) hormones; and, xxxi) neurotransmitters.

9. A system according to claim 1, wherein the system includes one or more switches for selectively connecting the signal generator to one or more microstructures of the plurality of microstructures, and wherein the one or more processing devices are configured to control the switches and the signal generator to thereby controllably release material from the one or more microstructures of the plurality of microstructures.

10. A system according to claim 1, wherein the one or more electronic processing devices are configured to:

a) perform an analysis, at least in part, using the measured response signals; and, b) use results of the analysis to control the at least one treatment delivery mechanism.

11. A system according to claim 1, wherein the system includes a monitoring device and a patch including the at least one substrate and the plurality of microstructures and wherein the monitoring device is configured to at least one of:

a) cause a measurement to be performed;

b) at least partially analyze measurements;

c) control delivery of therapy;

d) control stimulation applied to at least one microstructure of the plurality of microstructures;

e) generate an output; and, f) cause an action to be performed.

12. A system according to claim 1, wherein the system includes:

a) a wearable monitoring device configured to:

i) perform measurements; and, ii) control delivery of the treatment; and, b) a processing system that:

i) receives subject data derived from the measured response signals; and, ii) analyses the subject data to at least one of:

(1) generate at least one indicator, the at least one indicator being at least partially indicative of a physiological status associated with the subject;

(2) determine treatment requirements; and, (3) cause treatment to be delivered.

13. System according to claim 12, wherein the system includes a client device that:

a) receives measurement data from the wearable monitoring device;

b) generates subject data using the measurement data;

c) transfers the subject data to the processing system;

d) stores a representation of the at least one indicator;

e) receives the at least one indicator from the processing system; and, f) displays a representation of the at least one indicator.

14. A system according to claim 1, wherein at least some microstructures of the plurality of microstructures are plate microstructures having a substantially rounded rectangular cross sectional shape.

15. A system according to claim 1, wherein at least some microstructures of the plurality of microstructures have at least one of:

a) have a length that is at least one of:

i) less than 2500 μm;

ii) less than 1000 μm;

iii) less than 750 μm;

iv) less than 450 μm;

v) less than 300 μm;

vi) less than 250 μm;

vii) about 250 μm;

viii) about 150 μm;

ix) greater than 100 μm;

x) greater than 50 μm; and, xi) greater than 10 μm;

b) have a maximum width that is at least one of:

i) less than 2500 μm;

ii) less than 1000 μm;

iii) less than 750 μm;

iv) less than 450 μm;

v) less than 300 μm;

vi) less than 250 μm;

vii) of a similar order of magnitude to the length;

viii) greater than the length;

ix) about the same as the length;

x) about 250 μm;

xi) about 150 μm; and, xii) greater than 50 μm; and, c) have a maximum thickness that is at least one of:

i) less that the width;

ii) significantly less that the width;

iii) of a smaller order of magnitude to the length;

iv) less than 300 μm;

v) less than 200 μm;

vi) less than 50 μm;

vii) about 25 μm; and, viii) greater than 10 μm;

d) include a shoulder that is configured to abut against the stratum corneum to control a depth of penetration; and, e) include a shaft extending from a shoulder to a tip, the shaft being configured to control a position of the tip in the subject; and, f) have a density that is at least one of:

i) less than 5000 per cm$^2$;

ii) greater than 100 per cm$^2$; and, iii) about 600 per cm$^2$; and, g) have a spacing that is at least one of:

i) less than 1 mm;

ii) about 0.5 mm;

iii) about 0.2 mm;

iv) about 0.1 mm; and, v) more than 10 μm.

16. A system according to claim 1, wherein at least one microstructure of the plurality of microstructures include an electrode and wherein the electrode at least one of:

a) extends over a length of a distal portion of the at least one microstructure of the plurality of microstructures;

b) extends over a length of a portion of the at least one microstructure of the plurality of microstructures spaced from a tip;

c) is positioned proximate a distal end of the at least one microstructure of the plurality of microstructures;

d) is positioned proximate a tip of the at least one microstructure of the plurality of microstructures;

e) extends over at least 25% of a length of the at least one microstructure of the plurality of microstructures;

f) extends over less than 50% of a length of the at least one microstructure of the plurality of microstructures;

g) extends over about 60 μm of the at least one microstructure of the plurality of microstructures;

h) is configured to be positioned in a viable epidermis of the subject in use; and, i) has a surface area of at least one of:

i) less than 200,000 μm$^2$;

ii) about 22,500 μm$^2$; and, iii) at least 2,000 μm$^2$; and, j) interacts with one or more analytes of interest such that a response signal is dependent on a presence, absence, level or concentration of the one or more analytes of interest.

17. A method for delivering treatment to a biological subject, the method including:

a) using at least one substrate including a plurality of microstructures to breach a functional barrier of the subject;

b) using at least one sensor operatively connected to at least one microstructure of the plurality of microstructures to measure response signals from the at least one microstructure of the plurality of microstructures;

c) using at least one treatment delivery mechanism operatively coupled to at least one microstructure of the plurality of microstructures to deliver treatment via at least one microstructure of the plurality of microstructures, wherein the at least one treatment delivery mechanism includes a signal generator operatively connected to the at least one microstructure of the plurality of microstructures to send an electrical stimulation signal to the at least one microstructure of the plurality of microstructures, and thereby deliver the treatment; and, wherein the electrical stimulation signal is used to at least one of:

i) release material from a coating on the at least one microstructure of the plurality of microstructures;

ii) disrupt the coating on the at least one microstructure of the plurality of microstructures;

iii) dissolve the coating on the at least one microstructure of the plurality of microstructures; and, iv) release the coating on the at least one microstructure of the plurality of microstructures; and, d) in one or more electronic processing devices, controlling the at least one treatment delivery mechanism to thereby deliver treatment to the subject at least partially in accordance with the measured response signals.

18. A method according to claim 17, wherein the treatment is at least one of:

a) therapeutic; and, b) cosmetic.

19. A method for treating a biological subject, the method including:

a) using at least one substrate including a plurality of microstructures to breach a functional barrier of the subject;

b) using at least one sensor operatively connected to at least one microstructure of the plurality of microstructures to measure response signals from the at least one microstructure of the plurality of microstructures;

c) using at least one treatment delivery mechanism operatively coupled to at least one microstructure of the plurality of microstructures to deliver treatment via at least one microstructure of the plurality of microstructures, wherein the at least one treatment delivery mechanism includes a signal generator operatively connected to the at least one microstructure of the plurality of microstructures to send an electrical stimulation signal to the at least one microstructure of the plurality of microstructures, and thereby deliver the treatment; and, wherein the electrical stimulation signal is used to at least one of:

i) release material from a coating on the at least one microstructure of the plurality of microstructures;

ii) disrupt the coating on the at least one microstructure of the plurality of microstructures;

iii) dissolve the coating on the at least one microstructure of the plurality of microstructures; and, iv) release the coating on the at least one microstructure of the plurality of microstructures; and, d) in one or more electronic processing devices, controlling the at least one treatment delivery mechanism to thereby deliver treatment to the subject at least partially in accordance with the measured response signals.

\* \* \* \* \*

SEQUENCE LISTING

```
<160> NUMBER OF SEQ ID NOS: 26

<210> SEQ ID NO 1
<211> LENGTH: 76
<212> TYPE: DNA
<213> ORGANISM: Artificial Sequence
<220> FEATURE:
<223> OTHER INFORMATION: Synthetic

<400> SEQUENCE: 1
agtctccgct gtcctcccga tgcacttgac gtatgtctca ctttcttttc attgacatgg        60
gatgacgccg tgactg                                                        76

<210> SEQ ID NO 2
<211> LENGTH: 40
<212> TYPE: DNA
<213> ORGANISM: artificial sequence
<220> FEATURE:
<223> OTHER INFORMATION: Synthetic

<400> SEQUENCE: 2
cgtgcagtac gccaaccttt ctcatgcgct gcccctctta                              40

<210> SEQ ID NO 3
<211> LENGTH: 76
<212> TYPE: DNA
<213> ORGANISM: artificial sequence
<220> FEATURE:
<223> OTHER INFORMATION: Synthetic

<400> SEQUENCE: 3
agtctccgct gtcctcccga tgcacttgac gtatgtctca ctttcttttc attgacatgg        60
gatgacgccg tgactg                                                        76

<210> SEQ ID NO 4
<211> LENGTH: 40
<212> TYPE: DNA
<213> ORGANISM: Artificial Sequence
<220> FEATURE:
<223> OTHER INFORMATION: Synthetic

<400> SEQUENCE: 4
cgtgcagtac gccaaccttt ctcatgcgct gcccctctta                              40

<210> SEQ ID NO 5
<211> LENGTH: 40
<212> TYPE: DNA
<213> ORGANISM: Artificial Sequence
<220> FEATURE:
<223> OTHER INFORMATION: Synthetic
```

-continued

<400> SEQUENCE: 5
cgcatgccaa acgttgcctc atagttccct ccccgtgtcc                                          40

<210> SEQ ID NO 6
<211> LENGTH: 40
<212> TYPE: DNA
<213> ORGANISM: Artificial Sequence
<220> FEATURE:
<223> OTHER INFORMATION: Synthetic

<400> SEQUENCE: 6
tcacaccctc cctcccacat accgcataca ctttctgatt                                          40

<210> SEQ ID NO 7
<211> LENGTH: 40
<212> TYPE: DNA
<213> ORGANISM: Artificial Sequence
<220> FEATURE:
<223> OTHER INFORMATION: Synthetic

<400> SEQUENCE: 7
cccgaccacg tccctgccct ttcctaacct gtttgttgat                                          40

<210> SEQ ID NO 8
<211> LENGTH: 40
<212> TYPE: DNA
<213> ORGANISM: Artificial Sequence
<220> FEATURE:
<223> OTHER INFORMATION: Synthetic

<400> SEQUENCE: 8
atgcgttgaa ccctcctgac cgtttatcac atactccaga                                          40

<210> SEQ ID NO 9
<211> LENGTH: 40
<212> TYPE: DNA
<213> ORGANISM: Artificial Sequence
<220> FEATURE:
<223> OTHER INFORMATION: Synthetic

<400> SEQUENCE: 9
cgtgcagtac gccaaccttt ctcatgcgct gcccctctta                                          40

<210> SEQ ID NO 10
<211> LENGTH: 40
<212> TYPE: DNA
<213> ORGANISM: Artificial Sequence
<220> FEATURE:
<223> OTHER INFORMATION: Synthetic

<400> SEQUENCE: 10
caactgtaat gtaccctcct cgatcacgca ccacttgcat                                          40

<210> SEQ ID NO 11
<211> LENGTH: 40
<212> TYPE: DNA
<213> ORGANISM: Artificial Sequence
<220> FEATURE:
<223> OTHER INFORMATION: Synthetic

<400> SEQUENCE: 11
cgcatgccaa acgttgcctc atagttccct ccccgtgtcc                                          40

<210> SEQ ID NO 12

<211> LENGTH: 76
<212> TYPE: DNA
<213> ORGANISM: Artificial Sequence
<220> FEATURE:
<223> OTHER INFORMATION: Synthetic

<400> SEQUENCE: 12
agtctccgct gtcctcccga tgcacttgac gtatgtctca ctttcttttc attgacatgg        60
gatgacgccg tgactg                                                        76

<210> SEQ ID NO 13
<211> LENGTH: 40
<212> TYPE: DNA
<213> ORGANISM: Artificial Sequence
<220> FEATURE:
<223> OTHER INFORMATION: Synthetic

<400> SEQUENCE: 13
tcacaccctc cctcccacat accgcataca ctttctgatt                              40

<210> SEQ ID NO 14
<211> LENGTH: 40
<212> TYPE: DNA
<213> ORGANISM: Artificial Sequence
<220> FEATURE:
<223> OTHER INFORMATION: Synthetic

<400> SEQUENCE: 14
cccgaccacg tccctgccct ttcctaacct gtttgttgat                              40

<210> SEQ ID NO 15
<211> LENGTH: 40
<212> TYPE: DNA
<213> ORGANISM: Artificial Sequence
<220> FEATURE:
<223> OTHER INFORMATION: Synthetic

<400> SEQUENCE: 15
atgcgttgaa ccctcctgac cgtttatcac atactccaga                              40

<210> SEQ ID NO 16
<211> LENGTH: 40
<212> TYPE: DNA
<213> ORGANISM: Artificial Sequence
<220> FEATURE:
<223> OTHER INFORMATION: Synthetic

<400> SEQUENCE: 16
cgtgcagtac gccaaccttt ctcatgcgct gccctctta                               40

<210> SEQ ID NO 17
<211> LENGTH: 40
<212> TYPE: DNA
<213> ORGANISM: Artificial Sequence
<220> FEATURE:
<223> OTHER INFORMATION: Synthetic

<400> SEQUENCE: 17
caactgtaat gtaccctcct cgatcacgca ccacttgcat                              40

<210> SEQ ID NO 18
<211> LENGTH: 40
<212> TYPE: DNA
<213> ORGANISM: Artificial Sequence
<220> FEATURE:
<223> OTHER INFORMATION: Synthetic

<400> SEQUENCE: 18
cgcatgccaa acgttgcctc atagttccct ccccgtgtcc                                    40

<210> SEQ ID NO 19
<211> LENGTH: 40
<212> TYPE: DNA
<213> ORGANISM: Artificial Sequence
<220> FEATURE:
<223> OTHER INFORMATION: Synthetic

<400> SEQUENCE: 19
tcacaccctc cctcccacat accgcataca ctttctgatt                                    40

<210> SEQ ID NO 20
<211> LENGTH: 40
<212> TYPE: DNA
<213> ORGANISM: Artificial Sequence
<220> FEATURE:
<223> OTHER INFORMATION: Synthetic

<400> SEQUENCE: 20
cccgaccacg tccctgccct ttcctaacct gtttgttgat                                    40

<210> SEQ ID NO 21
<211> LENGTH: 40
<212> TYPE: DNA
<213> ORGANISM: Artificial Sequence
<220> FEATURE:
<223> OTHER INFORMATION: Synthetic

<400> SEQUENCE: 21
atgcgttgaa ccctcctgac cgtttatcac atactccaga                                    40

<210> SEQ ID NO 22
<211> LENGTH: 40
<212> TYPE: DNA
<213> ORGANISM: Artificial Sequence
<220> FEATURE:
<223> OTHER INFORMATION: Synthetic

<400> SEQUENCE: 22
caactgtaat gtaccctcct cgatcacgca ccacttgcat                                    40

<210> SEQ ID NO 23
<211> LENGTH: 40
<212> TYPE: DNA
<213> ORGANISM: Artificial Sequence
<220> FEATURE:
<223> OTHER INFORMATION: Synthetic

<400> SEQUENCE: 23
cgtgcagtac gccaaccttt ctcatgcgct gccctctta                                     40

<210> SEQ ID NO 24
<211> LENGTH: 40
<212> TYPE: DNA
<213> ORGANISM: Artificial Sequence
<220> FEATURE:
<223> OTHER INFORMATION: Synthetic

<400> SEQUENCE: 24
cgcatgccaa acgttgcctc atagttccct ccccgtgtcc                                    40

<210> SEQ ID NO 25

```
<211> LENGTH: 25
<212> TYPE: DNA
<213> ORGANISM: Artificial Sequence
<220> FEATURE:
<223> OTHER INFORMATION: Synthetic

<400> SEQUENCE: 25
gggatggggt gggtggccag cgatt                                    25

<210> SEQ ID NO 26
<211> LENGTH: 25
<212> TYPE: DNA
<213> ORGANISM: Artificial Sequence
<220> FEATURE:
<223> OTHER INFORMATION: Synthetic

<400> SEQUENCE: 26
ttaggggtgg tgtggttggc aattc                                    25
```